US012636370B2

(12) United States Patent
Duncan

(10) Patent No.: US 12,636,370 B2
(45) Date of Patent: May 26, 2026

(54) COMBINATION THERAPY FOR TREATMENT OF CANCER

(71) Applicant: Institute For Cancer Research, Philadelphia, PA (US)

(72) Inventor: James S. Duncan, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 908 days.

(21) Appl. No.: 17/633,307

(22) PCT Filed: Aug. 6, 2020

(86) PCT No.: PCT/US2020/045197
§ 371 (c)(1),
(2) Date: Feb. 7, 2022

(87) PCT Pub. No.: WO2021/026349
PCT Pub. Date: Feb. 11, 2021

(65) Prior Publication Data
US 2023/0011378 A1      Jan. 12, 2023

Related U.S. Application Data

(60) Provisional application No. 62/884,368, filed on Aug. 8, 2019.

(51) Int. Cl.
| | |
|---|---|
| *A61K 31/416* | (2006.01) |
| *A61K 31/436* | (2006.01) |
| *A61K 31/4375* | (2006.01) |
| *A61K 31/4439* | (2006.01) |
| *A61K 31/444* | (2006.01) |
| *A61K 31/4535* | (2006.01) |
| *A61K 31/4706* | (2006.01) |
| *A61K 31/4745* | (2006.01) |
| *A61K 31/496* | (2006.01) |
(Continued)

(52) U.S. Cl.
CPC ............ *A61K 47/55* (2017.08); *A61K 31/551* (2013.01); *A61K 45/06* (2013.01); *A61K 47/545* (2017.08); *A61P 35/00* (2018.01)

(58) Field of Classification Search
None
See application file for complete search history.

(56) References Cited

U.S. PATENT DOCUMENTS

2014/0038999 A1 * 2/2014 Vrudhula ................ A61P 25/02
546/110
2016/0058872 A1   3/2016 Crew et al.
(Continued)

FOREIGN PATENT DOCUMENTS

WO      2017212329      12/2017
WO      WO-2018033556 A1 *  2/2018  ............. A61K 45/06
(Continued)

OTHER PUBLICATIONS

Pei et al., RSC Adv., 2019, 9, 16967, Apr. 30, 2019 (Year: 2019).*
(Continued)

*Primary Examiner* — Kortney L. Klinkel
*Assistant Examiner* — Alison Azar Salamatian
(74) *Attorney, Agent, or Firm* — Ballard Spahr LLP

(57) ABSTRACT

Pharmaceutical compositions comprising: one or more bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents; and one or more kinase inhibitors, one or more KRAS inhibitors, or one or more autophagy inhibitors; and methods of treating cancer in a human patient by administering such pharmaceutical compositions are described herein.

BBI
JQ1
BBD
MZ1

8 Claims, 116 Drawing Sheets

(51) Int. Cl.

| | |
|---|---|
| *A61K 31/502* | (2006.01) |
| *A61K 31/5025* | (2006.01) |
| *A61K 31/506* | (2006.01) |
| *A61K 31/517* | (2006.01) |
| *A61K 31/519* | (2006.01) |
| *A61K 31/5377* | (2006.01) |
| *A61K 31/55* | (2006.01) |
| *A61K 31/551* | (2006.01) |
| *A61K 31/555* | (2006.01) |
| *A61K 31/69* | (2006.01) |
| *A61K 45/06* | (2006.01) |
| *A61K 47/54* | (2017.01) |
| *A61K 47/55* | (2017.01) |
| *A61P 35/00* | (2006.01) |
| *C07D 401/12* | (2006.01) |
| *C07D 401/14* | (2006.01) |
| *C07D 405/04* | (2006.01) |
| *C07D 413/04* | (2006.01) |
| *C07D 417/14* | (2006.01) |
| *C07D 471/04* | (2006.01) |
| *C07D 491/147* | (2006.01) |
| *C07D 495/14* | (2006.01) |

(56) References Cited

U.S. PATENT DOCUMENTS

| | | | |
|---|---|---|---|
| 2018/0161298 A1 | 6/2018 | Deretic et al. | |
| 2018/0228907 A1* | 8/2018 | Crew .................. | C07D 471/04 |
| 2019/0175612 A1 | 6/2019 | Pillow et al. | |
| 2023/0011378 A1 | 1/2023 | Duncan | |

FOREIGN PATENT DOCUMENTS

| | | |
|---|---|---|
| WO | 2019075114 | 4/2019 |
| WO | 2019079701 | 4/2019 |
| WO | 2021026349 | 2/2021 |
| WO | 2021142351 | 7/2021 |

OTHER PUBLICATIONS

Chen et al.,. Bioorganic Chemistry 81 (2018) 536-544 (Year: 2018).*

Grygier (J Med Chem. Mar. 8, 2023;66(6):4009-4024 (Year: 2023).*

Anonymous: "LY3023414 I PI3K inhibitor I Read Reviews & Product Use Citations", Aug. 5, 2018 (Aug. 5, 2018), XP093136708, https://web.archive.org/web/20180805205633/https://www.selleckchem.com/products/ly3023414.html.

Duarte Andressa et al, "The Role of the LY294002—A Non-Selective Inhibitor of Phosphatidylinositol 3-Kinase (PI3K) Pathway—in Cell Survival and Proliferation in Cell Line SCC-25", Asian Pacific Journal of Cancer Prevention, 20(11): 3377-3383 (2019).

Du Liyan et al., "Everolimus inhibits breast cancer cell growth through PI3K/AKT/mTOR signaling pathway", Molecular Medicine Reports, 17:7163-7169 (2018), XP093136692.

Pei et al., "Small molecule PROTACs: an emerging technology for targeted therapy in drug discovery", RSC Advances, 2019, 9, pp. 16967-16976.

Olson et al., "Pharmacological perturbation of CDK9 using selective CDK9 inhibition or degradation", Nature Chemical Biology, 2017, 14(2), pp. 163-170.

Robb et al., "Chemicially induced degradation of CDK9 by a proteolysis targeting chimera (PROTAC)", Chemical Communications, 2017, 53(54), pp. 7577-7580.

Saenz et al., "Novel BET protein proteolysis-targeting chimera exerts superior lethal activity than bromodomain inhibitor (BETi) against post-myeloproliferative neoplasm secondary (s) AML cells", Leukemia, 2017, 31(9), pp. 1951-1961.

Flanagan et al., "Abstract P5-04-18: ARV-471, an oral estrogen receptor PROTAC degrader for breast cancer", Cancer Research, 2019, 79 (4_Supplement), pp. 1-2.

Zhang et al., "Protein targeting chimeric molecules specific for bromodomain and extra-terminal motif family proteins are active against pre-clinical models of multiple myeloma", Leukemia, 2018, 32(10), pp. 2224-2239.

Sahni et al., "Targeting bromodomain and extraterminal proteins in breast cancer", Pharmacological Research, 2018, 129, pp. 156-176.

Cochran et al., "Bromodomains: a new target class for drug development", Nature Reviews Drug Discovery, 2019, 18(8), pp. 609-628.

Lim et al., "Proteolysis targeting chimeric molecules as therapy for multiple myeloma: efficacy, biomarker and drug combinations", Haematologica, 2019, 104(6), pp. 1209-1220.

Kurimchak et al., "Resistance to BET Bromodomain Inhibitors Is Mediated by Kinome Reprogramming in Ovarian Cancer", Cell Reports, 2016, 16(5), pp. 1273-1286.

Kurimchak et al., "MDR1 Drug Efflux Pump Promotes Intrinsic and Acquired Resistance to PROTACs in Cancer Cells", bioRxiv, 2021, pp. 1.

Kurimchak et al., "The Drug Efflux pump MDR1 promotes intrinsic and acquired resistance to PROTACs in cancer cells", Science Signaling, 2022, pp. 1-36.

* cited by examiner

RTK pY profiles

1. EGFR, 2. ERBB2, 3. ERBB3,
4. PDGFRB 5. INSR, 6. IGF1R,
7. AXL, 8. MET, 9. ROR

G.

H.

Kinases activated and/or upregulated by chronic BBD-treatment as determined by MIB-MS and KSEA (P<0.05)

D.

E.

F.

G.

I.

D.

E.

F.

G.

H.

A.

B.

C.

D.

E.

COV362

F.

OVCAR5

G.

H.

I.

J.

K.

L.

A.

—— drug    —— drug + JQ1    —— drug + MZ1    —— drug + cis-MZ1

A.

— drug     — drug + JQ1     — drug + MZ1     — drug + cis-MZ1

B.

B.

—— drug    —— drug + JQ1    —— drug + MZ1    —— drug + cis-MZ1

C.

OVCAR8

D.

OVCAR8

E.

F.

G.

H.

I.

J.

A.

B.

C.

D.

G.

H.

I.

J.

K.

M.

N.

O.

P.

A.

B.

G.

H.

I.

J.

K.

L.

A.

A.

B.

B.

C.

D.

E.

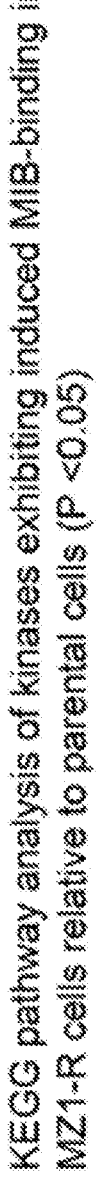
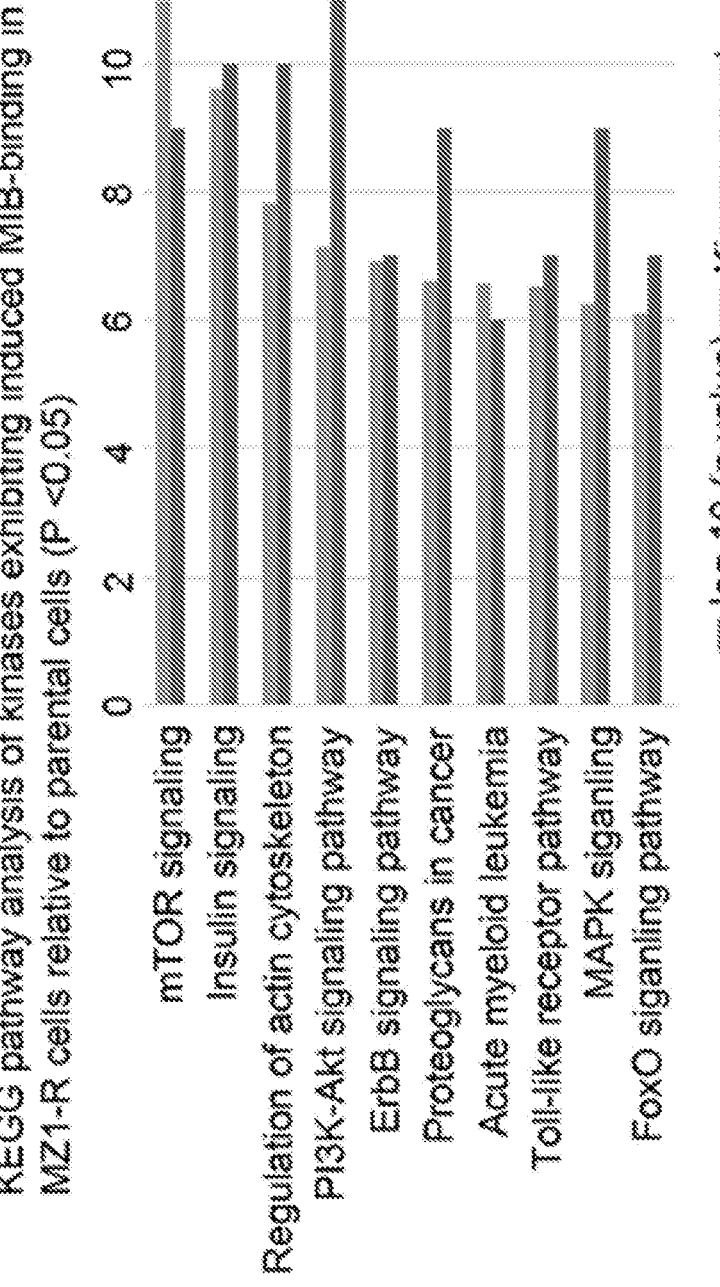

F.

KEGG pathway analysis of kinases exhibiting induced MIB-binding in MZ1-R cells relative to parental cells (P <0.05)

mTOR signaling
Insulin signaling
Regulation of actin cytoskeleton
PI3K-Akt signaling pathway
ErbB signaling pathway
Proteoglycans in cancer
Acute myeloid leukemia
Toll-like receptor pathway
MAPK siganling
FoxO siganling pathway ▦ log 10 (p value)　▦ Kinase count

— GSK1904529A
— MZ1 + GSK529A
— JQ1 + GSK529A

K.

K.

L.

L.

M.

N.

N.

A.

B.

Thal-R cells are grown in
500 nM Thal SNS 232

DLD-1
(*KRAS* G13D, *PIK3CA* E545K)

C)

Bliss synergy score: 24.117

D)

D)

E)

F)

G)

H)

I)

COMBINATION THERAPY FOR TREATMENT OF CANCER

REFERENCE TO GOVERNMENT GRANTS

This invention was made with government support under Grant Nos. CA211670 and CA006927 awarded by the National Institutes of Health. The government has certain rights in the invention.

FIELD

The present disclosure is directed to pharmaceutical compositions comprising: one or more bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents; and one or more kinase inhibitors, one or more KRAS inhibitors, or one or more autophagy inhibitors; and methods of treating cancer in a human patient by administering such pharmaceutical compositions.

BACKGROUND

Ovarian cancer represents the fifth-leading cause of death in women in the United States. High-Grade Serous Ovarian Carcinoma (HGSOC) is the most common and deadly subtype of epithelial ovarian cancer but currently has limited effective molecular targeted therapies. Recently, PROTAC (Proteolysis-Targeting Chimeras) degraders have emerged as promising anti-cancer drugs through utilization of the cancer cells own protein destruction machinery to selectively degrade essential tumor drivers. A number of BET protein degraders (BBD) have been identified including MZ1, which uses JQ1 as the bromodomain targeting molecule and recruits E3 ligases using a VHL-binding moiety, and ARV825 with OTX015 as the warhead and Cereblon (CRBN)-binding moiety for E3 ligase recruitment. Targeted degradation of BET proteins has been shown to cause significant tumor growth inhibition or regression in mouse models of prostate cancer, demonstrating the in vivo therapeutic potential of BBD. Notably, recent studies have suggested BET protein degradation differs from BET protein inhibition, where BBD treatment distinctly blocks transcriptional elongation in cancer cells providing superior antiproliferative and apoptosis inducing effects in cancer cells. Furthermore, BBD have been reported to have greater efficacy than traditional BBI in numerous cancer models, suggesting BET degradation may represent the more favorable method for targeting BET proteins in cancer. However, chronic exposure to BBD therapies triggers kinome reprogramming in cancer cells, which thus acquire resistance to BBD treatment thereby limiting the effectiveness of this therapy. Accordingly, there is a need for therapeutic approaches that overcome resistance to BBD treatment to maintain its efficiency.

SUMMARY

The present disclosure provides pharmaceutical compositions comprising: one or more bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents, or a combination thereof, and one or more kinase inhibitors, one or more KRAS inhibitors, or one or more autophagy inhibitors, or any combination thereof.

The present disclosure also provides methods for augmenting the therapeutic effect in a human cancer patient undergoing treatment with a BET-PROTAC therapeutic agent or CDK9-PROTAC therapeutic agent comprising administering one or more kinase inhibitors, one or more KRAS inhibitors, or one or more autophagy inhibitors, or any combination thereof, to the patient.

The present disclosure also provides methods of treating cancer in a human patient in need thereof, the method comprising administering to the patient a therapeutically effective amount of a pharmaceutical composition comprising: one or more BET-PROTAC therapeutic agents or one or more CDK9-PROTAC therapeutic agents, or a combination thereof; and one or more kinase inhibitors, one or more KRAS inhibitors, or one or more autophagy inhibitors, or any combination thereof.

MZ1-R or JQ1-R inhibitor treated cell viabilities were normalized to DMSO treated JQ1-R or MZ1-R cells, respectfully.

Figure 11:
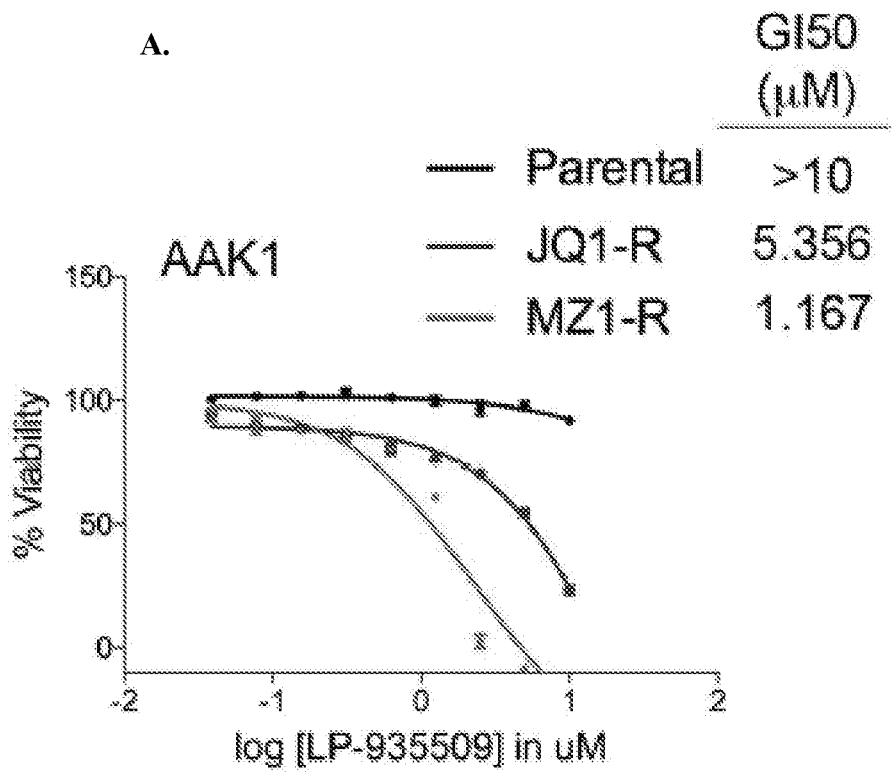
FIG. 11A shows parental, JQ1-R or MZ1-R OVCAR8 cells were treated with escalating doses of LP-935509 for 5 days and cell viability was assessed by CellTiter-Glo.
Figure 11:
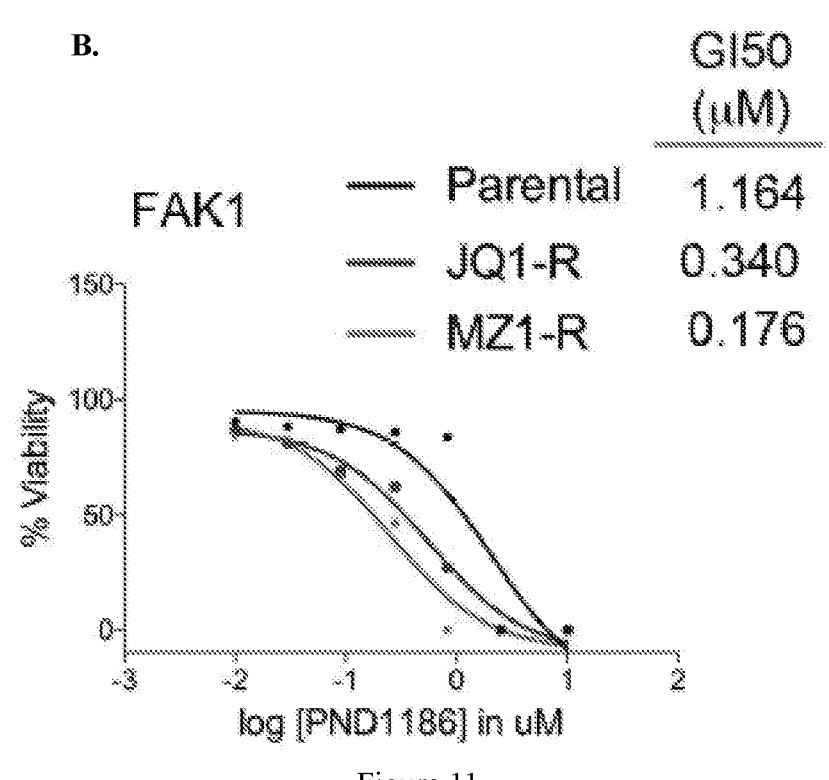
Figure 11:
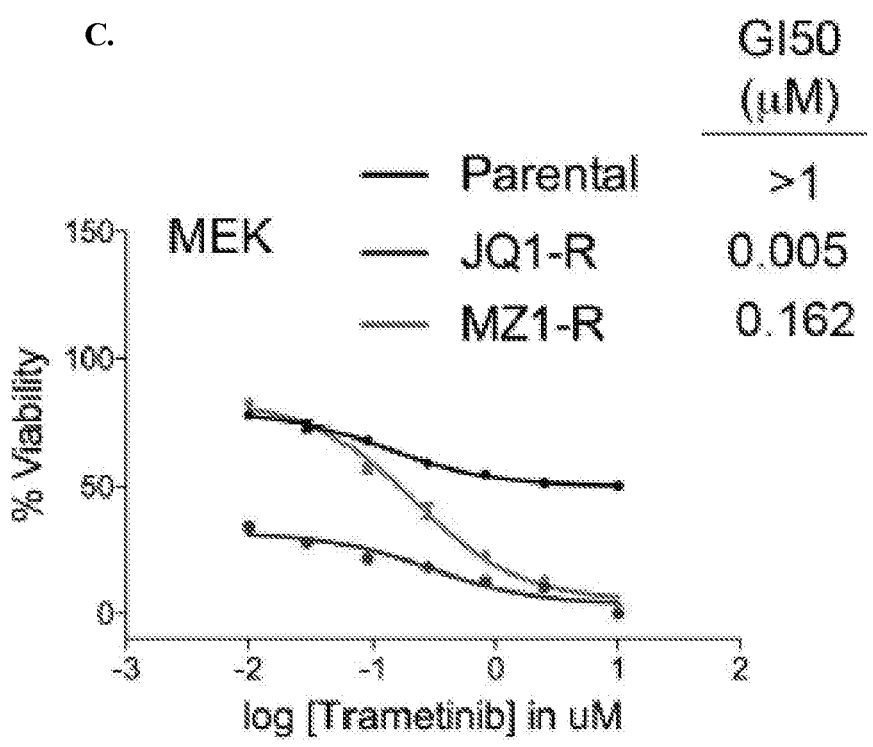
Figure 11:
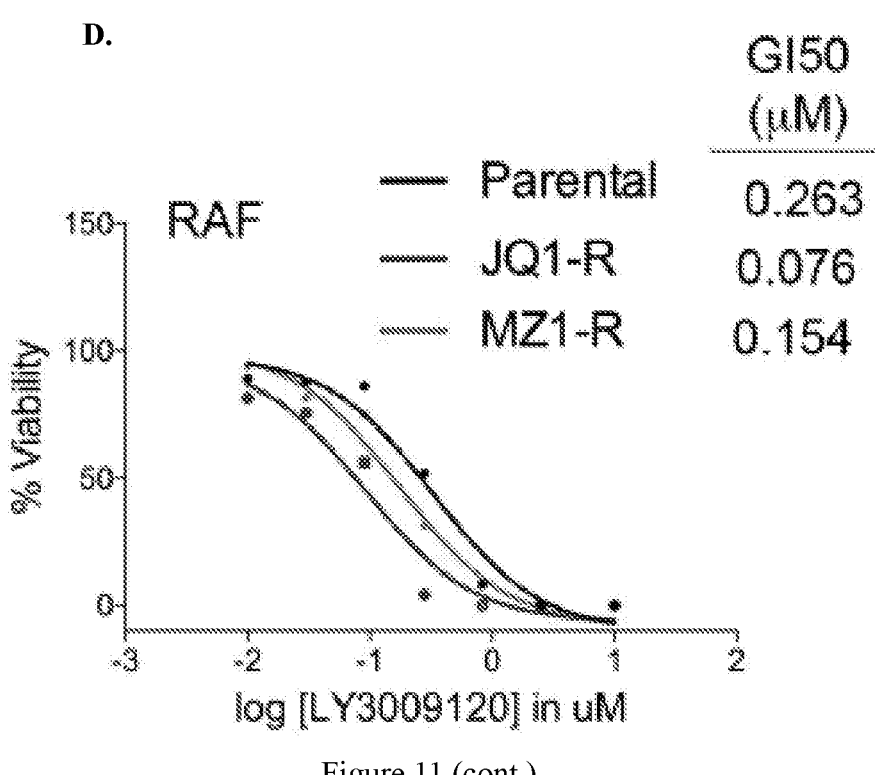
Figure 11:
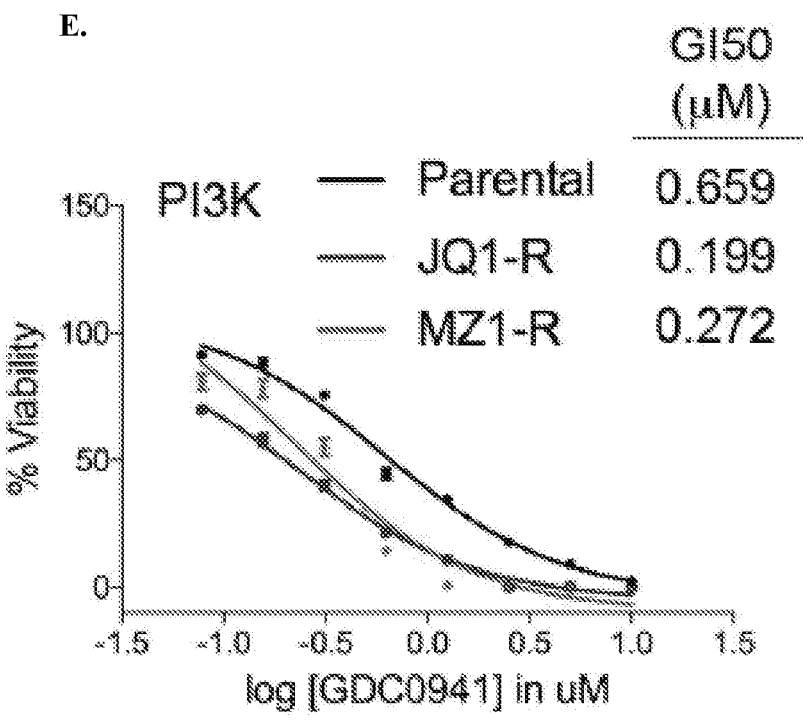
Figure 11:
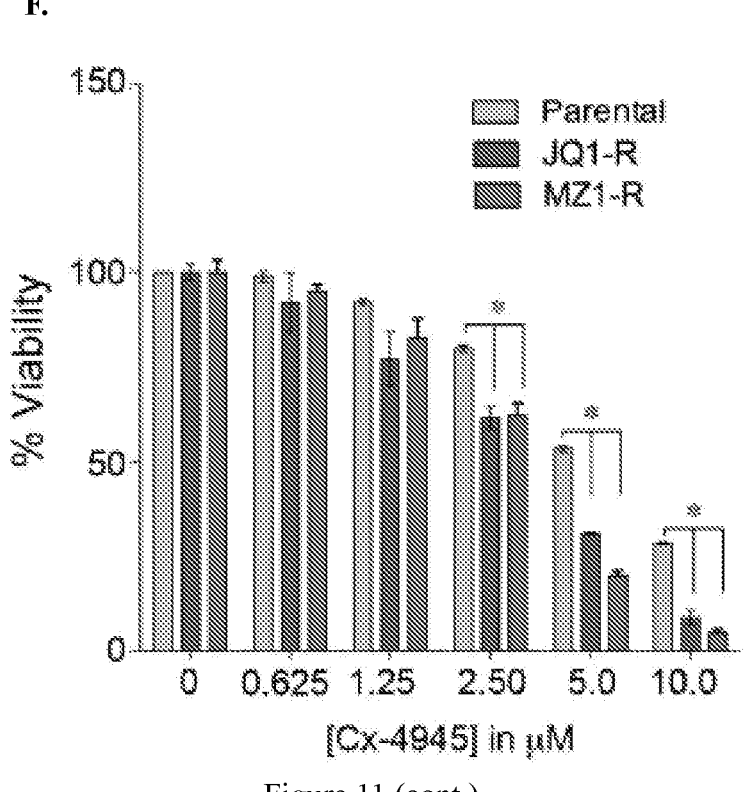
Figure 11:
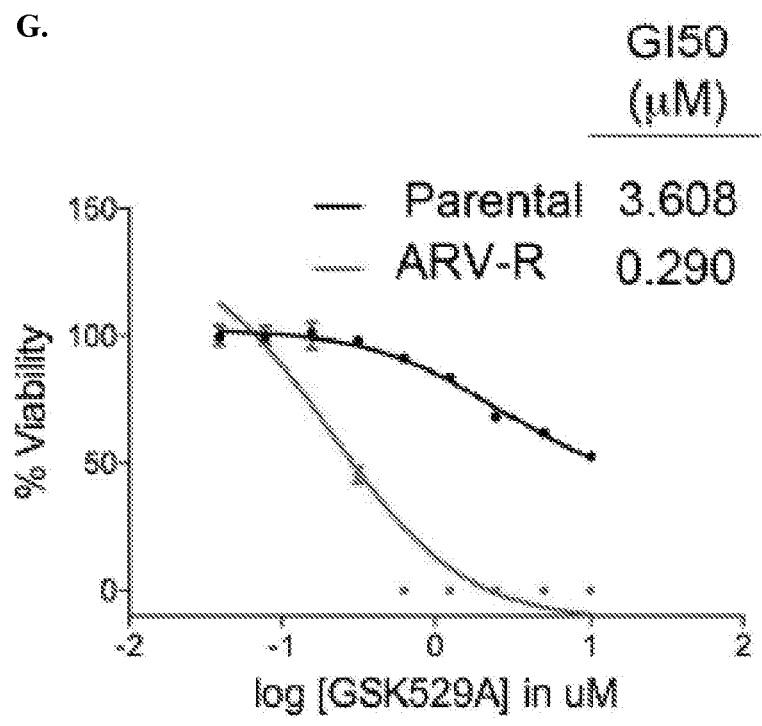
Figure 11:
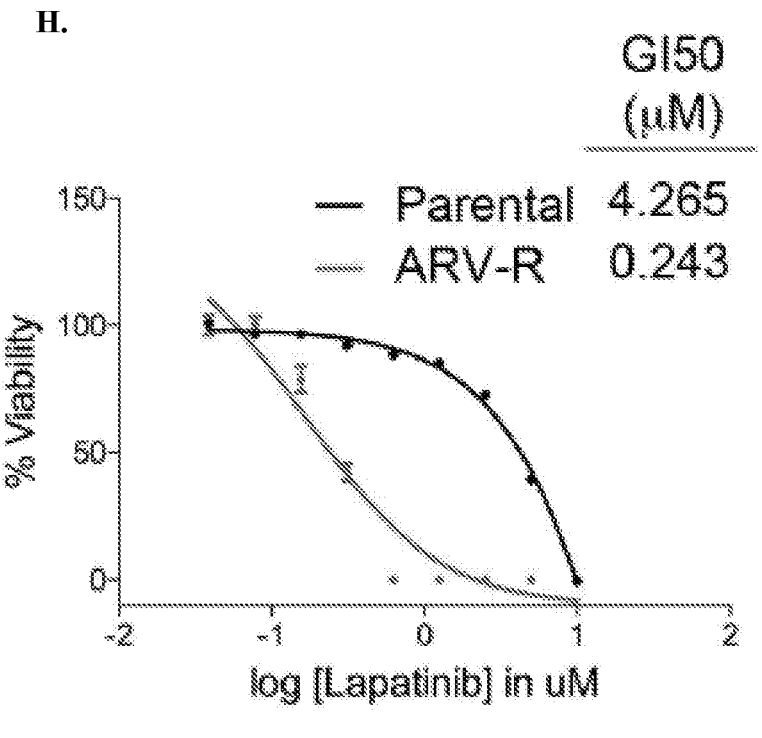
Figure 11:
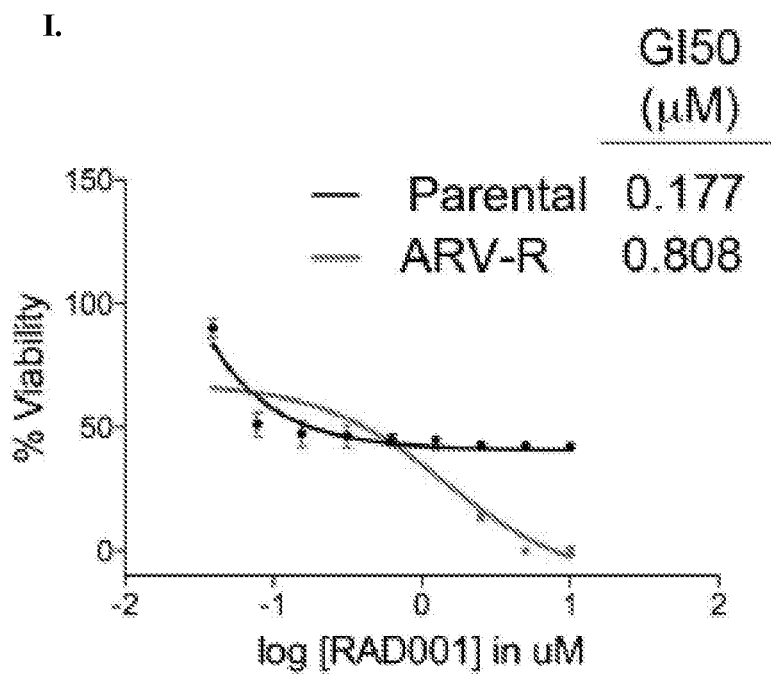
Figure 11:
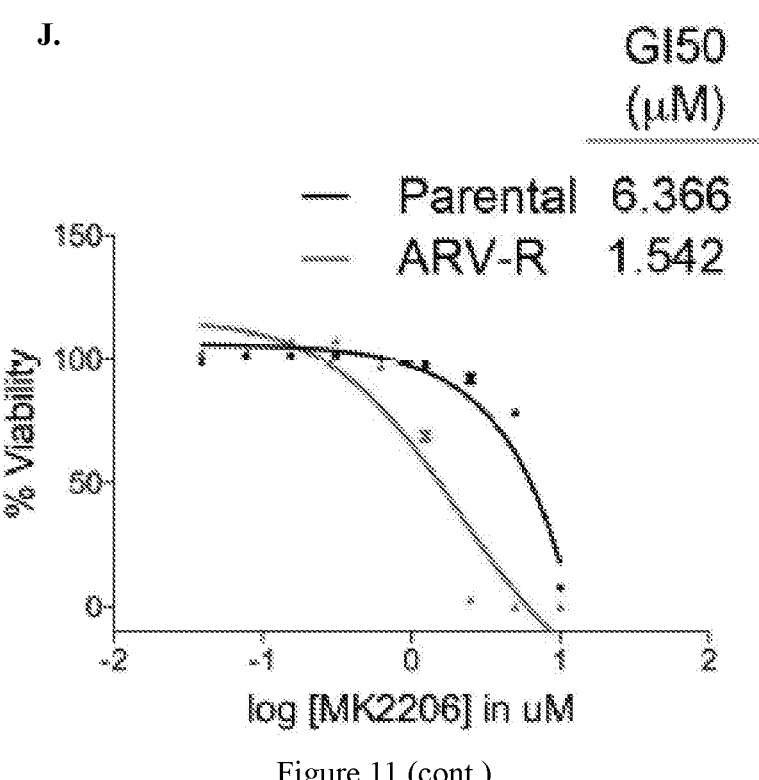
Figure 11:
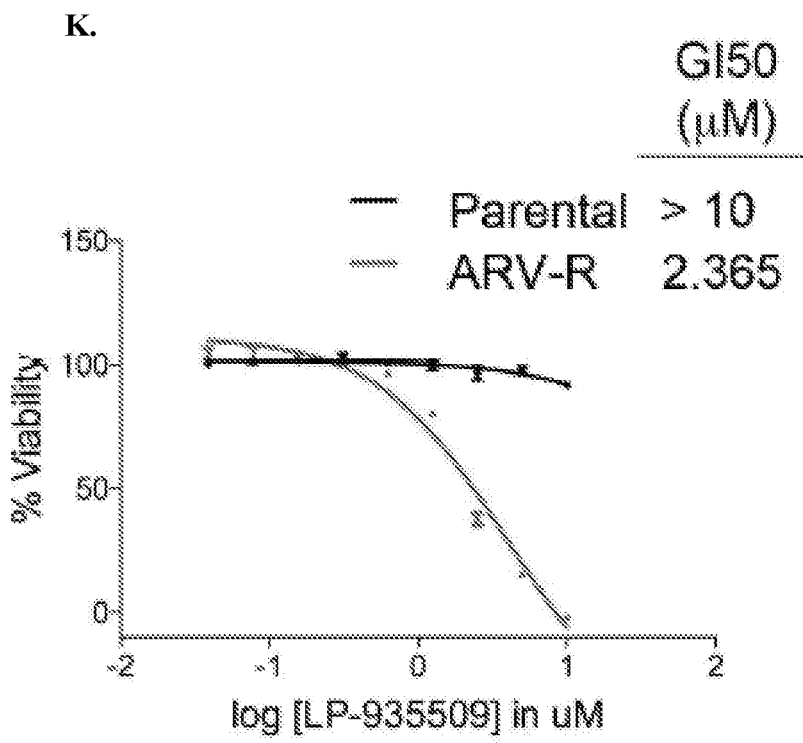
Figure 11:
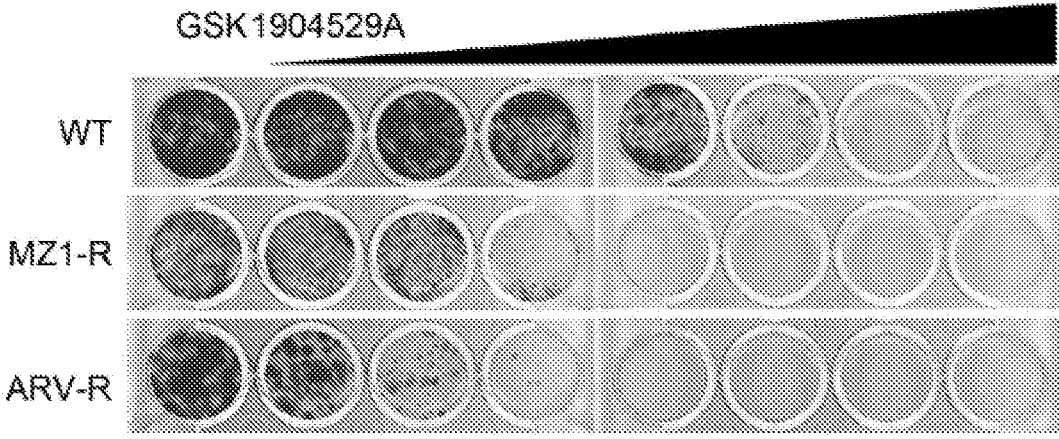

FIG. 11B shows parental, JQ1-R or MZ1-R OVCAR8 cells treated with escalating doses of PND11 for 5 days and cell viability was assessed by CellTiter-Glo; MZ1-R or JQ1-R inhibitor treated cell viabilities were normalized to DMSO treated JQ1-R or MZ1-R cells, respectfully.

FIG. 11C shows parental, JQ1-R or MZ1-R OVCAR8 cells treated with escalating doses of or Trametinib for 5 days and cell viability was assessed by CellTiter-Glo; MZ1-R or JQ1-R inhibitor treated cell viabilities were normalized to DMSO treated JQ1-R or MZ1-R cells, respectfully.

FIG. 11D shows parental, JQ1-R or MZ1-R OVCAR8 cells treated with escalating doses of or Y3009120 for 5 days and cell viability was assessed by CellTiter-Glo; MZ1-R or JQ1-R inhibitor treated cell viabilities were normalized to DMSO treated JQ1-R or MZ1-R cells, respectfully.

FIG. 11E shows parental, JQ1-R or MZ1-R OVCAR8 cells treated with escalating doses of or GDC0941 for 5 days and cell viability was assessed by CellTiter-Glo; MZ1-R or JQ1-R inhibitor treated cell viabilities were normalized to DMSO treated JQ1-R or MZ1-R cells, respectfully.

FIG. 11F shows parental, JQ1-R or MZ1-R OVCAR8 cells treated with escalating doses of or Cx-4945 for 5 days and cell viability was assessed by CellTiter-Glo; MZ1-R or JQ1-R inhibitor treated cell viabilities were normalized to DMSO treated JQ1-R or MZ1-R cells, respectfully.

FIG. 11G shows parental, ARV-R cells treated with escalating doses of GSK1904529A for 5 days and cell viability was assessed by CellTiter-Glo; ARV-R inhibitor treated cell viabilities were normalized to DMSO treated ARV-R cells, respectfully.

FIG. 11H shows parental, ARV-R cells treated with escalating doses of lapatinib for 5 days and cell viability was assessed by CellTiter-Glo; ARV-R inhibitor treated cell viabilities were normalized to DMSO treated ARV-R cells, respectfully.

FIG. 11I shows parental, ARV-R cells treated with escalating doses of or RAD001 for 5 days and cell viability was assessed by CellTiter-Glo; ARV-R inhibitor treated cell viabilities were normalized to DMSO treated ARV-R cells, respectfully.

FIG. 11J shows parental, ARV-R cells treated with escalating doses of MK2206 for 5 days and cell viability was assessed by CellTiter-Glo; ARV-R inhibitor treated cell viabilities were normalized to DMSO treated ARV-R cells, respectfully.

FIG. 11K shows parental, ARV-R cells treated with escalating doses of or LP-935509 for 5 days and cell viability was assessed by CellTiter-Glo; ARV-R inhibitor treated cell viabilities were normalized to DMSO treated ARV-R cells, respectfully.

FIG. 11L ARV-R cells are more sensitive to MTORC1 inhibition than parental cells; parental or MZ1-R OVCAR8 cells were treated with escalating doses of GSK1904529A for 5 days and cell viability assessed by CellTiter-Glo; ARV-R inhibitor treated cell viabilities normalized to DMSO treated JQ1-R or MZ1-R cells, respectfully.

Figure 12:
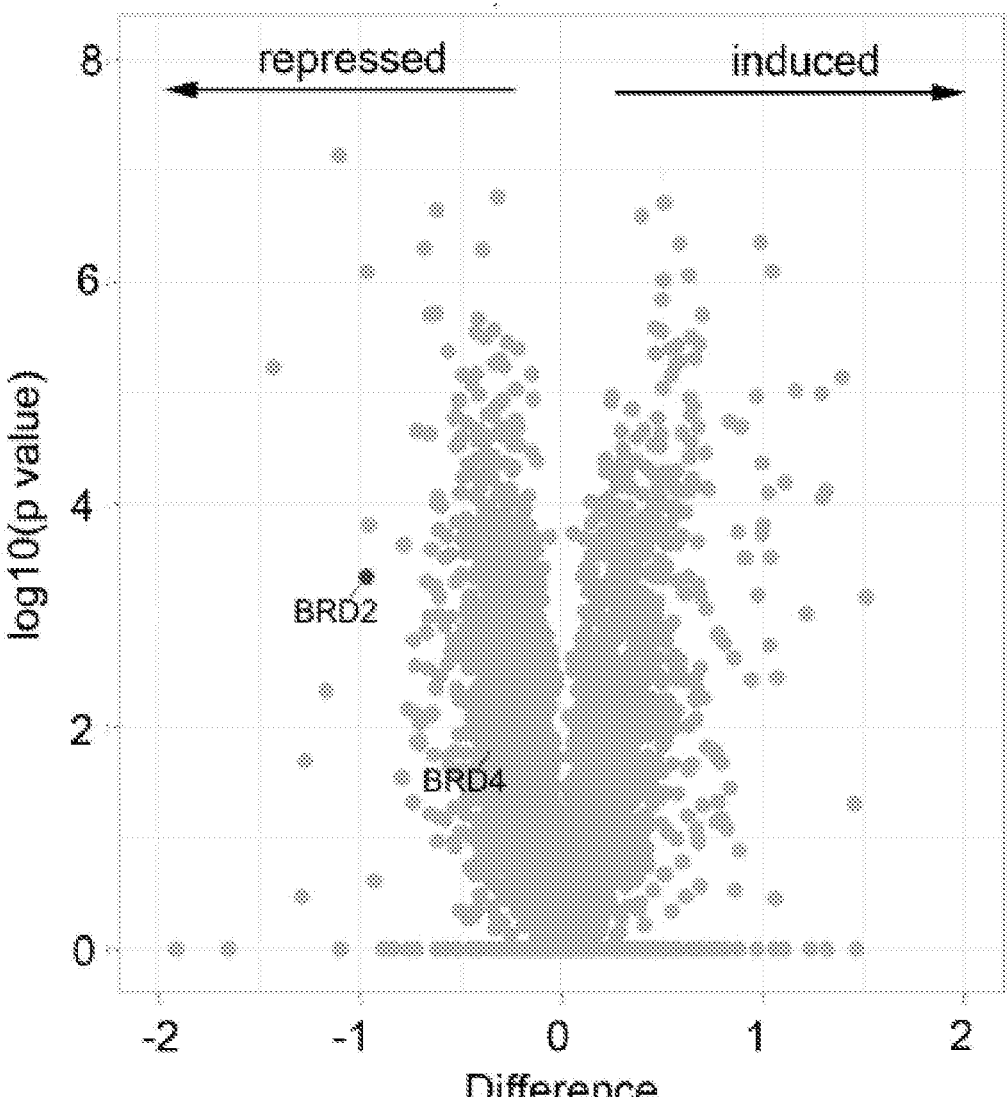
Figure 12:
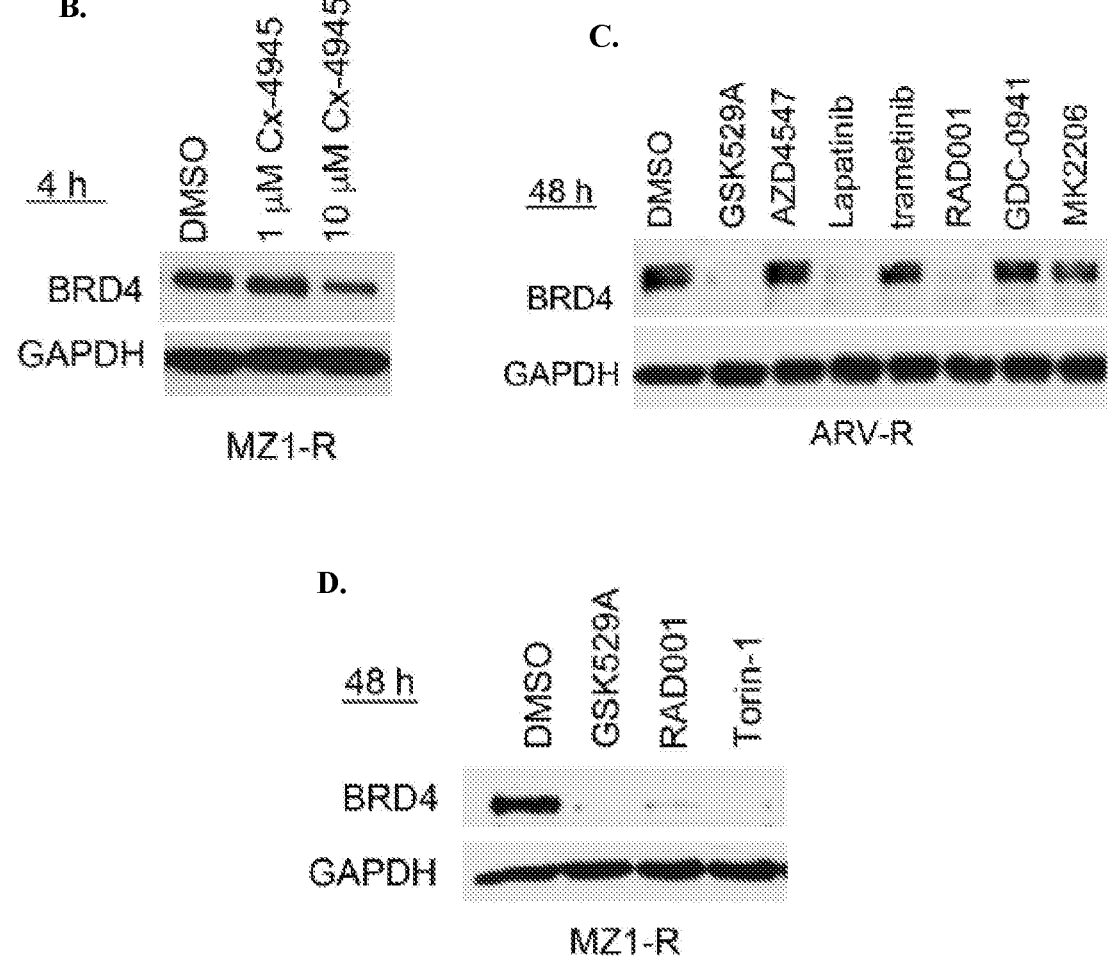
Figure 12:
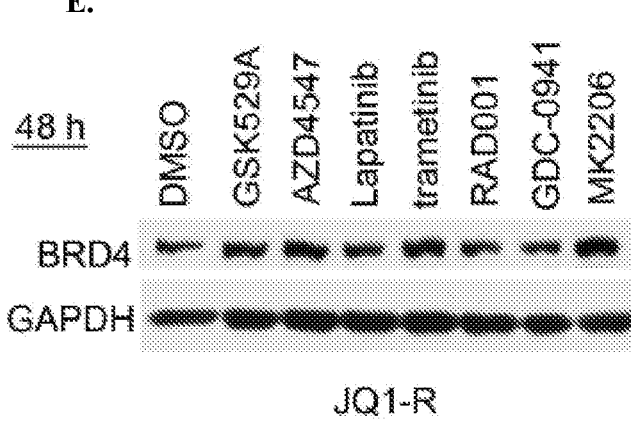

FIG. 12A shows proteome response to GSK529A in MZ1-R cells.

FIG. 12B shows MZ1-R OVCAR8 cells with escalating does of Ck-4945 or DMSO for 4 hours and BET protein levels were determined by Western blot.

FIG. 12C shows ARV-R OVCAR8 cells with 1 µM of kinase inhibitors or DMSO for 4 hours and BET protein levels were determined by Western blot.

FIG. 12D shows MZ1-R OVCAR8 cells with 1 µM of kinase inhibitors or DMSO for 4 hours and BET protein levels were determined by Western blot.

FIG. 12E shows JQ1-R OVCAR8 cells with 1 µM of kinase inhibitors or DMSO for 4 hours and BET protein levels were determined by Western blot.

Figure 13:
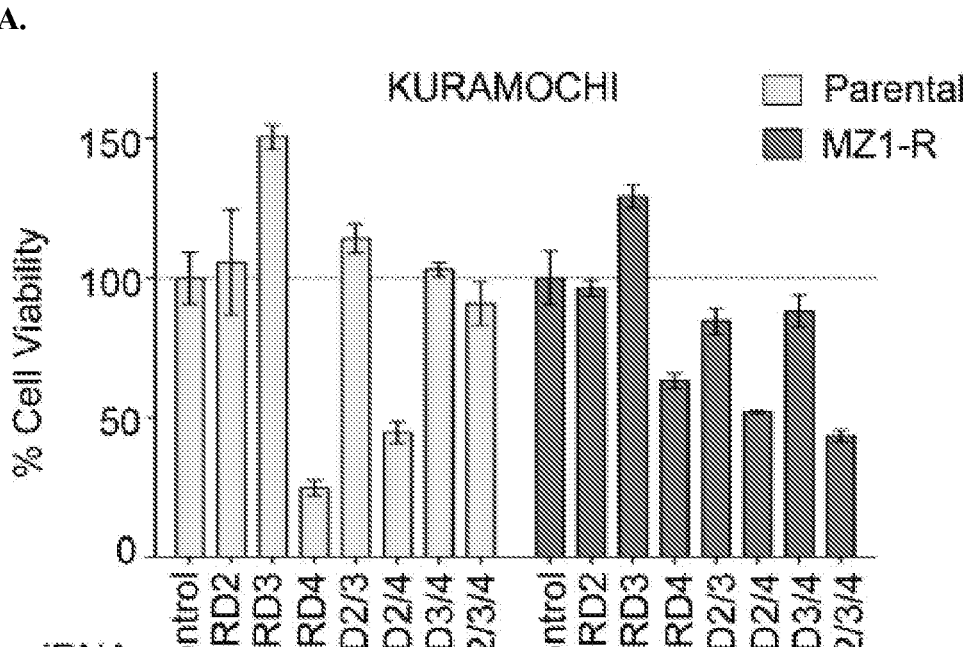
Figure 13:
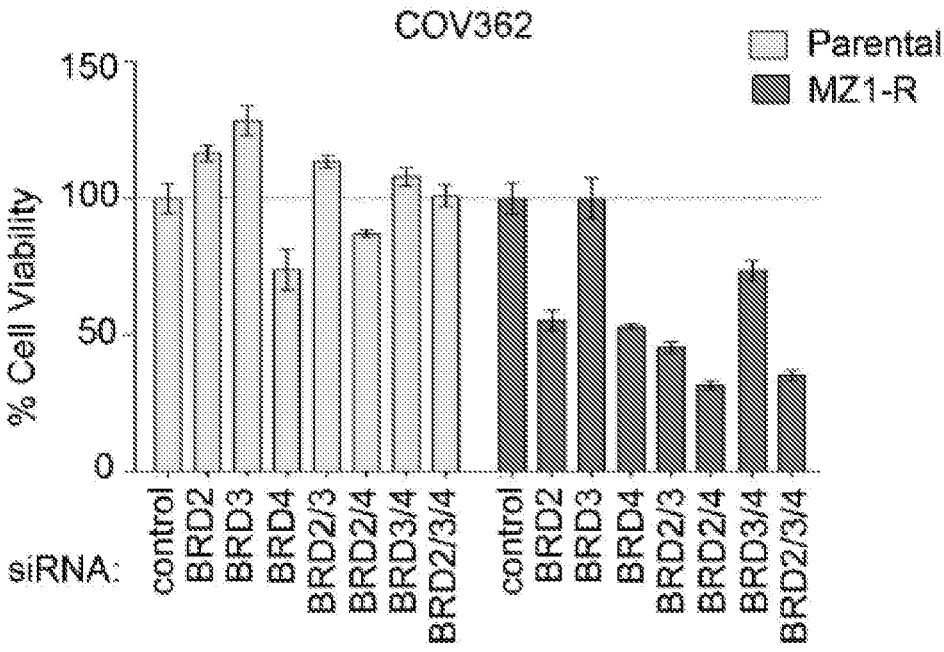
Figure 13:
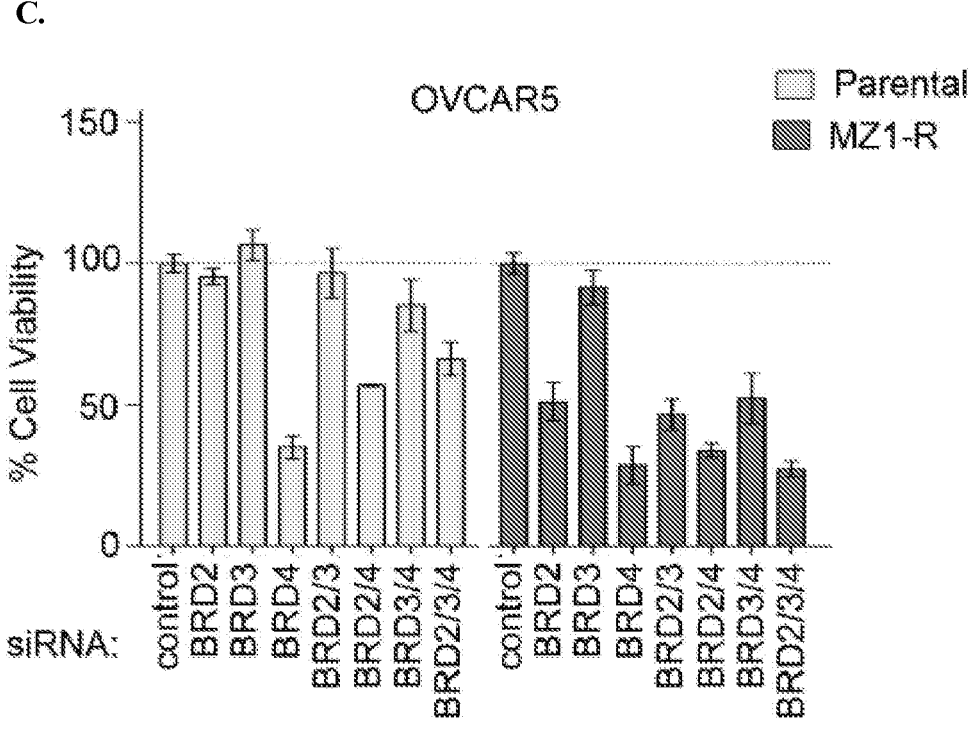
Figure 13:
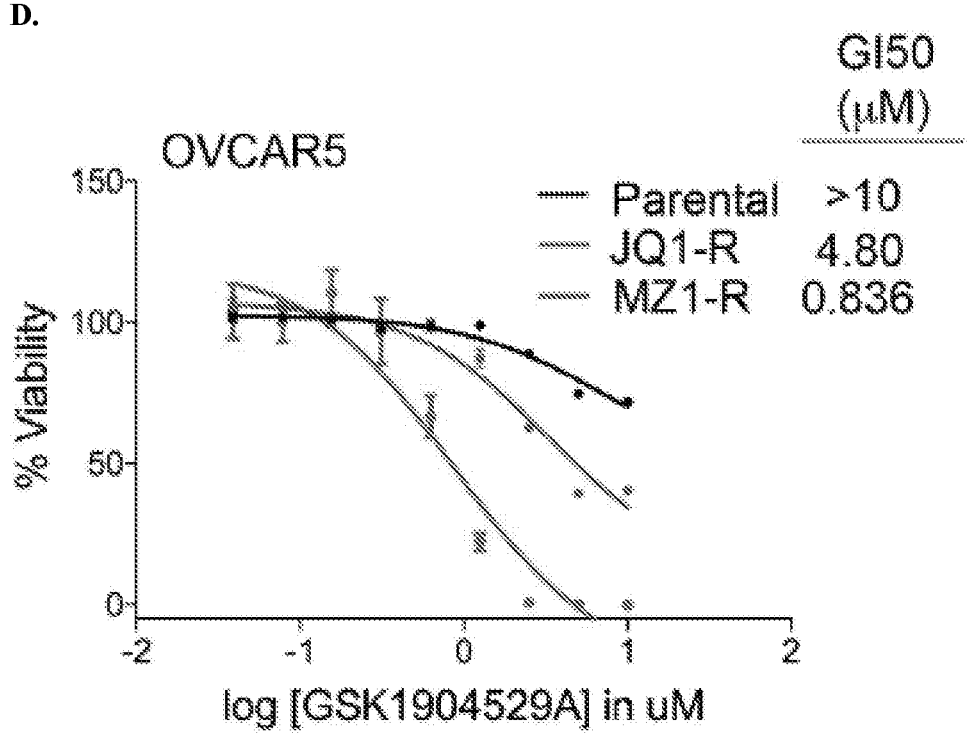
Figure 13:
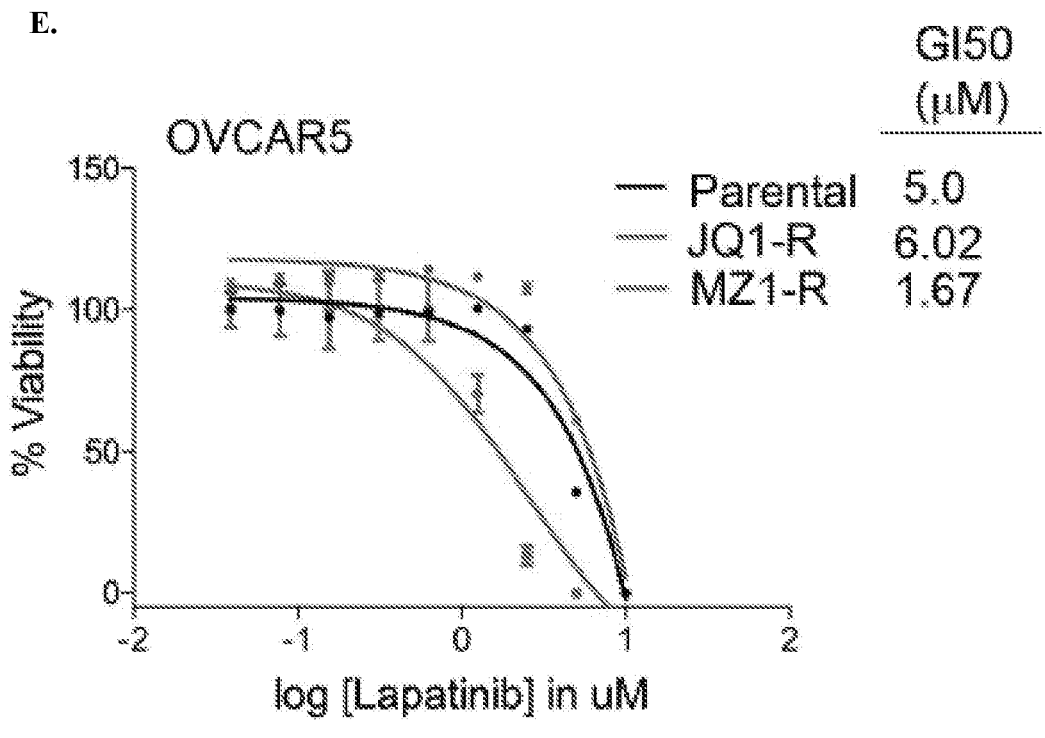
Figure 13:
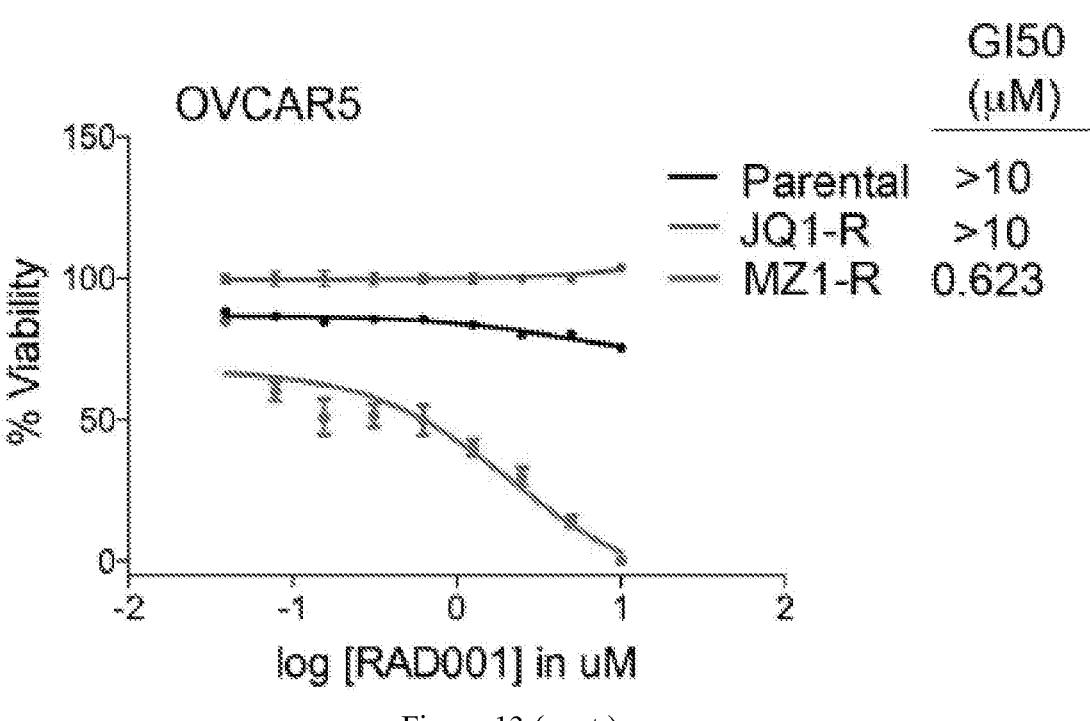

FIG. 13A shows that knockdown of BRD4 and to a lesser extent BRD2 inhibited cell viability of KURAMOCHI MZ1-R cells.

FIG. 13B shows that knockdown of BRD4 and to a lesser extent BRD2 inhibited cell viability of COV362 MZ1-R cells.

FIG. 13C shows that knockdown of BRD4 and to a lesser extent BRD2 inhibited cell viability of OVCAR5 MZ1-R cells.

FIG. 13D shows growth curves afret treatment of OVCAR5 JQ1-R cells with GSK529A.

FIG. 13E shows growth curves afret treatment of OVCAR5 JQ1-R cells with lapatinib.

FIG. 13F shows growth curves afret treatment of OVCAR5 JQ1-R cells with RAD001.

Figure 14:
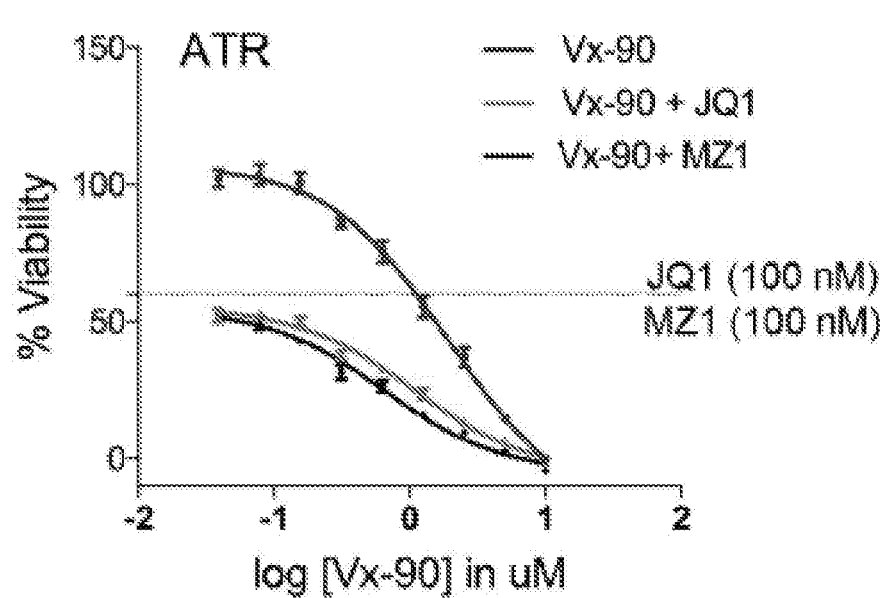
Figure 14:
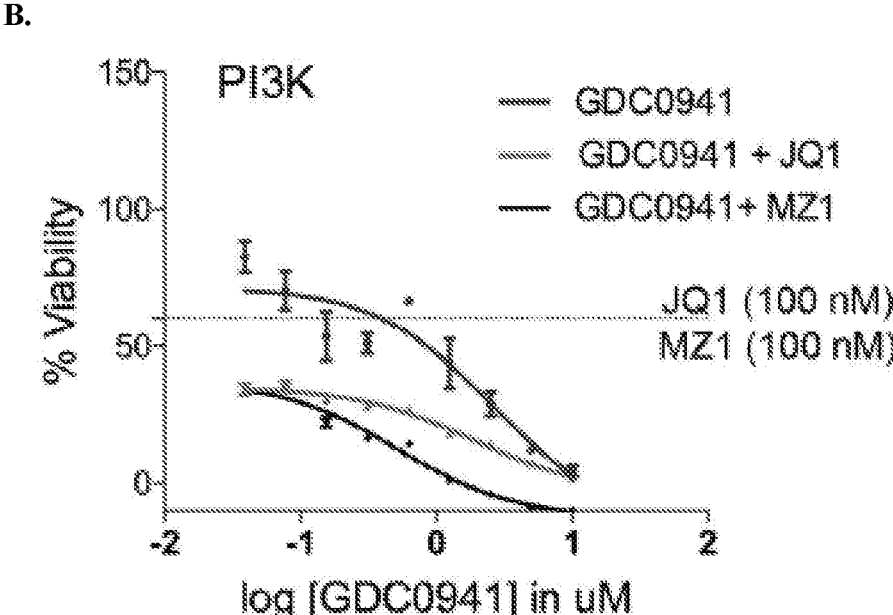
Figure 14:
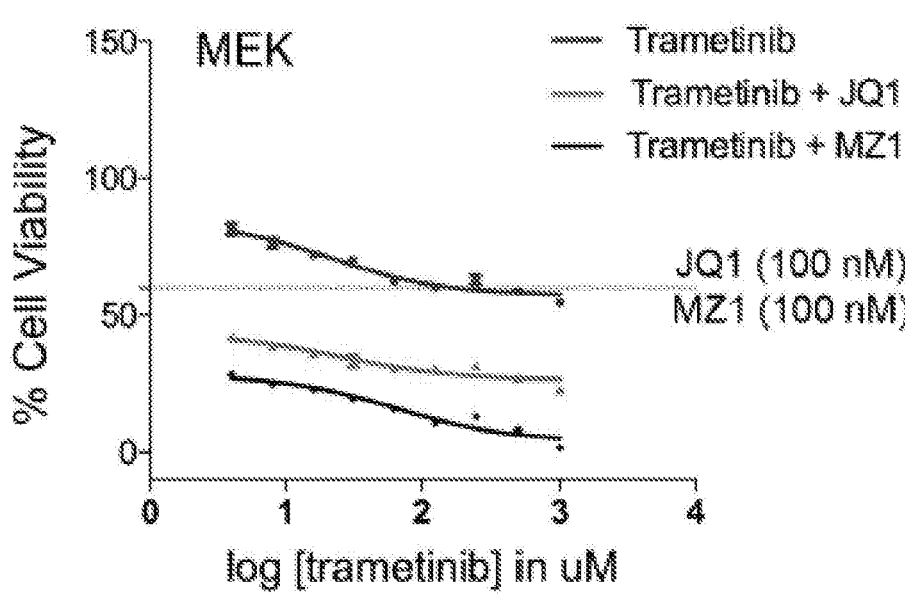
Figure 14:
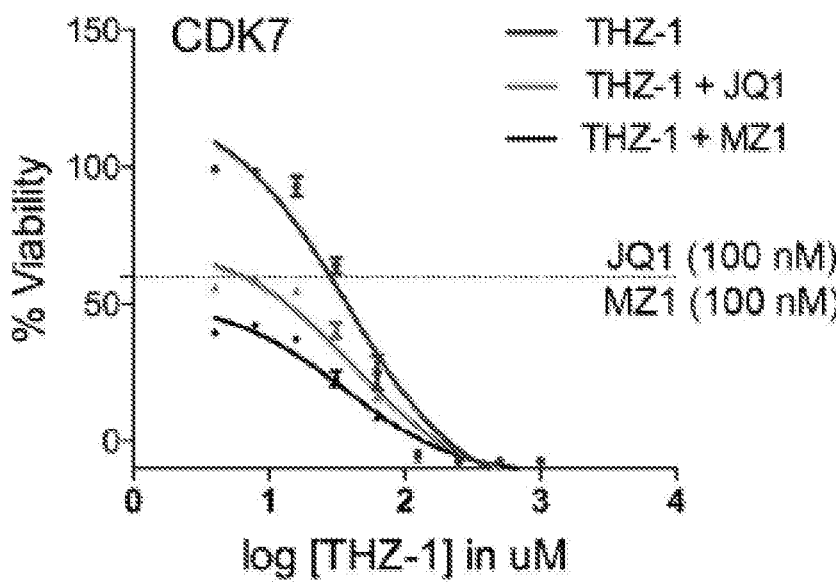
Figure 14:
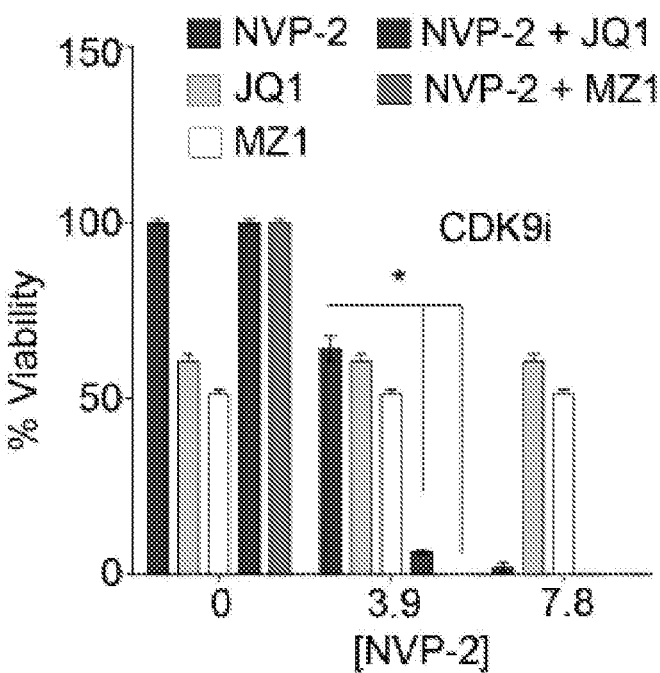
Figure 14:
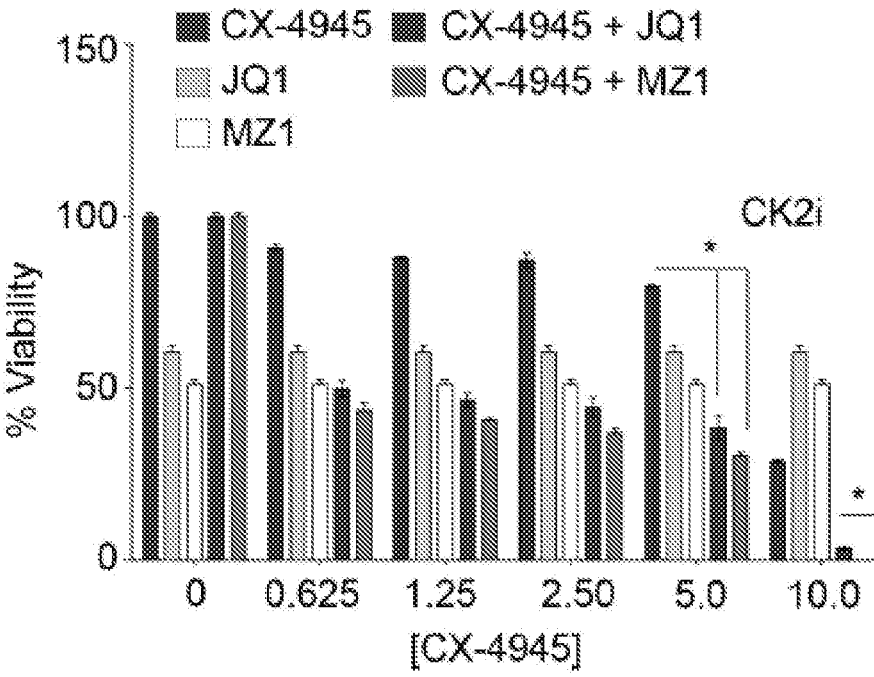
Figure 14:
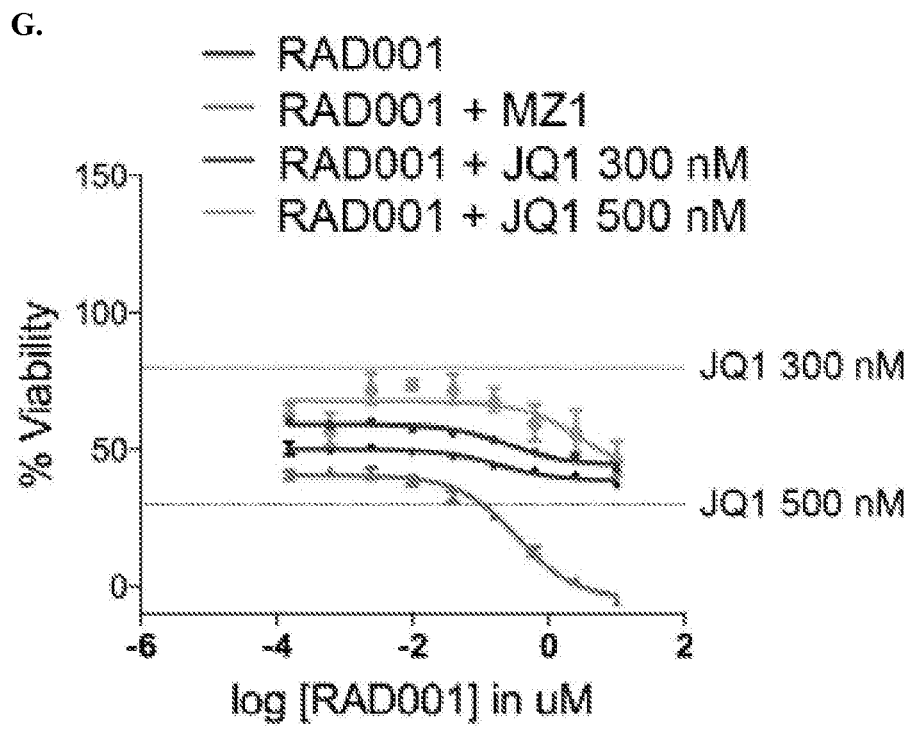
Figure 14:
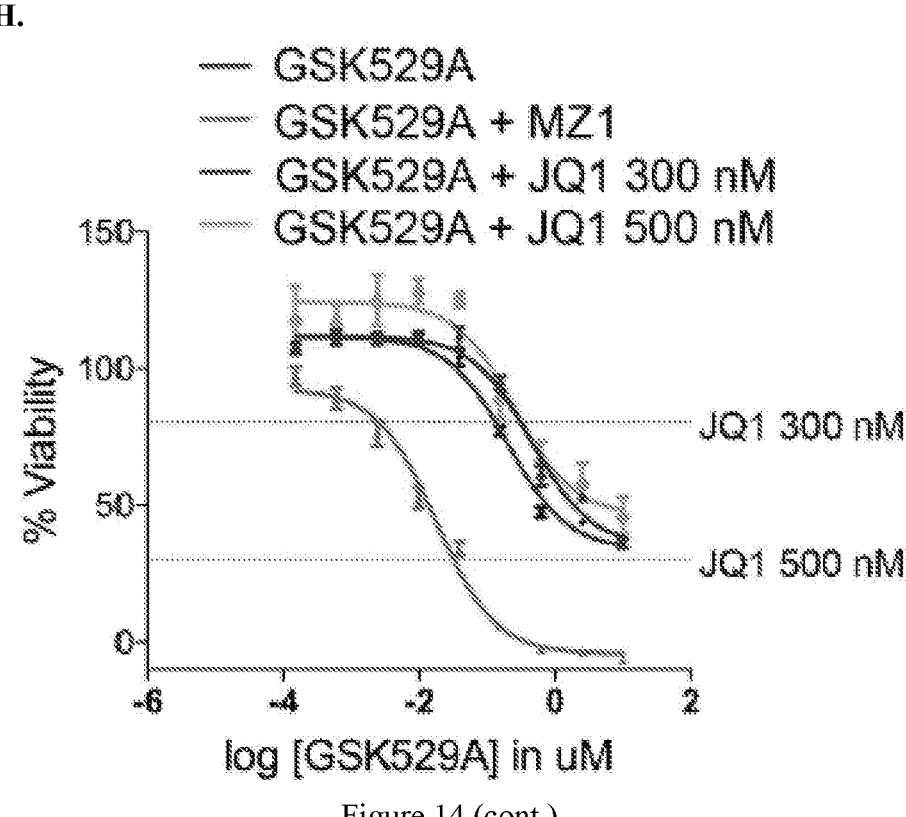
Figure 14:
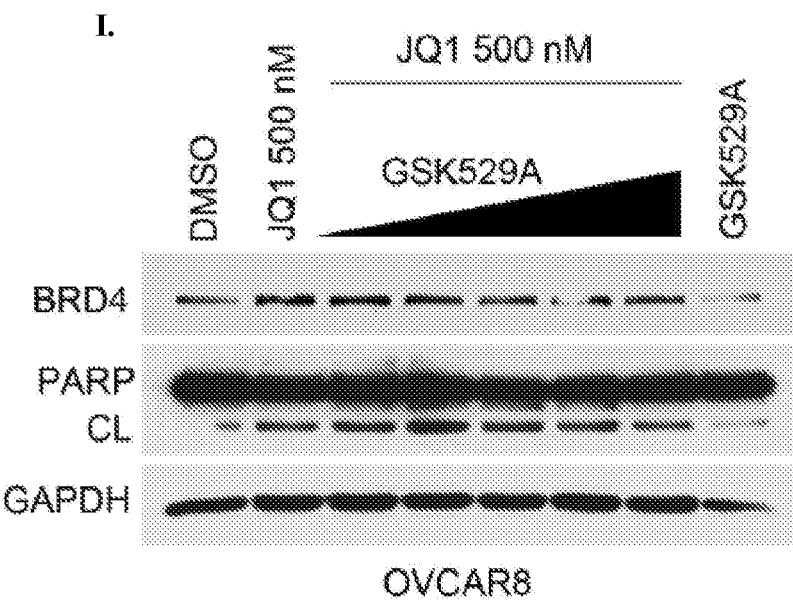
Figure 14:
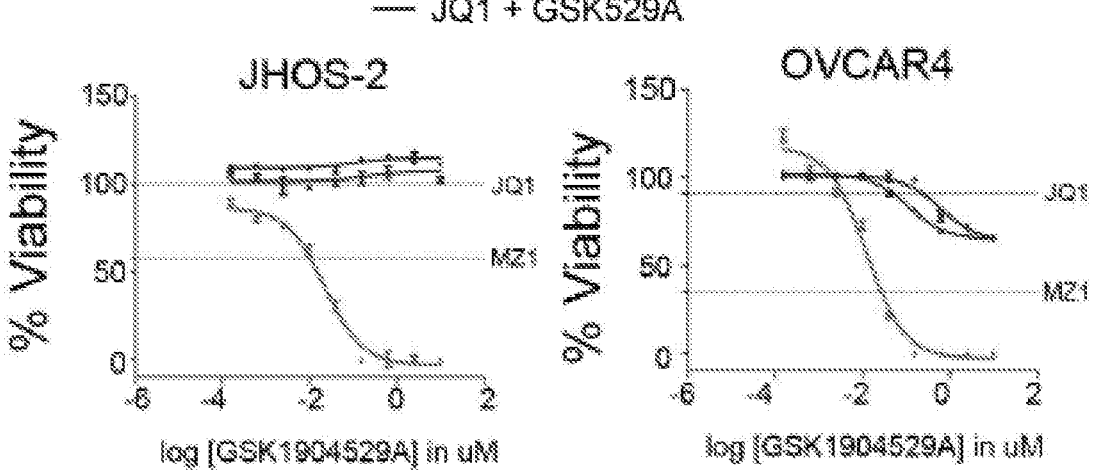
Figure 14:
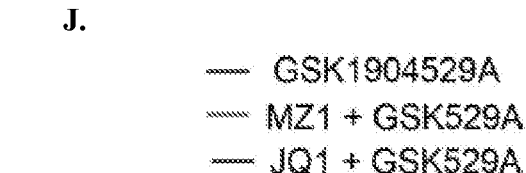
Figure 14:
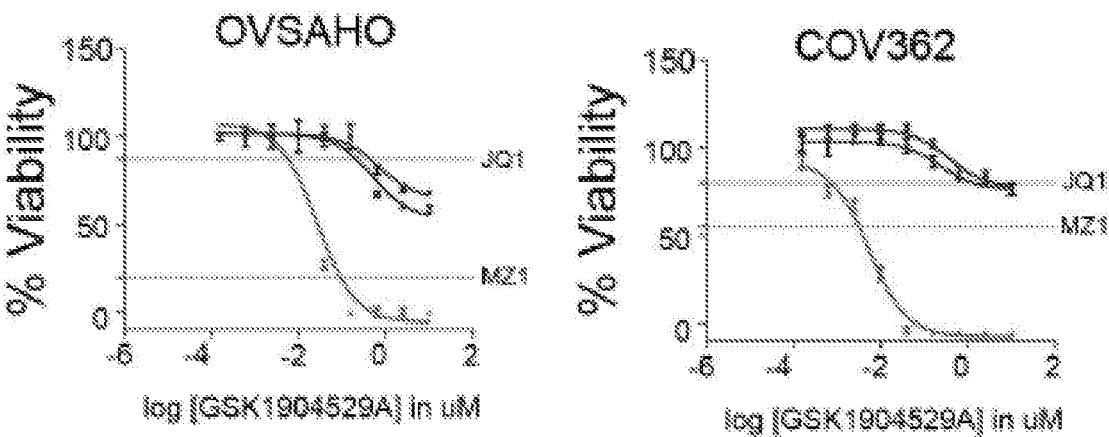
Figure 14:
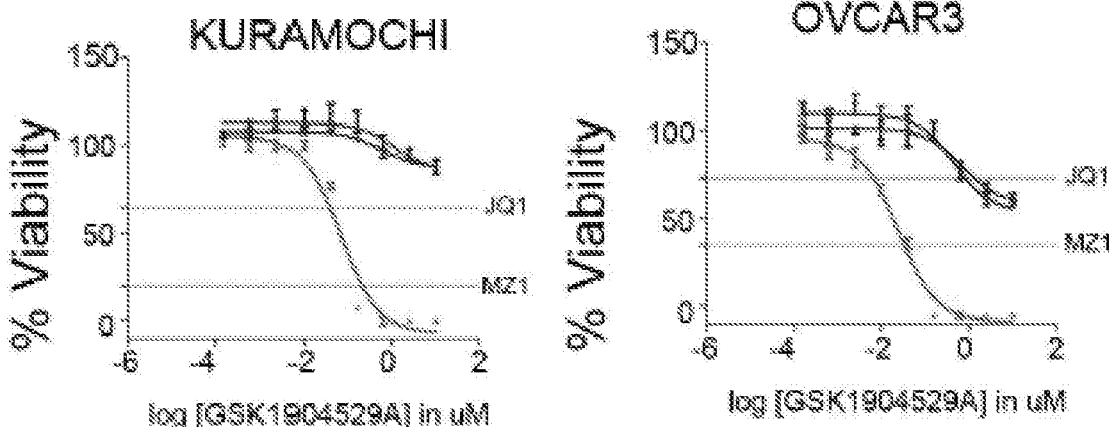
Figure 14:
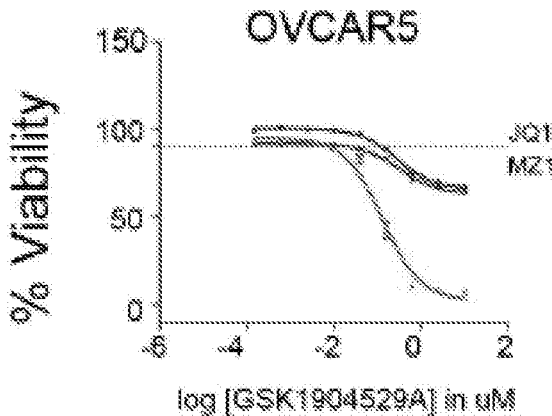
Figure 14:
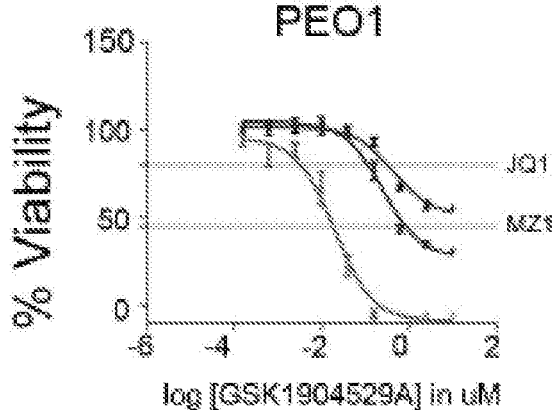
Figure 14:
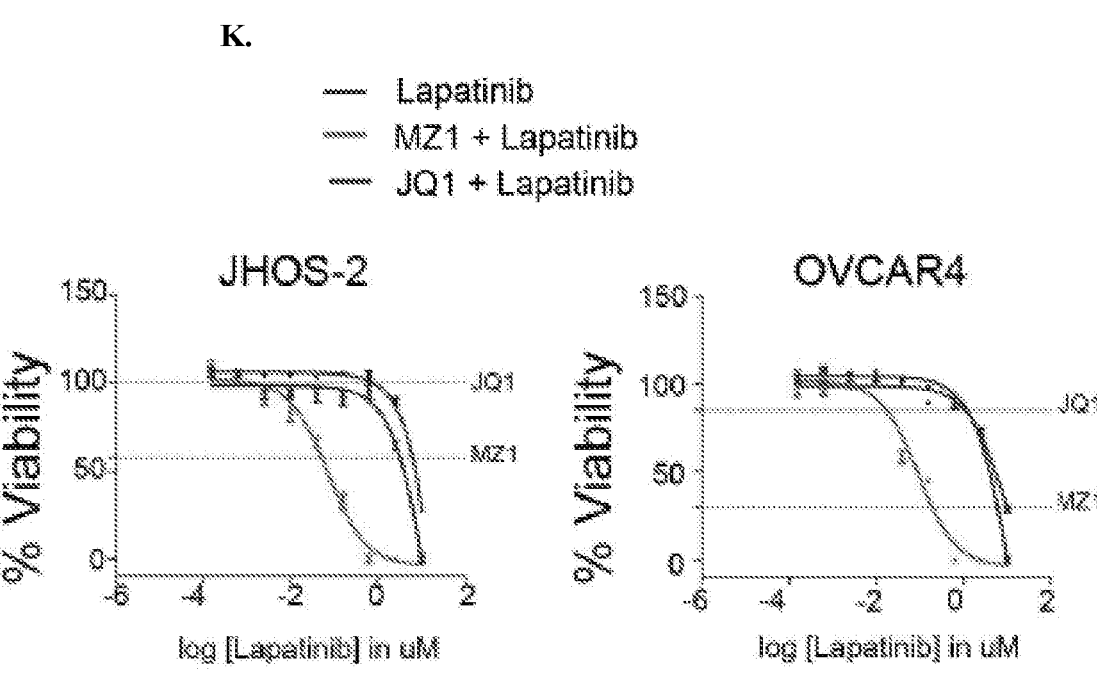
Figure 14:
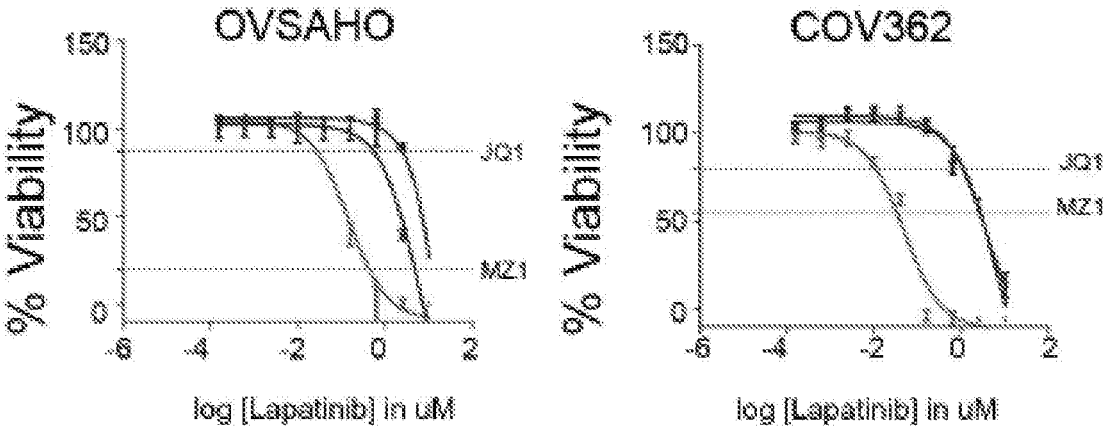
Figure 14:
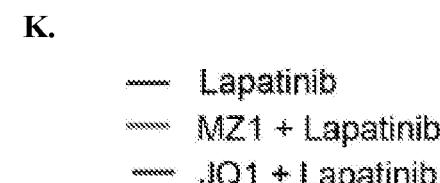
Figure 14:
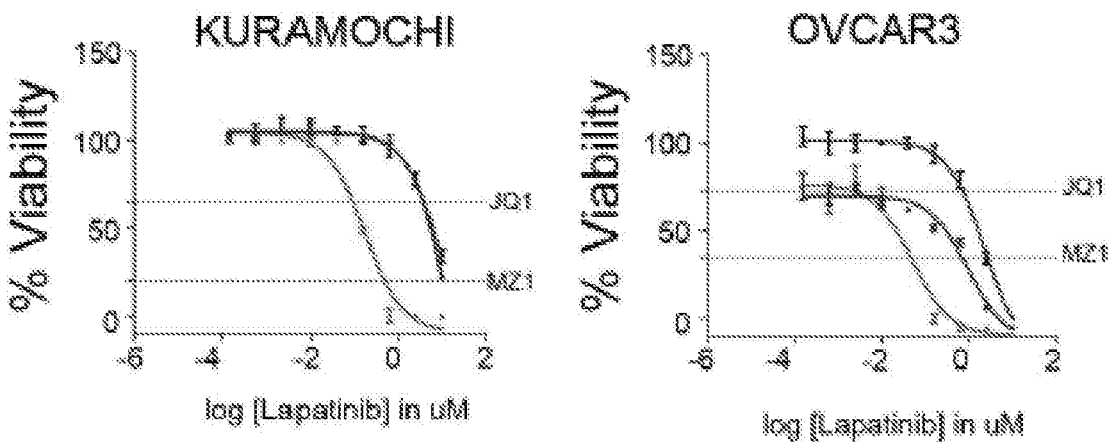
Figure 14:
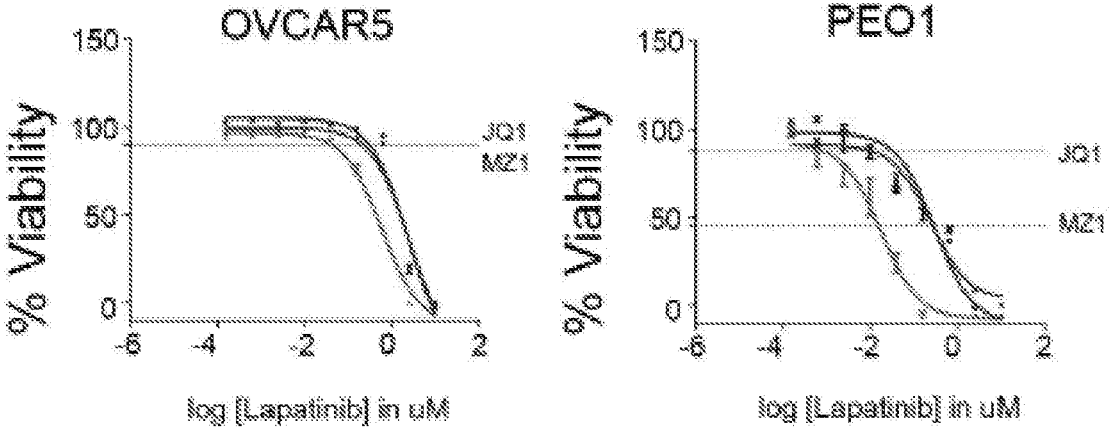
Figure 14:
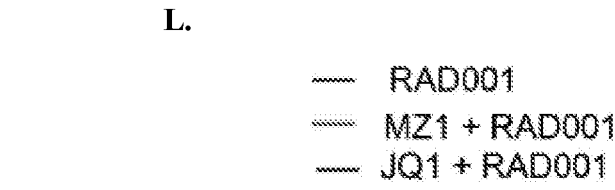
Figure 14:
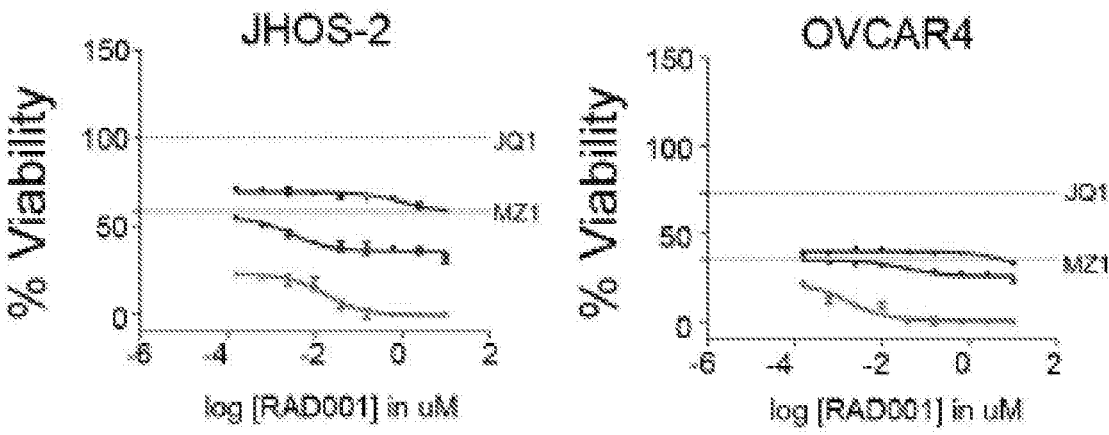
Figure 14:
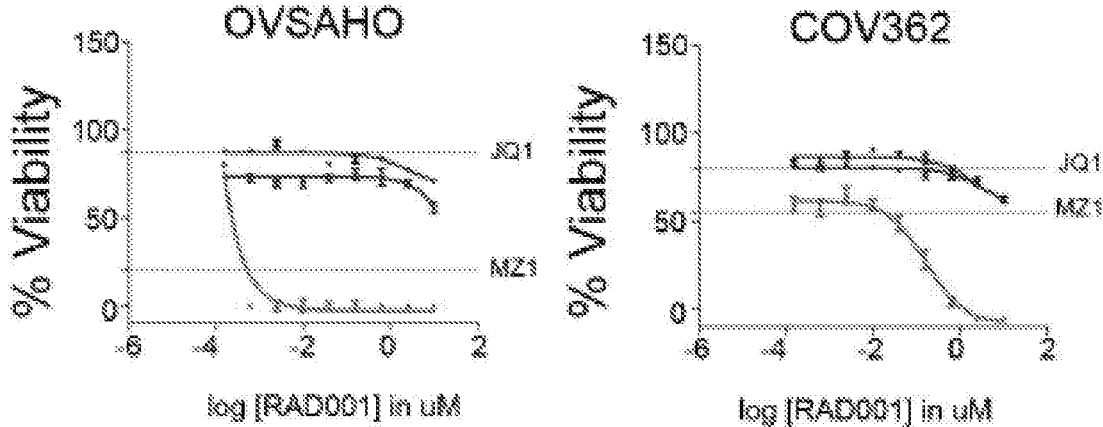
Figure 14:
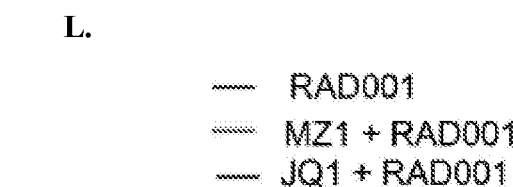
Figure 14:
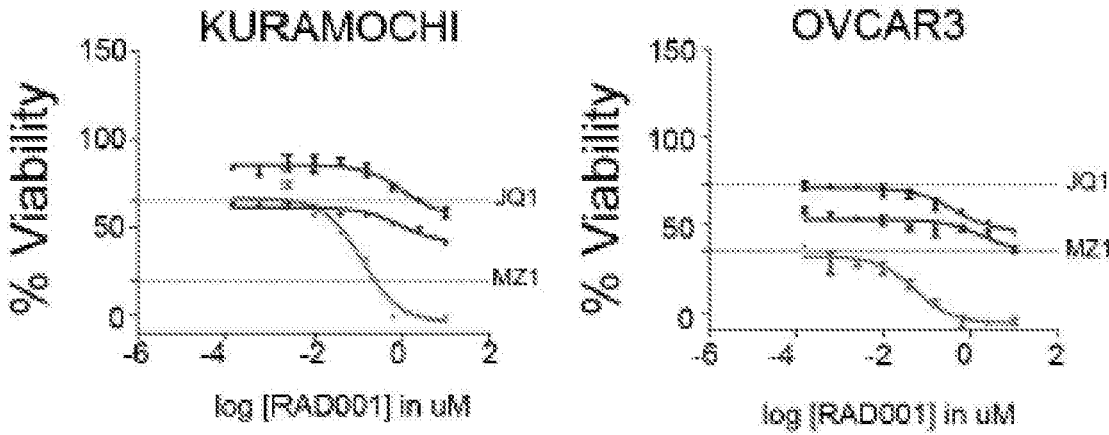
Figure 14:
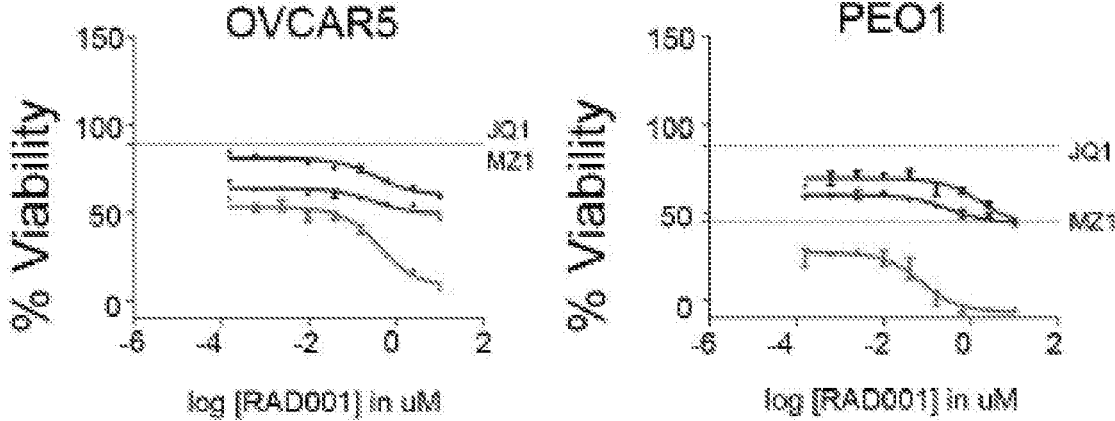
Figure 14:
Figure 14:
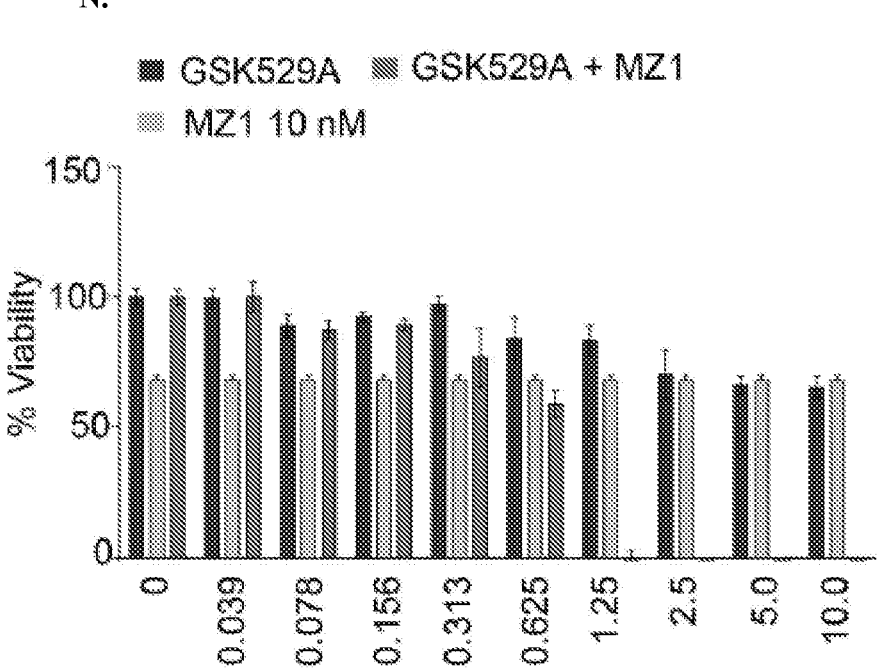
Figure 14:
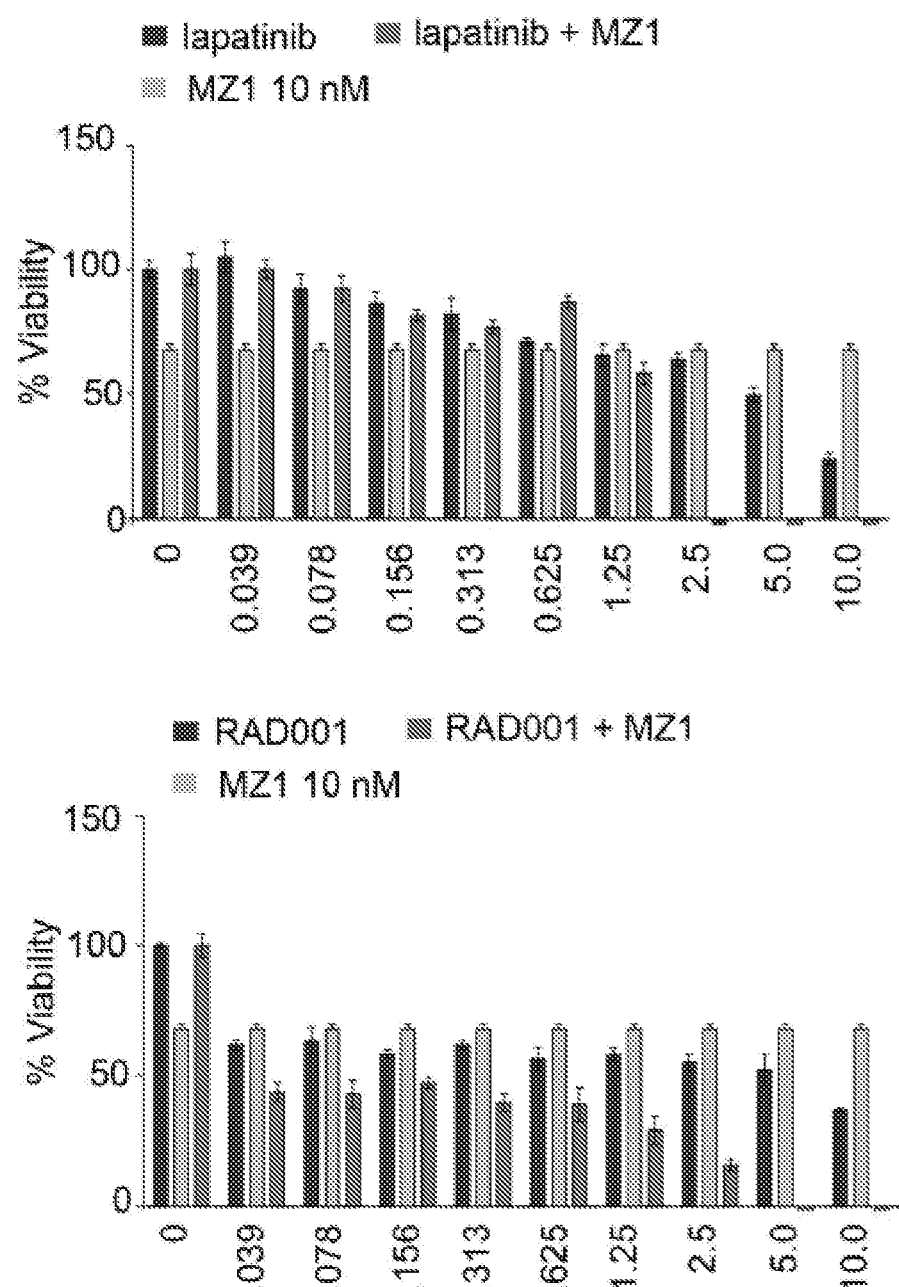

FIG. 14A shows combined treatment of OVCAR8 cells with JQ1 or MZ1 and Vx-90.

FIG. 14B shows combined treatment of OVCAR8 cells with JQ1 or MZ1 and GDC0941.

FIG. 14C shows combined treatment of OVCAR8 cells with JQ1 or MZ1 and trametinib.

FIG. 14D shows combined treatment of OVCAR8 cells with JQ1 or MZ1 and THZ-1.

FIG. 14E shows combined treatment of OVCAR8 cells with JQ1 or MZ1 and NVP-2.

FIG. 14F shows combined treatment of OVCAR8 cells with JQ1 or MZ1 and CX-4945.

FIG. 14G shows combined treatment of OVCAR8 cells with JQ1 or MZ1 and RAD001.

FIG. 14H shows combined treatment of OVCAR8 cells with JQ1 or MZ1 and GSK529A.

FIG. 14I shows BDT4 protein levels in OVCAR8 cells following combined treatment of with JQ1 and GSK529A.

FIG. 14J shows treatment of RAS-altered EOC cell lines OVCAR5, JHOS-2, A1847, COV362 and CAOV3, or PIK3CA mutant SKOV3 cells or KURMAOCHI with JQ1 or MZ1 and GSK1904529A.

FIG. 14K shows treatment of RAS-altered EOC cell lines OVCAR5, JHOS-2, A1847, COV362 and CAOV3, or PIK3CA mutant SKOV3 cells or KURAMOCHI with JQ1 or MZ1 and Lapatinib.

FIG. 14L shows treatment of RAS-altered EOC cell lines OVCAR5, JHOS-2, A1847, COV362 and CAOV3, or PIK3CA mutant SKOV3 cells or KURMAOCHI with JQ1 or MZ1 and RAD001.

FIG. 14M shows OVSAHO have the highest protein levels of BRD4 and they exhibit exhibit sensitivity towards the MZ1 and MTOR combination.

FIG. 14N shows treatment of OVSAHO cells with MZ1, GSK529A, lapatinib, or RAD001 alone, or a combination of MZ1 with each of GSK529A, lapatinib, or RAD001.

Figure 15:
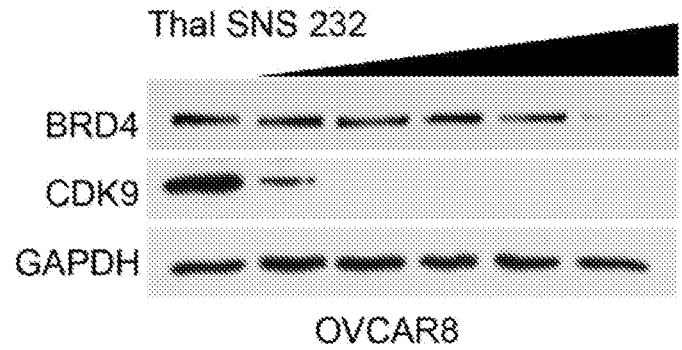
Figure 15:
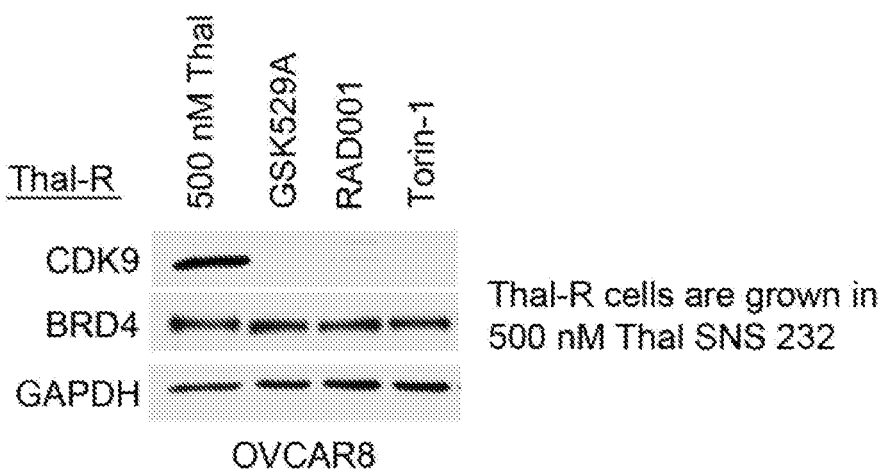
Figure 15:
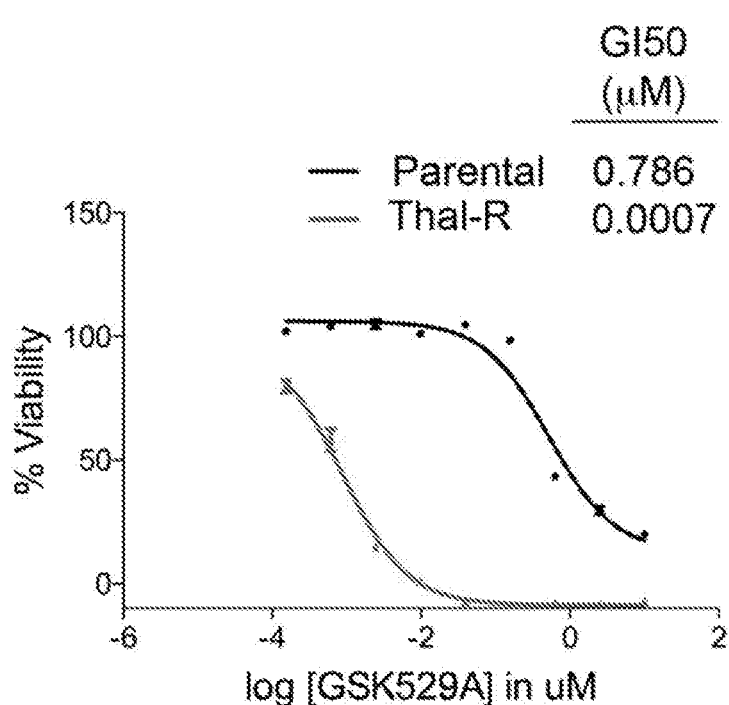
Figure 15:
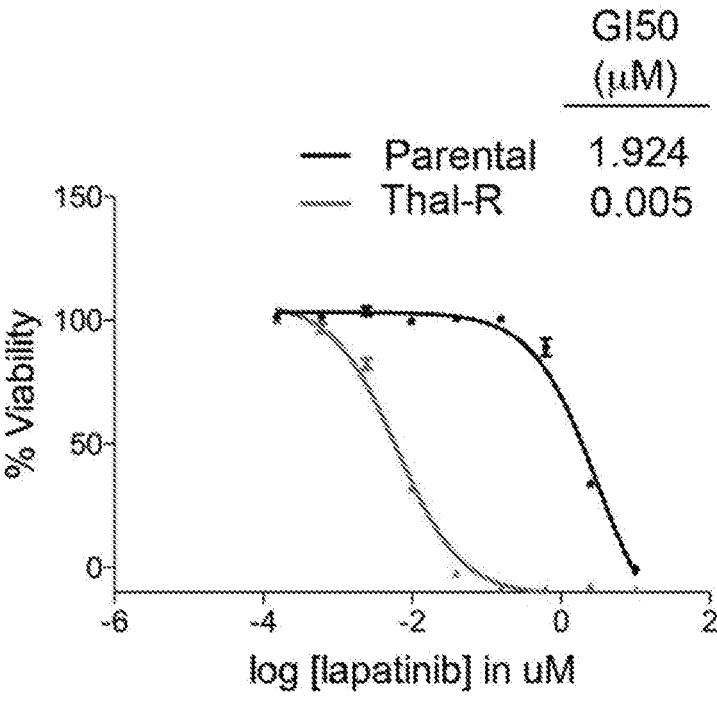
Figure 15:
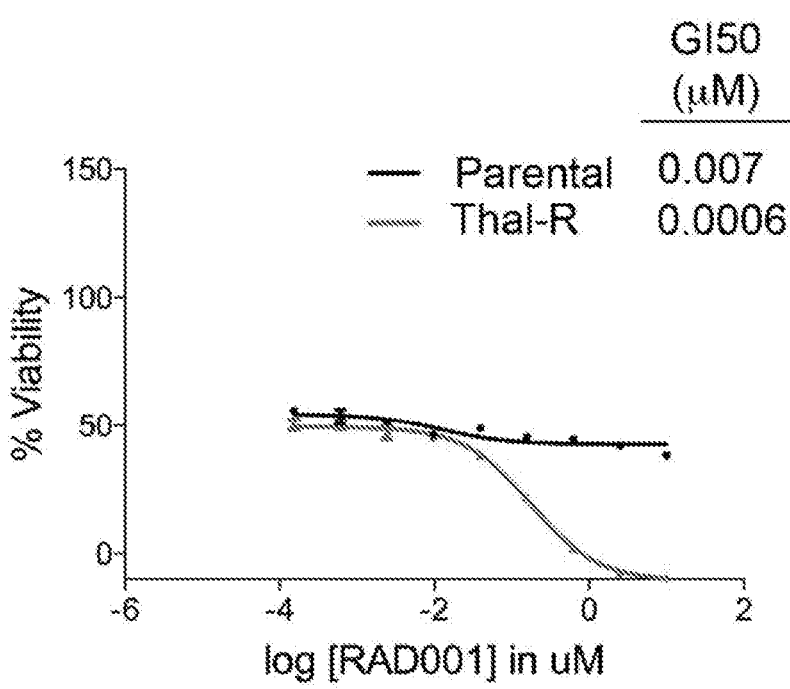
Figure 15:
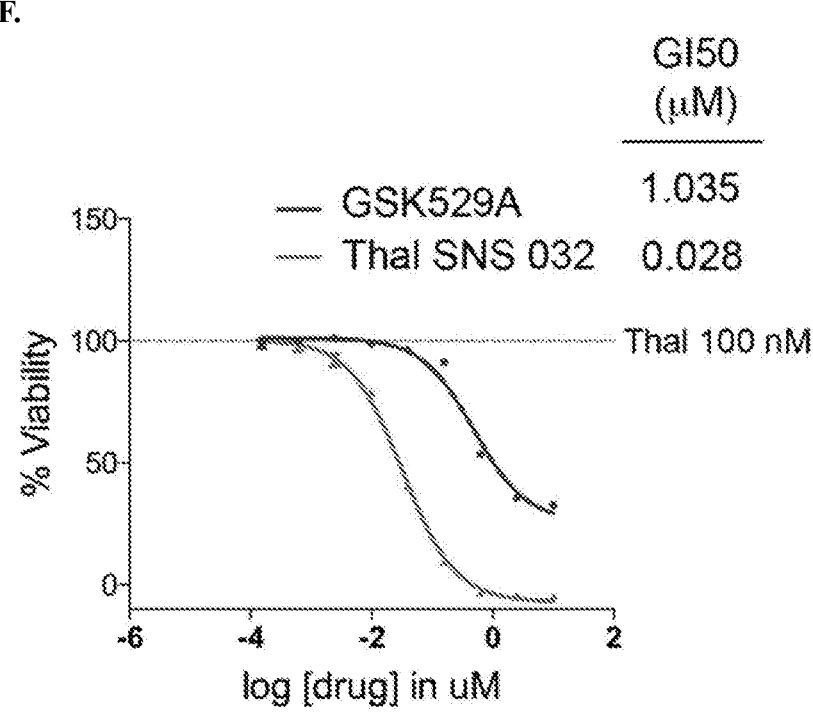

FIG. 15A shows treatment of OVCAR8 cells with CDK9-degrader Thal SNS 032 reduced CDK9 protein levels as determined by Western blot.

FIG. 15B shows chronic exposure to Thal SNS 032 failed to degrade CDK9 that is overcome by GSK529A, lapatinib or RAD001 treatment, where protein levels were assessed by Western blot.

FIG. 15C shows Thal-R cells were more sensitive to INSR inhibition than parental cells, where cell viability assessed by CellTiter-Glo.

FIG. 15D shows Thal-R cells were more sensitive to ErbB inhibition than parental cells, where cell viability assessed by CellTiter-Glo.

FIG. 15E shows Thal-R cells were more sensitive to MTORC1 inhibition than parental cells, where cell viability assessed by CellTiter-Glo.

FIG. 15F shows therapies involving GSK529A alone and the combination of GSK529A and Thal SNS 032, which improved growth repression of OVCAR8 cells, where cell viability was assessed by CellTiter-Glo.

FIG. 15G shows therapies involving RAD001 alone and the combination of RAD001 and Thal SNS 032, which improved growth repression of OVCAR8 cells, where cell viability was assessed by CellTiter-Glo.

Figure 16:
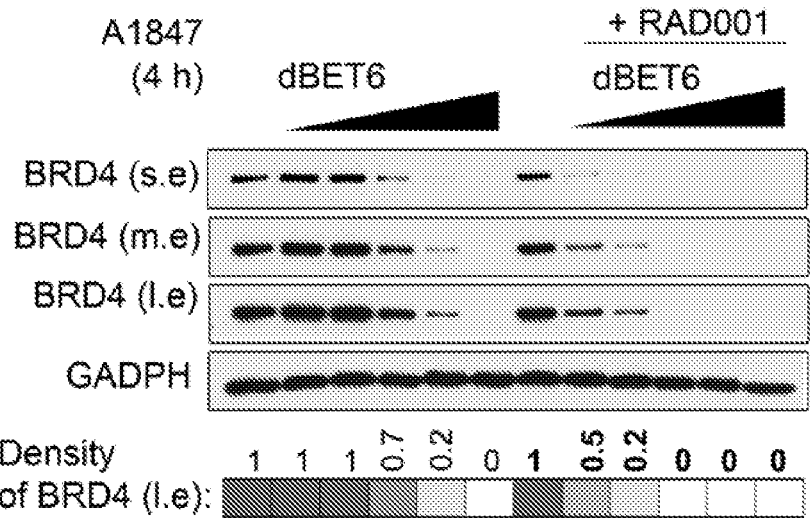
Figure 16:
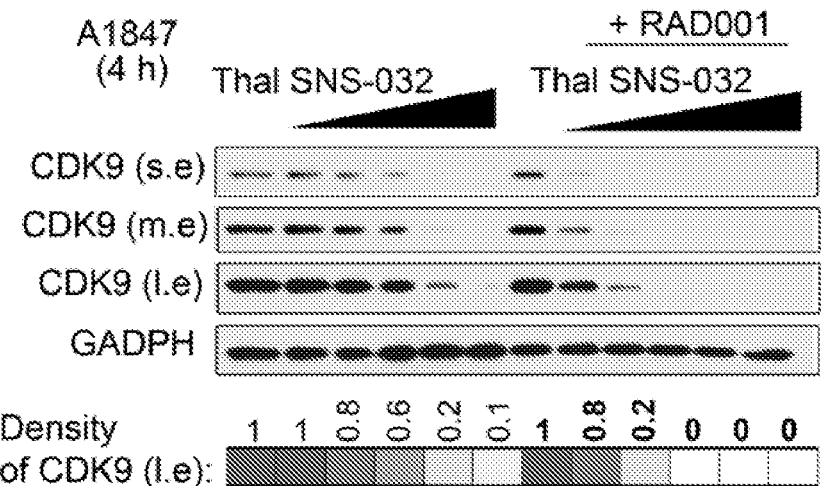

FIG. 16 shows MTORC1 inhibition enhances PROTAC-meditated degradation of BRD4, CDK9 or FAK1 proteins in cancer cells: treated with DMSO, RAD001, increasing doses of dBET6 or RAD001+increasing doses of dBET6 and BRD4 protein assessed by WB (Panel A); treated with DMSO, RAD001, increasing doses of Thal SNS 032 or RAD001+increasing doses of Thal SNS 032 and CDK9 protein assessed by WB (Panel B); and treated with DMSO, RAD001, increasing doses of FAK-Protac or RAD001+ increasing doses of FAK-Protac and CDK9 protein assessed by WB (Panel C).

Figure 17:
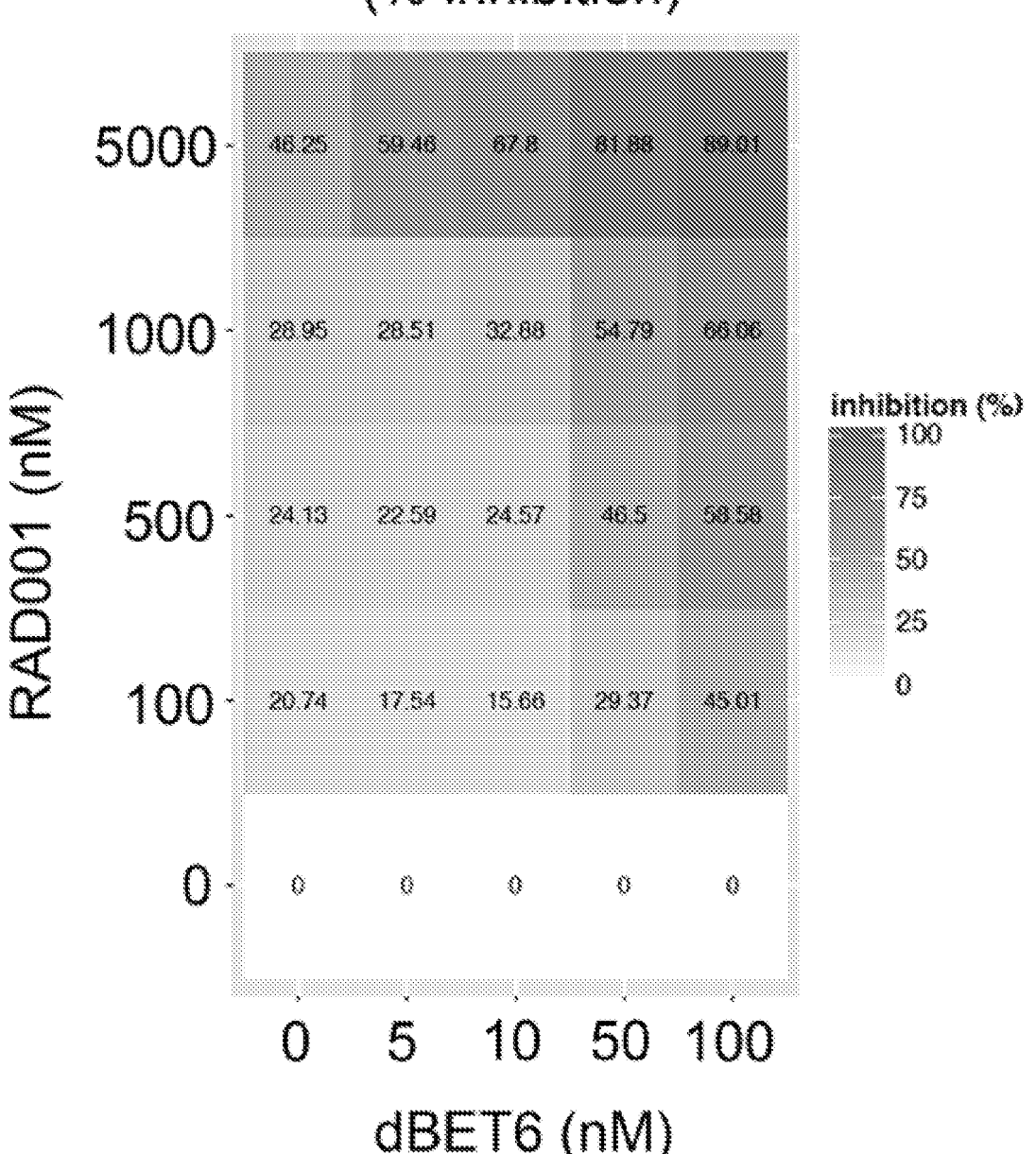
Figure 17:
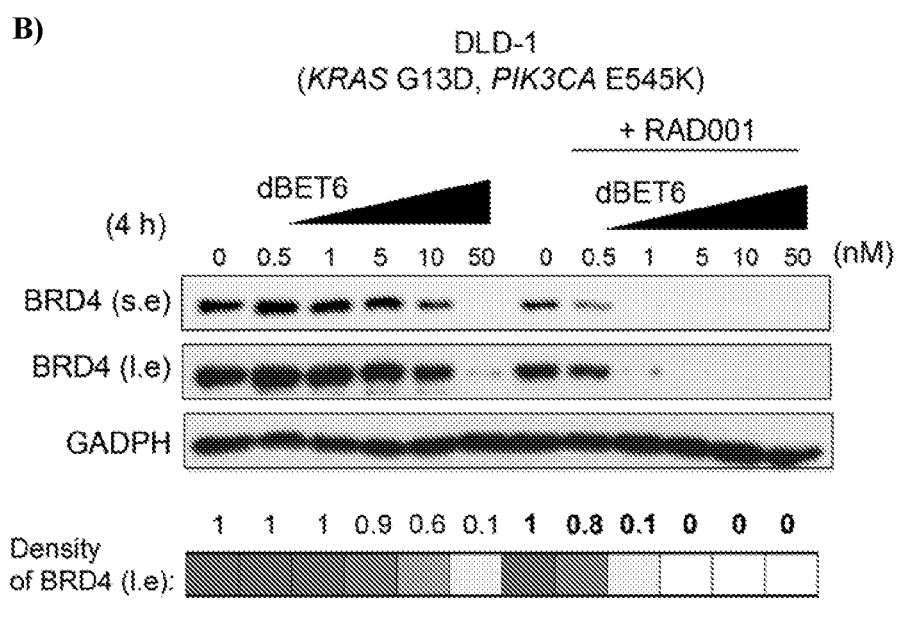
Figure 17:
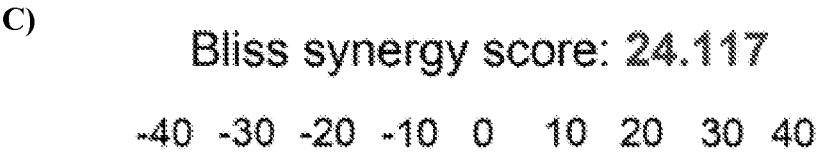
Figure 17:
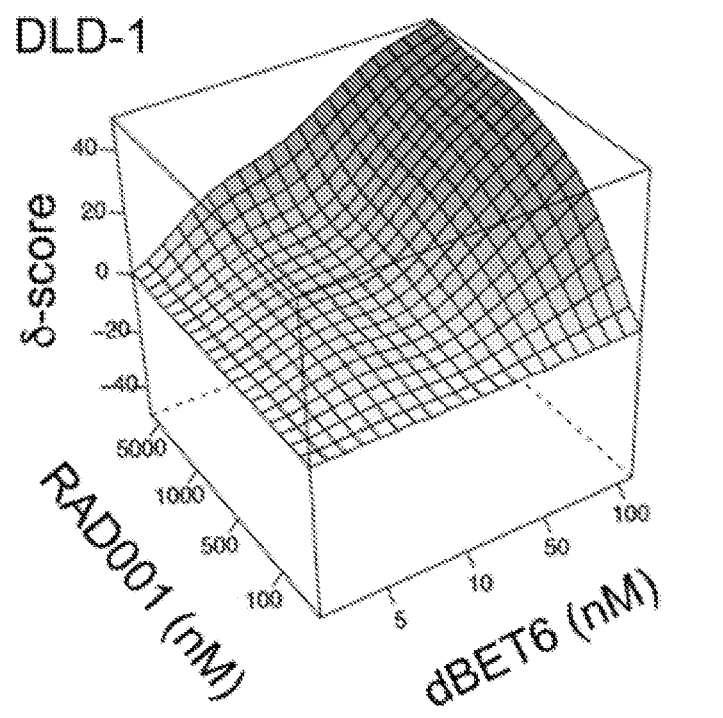
Figure 17:
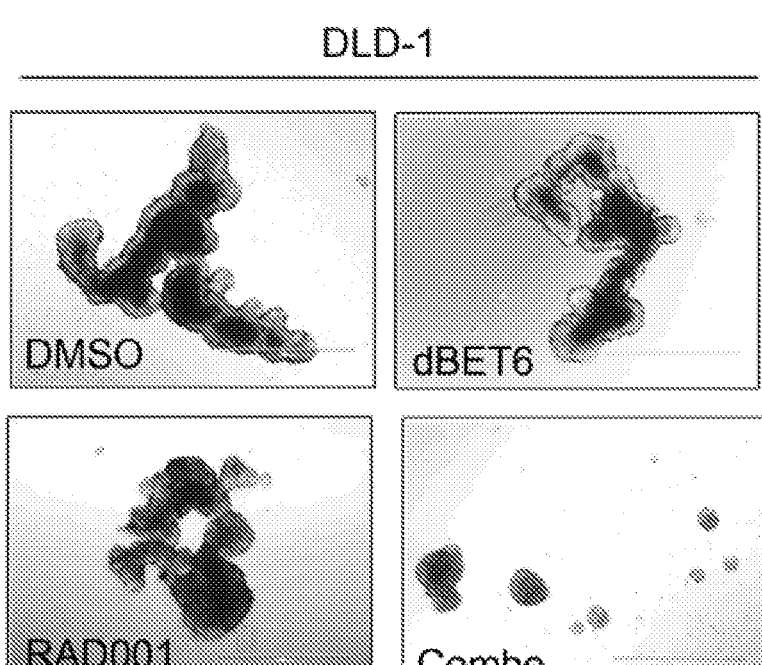

FIG. 17 shows the blockade of MTORC1 signaling sensitizes cancer cells resistant to BET-PROTACs by: a dose response matrix of RAD001 or dBET6 in A1847 cells (Panel A); immunoblot analysis of BRD4 protein levels (Panel B); drug synergy analysis of RAD001 and dBET6 in DLD-1 cells (Panel C); and spheroid assays (Panel D).

Figure 18:
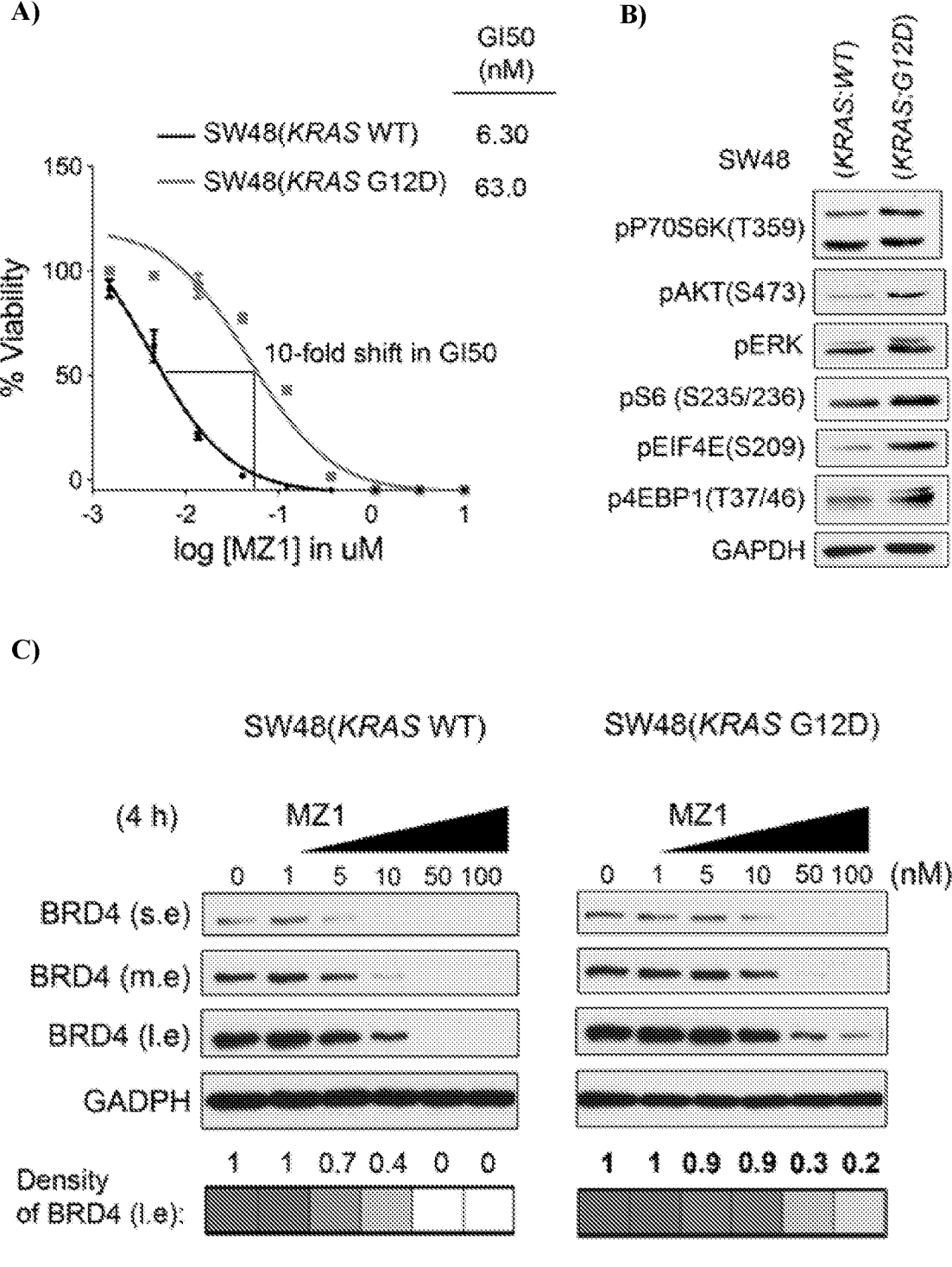
Figure 18:
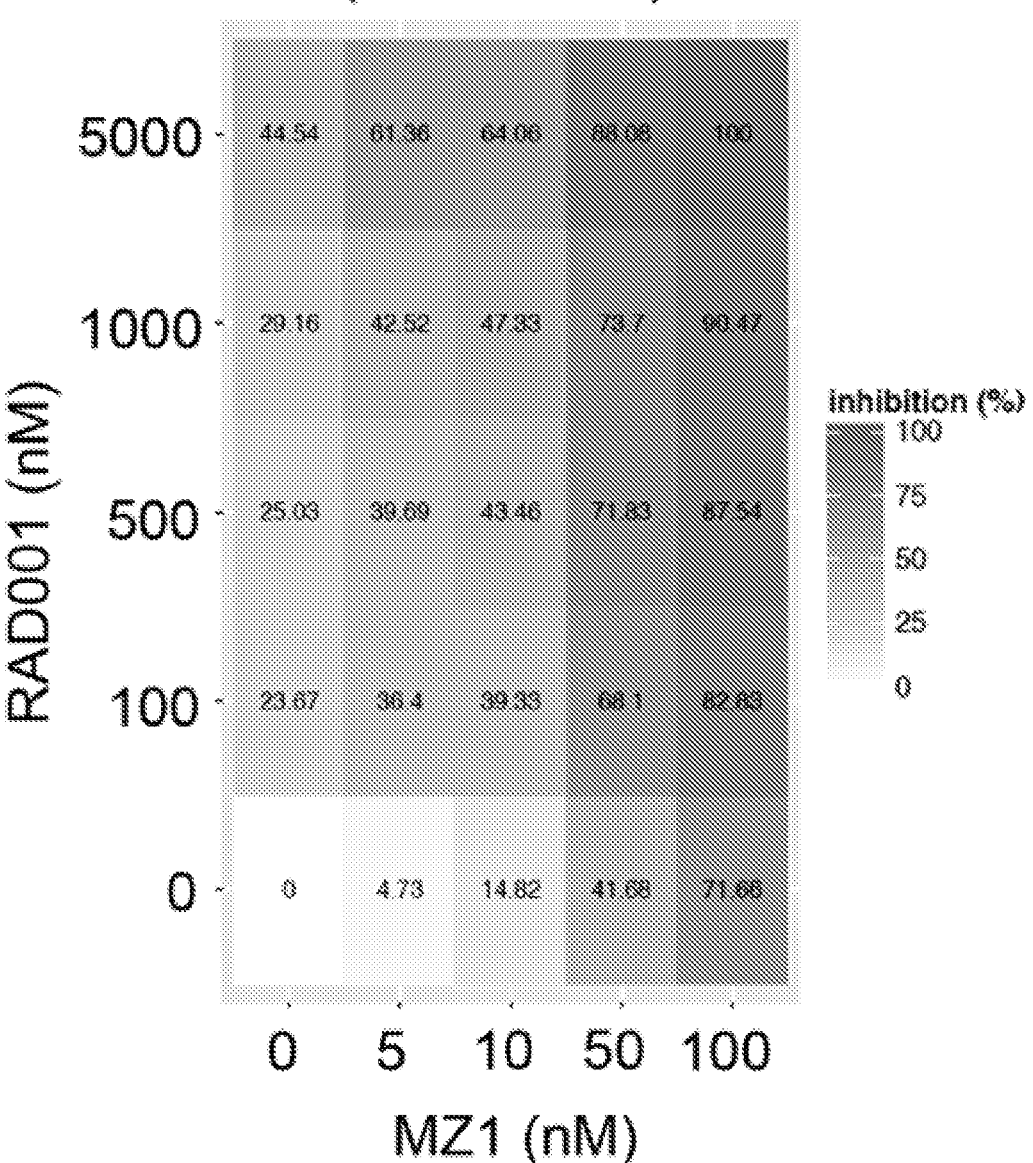
Figure 18:
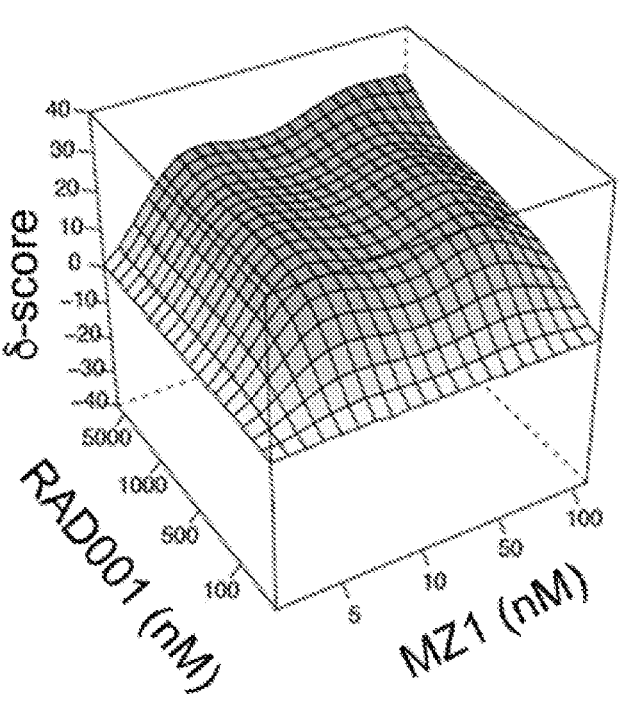
Figure 18:
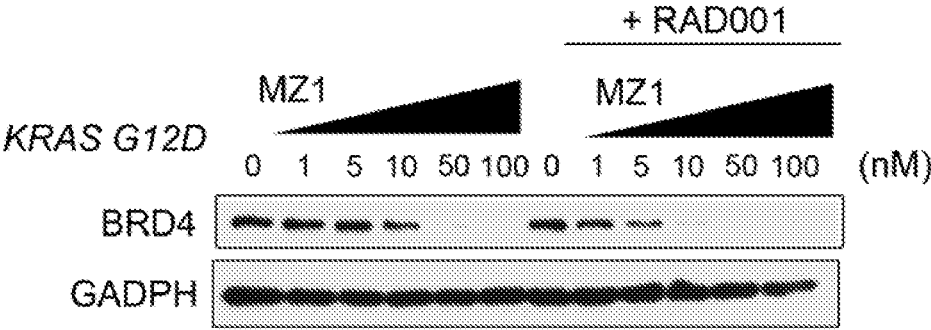
Figure 18:
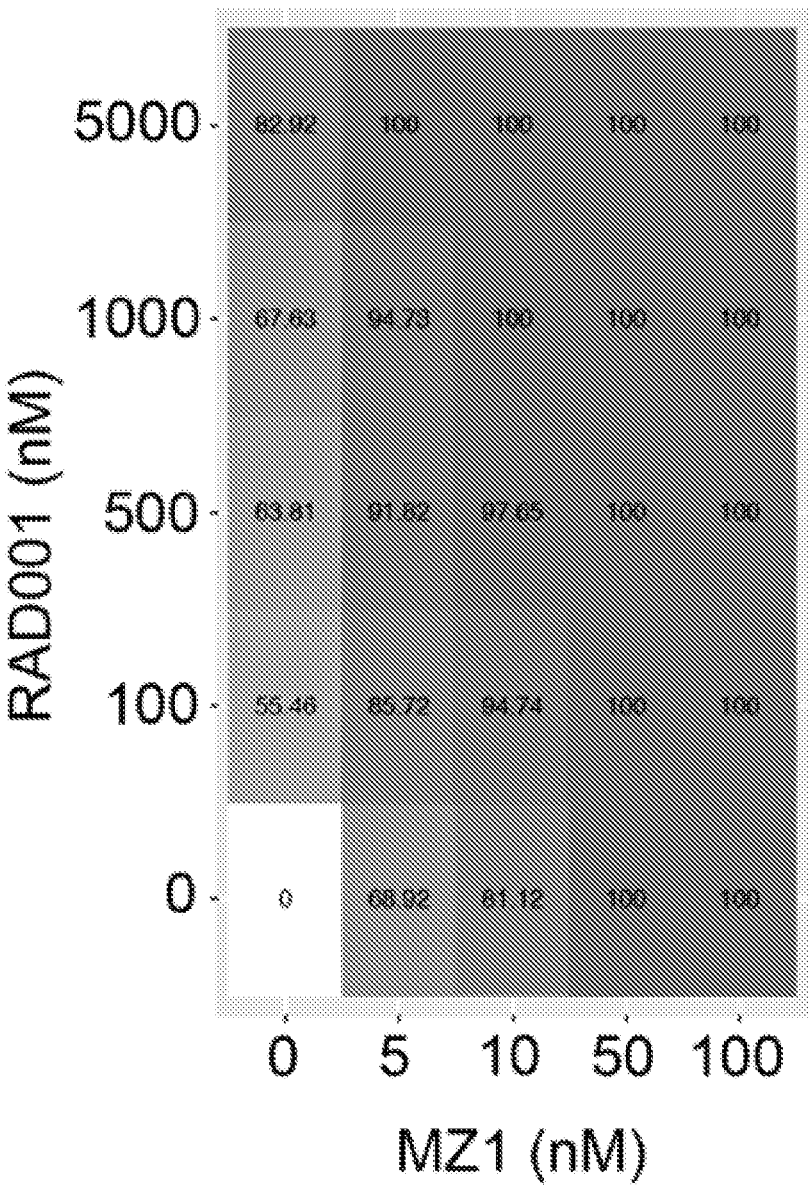
Figure 18:
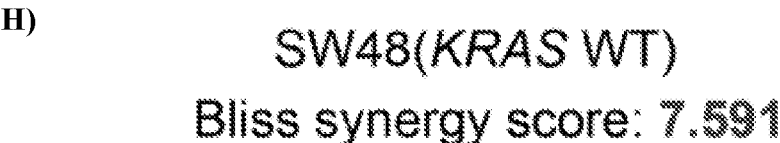
Figure 18:
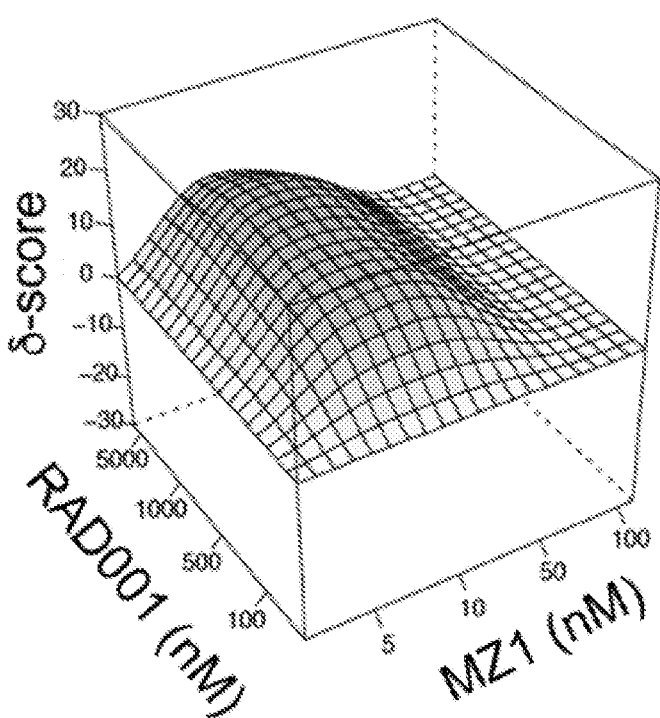
Figure 18:
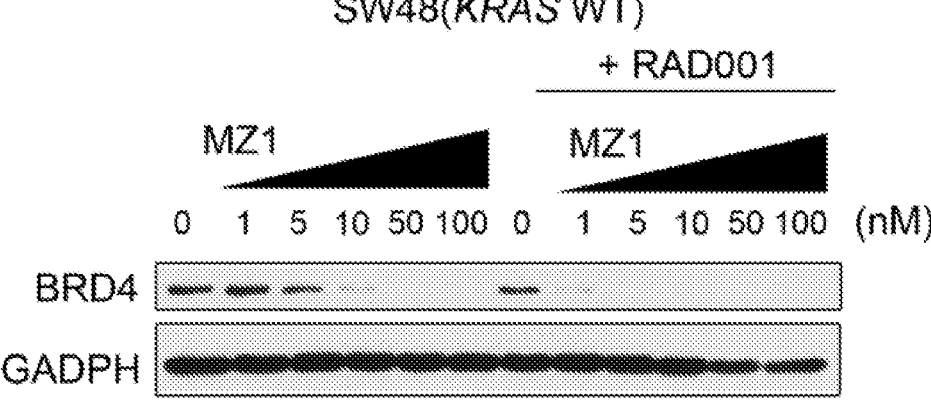

FIG. 18 shows activation of K-ras signaling promotes resistance to BET-PROTACs that can be reversed by MTORC1 inhibitors; expression of K-ras mutants promote resistance to MZ1 therapy (Panel A); immunoblot depicts activation of translation by forced expression of K-ras G12D mutants in SW48 cells (Panel B); immunoblot analysis of BRD4 protein levels (Panel C); dose synergy analysis of RAD001 or MZ1 in K-ras G12D mutant SW48 cells (Panels D and E); immunoblot for BRD4 protein levels in response to combination (Panel F); dose synergy analysis of RAD001 or MZ1 in K-ras wild-type SW48 cells (Panels G and H); and immunoblot for BRD4 protein levels in response to combination (Panel I).

DESCRIPTION OF EMBODIMENTS

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

In the claims, as well as in the specification above, all transitional phrases such as "comprising," "including," "carrying," "having," "containing," "involving," "holding," "composed of," and the like are to be understood to be open-ended, i.e., to mean including but not limited to.

It should also be understood that, in certain methods described herein that include more than one step or act, the order of the steps or acts of the method is not necessarily limited to the order in which the steps or acts of the method are recited unless the context indicates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

The terms "cancer" and "cancerous" refer to or describe the physiological condition in mammals that is typically characterized by unregulated cell growth/proliferation. A "tumor" comprises one or more cancerous cells. Examples of cancer are provided elsewhere herein.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It should be understood that stereoisomers (including diastereomers and enantiomers) of the compounds described herein, as well as mixtures thereof, are within the scope of the present disclosure. By way of non-limiting example, the mixture may be a racemate or the mixture may comprise unequal proportions of one particular stereoisomer over the other. Additionally, the compounds can be provided as a substantially pure stereoisomers. Diastereomers include, for example, cis-trans isomers, E-Z isomers, conformers, and rotamers. Methods of preparation of stereoisomers are known in the art, such as by resolution of racemic mixtures or by stereoselective synthesis. Many geometric isomers of olefins, C=N double bonds, and the like can also be present in the compounds described herein, and all such stable isomers are contemplated herein. Cis and trans geometric isomers of the compounds are also included herein and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Appropriate compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein also include hydrates and solvates, as well as anhydrous and non-solvated forms.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The present disclosure is based on a surprising and unexpected discovery that resistance of cancer to bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents can be overcome by inhibiting one or more cell signaling pathways including RTK signaling pathway, mTOR signaling pathway, CDK7 signaling pathway, KRAS signaling pathway or an autophagy signaling pathway.

The term "PROTAC" refers to proteolysis-targeting chimera molecules having generally three components, an E3 ubiquitin ligase binding group (E3LB), a linker L, and a protein binding group (PB).

The term "linker", "linker unit", or "link" as used herein means a chemical moiety comprising a chain of atoms that covalently attaches a PROTAC moiety to an antibody, or a component of a PROTAC to another component of the PROTAC. In some embodiments, a linker is a divalent radical.

The term "ubiquitin ligase" refers to a family of proteins that facilitate the transfer of ubiquitin to a specific substrate protein, targeting the substrate protein for degradation. For example, cereblon is an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

MTORC1 inhibition may represent a general therapeutic strategy to improve PROTAC-induced degradation of protein targets and improve efficacy of PROTACs by minimizing concentrations of PROTACs required for reduction of protein targets in cells. Without being limited to any particular theory, it is believed that chronic exposure to BET-PROTAC (which targets BRD4 for degradation) triggers reprogramming of cancer cell kinome via CDK9-dependent upregulation of BRD4 transcription and activation of INSR, ErbB and mTORC1-signaling, thereby protecting BRD4 from PROTAC-mediated degradation. This effect is believed to underlie BET-PROTAC therapy resistance in cancer cells. It is believed that inhibiting these signaling pathways may suppress this resistance mechanism thereby restoring cancer cell sensitivity to BRD4 for degradation. Thus, cancer cells intrinsically resistant to BET-PROTACs can be made sensitive by blocking mTORC1 signaling, supporting combination therapies involving MTORC1 and BET protein degraders for the treatment of these types of cancers.

Accordingly, the present disclosure provides pharmaceutical compositions comprising: one or more bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents, or a combination thereof and one or more kinase inhibitors, one or more KRAS inhibitors, or one or more autophagy inhibitors, or any combination thereof.

Proteolysis targeting chimeras are described, for example, in U.S. Patent Application Publication No. US 2019/0175612, U.S. Pat. No. 7,208,157, and PCT Publications No. WO2013/106643, WO2013/106646, and WO2015/. PROTACs have a general structure E3LB-L-PB; wherein, E3LB is an E3 ligase binding group covalently bound to L; L is a linker covalently bound to E3LB and PB; PB is a protein binding group covalently bound to L.

E3 ubiquitin ligases (of which over 600 are known in humans) confer substrate specificity for ubiquitination. There are known ligands which bind to these ligases. As described herein, an E3 ubiquitin ligase binding group is a peptide or small molecule that can bind an E3 ubiquitin ligase.

Specific E3 ubiquitin ligases include: von Hippel-Lindau (VHL); cereblon, XIAP, E3A; MDM2; Anaphase-promoting complex (APC); UBRS (EDD1); SOCS/BC-box/eloBC/CUL5/RING; LNXp80; CBX4; CBLL1; HACE1; HECTD1; HECTD2; HECTD3; HECW1; HECW2; HERC1; HERC2; HERC3; HERC4; HUWE1; ITCH; NEDD4; NEDD4L; PPIL2; PRPF19; PIAS1; PIAS2; PIAS3; PIAS4; RANBP2; RNF4; RBX1; SMURF1; SMURF2; STUB1; TOPORS; TRIP12; UBE3A; UBE3B; UBE3C; UBE4A; UBE4B; UBOX5; UBR5; WWP1; WWP2; Parkin; A20/TNFAIP3; AMFR/gp78; ARA54; beta-TrCP1/BTRC; BRCA1; CBL; CHIP/STUB1; E6; E6AP/UBE3A; F-box protein 15/FBXO15; FBXW7/Cdc4; GRAII/RNF128; HOIP/RNF31; cIAP-1/HIAP-2; cIAP-2/HIAP-1; cIAP (pan); ITCH/AIP4; KAP1; MARCH8; Mind Bomb 1/MIB1; Mind Bomb 2/MIB2; MuRF1/TRIM63; NDFIP1; NEDD4; NleL; Parkin; RNF2; RNF4; RNF8; RNF168; RNF43; SART1; Skp2; SMURF2; TRAF-1; TRAF-2; TRAF-3; TRAF-4; TRAF-5; TRAF-6; TRIM5; TRIM21; TRIM32; UBR5; and ZNRF3.

In some embodiments, E3 ubiquitin ligase is von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor $1\alpha$ (HIF-$1\alpha$), a transcription factor that upregulates genes such as the pro-angiogenic growth factor VEGF and the red blood cell inducing cytokine erythropoietin in response to low oxygen levels. Compounds that bind VHL may be hydroxyproline compounds such as those disclosed in WO2013/106643, and other compounds described in US2016/0045607, WO2014187777, US20140356322, and U.S. Pat. No. 9,249.

In some embodiments, E3 ubiquitin ligase is X-linked inhibitor of apoptosis (XIAP). XIAP is a protein that stops apoptotic cell death. Deregulation of XIAP has been associated with cancer, neurodegenerative disorders and autoimmunity. In the development of lung cancer, the overexpression of XIAP inhibits caspases. In developing prostate cancer, XIAP is one of four IAPs overexpressed in the prostatic epithelium. Mutations in the XIAP gene can result in a severe and rare type of inflammatory bowel disease. Defects in the XIAP gene can also result in an extremely rare condition called X-linked lymphoproliferative disease. Degradation of XIAP can enhance apoptosis by preventing XIAP from binding to caspases. This allows normal caspase activity to proceed.

Examples of small molecular binding compounds for XIAP include compounds disclosed in U.S. Pat. No. 9,096, 544; WO 2015187998; WO 2015071393; U.S. Pat. Nos. 9,278,978; 9,249,151; US 20160024055; US 20150307499; US 20140135270; US 20150284427; US 20150259359; US 20150266879; US 20150246882; US 20150252072; US 20150225449; U.S. Pat. No. 8,883,771, J. Med. Chem., 2015, 58(16) 6574-6588 and Small-molecule Pan-IAP Antagonists: A Patent Review (2010) Expert Opin Ther Pat; 20: 251-67 (Flygare & Fairbrother).

In some embodiments, E3 ubiquitin ligase is MDM2. Examples of small molecular binding compounds for MDM2 include the "nutlin" compounds, e.g., nutlin 3a and nutlin 3.

Thalidomide, lenalidomide, pomalidomide and analogs thereof are known to bind to cereblon. The crystal structure of cereblon (CRBN) with thalidomide and derivative compounds are described in US2015/0374678. Other small molecule compounds that bind to cereblon are also known, e.g., the compounds disclosed as an in US2016/0058872 and US2015/0291562. Further, phthalimide conjugation with binders, such as antagonists, of BET bromodomains can provide PROTACs with highly-selective cereblon-dependent BET protein degradation. Winter et al., Science, Jun. 19, 2015, 1376. Such PROTACs can be conjugated to an antibody as described herein to form a PAC. Additional E3 ligase binding groups are described, for example, in the U.S. Patent Application Publication No. 2019/0175612.

The PB component is a group which binds to a target protein intended to be degraded. The term "protein" includes oligopeptides and polypeptide sequences of sufficient length that they can bind to a PB group. Any protein in a eukaryotic system or a microbial system, including a virus, bacteria or fungus, as otherwise described herein, are targets for ubiquitination mediated by the compounds described herein.

PB groups include, for example, any moiety which binds to a protein specifically (binds to a target protein) and includes the following non-limiting examples of small molecule target protein moieties: Hsp90 inhibitors, kinase inhibitors (such as CDK9 inhibitors), MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others.

In some embodiments, PB group specifically binds one or more Bromodomain and Extra-Terminal motif (BET) proteins. BET is a subfamily of proteins responsible for recognition acetylated lysine residues, such as those on the N-terminal tails of histones, and include BRD2, BRD3, BRD4 and BRDT (see WO 2011/143669). In some embodiments, the BET-specific PB group comprises an anti-BET antibody. In some embodiments the BET-specific PB group comprises a BET inhibitor that is specific for one or more BET proteins. Numerous BET inhibitors are known in the art and are described, for example in Doroshow et al., Annals of Oncology, 2017, 28, 1776-1787; Pérez-Salviaa and Esteller Epigenetics, 2017, 12, 323-339; Klein, RMD Open, 2018, 4: e000744; Ocana et al., Oncotarget, 2017, 8, 71285-71291; Hogg et al., Blood, 2017, 130, 2537; U.S. Patent Application Publications 2018/0117030, 2016/

0095867, 2018/0117165, PCT Publications WO 2011/054843, WO 2009/084693, 20180117165, and JP2008-156311.

In some embodiments, the BET inhibitors include, without limitation, olinone, JQ1, iBET, RVX-208, PF-1, ABBV-075, BAY1238097, BI 894999, BMS-986158, CPI-0610, FT-1101, GS-5829, GSK525762/I-BET762, GSK2820151/I-BET151, INCB054329, OTX015/MK-8628, PLX51107, R06870810/TEN-010, ZEN003694, CPI203, PFI-1, MS436, RVX2135, BAY-299, I-BET762, RVX297, SF1126, INCB054329, INCB057643, RO6870810, LY294002, AZD5153, MT-1, MS645 and RG6146.

In some embodiments PB group specifically binds Cyclin-Dependent Kinase 9 (CDK9) Protein. In some embodiments, the CDK9-specific PB group comprises an anti-CDK9 antibody.

In some embodiments the CDK9-specific PB group comprises a CDK9 inhibitor. Numerous BET inhibitors are described, for example in Krystof, Medicinal Research Reviews, 2009, DOI 10.1002/med.24172; U.S. Patent Application Publications 2017/0304315, 2017/0173021, 2015/0329537, 2014/0287454, and PCT Publications WO 2009/047359, WO 2010/003133, WO 2008/79933 and WO 2011/012661.

In some embodiments, the CDK9 inhibitors include, without limitation, NVP-2, LDC000067, SNS-032 (BMS-387032), AT7519, P-276-00, AZD5438, PHA-767491, PHA-793887, PHA-848125, BAY 1143572, BAY 1112054, Cdk9 inhibitor II (CAS 140651-18-9 from Calbiochem), DRB, AZD-5438, SNS-032, dinaciclib, LY2857785, flavopiridol, purvalanol B, CDKI-71, CDKI-73, CAN508, FIT-039, CYC065, Ro-3306, 3,4-dimethyl-5-[2-(4-piperazin-1-yl-phenylamino)-pyrimidin-4-yl]-3H-thiazol-2-one, wogonin, apigenin, chrysin, luteolin, 4-methyl-5-[2-(3-nitroanilino)pyrimidin-4-yl]-1,3-thiazol-2-amine, 1073485-20-7P and Cpd B1.

The E3LB and PB groups of PROTACs as described herein can be connected with linker (L). In certain embodiments, the linker group L is a group comprising one or more covalently connected structural units of A (e.g., $-A_1 \ldots A_q-$), wherein $A_1$ is a group coupled to at least one of a E3LB, a PB, or a combination thereof. In certain embodiments, $A_1$ links a E3LB, a PB, or a combination thereof directly to another E3LB, PB, or combination thereof. In other embodiments, $A_1$ links a EL3B, a PB, or a combination thereof indirectly to another E3LB, PB, or combination thereof through $A_q$.

In certain embodiments, q is an integer greater than or equal to 0. In certain embodiments, q is an integer greater than or equal to 1.

In some embodiments, e.g., where q is greater than 2, $A_q$ is a group which is connected to an E3LB moiety, and $A_1$ and $A_q$ are connected via structural units of A (number of such structural units of A: q-2). In some embodiments, e.g., where q is 2, $A_q$ is a group which is connected to $A_1$ and to an E3LB moiety. In some embodiments, e.g., where q is 1, the structure of the linker group and L-$A_1$-, and $A_1$ is a group which is connected to an E3LB moiety and a PB moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In some embodiments, the linker group is an optionally substituted (poly)ethyleneglycol having from 1 to about 100 ethylene glycol units, from 1 to about 50 ethylene glycol units, from 1 to about 25 ethylene glycol units, from 1 to about 10 ethylene glycol units, from 1 to about 8 ethylene glycol units, and from 1 to about 6 ethylene glycol units, from 2 to 4 ethylene glycol units, or optionally substituted alkyl groups interdispersed with optionally substituted, O, N, S, P or Si atoms. In some embodiments, the linker is substituted with an aryl, phenyl, benzyl, alkyl, alkylene, or heterocycle group. In some embodiments, the linker may be asymmetric or symmetrical.

In any of the embodiments of the compounds described herein, the linker group may be any suitable moiety as described herein. In some embodiments, the linker is a substituted or unsubstituted polyethylene glycol group ranging in size from about 1 to about 12 ethylene glycol units, from 1 to about 10 ethylene glycol units, from 2 to about 6 ethylene glycol units, from 2 to about 5 ethylene glycol units, or from 2 to 4 ethylene glycol units.

Although the E3LB group and PB group may be covalently linked to the linker group through any group which is appropriate and stable to the chemistry of the linker. The linker can be independently covalently bonded to the E3LB group and the PB group preferably through an amide, ester, thioester, keto group, carbamate (urethane), carbon or ether, each of which groups may be inserted anywhere on the E3LB group and PB group to provide maximum binding of the E3LB group on the ubiquitin ligase and the PB group on the target protein to be degraded. In some embodiments where the PB group is an E3LB group, the target protein for degradation may be the ubiquitin ligase itself. In some embodiments, the linker may be linked to an optionally substituted alkyl, alkylene, alkene or alkyne group, an aryl group or a heterocyclic group on the E3LB and/or PB groups. It is noted that an E3LB group or a PB group may need to be derivatized to make a chemical functional group that is reactive with a chemical functional group on the linker. Alternately, the linker may need to be derivatized to include a chemical functional group that can react with a functional group found on E3LB and/or PB.

Although the E3LB group and PB group may be covalently linked to the linker group through any group which is appropriate and stable to the chemistry of the linker, in preferred aspects, the linker is independently covalently bonded to the E3LB group and the PB group through an amide, ester, thioester, keto group, carbamate (urethane) or ether, each of which groups may be inserted anywhere on the E3LB group and PB group to allow binding of the E3LB group to the ubiquitin ligase and the PB group to the target protein to be degraded. In other words, as shown herein, the linker can be designed and connected to E3LB and PB to minimize, eliminate, or neutralize any impact its presence might have on the binding of E3LB and PB to their respective binding partners. In certain aspects, the targeted protein for degradation may be a ubiquitin ligase.

Additional linkers L are disclosed in US Application Publication Nos. 2019/0175612, 2016/0058872; 2016/0045607; 2014/0356322; and 2015/0291562, and WO2014/063061.

Multiple BET-specific POTACS assembled from, inter alia, the components described above are described in, for example in Sun et al., Leukemia, 2018, 32, 343-352; Zhang et al., Mol. Cancer Ther., 2019, 18, 1302-1311; Yang et al., Drug Discovery Today: Technologies, 2019, 31, 43-51; Raina et al., PNAS, 2016, 113, 7124-7129; and Zou et al, Cell Biochem Funct., 2019, 37, 21-30; An and Fu, EBioMedicine, 2018, 36, 553-562.

In some embodiments, the BET-PROTACS include, without limitation, MZ1, ARV-771, AT1, MZP-61, MZP-51, MZP-55, ARV825, dBET6, dBET57, dBET23, ZXH 3-26, BETd246, BETd260, QCA570, or ARCC-29, A1874, and CFT-2718.

Multiple CDK9-specific POTACS assembled, inter alia, from the components described above are described in, for example in Olson et al., Nat. Chem. Biol., 2018, 14, 163-170 and Robb et al, Chem. Commun. (Camb), 2017, 53, 7577-7580.

In some embodiments, the CDK9-PROTACS include, without limitation, THAL SNS 032, PROTAC3, and CDK9 Degrader-1.

In some embodiments, the compositions comprise a single PROTAC therapeutic agent. In some embodiments, the compositions comprise multiple PROTAC agents comprising any combination of the PROTAC agents described herein.

In some embodiments, the compositions further comprise one or more kinase inhibitors, one or more KRAS inhibitors, or one or more autophagy inhibitors. In some embodiments the kinase pathway inhibitors inhibit kinase signaling pathways including, without limitation, a receptor tyrosine kinase (RTK) pathway inhibitor, a mammalian target of rapamycin (MTOR) pathway inhibitor, or a CDK7 pathway inhibitor.

RTK family of kinases are described, for example, by Bertrand et al., The International Journal of Developmental Biology, 61(10-11-12), 697-722 and Regad, Cancers 2015, 7, 1758-1784. In addition to RTK, the family includes, inter alia, Insulin Receptor (INSR/IGF1R), Epidermal Growth Factor Receptor family (EGFR/ERBB/HER2/HER3/HER4), Proto-Oncogene Tyrosine-Protein Kinase (MERTK), Macrophage-Stimulating Protein Receptor 1 (MST1R) and Fibroblast Growth Factor Receptor 1 (FGFR1), any of which can be targeted for inhibition according to the methods of the present disclosure. In some embodiments, the RTK pathway inhibitor targets RTK directly. RTK inhibitors include, without limitation, GTP14564, R 1530, imatinib, Sorafenib, Pazopanib, Cabozantinib, Sunitinib, Crizitonib, Regorafenib, and Dovitinib. In some embodiments, the RTK pathway inhibitor is an EGFR inhibitor. EGFR inhibitors include, without limitation, Trastuzumab, Panitumumab, Cetuximab, Afatinib, Sapitinib, Neratinib, Theliatinib, Avitinib, Canertinib, AG-490, CP-724714, Dacomitinib, WZ4002, CUDC-101, AG-1478, PD153035, Pelitinib, AC480, AEE788, OSI-420, WZ3146, ARRY-380, AST-1306, Rociletinib, Genistein, Varlitinib, Icotinib, TAK-285, WHI-P154, Daphnetin, PD168393, Tyrphostin 9, CNX-2006, AG-18, AZ5104, Osimertinib, CL-387785, Olmutinib, (–)-Epigallocatechin Gallate (EGCG), AZD3759, Poziotinib, Naquotinib, Chrysophanol, Nazartinib, Norcantharidin, Lifirafenib, Lidocaine hydrochloride, Butein, EA1045, NSC228155, Erlotinib, Gefitinib, and Lapatinib. In some embodiments, the RTK pathway inhibitor is an MERTK inhibitor. MERTK inhibitors include, without limitation, UNC1062, MRX-2843, RXDX-106, UNC2541, and unc2025. In some embodiments, the RTK pathway inhibitor is an MST1R inhibitor. MST1R inhibitors include, without limitation, LY2801653 dihydrochloride, BMS777607, and PHA 665752. In some embodiments, the RTK pathway inhibitor is an FGFR1 inhibitor. FGFR1 inhibitors include, without limitation, Ponatinib, BGJ398, Nintedanib, PD173074, Dovitinib, Alofanib, Gambogenic Acid, Derazantinib, Nintedanib, AZD4547, Danusertib, Brivanib, Dovitinib Dilactic acid, Dovitinib Lactate, MK-2461, SSR128129E, LY2874455, H3B-6527, Erdafitinib, NSC12, 549076, BLU-554, PRN1371, PD-166866, PD-166866, FIIN-2, CH5183284, BLU9931, and SUN11602.

mTOR pathway inhibitors are described, for example, by Harter et al., PLoS ONE, 2015, 10, e0127123. In addition to MTOR, the signaling pathway includes, inter alia, Phospho-inositide 3-Kinase (PI3K), p70S6 kinase (P70S6K), Phosphatidylinositol 4-Kinase Type 2 Alpha (PI4K2A), and CDK9, any of which can be targeted for inhibition according to the methods of the present disclosure. In some embodiments, the mTOR inhibitor targets the mTOR kinase directly. mTOR inhibitors include, without limitation, Dactolisib (BEZ235 or NVP-BEZ235), Rapamycin (Sirolimus), Everolimus (RAD001), AZD8055, Temsirolimus (CCI-779 or NSC 683864), PI-103, KU-0063794, Torkinib (PP242), Tacrolimus (FK506), Ridaforolimus (Deforolimus or MK-8669), Sapanisertib (INK 128, MLN0128, or TAK-228), Voxtalisib (SAR245409 or XL765) Analogue, Torin 1, Omipalisib (GSK2126458 or GSK458), OSI-027, PF-04691502, Apitolisib (GDC-0980 or RG7422), GSK1059615, WYE-354, Gedatolisib (PF-05212384 or PKI-587), Torin 2, WYE-125132 (WYE-132), Vistusertib (AZD2014), BGT226 (NVP-BGT226), Palomid 529 (P529), PP121, WYE-687, WAY-600, ETP-46464, GDC-0349, XL388, Zotarolimus (ABT-578), LY3023414, CC-115, MHY1485, CZ415, GDC-0084, Voxtalisib (XL765 or SAR245409), 3BDO, Bimiralisib (PQR309), CC-223, and SF2523. In some embodiments, the mTOR pathway inhibitor is an PI3K inhibitor. PI3K inhibitors include, without limitation, compound 7n, Dactolisib, Pictilisib (GDC-0941), LY294002, Buparlisib, IC-87114, Wortmannin, XL147 analogue, ZSTK474, Apitolisib, AS-605240, 3-Methyladenine, PIK-90, PF-04691502, AZD6482, Apitolisib, GSK1059615, Duvelisib, Gedatolisib, TG100-115, AS-252424, BGT226, CUDC-907, AS-604850, GSK2636771, Copanlisib, CH5132799, CAY10505, PIK-293, PKI-402, TG100713, VS-5584, Taselisib, CZC24832, SF2523, AZD8835, AMG319, Seletalisib, TGR-1202, Pilaralisib, Bimiralisib, IPI-549, GDC-0084, Voxtalisib, HS-173, PF-4989216, Tenalisib, 740 Y-P, Leniolisib, GNE-317, LY3023414, GSK2292767, AZD8186, 2-D08, Nemiralisib, PI-103, Vistusertib, BGT226, and CC-223. In some embodiments, the mTOR pathway inhibitor is an P70S6K inhibitor. P70S6K inhibitors include, without limitation, BI-D1870, AT7867, PF-4708671, AD80, AT13148, LY2584702, and LY2584702 Tosylate. In some embodiments, the mTOR pathway inhibitor is an PI4K2A inhibitor. PI4K2A inhibitors include, without limitation, PIK-93, PI-273, NA04, NB04, NE02, NCO2, NC03, NB02, NC04, ND02, NE03, NF03, NF04, NG02, NG03, NH02, NCO2-567, and NCO2-770 (see Sengupta et al., 2019 The Journal of Lipid Research, 60(3):683-693). In some embodiments, the mTOR pathway inhibitor is an CDK9 inhibitor. CDK9 inhibitors include, without limitation, NVP-2, LDC000067, SNS-032 (BMS-387032), AT7519, P-276-00, AZD5438, PHA-767491, PHA-793887, PHA-848125, BAY 1143572, BAY 1112054, Cdk9 inhibitor II (CAS 140651-18-9 from Calbiochem), DRB, AZD-5438, SNS-032, dinaciclib, LY2857785, flavopiridol, purvalanol B, CDKI-71, CDKI-73, CAN508, FIT-039, CYC065, Ro-3306, 3,4-dimethyl-5-[2-(4-piperazin-1-yl-phenylamino)-pyrimidin-4-yl]-3H-thiazol-2-one, wogonin, apigenin, chrysin, luteolin, 4-methyl-5-[2-(3-nitroanilino)pyrimidin-4-yl]-1,3-thiazol-2-amine, 1073485-20-7P and Cpd B1.

The combination therapies described herein are considered to be global to improve the efficacy of PROTACs independent of the therapeutic target. Thus, MTOR inhibitors can be combined with any and all PROTACs, not just BET protein or CDK9 PROTACs.

In some embodiments, the kinase inhibitor is a CDK7 inhibitor. CDK7 inhibitors include, without limitation, THZ1, AT7519, LDC4297, LY2857785, BS-181 HC, SNS-032, R547, Flavopiridol, AT7519, PHA-793887, and Flavopiridol-HCl.

In some embodiments, the kinase inhibitor is a Casein kinase 2 (CK2) inhibitor. CK2 inhibitors include, without limitation, Silmitasertib, GSK269962, and TBB.

In some embodiments, the kinase inhibitor is a RAC-alpha serine/threonine-protein kinase 1 and 2 (AKT1/2) inhibitor. AKT1/2 inhibitors include, without limitation, Akti-1/2, MK-2206, Perifosine, GSK690693, Ipatasertib, AZD5363, AT7867, Triciribine, CCT128930, A-674563, Miltefosine, TIC10, SC66, Afuresertib, AT13148, Uprosertib, SC79, and ARQ 092.

In some embodiments, the kinase inhibitor is an Adaptor-associated kinase 1 (AAK1) inhibitor. AAK1 inhibitors include, without limitation, LP-935509, LP-922761, BMT-090605, BMT-124110, LP-927443, and BMS-901715 (see, Kostich et al., J. Pharmacol. Exp. Ther., 2016, 358, 371-386).

In some embodiments, the kinase inhibitor is a focal adhesion kinase (FAK1) inhibitor. FAK1 inhibitors include, without limitation, PF-00562271, PF-573228, TAE226, PF-03814735, Defactinib, GSK2256098, PF-431396, Y15, and PND-1186.

In some embodiments, the kinase inhibitor is a mitogen-activated protein kinase kinase (MEK) inhibitor. MEK inhibitors include, without limitation, Binimetinib, Selumetinib, PD0325901, Trametinib, U0126-EtOH, PD184352, PD98059, Pimasertib, TAK-733, AZD8330, PD318088, SL327, Refametinib, GDC-0623, Cobimetinib, and BI-847325.

In some embodiments, the kinase inhibitor is a Rapidly Accelerated Fibrosarcoma (RAF) kinase inhibitor. RAF kinase inhibitors include, without limitation, Sorafenib, Vemurafenib, Regorafenib, Sorafenib Tosylate, Dabrafenib, AZ304, Belvarafenib, ERK-IN-1, PLX8394, Doramapimod, PLX-4720, LY3009120, RAF265, GW 5074, Dabrafenib Mesylate, LXH254, Agerafenib, GDC-0879, AZ 628, Ro 5126766, TAK-632, Regorafenib Hydrochloride, PLX7904, CCT196969, HG6-64-1, TAK-580, ZM 336372, AD80, SB-590885, Regorafenib monohydrate, Lifirafenib, L-779450, P-0850, B-Raf inhibitor 1, Belvarafenib, B-Raf IN 1, LUT014, BI-882370, Agerafenib hydrochloride, and B-Raf inhibitor 1 dihydrochloride.

In some embodiments, the compositions further comprise a KRAS inhibitor. KRAS inhibitors include, without limitation, K-Ras(G12C) inhibitors 1-12, Olaparib, AMG-510, Deltarasin, 6H05, ARS-1620, KRpep-2d, ARS-853, Lonafarnib, MRTX-1257, PHT-7.3, ARS-1323 and MRTX849.

In some embodiments, the compositions further comprise an autophagy inhibitor. Autophagy inhibitors include, without limitation, Nimodipine, Lucanthone, Liensinine, Autophinib, DC661, EAD1, Spautin-1, ROC-325, PIK-III, PHY34, MHY1485, Hydroxychloroquine Sulfate, CA-5f, Bafilomycin Al, Daurisoline, 3BDO, SAR405, Elaiophylin, Autogramin-2, Lys05, DC661, IITZ-01, SBI-0206965, AS1842856, Chloroquine, 3-Methyladenine, ULK-101, J22352, LYN-1604, MRT68921 HCl, and hydroxychloroquine.

In some embodiments, the compositions comprise one or more BET-PROTAC therapeutic agents and one or more MTOR signaling pathway inhibitors. In some embodiments, the compositions comprise MZ1 and one or more MTOR signaling pathway inhibitors. In some embodiments, the compositions comprise MZ1 and one or more of RAD001, Torin-1, GDC-0941, LY2584702, PI-273, or NVP-2. In some embodiments, the compositions comprise MZ1 and GDC-0941. In some embodiments, the compositions comprise MZ1 and lapatinib. In some embodiments, the compositions comprise MZ1 and RAD001. In some embodiments, the compositions comprise MZ1 and LY2584702. In some embodiments, the compositions comprise MZ1 and PI-273. In some embodiments, the compositions comprise MZ1 and NVP-2. In some embodiments, the compositions comprise ARV825 and one or more MTOR signaling pathway inhibitors. In some embodiments, the compositions comprise ARV825 and one or more of RAD001, Torin-1, GDC-0941, LY2584702, PI-273, or NVP-2. In some embodiments, the compositions comprise ARV825 and GDC-0941. In some embodiments, the compositions comprise ARV825 and lapatinib. In some embodiments, the compositions comprise ARV825 and RAD001. In some embodiments, the compositions comprise ARV825 and LY2584702. In some embodiments, the compositions comprise ARV825 and PI-273. In some embodiments, the compositions comprise ARV825 and NVP-2. In some embodiments, the compositions comprise dBET1 and one or more MTOR signaling pathway inhibitors. In some embodiments, the compositions comprise dBET1 and one or more of RAD001, Torin-1, GDC-0941, LY2584702, PI-273, or NVP-2. In some embodiments, the compositions comprise dBET1 and GDC-0941. In some embodiments, the compositions comprise dBET1 and lapatinib. In some embodiments, the compositions comprise dBET1 and RAD001. In some embodiments, the compositions comprise dBET1 and LY2584702. In some embodiments, the compositions comprise dBET1 and PI-273. In some embodiments, the compositions comprise dBET1 and NVP-2. In some embodiments, the compositions comprise A1874 and one or more MTOR signaling pathway inhibitors. In some embodiments, the compositions comprise A1874 and one or more of RAD001, Torin-1, GDC-0941, LY2584702, PI-273, or NVP-2. In some embodiments, the compositions comprise A1874 and GDC-0941. In some embodiments, the compositions comprise A1874 and lapatinib. In some embodiments, the compositions comprise A1874 and RAD001. In some embodiments, the compositions comprise A1874 and LY2584702. In some embodiments, the compositions comprise A1874 and PI-273. In some embodiments, the compositions comprise A1874 and NVP-2. In some embodiments, the compositions comprise CFT-2718 and one or more MTOR signaling pathway inhibitors. In some embodiments, the compositions comprise CFT-2718 and one or more of RAD001, Torin-1, GDC-0941, LY2584702, PI-273, or NVP-2. In some embodiments, the compositions comprise CFT-2718 and GDC-0941. In some embodiments, the compositions comprise CFT-2718 and lapatinib. In some embodiments, the compositions comprise CFT-2718 and RAD001. In some embodiments, the compositions comprise CFT-2718 and LY2584702. In some embodiments, the compositions comprise CFT-2718 and PI-273. In some embodiments, the compositions comprise CFT-2718 and NVP-2.

In some embodiments, the compositions comprise one or more BET-PROTAC therapeutic agents and one or more RTK signaling pathway inhibitors. In some embodiments, the compositions comprise MZ1 and one or more RTK signaling pathway inhibitors. In some embodiments, the compositions comprise MZ1 and one or more of GSK1904529A, lapatinib, imatinib, MRX-2843, LY2801653 dihydrochloride and PD173074. In some embodiments, the compositions comprise MZ1 and GSK1904529A. In some embodiments, the compositions comprise MZ1 and lapatinib. In some embodiments, the compositions comprise MZ1 and imatinib. In some embodiments, the compositions comprise MZ1 and MRX-2843. In some embodiments, the compositions comprise MZ1 and LY2801653 dihydrochloride. In some embodiments, the compositions comprise MZ1 and PD173074. In some embodiments, the compositions comprise ARV825 and one or more RTK signaling pathway inhibitors. In some embodiments, the compositions comprise ARV825 and one or more of GSK1904529A, lapatinib, imatinib, MRX-2843, LY2801653 dihydrochloride and PD173074. In some embodiments, the compositions comprise ARV825 and GSK1904529A. In some embodiments, the compositions comprise ARV825 and lapatinib. In some embodiments, the compositions comprise ARV825 and imatinib. In some embodiments, the compositions comprise ARV825 and MRX-2843. In some embodiments, the compositions comprise ARV825 and LY2801653 dihydrochloride. In some embodiments, the compositions comprise ARV825 and PD173074. In some embodiments, the compositions comprise dBET1 and one or more RTK signaling pathway inhibitors. In some embodiments, the compositions comprise dBET1 and one or more of GSK1904529A, lapatinib, imatinib, MRX-2843, LY2801653 dihydrochloride and PD173074. In some embodiments, the compositions comprise dBET1 and GSK1904529A. In some embodiments, the compositions comprise dBET1 and lapatinib. In some embodiments, the compositions comprise dBET1 and imatinib. In some embodiments, the compositions comprise dBET1 and MRX-2843. In some embodiments, the compositions comprise dBET1 and LY2801653 dihydrochloride. In some embodiments, the compositions comprise dBET1 and PD173074. In some embodiments, the compositions comprise A1874 and one or more RTK signaling pathway inhibitors. In some embodiments, the compositions comprise A1874 and one or more of GSK1904529A, lapatinib, imatinib, MRX-2843, LY2801653 dihydrochloride and PD173074. In some embodiments, the compositions comprise A1874 and GSK1904529A. In some embodiments, the compositions comprise A1874 and lapatinib. In some embodiments, the compositions comprise A1874 and imatinib. In some embodiments, the compositions comprise A1874 and MRX-2843. In some embodiments, the compositions comprise A1874 and LY2801653 dihydrochloride. In some embodiments, the compositions comprise A1874 and PD173074. In some embodiments, the compositions comprise CFT-2718 and one or more RTK signaling pathway inhibitors. In some embodiments, the compositions comprise CFT-2718 and one or more of GSK1904529A, lapatinib, imatinib, MRX-2843, LY2801653 dihydrochloride and PD173074. In some embodiments, the compositions comprise CFT-2718 and GSK1904529A. In some embodiments, the compositions comprise CFT-2718 and lapatinib. In some embodiments, the compositions comprise CFT-2718 and imatinib. In some embodiments, the compositions comprise CFT-2718 and MRX-2843. In some embodiments, the compositions comprise CFT-2718 and LY2801653 dihydrochloride. In some embodiments, the compositions comprise CFT-2718 and PD173074.

In some embodiments, the compositions comprise one or more BET-PROTAC therapeutic agents and one or more KRAS inhibitors. In some embodiments, the compositions comprise MZ1 and one or more KRAS inhibitors. In some embodiments, the compositions comprise MZ1 and one or more of ARS-1620 and MRTX849. In some embodiments, the compositions comprise MZ1 and ARS-1620. In some embodiments, the compositions comprise MZ1 and MRTX849. In some embodiments, the compositions comprise ARV825 and one or more of ARS-1620 and MRTX849. In some embodiments, the compositions comprise ARV825 and ARS-1620. In some embodiments, the compositions comprise ARV825 and MRTX849. In some embodiments, the compositions comprise dBET1 and one or more KRAS inhibitors. In some embodiments, the compositions comprise dBET1 and one or more of ARS-1620 and MRTX849. In some embodiments, the compositions comprise dBET1 and ARS-1620. In some embodiments, the compositions comprise dBET1 and MRTX849. In some embodiments, the compositions comprise A1874 and one or more KRAS inhibitors. In some embodiments, the compositions comprise A1874 and one or more of ARS-1620 and MRTX849. In some embodiments, the compositions comprise A1874 and ARS-1620. In some embodiments, the compositions comprise A1874 and MRTX849. In some embodiments, the compositions comprise CFT-2718 and one or more KRAS inhibitors. In some embodiments, the compositions comprise CFT-2718 and one or more of ARS-1620 and MRTX849. In some embodiments, the compositions comprise CFT-2718 and ARS-1620. In some embodiments, the compositions comprise CFT-2718 and MRTX849.

In some embodiments, the compositions comprise one or more BET-PROTAC therapeutic agents and one or more autophagy inhibitors. In some embodiments, the compositions comprise MZ1 and one or more autophagy inhibitors. In some embodiments, the compositions comprise MZ1 and one or more of SAR405, Autophinib, PIK-III, LYN-1604, SBI-0206965, MRT68921 HCl, ULK-101, and hydroxychloroquine. In some embodiments, the compositions comprise MZ1 and SAR405. In some embodiments, the compositions comprise MZ1 and Autophinib. In some embodiments, the compositions comprise MZ1 and PIK-III. In some embodiments, the compositions comprise MZ1 and LYN-1604. In some embodiments, the compositions comprise MZ1 and SBI-0206965. In some embodiments, the compositions comprise MZ1 and MRT68921 HCl. In some embodiments, the compositions comprise MZ1 and ULK-101. In some embodiments, the compositions comprise MZ1 and hydroxychloroquine. In some embodiments, the compositions comprise ARV825 and one or more autophagy inhibitors. In some embodiments, the compositions comprise ARV825 and one or more of SAR405, Autophinib, PIK-III, LYN-1604, SBI-0206965, MRT68921 HCl, ULK-101, and hydroxychloroquine. In some embodiments, the compositions comprise ARV825 and SAR405. In some embodiments, the compositions comprise ARV825 and Autophinib. In some embodiments, the compositions comprise ARV825 and PIK-III. In some embodiments, the compositions comprise ARV825 and LYN-1604. In some embodiments, the compositions comprise ARV825 and SBI-0206965. In some embodiments, the compositions comprise ARV825 and MRT68921 HCl. In some embodiments, the compositions comprise ARV825 and ULK-101. In some embodiments, the compositions comprise ARV825 and hydroxychloroquine. In some embodiments, the compositions comprise dBET1 and one or more autophagy inhibitors. In some embodiments, the compositions comprise dBET1 and one or more of SAR405, Autophinib, PIK-III, LYN-1604, SBI-0206965, MRT68921 HCl, ULK-101, and hydroxychloroquine. In some embodiments, the compositions comprise dBET1 and SAR405. In some embodiments, the compositions comprise dBET1 and Autophinib. In some embodiments, the compositions comprise dBET1 and PIK-III. In some embodiments, the compositions comprise dBET1 and LYN-1604. In some embodiments, the compositions comprise dBET1 and SBI-0206965. In some embodiments, the compositions comprise dBET1 and MRT68921 HCl. In some embodiments, the compositions comprise dBET and ULK-101. In some embodiments, the compositions comprise dBET and hydroxychloroquine. In some embodiments, the compositions comprise A1874 and one or more autophagy inhibitors. In some embodiments, the compositions comprise A1874 and one or more of SAR405, Autophinib, PIK-III, LYN-1604, SBI-0206965, MRT68921 HCl, ULK-101, and hydroxychloroquine. In some embodiments, the compositions comprise A1874 and SAR405. In some embodiments, the compositions comprise A1874 and Autophinib. In some embodiments, the compositions comprise A1874 and PIK-III. In some embodiments, the compositions comprise A1874 and LYN-1604. In some embodiments, the compositions comprise A1874 and SBI-0206965. In some embodiments, the compositions comprise A1874 and MRT68921 HCl. In some embodiments, the compositions comprise A1874 and ULK-101. In some embodiments, the compositions comprise A1874 and hydroxychloroquine. In some embodiments, the compositions comprise CFT-2718 and one or more autophagy inhibitors. In some embodiments, the compositions comprise CFT-2718 and one or more of SAR405, Autophinib, PIK-III, LYN-1604, SBI-0206965, MRT68921 HCl, ULK-101, and hydroxychloroquine. In some embodiments, the compositions comprise CFT-2718 and SAR405. In some embodiments, the compositions comprise CFT-2718 and Autophinib. In some embodiments, the compositions comprise CFT-2718 and PIK-III. In some embodiments, the compositions comprise CFT-2718 and LYN-1604. In some embodiments, the compositions comprise CFT-2718 and SBI-0206965. In some embodiments, the compositions comprise CFT-2718 and MRT68921 HCl. In some embodiments, the compositions comprise CFT-2718 and ULK-101. In some embodiments, the compositions comprise CFT-2718 and hydroxychloroquine.

In some embodiments, the compositions comprise one or more CDK9-PROTAC therapeutic agents and one or more MTOR signaling pathway inhibitors. In some embodiments, the compositions comprise THAL SNS 032 and one or more MTOR signaling pathway inhibitors. In some embodiments, the compositions comprise THAL SNS 032 and one or more of RAD001, Torin-1, GDC-0941, LY2584702, PI-273, or NVP-2. In some embodiments, the compositions comprise THAL SNS 032 and GDC-0941. In some embodiments, the compositions comprise THAL SNS 032 and lapatinib. In some embodiments, the compositions comprise THAL SNS 032 and RAD001. In some embodiments, the compositions comprise THAL SNS 032 and LY2584702. In some embodiments, the compositions comprise THAL SNS 032 and PI-273. In some embodiments, the compositions comprise THAL SNS 032 and NVP-2. In some embodiments, the compositions comprise NVP-2 and one or more MTOR signaling pathway inhibitors. In some embodiments, the compositions comprise NVP-2 and one or more of RAD001, Torin-1, GDC-0941, LY2584702, or PI-273. In some embodiments, the compositions comprise NVP-2 and GDC-0941. In some embodiments, the compositions comprise NVP-2 and lapatinib. In some embodiments, the compositions comprise NVP-2 and RAD001. In some embodiments, the compositions comprise NVP-2 and LY2584702. In some embodiments, the compositions comprise NVP-2 and PI-273. In some embodiments, the compositions comprise CDK9 Degrader-1 and one or more MTOR signaling pathway inhibitors. In some embodiments, the compositions comprise CDK9 Degrader-1 and one or more of RAD001, Torin-1, GDC-0941, LY2584702, PI-273, or NVP-2. In some embodiments, the compositions comprise CDK9 Degrader-1 and GDC-0941. In some embodiments, the compositions comprise CDK9 Degrader-1 and lapatinib. In some embodiments, the compositions comprise CDK9 Degrader-1 and RAD001. In some embodiments, the compositions comprise CDK9 Degrader-1 and LY2584702. In some embodiments, the compositions comprise CDK9 Degrader-1 and PI-273. In some embodiments, the compositions comprise CDK9 Degrader-1 and NVP-2.

In some embodiments, the compositions comprise one or more CDK9-PROTAC therapeutic agents and one or more RTK signaling pathway inhibitors. In some embodiments, the compositions comprise THAL SNS 032 and one or more RTK signaling pathway inhibitors. In some embodiments, the compositions comprise THAL SNS 032 and one or more of GSK1904529A, lapatinib, imatinib, MRX-2843, LY2801653 dihydrochloride and PD173074. In some embodiments, the compositions comprise THAL SNS 032 and GSK1904529A. In some embodiments, the compositions comprise THAL SNS 032 and lapatinib. In some embodiments, the compositions comprise THAL SNS 032 and imatinib. In some embodiments, the compositions comprise THAL SNS 032 and MRX-2843. In some embodiments, the compositions comprise THAL SNS 032 and LY2801653 dihydrochloride. In some embodiments, the compositions comprise THAL SNS 032 and PD173074. In some embodiments, the compositions comprise NVP-2 and one or more RTK signaling pathway inhibitors. In some embodiments, the compositions comprise NVP-2 and one or more of GSK1904529A, lapatinib, imatinib, MRX-2843, LY2801653 dihydrochloride and PD173074. In some embodiments, the compositions comprise NVP-2 and GSK1904529A. In some embodiments, the compositions comprise NVP-2 and lapatinib. In some embodiments, the compositions comprise NVP-2 and imatinib. In some embodiments, the compositions comprise NVP-2 and MRX-2843. In some embodiments, the compositions comprise NVP-2 and LY2801653 dihydrochloride. In some embodiments, the compositions comprise NVP-2 and PD173074. In some embodiments, the compositions comprise CDK9 Degrader-1 and one or more RTK signaling pathway inhibitors. In some embodiments, the compositions comprise CDK9 Degrader-1 and one or more of GSK1904529A, lapatinib, imatinib, MRX-2843, LY2801653 dihydrochloride and PD173074. In some embodiments, the compositions comprise CDK9 Degrader-1 and GSK1904529A. In some embodiments, the compositions comprise CDK9 Degrader-1 and lapatinib. In some embodiments, the compositions comprise CDK9 Degrader-1 and imatinib. In some embodiments, the compositions comprise CDK9 Degrader-1 and MRX-2843. In some embodiments, the compositions comprise CDK9 Degrader-1 and LY2801653 dihydrochloride. In some embodiments, the compositions comprise CDK9 Degrader-1 and PD173074.

In some embodiments, the compositions comprise one or more CDK9-PROTAC therapeutic agents and one or more KRAS inhibitors. In some embodiments, the compositions comprise THAL SNS 032 and one or more KRAS inhibitors. In some embodiments, the compositions comprise THAL SNS 032 and one or more of ARS-1620 and MRTX849. In some embodiments, the compositions comprise THAL SNS 032 and ARS-1620. In some embodiments, the compositions comprise THAL SNS 032 and MRTX849. In some embodiments, the compositions comprise NVP-2 and one or more of ARS-1620 and MRTX849. In some embodiments, the compositions comprise NVP-2 and ARS-1620. In some embodiments, the compositions comprise NVP-2 and MRTX849. In some embodiments, the compositions comprise CDK9 Degrader-1 and one or more KRAS inhibitors. In some embodiments, the compositions comprise CDK9 Degrader-1 and one or more of ARS-1620 and MRTX849. In some embodiments, the compositions comprise CDK9 Degrader-1 and ARS-1620. In some embodiments, the compositions comprise CDK9 Degrader-1 and MRTX849.

In some embodiments, the compositions comprise one or more CDK9-PROTAC therapeutic agents and one or more autophagy inhibitors. In some embodiments, the compositions comprise THAL SNS 032 and one or more autophagy inhibitors. In some embodiments, the compositions comprise THAL SNS 032 and one or more of SAR405, Autophinib, PIK-III, LYN-1604, SBI-0206965, MRT68921 HCl, ULK-101, and hydroxychloroquine. In some embodiments, the compositions comprise THAL SNS 032 and SAR405. In some embodiments, the compositions comprise THAL SNS 032 and Autophinib. In some embodiments, the compositions comprise THAL SNS 032 and PIK-III. In some embodiments, the compositions comprise THAL SNS 032 and LYN-1604. In some embodiments, the compositions comprise THAL SNS 032 and SBI-0206965. In some embodiments, the compositions comprise THAL SNS 032 and MRT68921 HCl. In some embodiments, the compositions comprise THAL SNS 032 and ULK-101. In some embodiments, the compositions comprise THAL SNS 032 and hydroxychloroquine. In some embodiments, the compositions comprise NVP-2 and one or more autophagy inhibitors. In some embodiments, the compositions comprise NVP-2 and one or more of SAR405, Autophinib, PIK-III, LYN-1604, SBI-0206965, MRT68921 HCl, ULK-101, and hydroxychloroquine. In some embodiments, the compositions comprise NVP-2 and SAR405. In some embodiments, the compositions comprise NVP-2 and Autophinib. In some embodiments, the compositions comprise NVP-2 and PIK-III. In some embodiments, the compositions comprise NVP-2 and LYN-1604. In some embodiments, the compositions comprise NVP-2 and SBI-0206965. In some embodiments, the compositions comprise NVP-2 and MRT68921 HCl. In some embodiments, the compositions comprise NVP-2 and ULK-101. In some embodiments, the compositions comprise NVP-2 and hydroxychloroquine. In some embodiments, the compositions comprise CDK9 Degrader-1 and one or more autophagy inhibitors. In some embodiments, the compositions comprise CDK9 Degrader-1 and one or more of SAR405, Autophinib, PIK-III, LYN-1604, SBI-0206965, MRT68921 HCl, ULK-101, and hydroxychloroquine. In some embodiments, the compositions comprise CDK9 Degrader-1 and SAR405. In some embodiments, the compositions comprise CDK9 Degrader-1 and Autophinib. In some embodiments, the compositions comprise CDK9 Degrader-1 and PIK-III. In some embodiments, the compositions comprise CDK9 Degrader-1 and LYN-1604. In some embodiments, the compositions comprise CDK9 Degrader-1 and SBI-0206965. In some embodiments, the compositions comprise CDK9 Degrader-1 and MRT68921 HCl. In some embodiments, the compositions comprise CDK9 Degrader-1 and ULK-101. In some embodiments, the compositions comprise CDK9 Degrader-1 and hydroxychloroquine.

The present disclosure further provides methods for augmenting the therapeutic effect in a human cancer patient undergoing treatment with a BET-PROTAC therapeutic agent or CDK9-PROTAC therapeutic agent comprising administering one or more kinase inhibitors, one or more KRAS inhibitors, or one or more autophagy inhibitors, or any combination thereof, to the patient.

As used herein, the term "augment" or "augmenting" as used herein, for therapeutic purposes, generally refers to an improvement in the pharmacodynamic effect (referred to as the efficacy) of a therapeutic agent. Thus, the term "augment" refers to the ability of the kinase inhibitors, KRAS inhibitors, or autophagy inhibitors to raise the efficacy of a PROTACs leading to the killing of a greater number of cancer cells over the same unit of time (e.g., 24, 48, or 72 hour period) when the kinase inhibitors, KRAS inhibitors, or autophagy inhibitors are administered prior to, along with, or after the PROTACs as compared to the PROTACs alone.

The present disclosure also provides methods of treating cancer in a human patient in need thereof, the method comprising administering to the patient a therapeutically effective amount of a pharmaceutical composition comprising one or more BET-PROTAC therapeutic agents or one or more CDK9-PROTAC therapeutic agents, or a combination thereof and one or more kinase inhibitors, one or more KRAS inhibitors, or one or more autophagy inhibitors, or any combination thereof.

The present disclosure also provides methods of overcoming resistance to BET-PROTAC therapeutic agents or CDK9-PROTAC therapeutic in a human patient, the method comprising administering to the patient a therapeutically effective amount of a pharmaceutical composition comprising one or more BET-PROTAC therapeutic agents or one or more CDK9-PROTAC therapeutic agents, or a combination thereof and one or more kinase inhibitors, one or more KRAS inhibitors, or one or more autophagy inhibitors, or any combination thereof In some embodiments, the BET-PROTAC or CDK9-PROTAC is administered prior to the administration of the one or more kinase inhibitors, one or more KRAS inhibitors, or one or more autophagy inhibitors or after administration of the one or more kinase inhibitors, one or more KRAS inhibitors, or one or more autophagy inhibitors. In some embodiments, the BET-PROTAC or CDK9-PROTAC is administered prior to the administration of the one or more kinase inhibitors, one or more KRAS inhibitors, or one or more autophagy inhibitors. In some embodiments, the BET-PROTAC or CDK9-PROTAC is administered after administration of the one or more kinase inhibitors, one or more KRAS inhibitors, or one or more autophagy inhibitors. In some embodiments, the BET-PROTAC or CDK9-PROTAC is administered concurrently with administration of the one or more kinase inhibitors, one or more KRAS inhibitors, or one or more autophagy inhibitors, or any combination thereof As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, compositions described herein are used to delay development of a disease or to slow the progression of a disease. In some embodiments, compositions described herein are used to increase survival of a patient having a disease. In some embodiments, compositions described herein are used to increase or extend survival of a patient having a disease.

As used herein, the term "survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

As used herein, the term "progression-Free Survival" (PFS) is the time from the first day of treatment to documented disease progression (including isolated CNS progression) or death from any cause on study, whichever occurs first.

As used herein, the term "disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the subject matter described herein, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g, breast cancer recurrence or second primary cancer).

As used herein, the term "overall survival" refers to the patient remaining alive for a defined period of time, such as about 1 year, about 2 years, about 3 years, about 4 years, about 5 years, about 10 years, etc., from initiation of treatment or from initial diagnosis.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

The term "effective" is used to describe an amount of a compound, composition or component which, when used within the context of its intended use, effects an intended result. The term effective subsumes all other effective amount or effective concentration terms, which are otherwise described or used in the present application.

An "effective amount" of an agent, e.g., a pharmaceutical formulation, refers to an amount effective, at dosages and for periods of time necessary, to achieve the desired therapeutic or prophylactic result. For example, an effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a PAC, as well as salts thereof, may be administered as the raw chemical. Additionally, the active ingredient may be presented as a pharmaceutical composition.

The present disclosure also provides methods for killing or inhibiting growth of a cancer cell comprising comprising contacting the cancer cell with any of the combinations of compounds, or compositions comprising the same as described herein. In some embodiments, one or more compounds may be combined in the same composition for any of the methods disclosed herein.

Thus, the compounds and compositions can be used as anti-cancer and anti-tumor agents, e.g., the compounds can kill or inhibit the growth of cancer cells. The compounds and compositions can also be used in methods of reducing cancer in an animal, or in methods of treating or preventing the spread or metastasis of cancer in an animal, or in methods of treating an animal afflicted with cancer. The compounds and compositions can also be used in methods of killing or inhibiting the growth of a cancer cell, or in methods of inhibiting tumor growth.

Cancers that are treatable are broadly divided into the categories of carcinoma, lymphoma and sarcoma. Examples of carcinomas include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas include, but are not limited to: Hodgkin's disease and lymphocytic lymphomas, such as Burkitt's lymphoma, NPDL, NML, NH and diffuse lymphomas.

Examples of cancers which may be treated by the compositions include, but are not limited to acute myeloid leukemia, acute monocytic leukemia, prostatic adenocarcinoma, ovarian carcinoma, or epithelial ovarian cancer, such as High-Grade Serous Ovarian Carcinoma (HGSOC). In some embodiments, the cancers which may be treated by the compositions include KRAS cancers (including, but not limited to non-small cell lung cancer (NSCLC), colorectal cancer, and pancreatic cancer), PIK3CA cancers (including, but not limited to breast cancer, colon cancer, endometrial cancer, glioblastoma multiformes, epidermal nevi, seborrheic keratoses (SK), ovarian cancer, gastric cancer, squamous cell carcinoma, thyroid cancer, oral squamous cell carcinoma, nasopharyngeal carcinoma, cervical cancer, papillary mucinous carcinoma of the pancreas, squamous cell carcinoma of the esophagus, adenocarcinomas of the esophagus, gallbladder carcinoma, cholangiocarcinoma, invasive pituitary tumors, penile tumors, bladder cancer, and diffuse large B cell lymphomas) or PTEN cancers (including, but not limited to glioblastoma, endometrial cancer, breast cancer, Endometrial Cancer, and prostate cancer). Thus, cancer cells harboring K-Ras mutations or other mutations (such as Kras-amplification, PIK3CA-mutations, PTEN-loss, EGFR-mutants, HER2 overexpression, and AKT amplification) that strongly activate mTORC1 signaling can promote intrinsic resistance to BBDs representing a patient population that may benefit from combined mTORC1 and PROTAC-treatment.

The compounds and compositions can be used in methods of killing or inhibiting the growth of cancer cells, either in vivo or in vitro, or inhibiting the growth of a cancerous tumor.

In some embodiments, the compounds and compositions are used in conjunction with other therapies, such as standard immunotherapy, neoadjuvant therapy, radiotherapy, tumor surgery, and conventional chemotherapy directed against solid tumors and for the control of establishment of metastases. Additionally, the compounds and compositions can be administered after surgery where solid tumors have been removed as a prophylaxis against metastasis. Cytotoxic or chemotherapeutic agents include, but are of limited to, aziridine thiotepa, alkyl sulfonate, nitrosoureas, platinum complexes, NO classic alkylators, folate analogs, purine analogs, adenosine analogs, pyrimidine analogs, substituted urea, antitumor antibiotics, microtubulle agents, and asprignase.

In some embodiments, the subject is also administered radiation therapy, immunotherapy, and/or neoadjuvant therapy. In some embodiments, the subject is also administered radiation therapy. In some embodiments, the subject is also administered immunotherapy. In some embodiments, the subject is also administered neoadjuvant therapy.

The present disclosure provides pharmaceutical formulations comprising one or more bromodomain and extra terminal domain (BET) proteolysis targeting chimera (PROTAC) (BET-PROTAC) therapeutic agents or one or more cyclin-dependent kinase 9 (CDK9) PROTAC (CDK9-PROTAC) therapeutic agents, or a combination thereof; one or more kinase inhibitors, one or more KRAS inhibitors, or one or more autophagy inhibitors, or any combination thereof and a pharmaceutically acceptable carrier or excipient.

In some embodiments, the ratio of the BET-PROTAC or CDK9-PROTAC to the one or more kinase inhibitors, one or more KRAS inhibitors, or one or more autophagy inhibitors is from about 0.01:1 to about 100:1 (w/w), from about 0.1:1 to about 10:1 (w/w), or from about 1:1 to about 5:1 (w/w). In some embodiments, the ratio of the BET-PROTAC or CDK9-PROTAC to the one or more kinase inhibitors, one or more KRAS inhibitors, or one or more autophagy inhibitors is from about 0.01:1 to about 100:1 (w/w). In some embodiments, the ratio of the BET-PROTAC or CDK9-PROTAC to the one or more kinase inhibitors, one or more KRAS inhibitors, or one or more autophagy inhibitors is from about 0.1:1 to about 10:1 (w/w). In some embodiments, the ratio of the BET-PROTAC or CDK9-PROTAC to the one or more kinase inhibitors, one or more KRAS inhibitors, or one or more autophagy inhibitors is from about 1:1 to about 5:1 (w/w).

In some embodiments, the BET-PROTAC or CDK9-PROTAC is present in an amount from about 1 mg to about 100 mg, from about 5 mg to about 75 mg, from about 10 mg to about 60 mg, or from about 12.5 mg to about 50 mg, and the one or more kinase inhibitors, one or more KRAS inhibitors, or one or more autophagy inhibitors is present in an amount from about 1 mg to about 500 mg, from about 50 mg to about 400 mg, from about 75 mg to about 300 mg, or from about 100 mg to about 200 mg. In some embodiments, the BET-PROTAC or CDK9-PROTAC is present in an amount from about 1 mg to about 100 mg. In some embodiments, the BET-PROTAC or CDK9-PROTAC is present in an amount from about 5 mg to about 75 mg. In some embodiments, the BET-PROTAC or CDK9-PROTAC is present in an amount from about 10 mg to about 60 mg. In some embodiments, the BET-PROTAC or CDK9-PROTAC is present in an amount from about 12.5 mg to about 50 mg. In some embodiments, the one or more kinase inhibitors, one or more KRAS inhibitors, or one or more autophagy inhibitors is present in an amount from about 1 mg to about 500 mg. In some embodiments, the one or more kinase inhibitors, one or more KRAS inhibitors, or one or more autophagy inhibitors is present in an amount from about 50 mg to about 400 mg. In some embodiments, the one or more kinase inhibitors, one or more KRAS inhibitors, or one or more autophagy inhibitors is present in an amount from about 75 mg to about 300 mg. In some embodiments, the one or more kinase inhibitors, one or more KRAS inhibitors, or one or more autophagy inhibitors is present in an amount from about 100 mg to about 200 mg.

In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced compared to the amount of the BET-PROTAC therapeutic agent or CDK9-PROTAC therapeutic agent administered to the human patient in the absence of receiving administration of one or more kinase inhibitors, one or more KRAS inhibitors, or one or more autophagy inhibitors. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 10%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 15%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 20%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 25%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 30%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 35%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 40%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 45%. In some embodiments, the amount of the BET-PROTAC therapeutic agent or CDK9-PROTAC therapeutic agent administered to the human patient receiving administration of one or more kinase inhibitors, one or more KRAS inhibitors, or one or more autophagy inhibitors is reduced by 50% compared to the amount of the BET-PROTAC therapeutic agent or CDK9-PROTAC therapeutic agent administered to the human patient in the absence of receiving administration of one or more kinase inhibitors, one or more KRAS inhibitors, or one or more autophagy inhibitors.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative. The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

In some embodiments, the BET-PROTAC or CDK9-PROTAC and the one or more kinase inhibitors, one or more KRAS inhibitors, or one or more autophagy inhibitors are co-administered to the subject together in a single pharmaceutical composition. In some embodiments, the single pharmaceutical composition is an oral dosage form, an intravenous dosage form, a topical dosage form, an intraperitoneal dosage form, or an intrathecal dosage form. In some embodiments, the single pharmaceutical composition is an oral dosage form or an intravenous dosage form. In some embodiments, the single pharmaceutical composition is an oral dosage form. In some embodiments, the single pharmaceutical composition is an intravenous dosage form. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

In some embodiments, the pharmaceutical composition is an oral dosage form, an intravenous dosage form, a topical dosage form, an intraperitoneal dosage form, or an intrathecal dosage form. In some embodiments, the pharmaceutical composition is an oral dosage form or an intravenous dosage form. In some embodiments, the pharmaceutical composition is an oral dosage form.

In some embodiments, the oral dosage form is a pill, tablet, capsule, cachet, gel-cap, pellet, powder, granule, or liquid. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

In some embodiments, the oral dosage form is protected from light and present within a blister pack, bottle, or intravenous bag. In some embodiments, the oral dosage form is present within a blister pack, bottle, or intravenous bag. In some embodiments, the oral dosage form is present within a blister pack. In some embodiments, the oral dosage form is present within a bottle. In some embodiments, the oral dosage form is present within an intravenous bag.

The compounds and compositions described herein can be administered by any route of administration including, but not limited to, oral, intravenous, topical, intraperitoneal, and intrathecal. In some embodiments, the administration is oral, intravenous, intraperitoneal, or intrathecal. In some embodiments, the administration is oral, intravenous, or intraperitoneal. In some embodiments, the administration is oral or intravenous. In some embodiments, the administration is oral or topical. In some embodiments, the administration is oral or intraperitoneal. In some embodiments, the administration is oral or intrathecal. The route of administration can depend on the particular disease, disorder, or condition being treated and can be selected or adjusted by the clinician according to methods known to the clinician to obtain desired clinical responses. Methods for administration are known in the art and one skilled in the art can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

In some embodiments, it may be desirable to administer one or more compounds, or a pharmaceutically acceptable salt thereof, or composition(s) comprising the same to a particular area in need of treatment. This may be achieved, for example, by local infusion (for example, during surgery), topical application (for example, with a wound dressing after surgery), or by injection (for example, by depot injection). Formulations for injection can be presented in unit dosage form, such as in ampoules or in multi-dose containers, with an added preservative.

The compounds and compositions described herein can be formulated for parenteral administration by injection, such as by bolus injection or continuous infusion. The compounds and compositions can be administered by continuous infusion subcutaneously over a period of about 15 minutes to about 24 hours. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds and compositions described herein can be formulated by combining the compounds with pharmaceutically acceptable carriers. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a subject to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations including, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, including, but not limited to, the cross-linked polyvinyl pyrrolidone, agar, or alginic acid or a salt thereof such as sodium alginate.

Orally administered compounds and compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as, for example, mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

In transdermal administration, the compounds and compositions can be applied to a plaster, or can be applied by transdermal, therapeutic systems that are consequently supplied to the organism. In some embodiments, the compounds and compositions are present in creams, solutions, powders, fluid emulsions, fluid suspensions, semi-solids, ointments, pastes, gels, jellies, and foams, or in patches containing any of the same.

The compounds and compositions described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds and compositions can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds and compositions can be delivered in a controlled release system. In some embodiments, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In some embodiments, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)).

Other controlled-release systems discussed in the review by Langer, Science, 1990, 249, 1527-1533) may be used.

The compounds and compositions described herein can be contained in formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol). Pharmaceutical carriers can be liquids, such as water and oils, including those of petroleum, animal, vegetable or synthetic origin, such as peanut oil, soybean oil, mineral oil, sesame oil, and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

In some embodiments, the compounds and compositions described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

The compositions described herein can be administered either alone (as a single composition comprising the compounds described herein) or in combination (concurrently or serially) with other pharmaceutical agents. For example, the compounds and compositions can be administered in combination with anti-cancer or anti-neoplastic agents (for example, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel) or therapies (for example, surgery or radiotherapy).

The amount of any particular compound to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the disease, condition, or disorder, and can be easily determined by one skilled in the art (e.g., by the clinician). The selection of the specific dose regimen can be selected or adjusted or titrated by the clinician according to methods known to the clinician to obtain the desired clinical response. In addition, in vitro or in vivo assays may optionally be employed to help identify optimal dosage ranges. The precise dose to be employed in the compositions may also depend on the route of administration, and should be decided according to the judgment of the practitioner and each patient's circumstances.

Suitable compositions include, but are not limited to, oral non-absorbed compositions. Suitable compositions also include, but are not limited to saline, water, cyclodextrin solutions, and buffered solutions of pH 3-9.

The compounds and compositions described herein can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water. In some embodiments, the excipient is chosen from 50% w/v propylene glycol in purified water, 15% w/v glycerin in purified water, 20% w/v Kleptose in purified water, 40% w/v Kleptose in purified water, and 25% w/v Captisol in purified water. In some embodiments, the excipient is chosen from 20% w/v Kleptose in purified water, 20% w/v propylene glycol in purified water, and 15% w/v glycerin in purified water.

In some embodiments, the compounds and compositions described herein can be lyophilized to a solid and reconstituted with, for example, water prior to use.

When administered to a human, the compounds and compositions can be sterile. Water is a suitable carrier when the compound and composition is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds and compositions are formulated in accordance with routine procedures as pharmaceutical compositions adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound or composition is to be administered by infusion, it can be dispensed, for example, with an infusion bottle containing sterile pharmaceutical grade water or saline.

Where the compound or composition is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition is in the form of a liquid wherein the active agents are present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is an in situ gellable aqueous solution, suspension or solution/suspension, comprising about from 0.2% to about 3% or from about 0.5% to about 1% by weight of a gelling polysaccharide, chosen from gellan gum, alginate gum and chitosan, and about 1% to about 50% of a water-soluble film-forming polymer, preferably selected from alkylcelluloses (e.g., methylcellulose, ethylcellulose), hydroxyalkylcelluloses (e.g., hydroxyethylcellulose, hydroxypropyl methylcellulose), hyaluronic acid and salts thereof, chondroitin sulfate and salts thereof, polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carrageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin.

In some embodiments, the composition is an in situ gellable aqueous solution, suspension or solution/suspension comprising about 0.1% to about 5% of a carrageenan gum, e.g., a carrageenan gum having no more than 2 sulfate groups per repeating disaccharide unit, such as e.g., kappa-carrageenan, having 18-25% ester sulfate by weight, iota-carrageenan, having 25-34% ester sulfate by weight, and mixtures thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

The present disclosure also provides combinations of a BET-PROTAC or a CDK9-PROTAC, or a pharmaceutically acceptable salt thereof, and one or more kinase inhibitors, one or more KRAS inhibitors, or one or more autophagy inhibitors, or any combination thereof, or a pharmaceutically acceptable salt thereof, for use in the manufacture of a medicament for treating cancer. Any of the combinations described herein can be used in the manufacture of a medicament for treating any of the cancers described herein.

The present disclosure also provides uses of a pharmaceutical composition comprising a BET-PROTAC or a CDK9-PROTAC, or a pharmaceutically acceptable salt thereof, and one or more KRAS inhibitors, or one or more autophagy inhibitors, or any combination thereof, or a pharmaceutically acceptable salt thereof, for treating cancer. Any of the combinations described herein can be used for treating any of the cancers described herein.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Figure 8:
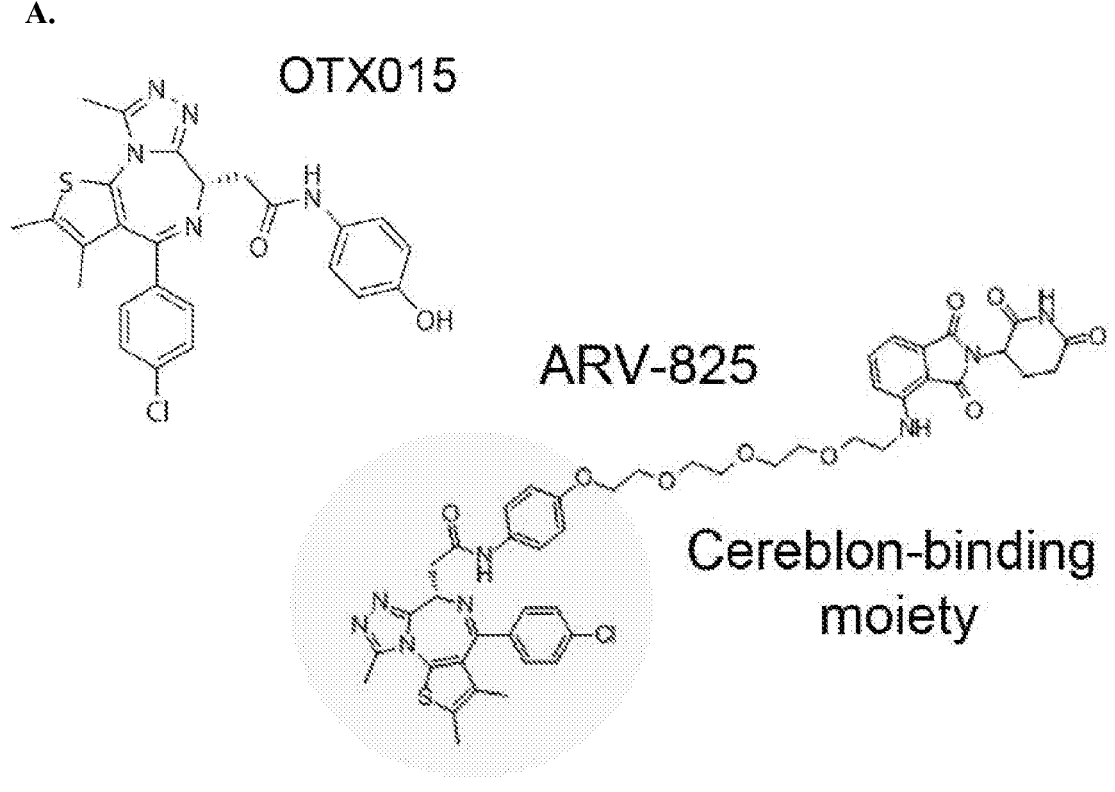
FIG. 8A shows BBD ARV825 with OTX015 as the warhead and a Cereblon-binding moiety for E3 ligase recruitment.
FIG. 8B shows that BBD-treatment reduces BET proteins inducing apoptosis to a greater extent than BBI-treatment; OVCAR8 cells were treated with increasing doses of ARV-825 and BET protein levels were determined by Western blot; apoptosis was measured by assessing cleaved PARP levels by blot.
FIG. 8C shows a more pronounced cleavage of PARP at lower doses with BBD-treatment single-run proteome analysis.
FIG. 8D shows that BRD2, BRD3 and BRD4 proteins were reduced by BBD but not BBI-treatment, and induced protein levels of HEXIM1 was observed only with BBI-treatment.
FIG. 8E shows reactome pathways upregulated by 48 hours of BBD threapy.
FIG. 8F shows reactome pathways upregulated by 48 hours of BBI threapy.
FIG. 8G shows analysis of global expression changes in response to MZ1 or JQ1 by RNA-seq.
FIG. 8H shows analysis of global expression changes in response to MZ1 or JQ1 by RNA-seq.
FIG. 8I shows proteins significantly repressed by 48 hours of BBD-treatment.
FIG. 8J shows BET inhibitor MIB-signature (P<0.05).
FIG. 8K shows PROTAC MIB-signature.
FIG. 8L shows kinases exhibiting increased MIB-binding in response to BBI treatment.
FIG. 8M shows common MIB-MS & RNA-seq response signatures for MZ1.
FIG. 8N shows common MIB-MS & RNA-seq response signatures for JQ1.
FIG. 8O shows RTK reprogramming induced by JQ1-treatment are blocked by using BBDs; KURAMOCHI cells were treated with DMSO, JQ1 (500 nM) or MZ1 (500 nM) for 48 hours and protein levels determined by Western blot.
FIG. 8P shows RTK reprogramming induced by JQ1-treatment are blocked by using BBDs; COV362 cells were treated with DMSO, JQ1 (500 nM) or MZ1 (500 nM) for 48 hours and protein levels determined by Western blot.
Figure 8:
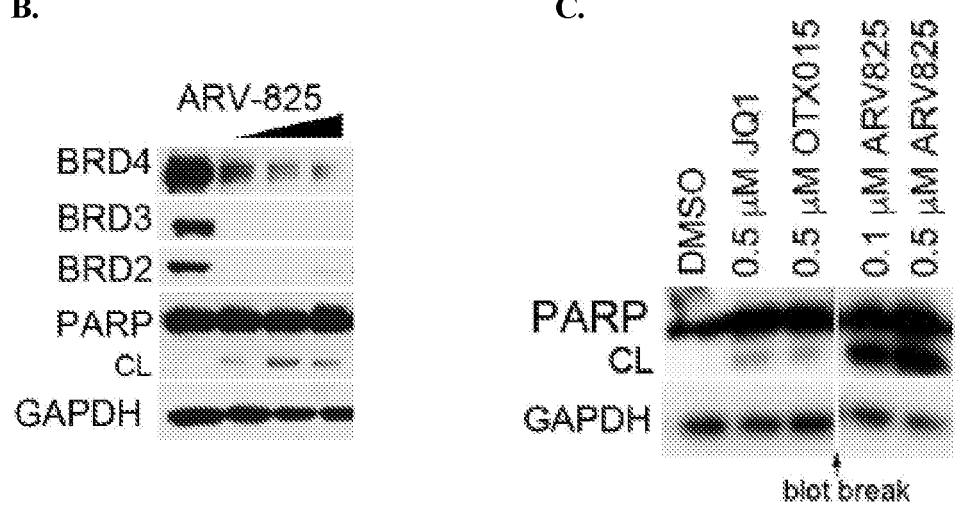
Figure 8:
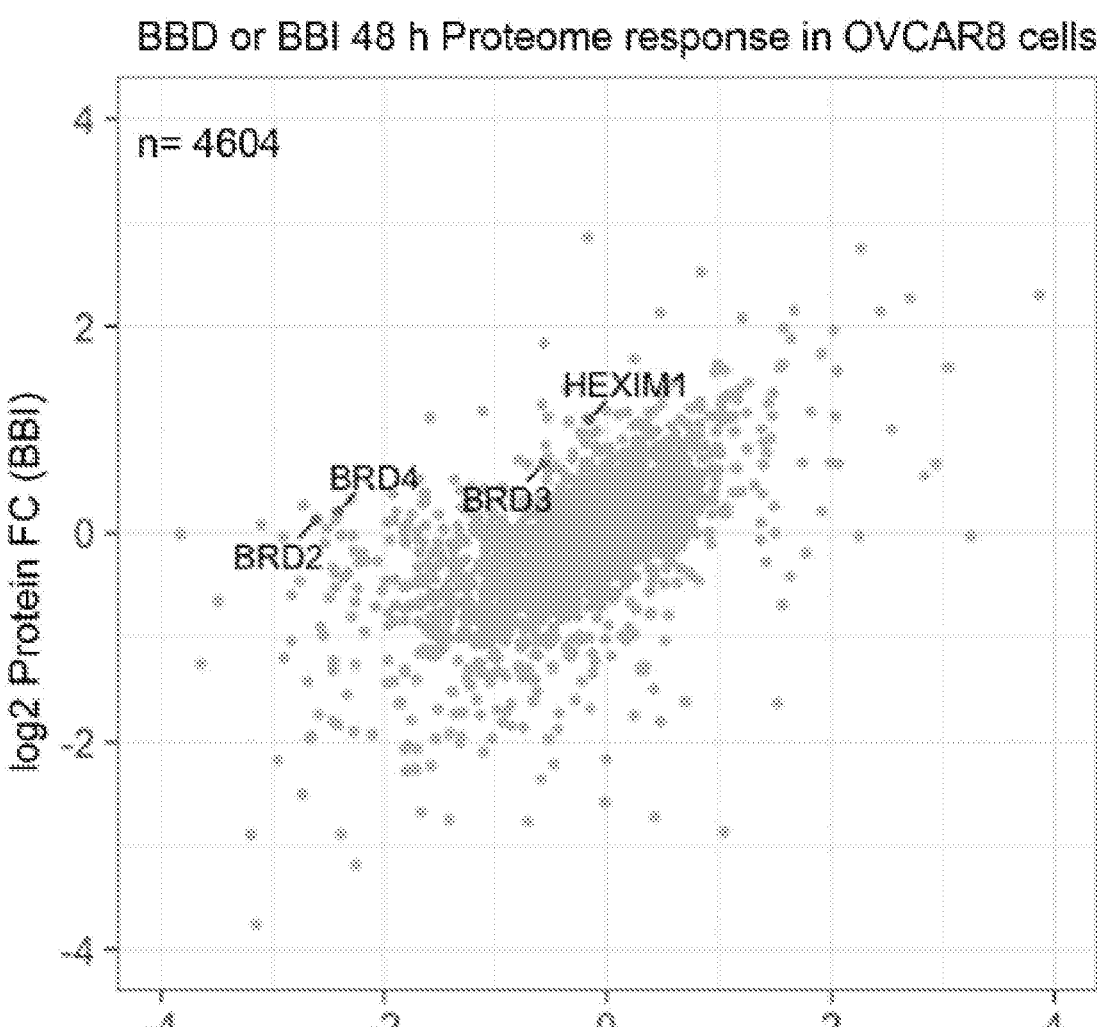
Figure 8:
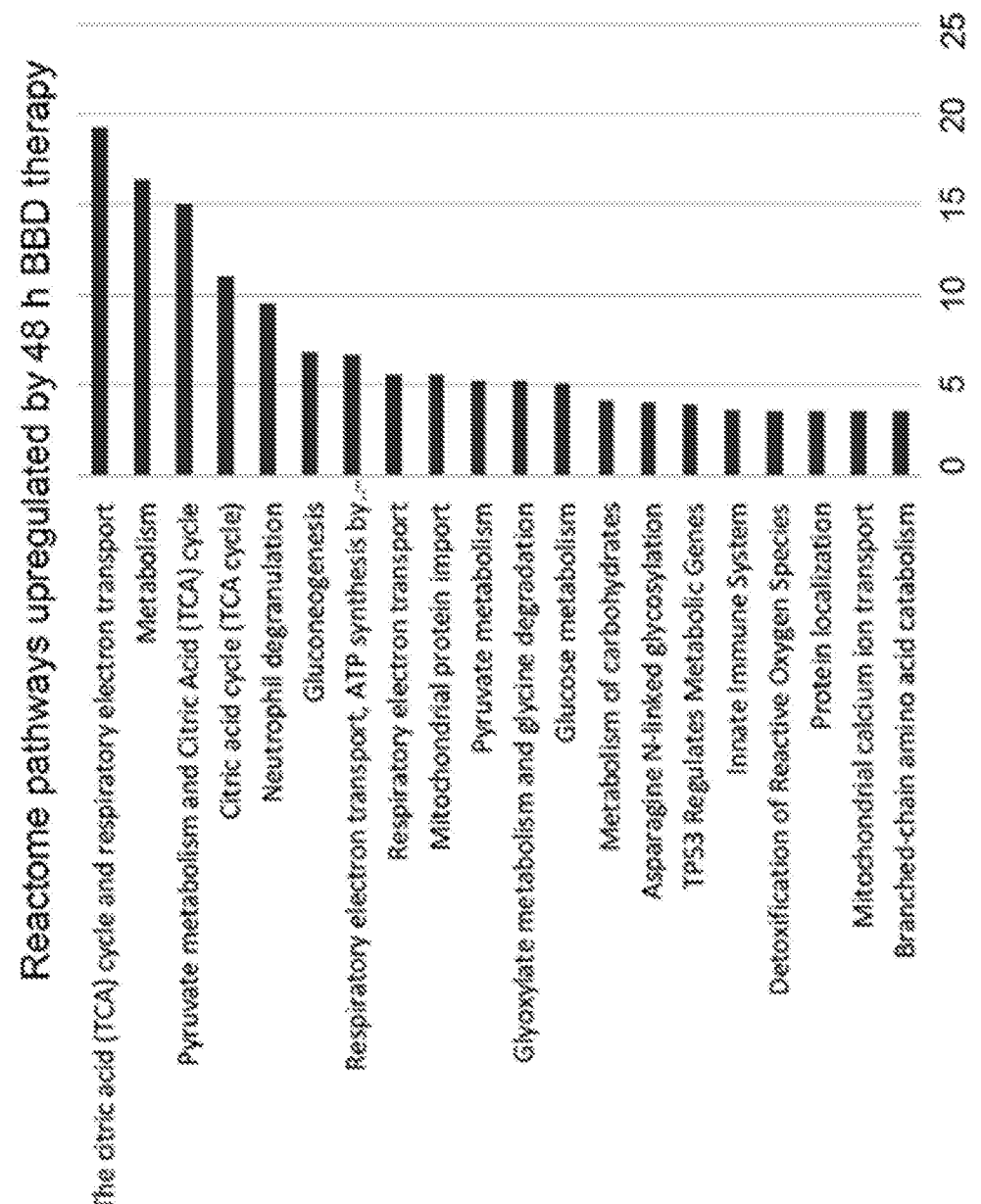
Figure 8:
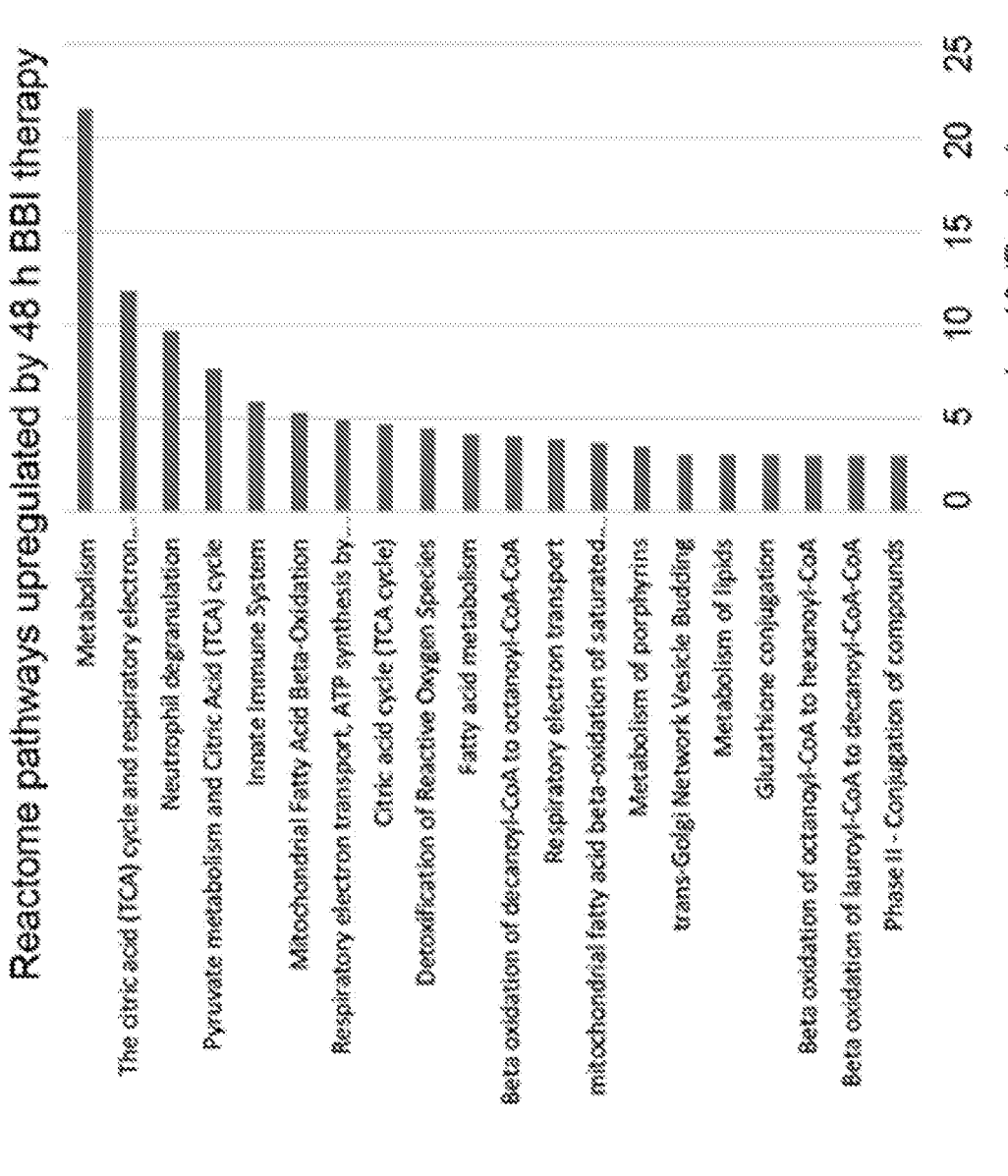
Figure 8:
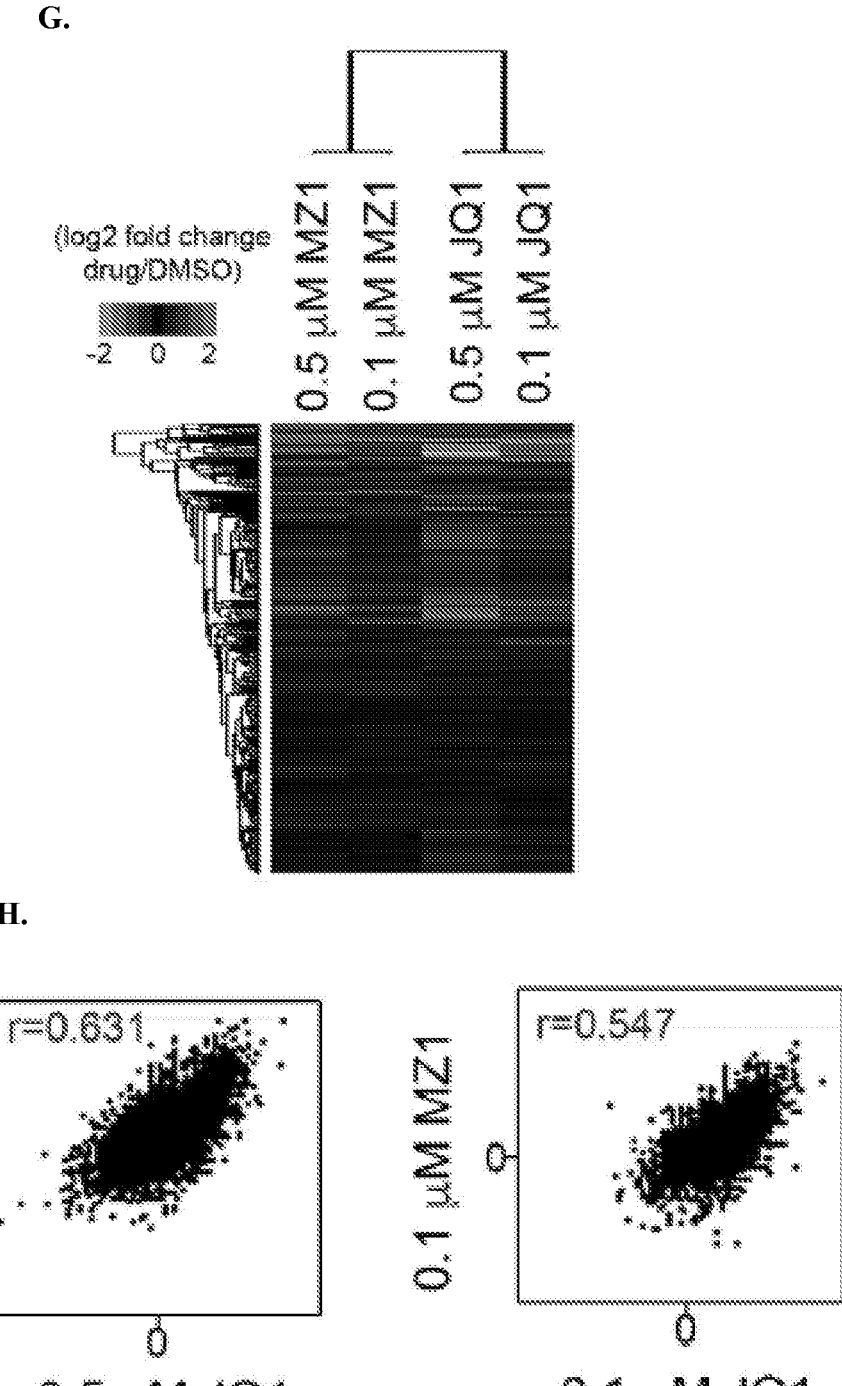
Figure 8:
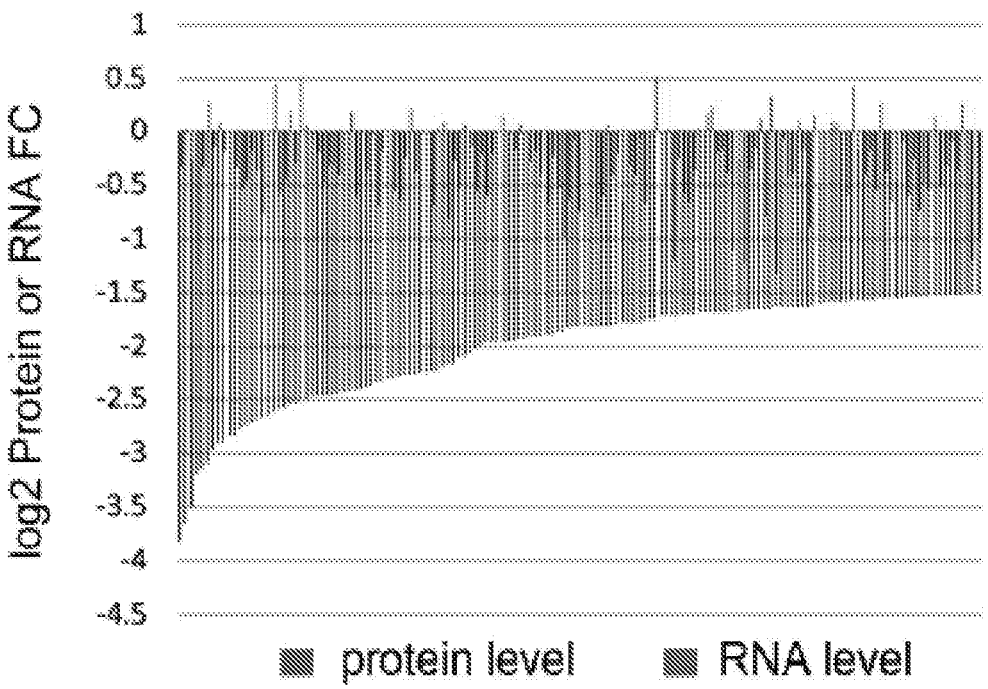
Figure 8:
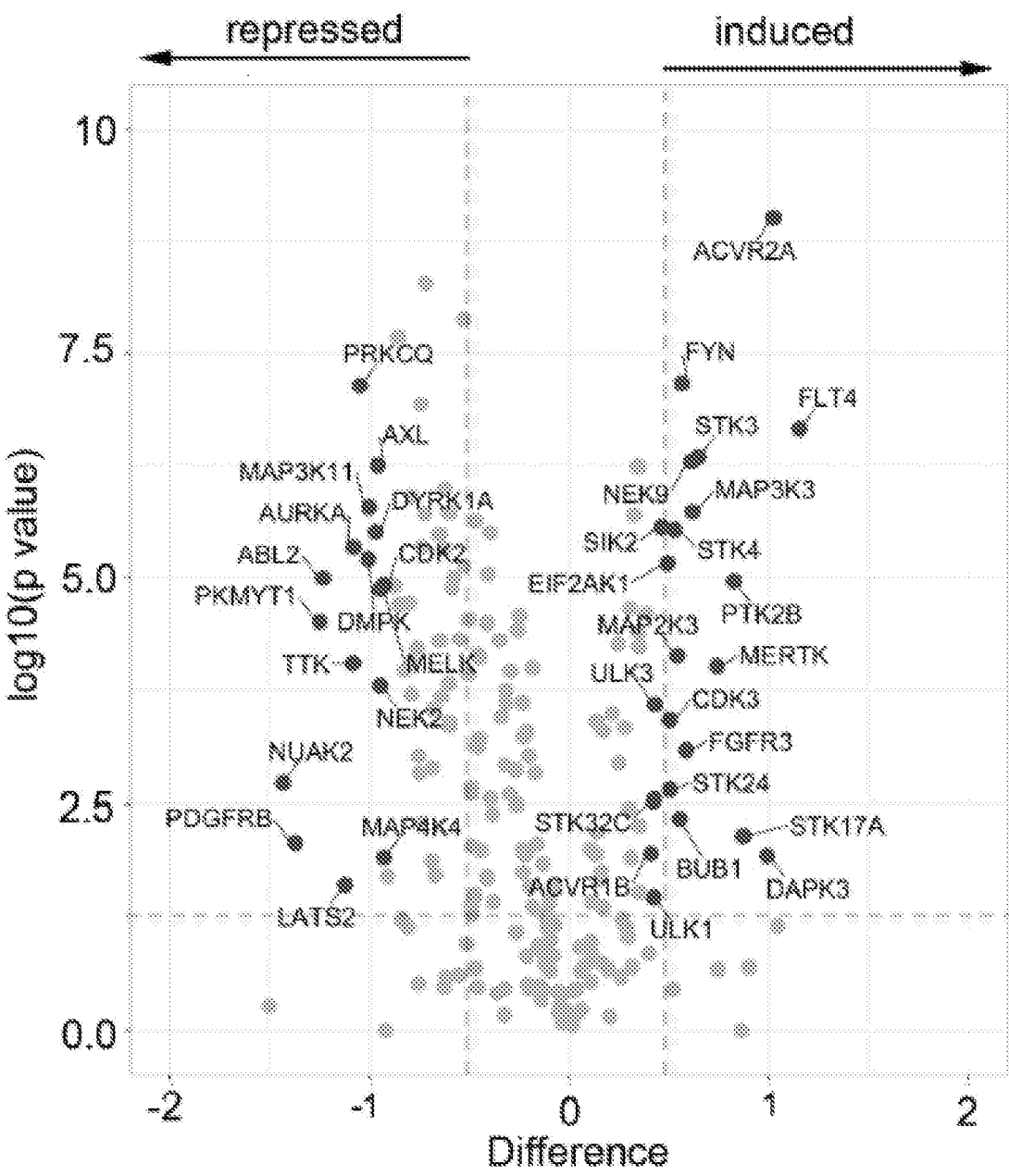
Figure 8:
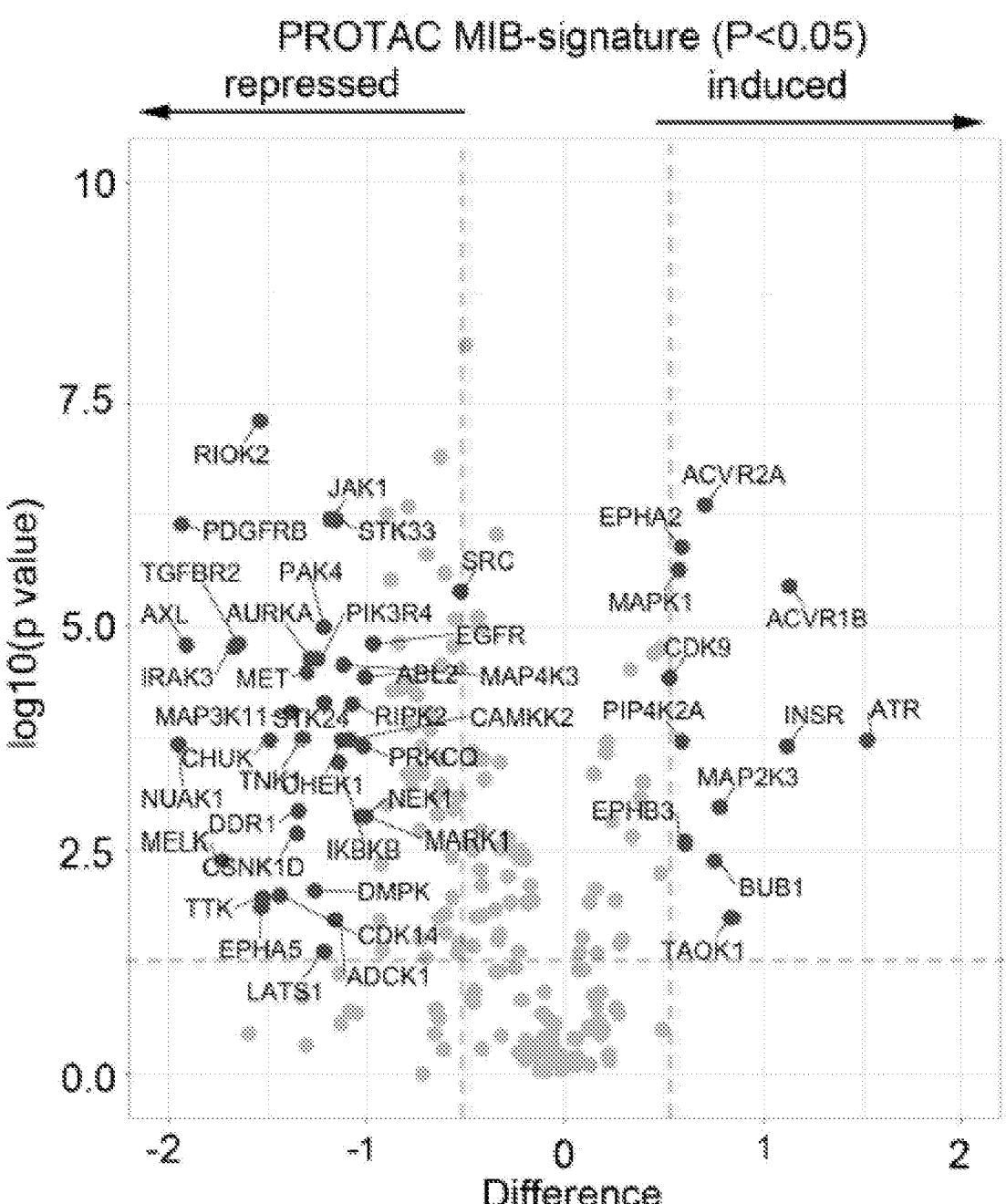
Figure 8:
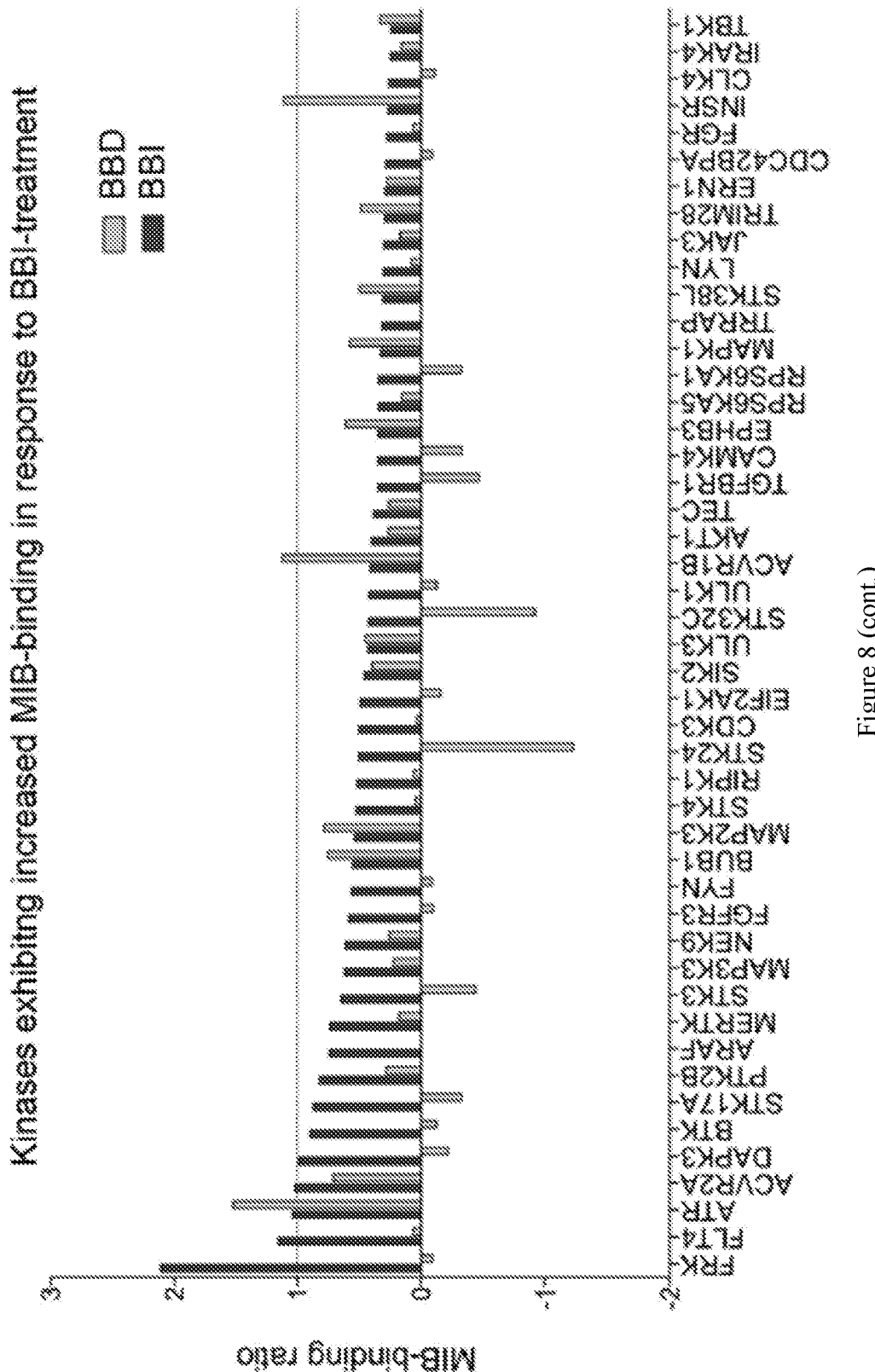
Figure 8:
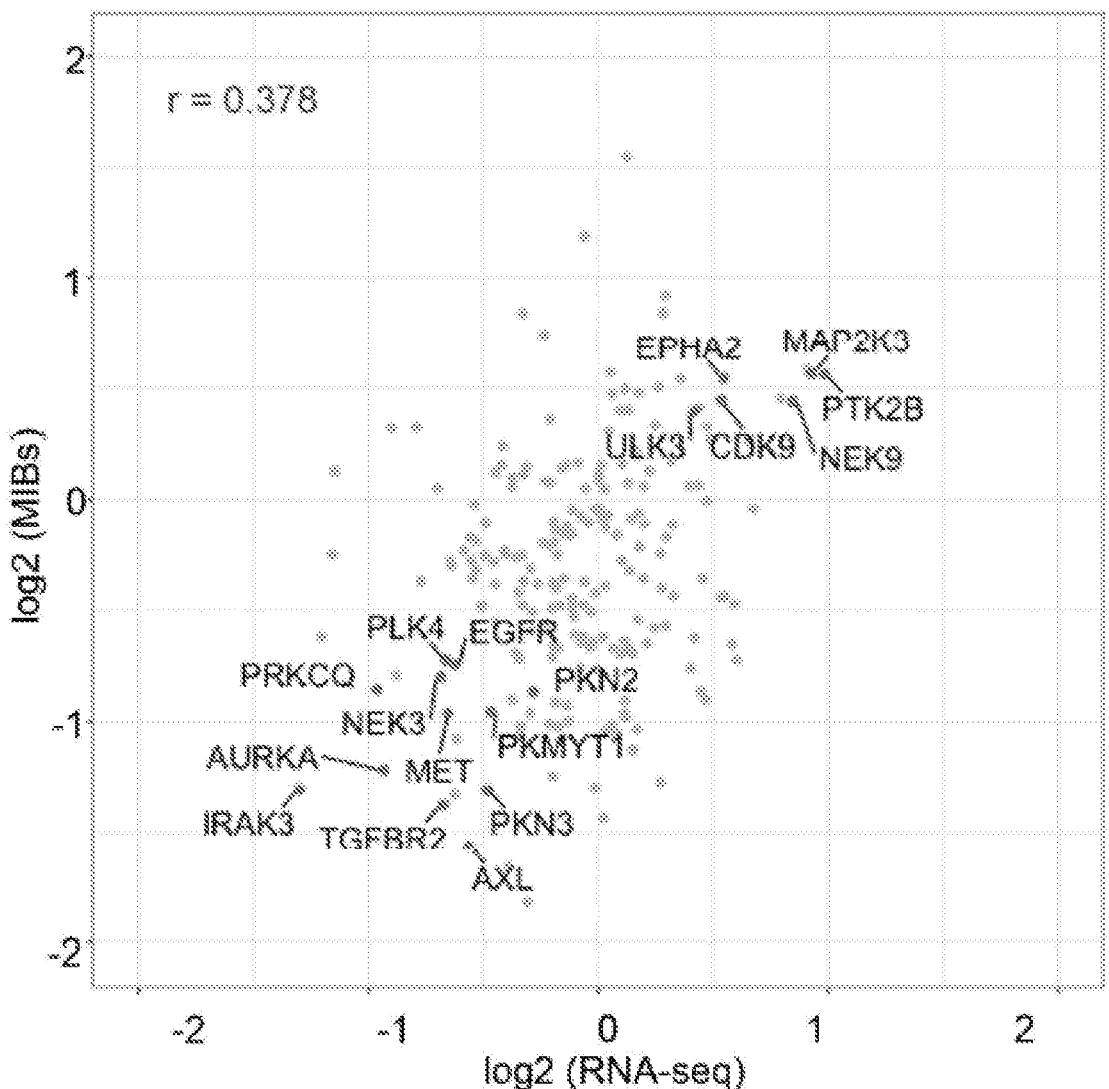
Figure 8:
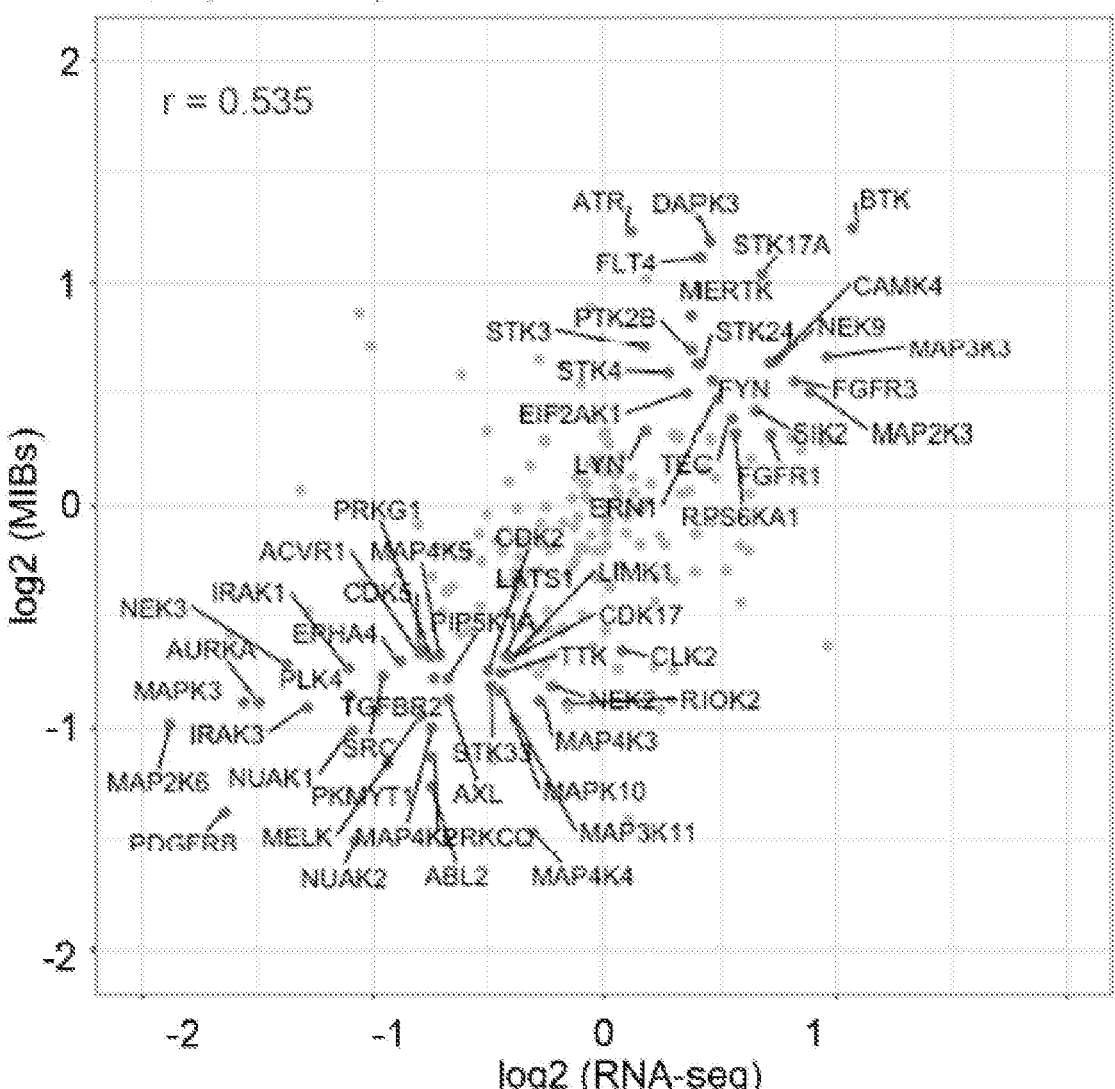
Figure 8:
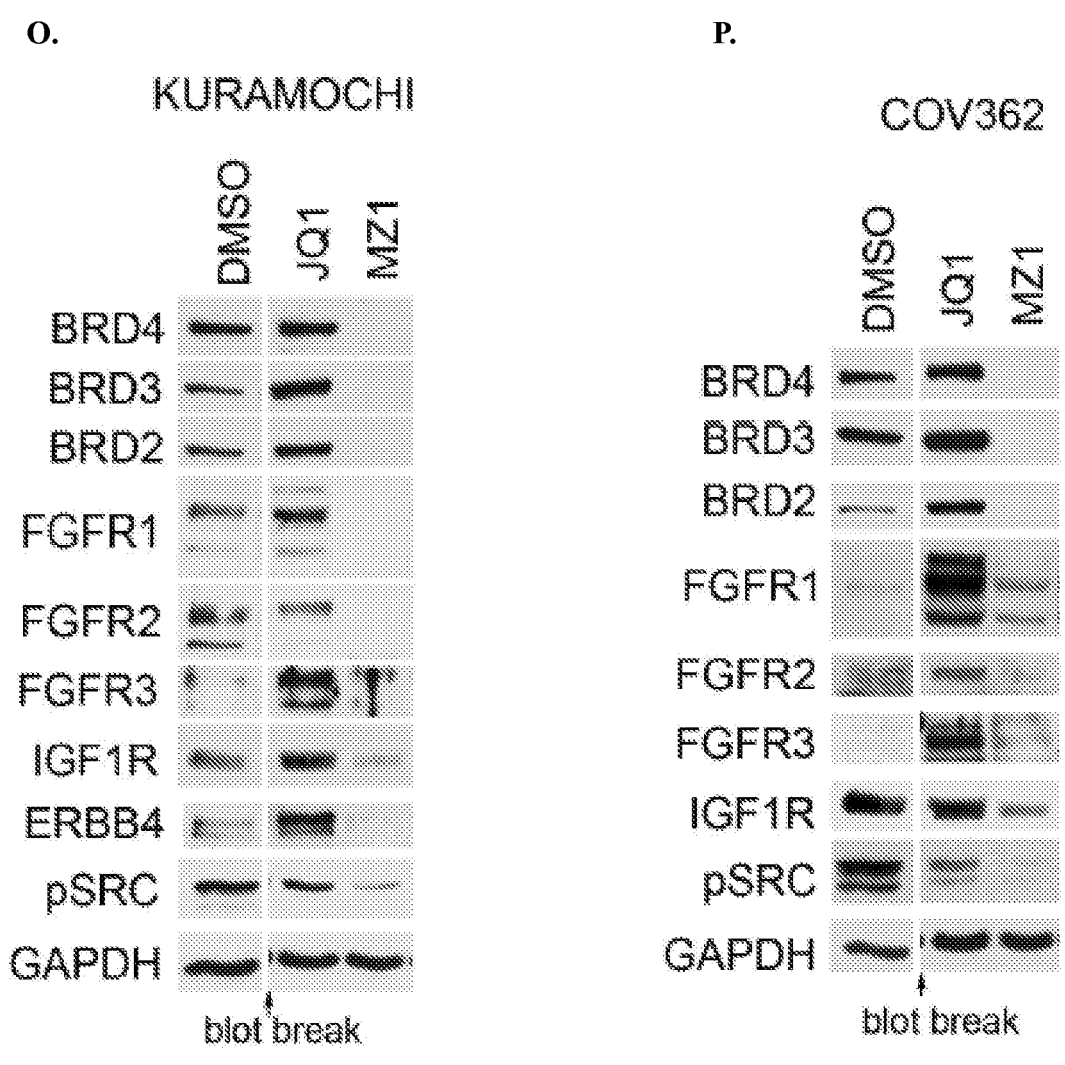

Example 1: BET Degrader Therapies Uniquely Block Translation Signaling in OC Cells Promoting Kinome Destabilization and Apoptosis To functionally explore the distinct methods of targeting BET proteins in ovarian cancer, a detailed proteomics characterization of OC cells treated with BBDs (MZ1 or ARV825) or BBIs (JQ1, or OTX015) was carried out. The BBDs used in the study were, MZ1, which uses JQ1 as the bromodomain targeting molecule and recruits E3 ligases using a VHL-binding moiety, and ARV825 with OTX015 as the warhead and a Cereblon-binding moiety for E3 ligase recruitment (FIGS. 1A and 8A). The established epithelial ovarian cancer cell line OVCAR8 was selected for the studies as it has previously been shown to require BRD4 for tumor formation. Knockdown of BRD4 induced apoptosis in OVCAR8 cells confirming BRD4-dependency (FIG. 1B).

Figure 1:
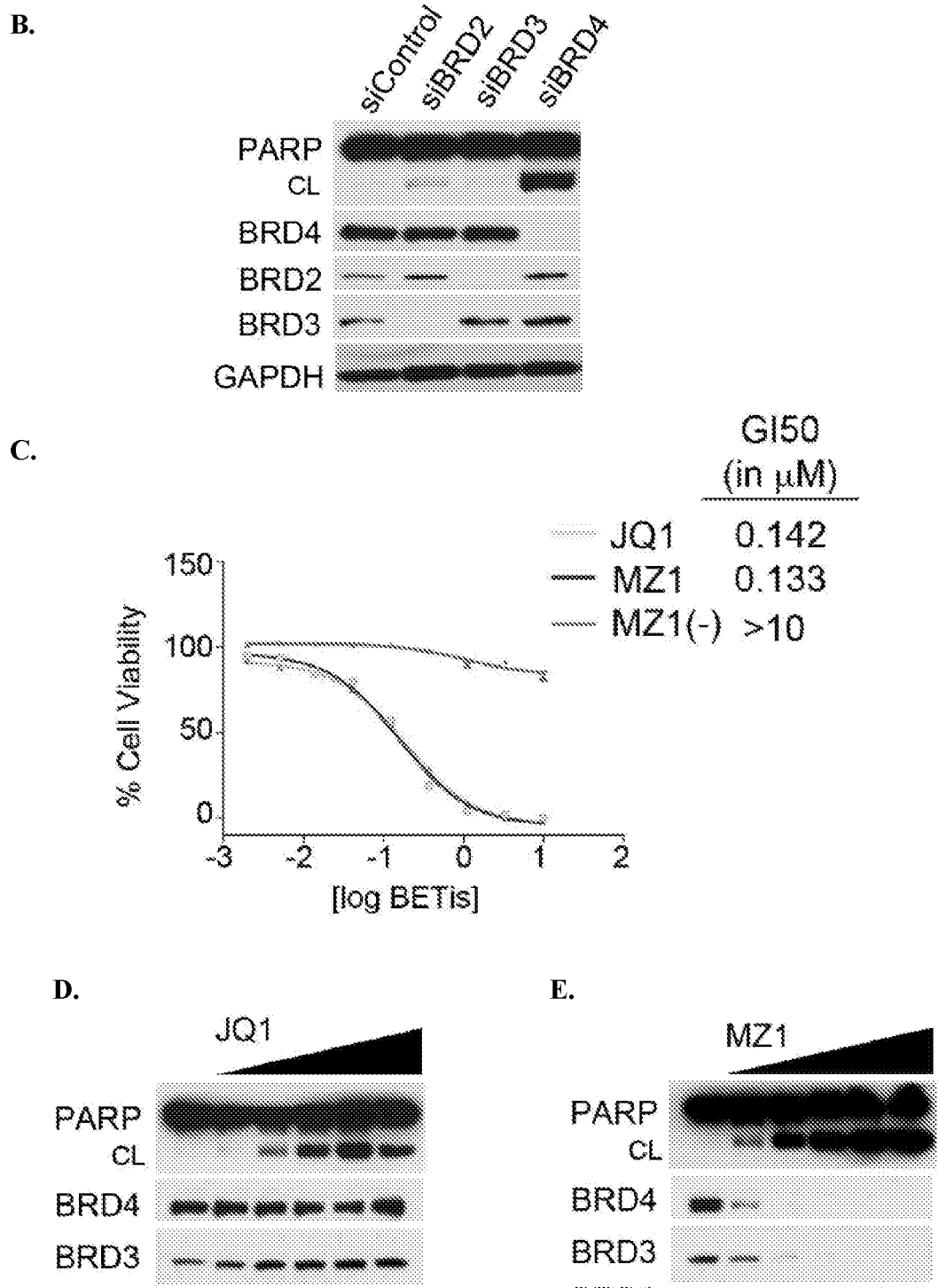
FIG. 1A shows BBI, JQ1 or BBD, MZ1, which uses JQ1 as bromodomain targeting molecule, were used for proteogenomics studies.
FIG. 1B shows that knockdown of BRD4 induced apoptosis in OVCAR8 cells confirming BRD4-dependency; OVCAR8 cells were transfected with siRNAs targeting BRD2, BRD3, BRD4 or control siRNA and cultured for 120 hours. Apoptosis was measured by assessing cleaved PARP by Western blot.
FIG. 1C shows that treatment of OVCAR8 cells with JQ1 or MZ1 but not cis-MZ1 blocked cell viability; cells were treated with increasing doses of drug for 5 days and viability was assessed by CellTiter-Glo assays; Cis-MZ1 was used as a negative control which cannot recruit VHL.
FIG. 1D shows that BBD-treatment reduces BET proteins inducing apoptosis to a greater extent than BBI-treatment; OVCAR8 cells were treated with increasing doses of JQ1 and BET protein levels was determined by Western blot; apoptosis was measured by assessing cleaved PARP levels by blot.
FIG. 1E shows that BBD-treatment reduces BET proteins inducing apoptosis to a greater extent than BBI-treatment; OVCAR8 cells were treated with increasing doses of MZ1 and BET protein levels was determined by Western blot; apoptosis was measured by assessing cleaved PARP levels by blot.
FIG. 1F shows that Short-term BBD-treatment induces differential proteome response than BBI-treatment; hierarchical clustering of protein log 2 LFQ z-scores of OVCAR8 cells treated with DMSO, BBIs (JQ1 or OTX015) or BBDs (MZ1 or ARV825) for 48 hours; heat map depicts log 2 LFQ z-scores for 4604 proteins measured by single-run proteome analysis.
FIG. 1G shows that BBD and BBI-induced proteome responses exhibit poor correlation; Pearson correlations of single-run proteome profiles of OVCAR8 cells treated with BBIs (JQ1 or OTX015) or BBDs (MZ1 or ARV825) for 48 hours; correlation plots of SILAC-determined log 2-fold changes in protein levels as a ratio of (drug/control) were generated using Perseus Software.
FIG. 1H shows Pearson correlation analysis of log 2-fold changes in RNA and those proteins exhibiting statistically significant changes following BBI therapies was determined using Perseus Software; BBD-induced proteome and RNA response exhibits poor correlation in contrast to BBI-therapy; OVCAR8 cells were treated with 500 nM JQ1 or MZ1 for 48 hours and global changes in protein or RNA levels was determined by single-run proteome and RNA-seq analysis.
FIG. 1I shows Pearson correlation analysis of log 2-fold changes in RNA and those proteins exhibiting statistically significant changes following BBD therapies was determined using Perseus Software.
FIG. 1J shows that BBD-therapy uniquely represses translation markers, translational elongation and MYC protein levels; characterization of BBD or BBI therapies on translation, BET proteins, BRD4-targets and MYC signaling were determined by Western blot; OVCAR8 cells were treated with 500 nM MZ1, JQ1, cis-MZ1 or DMSO for 48 hours and characterization of BBD or BBI therapies on translation, BET proteins, BRD4-targets and MYC signaling determined by Western blot.
FIG. 1K shows that distinct remodeling of the kinome to 48 hours MZ1 or JQ1 (500 nM) treatment in OVCAR8 cells; unsupervised hierarchical clustering of SILAC-determined log 2-fold changes in MIB binding of 237 kinases as a ratio of drug/DMSO.
FIG. 1L shows Pearson correlations plots of kinome response signatures to MZ1 vs JQ1 or ARV825 vs OTX015; heat map and correlation plots were generated in Perseus Software.
FIG. 1M shows the kinases distinctly induced or repressed by BBD therapy; MIB-MS kinome profile of OVCAR8 cells following a 48 hour treatment with BBDs (MZ1, ARV825) or BBIs (JQ1, OTX015); volcano plot depicts SILAC determined log 2-fold changes in MIB binding as a ratio of BBDs/BBIs; statistical changes in SILAC determined MIB-binding were determined by paired T-Test (P<0.05) using Perseus Software.
FIG. 1N shows that BBD-treatment blocks kinome remodeling observed with BBI-therapies; OVCAR8 cells were treated with 500 nM of JQ1 or MZ1 for 48 hours and kinase protein levels determined by Western blot.
Figure 1:
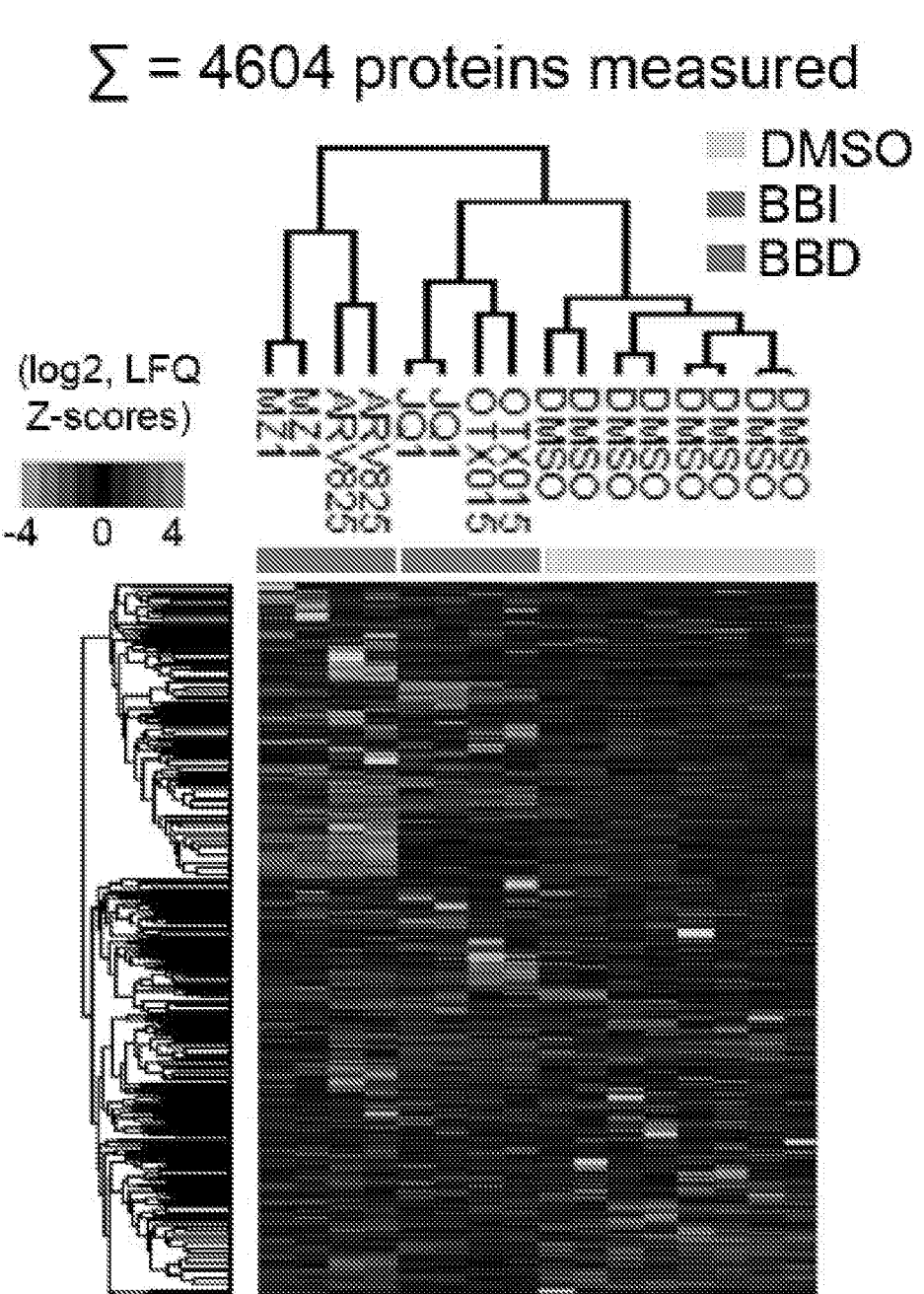
Figure 1:
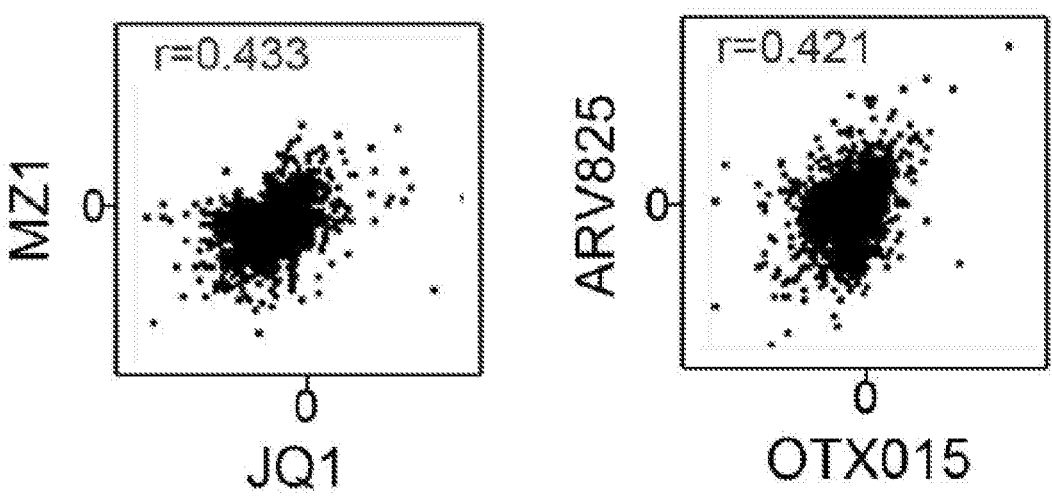
Figure 1:
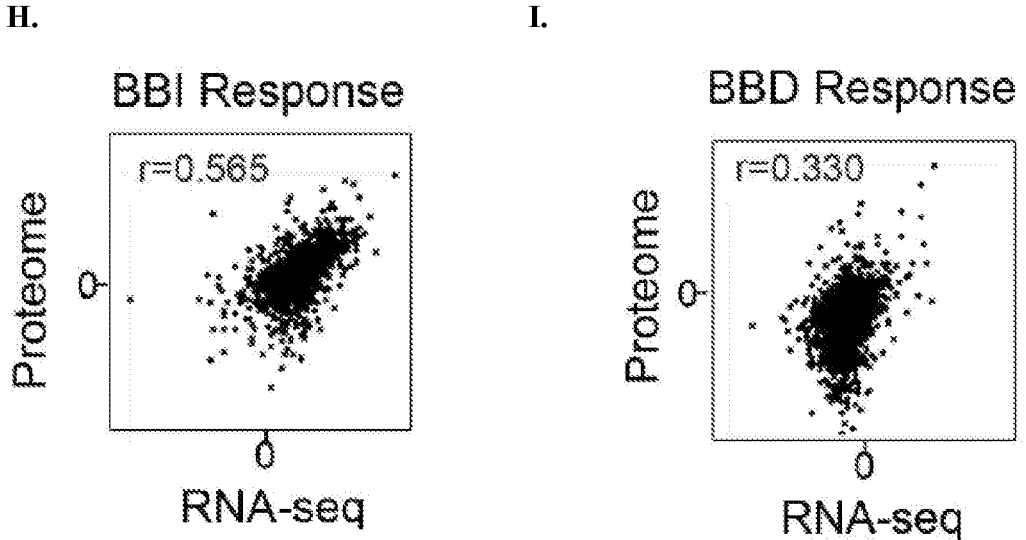
Figure 1:
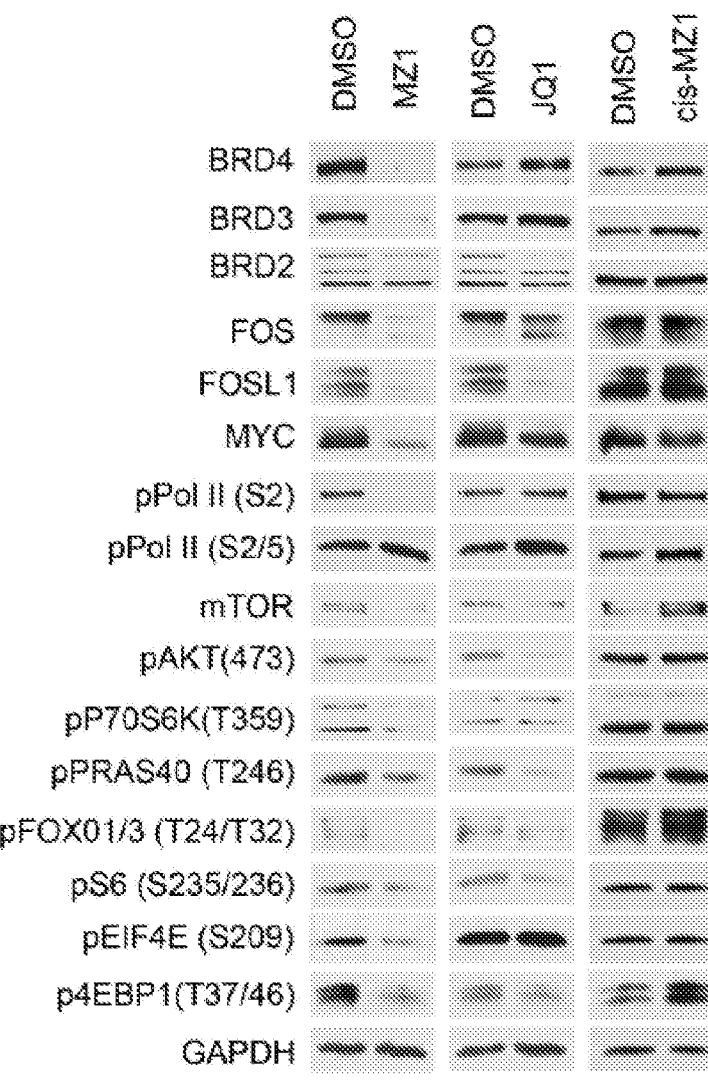
Figure 1:
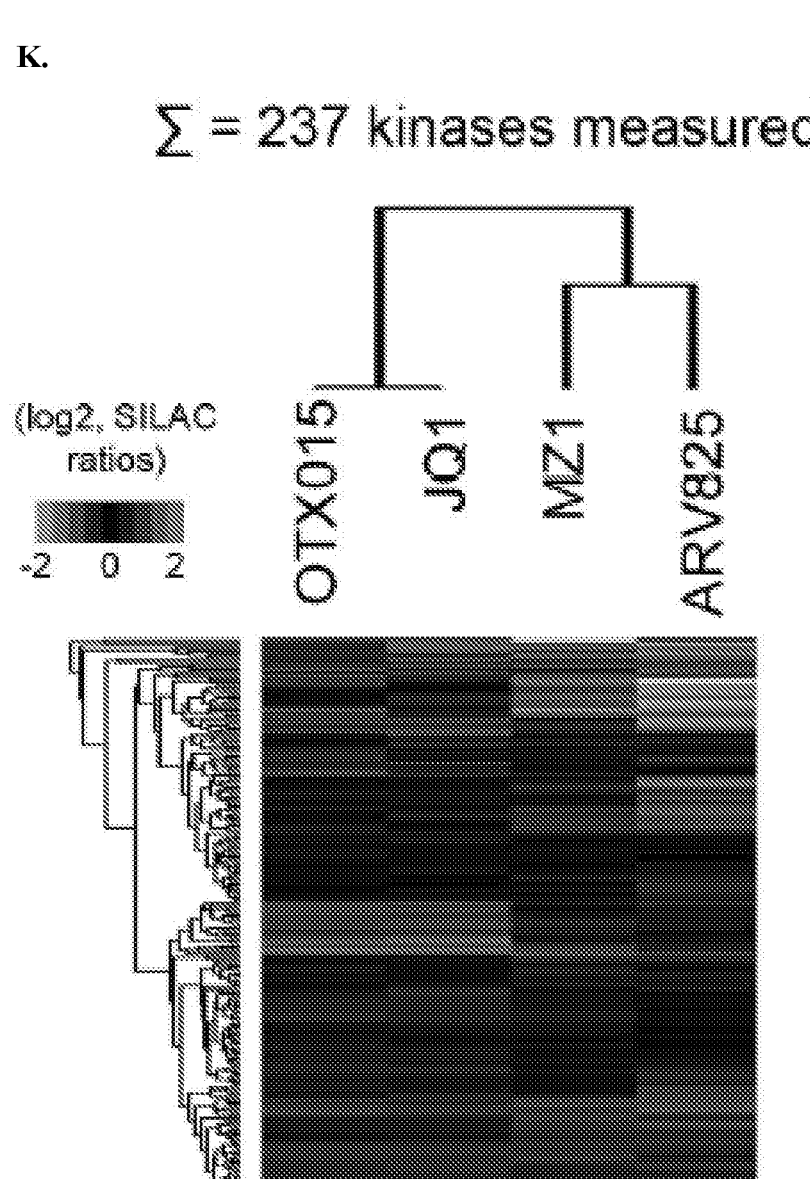
Figure 1:
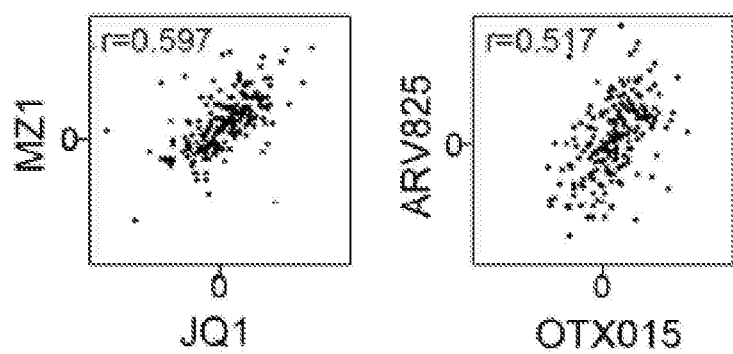
Figure 1:
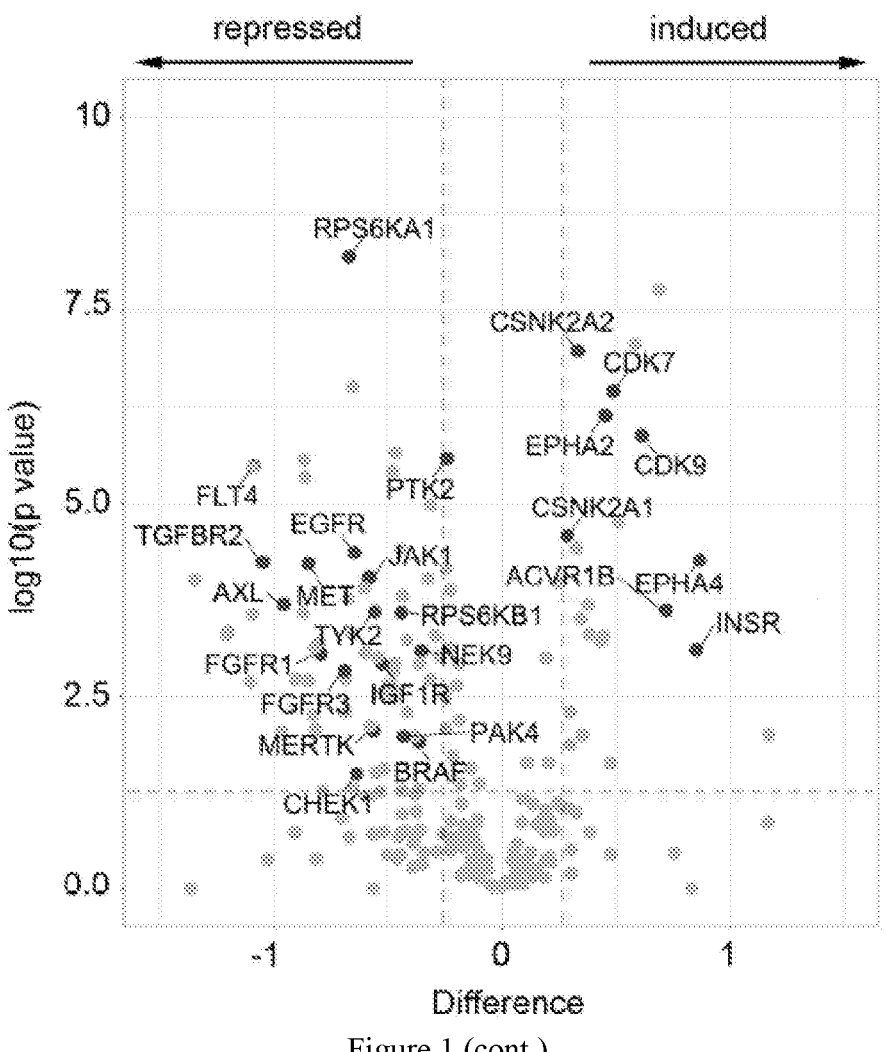
Figure 1:
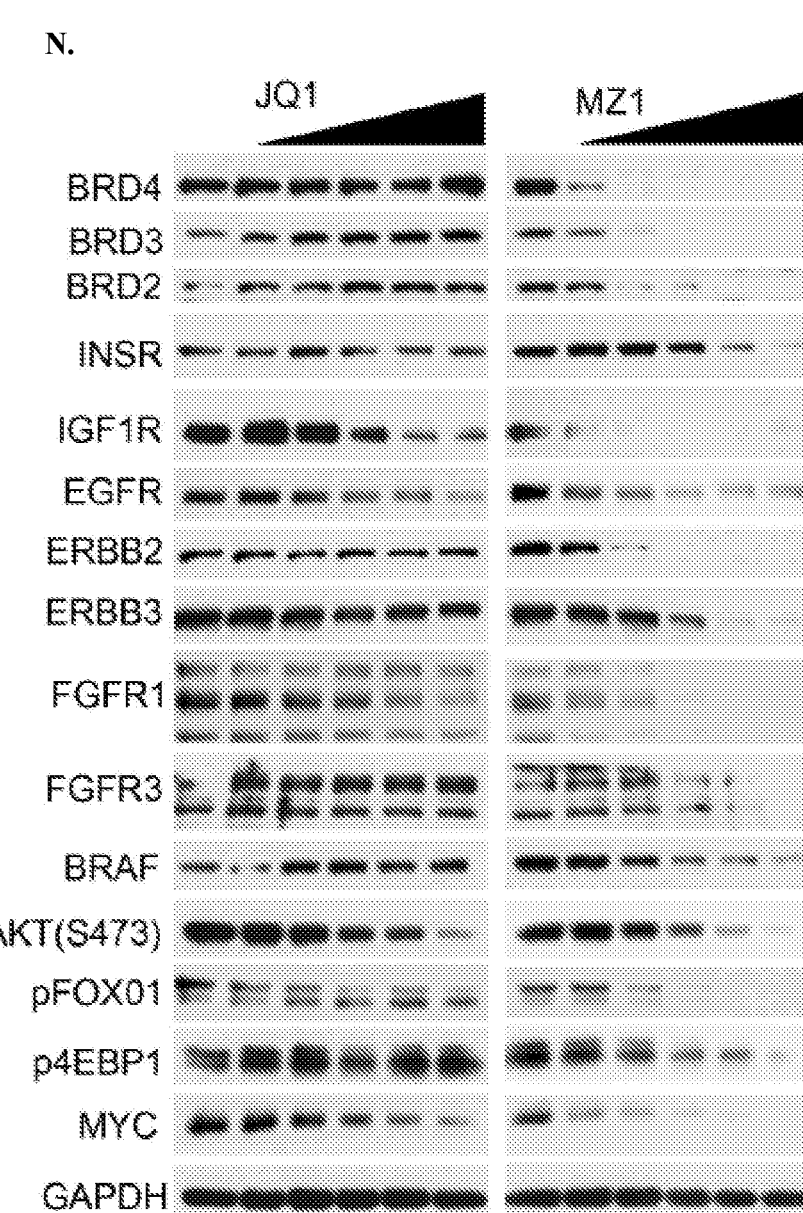

Dose escalation of JQ1 or MZ1 but not cis-MZ1, a negative control unable to recruit VHL, in OVCAR8 cells inhibited cell viability similarly, with GI50 values 133 nM (JQ1) and 142 nM (MZ1) (FIG. 1C). BBDs MZ1 or ARV825 degraded BET proteins in a concentration-dependent manner in OVCAR8 cells (FIGS. 1D, 1E and 8B). Treatment with BBIs or BBDs induced apoptosis in OVCAR8 cells, however, a more pronounced cleavage of PARP at lower doses was observed with BBD-treatment (FIGS. 1D, 1E and 8C), demonstrating BET protein degradation was superior at inducing apoptosis in cancer cells than BET bromodomain inhibition.

Global proteomic characterization of BBD or BBI treated OVCAR8 cells using single-run proteome analysis demonstrated MZ1 or ARV825 promoted distinct changes in global protein levels compared to BBI treatment (FIGS. 1F and 1G). As expected, BRD2, BRD3 and BRD4 proteins were reduced by BBD but not BBI-treatment, and induced protein levels of HEXIM1 was observed only with BBI-treatment, consistent with previous reports (FIG. 8D). Short-term exposure to BBI or BBD therapies commonly induced proteins involved in metabolism signaling, including citric acid (TCA) cycle and pyruvate metabolism (FIGS. 8E and 8F).

Notably, MZ1 or ARV825-treatment uniquely downregulated proteins involved in ribosome and translation signaling, in addition to those regulating transcription and cell cycle signaling observed with BBI-treatment. Enrichment maps of pathways repressed by short-term BBD generated from single-run proteome profiles of OVCAR8 cells treated with BBDs (MZ1 or ARV825) for 48 hours were prepared (data not shown). Statistical differences in protein log 2 LFQ z-scores comparing BBDs or BBIs to control treated cells was determined by paired T-Test Benjamini-Hochberg adjusted p values at FDR of <0.05 using Perseus Software. Proteins significantly repressed by BBD or BBI therapies were then analyzed by gProfiler to determine pathway enrichments (BH P<05). Enrichment maps were generated in Cytoscape using the Enrichment Map app v2.2.1. Enrichment maps of pathways repressed by short-term BBI generated from single-run proteome profiles of OVCAR8 cells treated with BBIs (JQ1 or OTX015) for 48 hours were also prepared (data not shown). Statistical differences in protein log 2 LFQ z-scores comparing BBDs or BBIs to control treated cells was determined.

Analysis of global expression changes in response to MZ1 or JQ1 by RNA-seq showed the treatments differentially altered the transcriptome landscape (FIGS. 8G and 8H). Comparison of global protein and RNA changes following BBD or BBI-treatment, revealed many of the proteins altered by BBI-treatment were commonly induced or repressed at the RNA level (r=0.565) (FIG. 1H). In contrast, BBD-induced changes in RNA and protein levels were less correlated (r=0.330), with many genes downregulated at the protein level but not RNA, suggesting a significant component of the molecular response to BET protein degradation occurred post-transcriptionally (FIGS. 1I and 8I).

Western blot analysis of JQ1 or MZ1 treated OVCAR8 cells confirmed the repression of translational signaling by BBD therapies. MZ1-treatment distinctly reduced phosphorylation of FOX01/3 (T24/32), P70S6 Kinase (T389), pEIF4E (S209) and p4EBP1 (T37/46) relative to cis-MZ1 or JQ1 treatment (FIG. 1J). Previous studies have shown BRD4 degradation blocks RNA pol II (S2) phosphorylation inhibiting transcriptional elongation. Consistent with these findings, BBD-treatment of OVCAR8 cells reduced RNA pol II (S2) phosphorylation that was not observed with JQ1. Moreover, in contrast to JQ1 therapy, MZ1-treatment reduced MYC protein levels, demonstrating BRD4 degradation but not inhibition can block MYC signaling in OVCAR8 cells.

Kinome profiling of BBD or BBI treated OC cells using MIB-MS showed dynamic reprogramming of kinase signaling was similar within BBDs (ARV825 and MZ1) or BBIs (JQ1 and OTX015), but less similar amongst BBD and BBI (FIGS. 1K and 1L). Consistent with BBD-mediated translational repression, the majority of kinases induced by BBI treatment were unaltered or inhibited by BBD treatment, many encompassing the published JQ1-kinome response signature (FIG. 8J). MZ1-treatment uniquely increased MIB-binding of INSR, CDK7, EPHA4 and EPHA2, as well as established BRD4 interacting proteins CSNK2A1, CSNK2A2, and CDK9 (FIG. 1M). Overall, BBD-treatment significantly reduced kinase MIB-binding relative to BBI therapy, including the inhibition of established OC driver kinases EGFR, FGFR1, FGFR3, MET, BRAF, PTK2, PAK4, CHEK1 and RPS6KB1. MZ1-induced changes in kinase RNA and MIB-binding exhibited poor correlation (r=0.394) compared to JQ1-treatment (r=0.595) illustrating the profound impact of BET protein degradation on kinase protein stability in OVCAR8 cells (FIGS. 8K and 8L). Western blot analysis of JQ1 or MZ1 treated OVCAR8 cells confirmed the distinct consequence of BET degradation, including the MZ1-specific reduction of RTKs, EGFR, ERBB2, ERBB3, FGFR1, and IGF1R (FIG. 1N). Similarly, the majority of kinases induced by BBI treatment in additional OC cell lines KURAMOCHI or COV362 were either unaltered or reduced by BBD therapy, demonstrating BBD-treatment uniquely blocks compensatory kinome reprogramming observed with BBI-treatment (FIGS. 8M and 8N). Ovarian cancer cell lines KURAMOCHI and COV362 were treated with BET PROTAC MZ1 for 48 hours, which causes downregulation of RTKs protein levels such as FGFR1, FGFR2, FGFR3, IGF1R and ERBB4 that was not observed with BET inhibitor JQ1 (FIGS. 8O and 8P).

Together, proteogenomic characterization of BET protein degradation or inhibition in BRD4-driven OVCAR8 cells revealed BBD therapies uniquely inhibited translation, blocked kinome reprogramming observed with BBI therapies, as well as reduced MYC protein levels leading to enhanced apoptosis of OVCAR8 cells.

Figure 2:
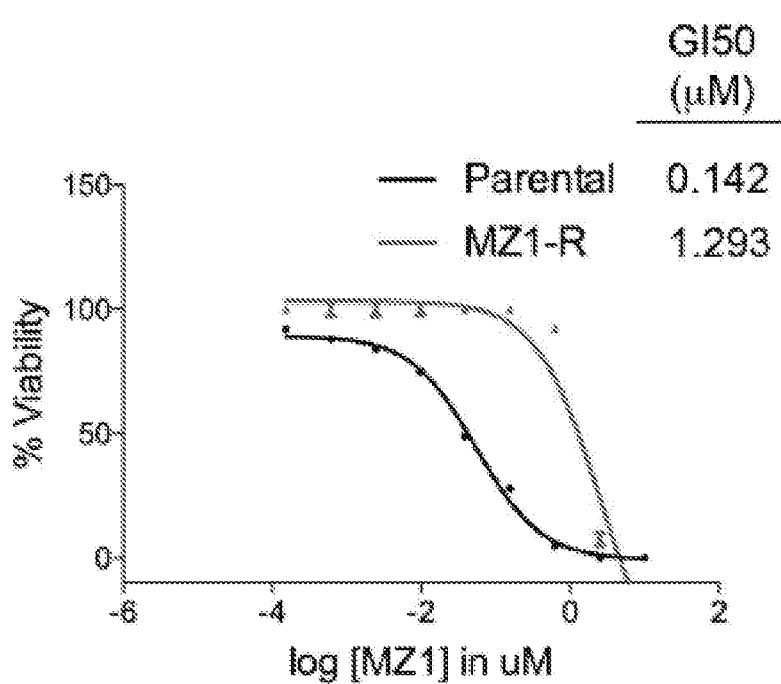
FIG. 2A shows that OVCAR8 cells acquire resistance to MZ1 or ARV825; parental and BBD-resistant cells were treated with escalating doses of MZ1 for 5 days and cell viability assessed by CellTiter-Glo; BBD-R treated cell viabilities normalized to DMSO treated BBD-R cells.
FIG. 2B shows that OVCAR8 cells acquire resistance to MZ1 or ARV825; parental and BBD-resistant cells were treated with escalating doses of ARV825 for 5 days and cell viability assessed by CellTiter-Glo; BBD-R treated cell viabilities normalized to DMSO treated BBD-R cells.
FIG. 2C shows that escalating doses of BBDs fails to promote degradation of BET proteins in BBD-R cells; OVCAR8 parental cells were treated with escalating doses of MZ1 for 24 hours and BET proteins and BRD4-target FOSL1 were determined by Western blot.
FIG. 2D shows that escalating doses of BBDs fails to promote degradation of BET proteins in BBD-R cells; OVCAR8 parental cells were treated with escalating doses of ARV825 for 24 hours and BET proteins and BRD4-target FOSL1 were determined by Western blot.
FIG. 2E shows that BET proteins remained reduced in cells chronically exposed to BBD-therapies; BET protein levels were determined by blot in parental cells, parental cells treated with MZ1 (100 nM), MZ1-R or in MZ1-R cells where MZ1 was removed from media for 48 hours.
FIG. 2F shows BET protein levels were determined by blot in parental cells, parental cells treated with ARV825 (100 nM), ARV-R or in ARV-R cells where MZ1 was removed from media for 48 hours.
FIG. 2G shows that Cells resistant to BBI or BBDs are dependent on BRD4 for growth; OVCAR8 parental, JQ1-R, MZ1-R or ARV-R cells were transfected with siRNAs targeting individual BRD2, BRD3 or BRD4, combinations of BRDs or control siRNA, cultured for 120 hours and viability was assessed by CellTiter-Glo.
FIG. 2H shows that cells resistant to MZ1 require BRD4 for MYC signaling and cell survival; OVCAR8 MZ1-R cells were transfected with siRNAs targeting individual BRD2, BRD3, BRD4, BRD2/3/4 or control siRNA, cultured for 120 hours and apoptosis and BRD4-targets were assessed by Western blot.
FIG. 2I and shows that cells resistant to MZ1 are cross-resistant to VHL-based BBDs but sensitive to CRBN-based BBDs; OVCAR8 parental or MZ1-R cells were treated with increasing doses of VHL-based BBD ARV-771 for 5 days and cell viability was assessed by CellTiter-Glo.
FIG. 2J shows that cells resistant to MZ1 are cross-resistant to VHL-based BBDs but sensitive to CRBN-based BBDs; OVCAR8 parental or MZ1-R cells were treated with increasing doses of CRBN-based BBD, ARV825 for 5 days and cell viability was assessed by CellTiter-Glo.
FIG. 2K shows that treatment of MZ1-R cells with CRBN-based BBD ARV825 promotes degradation of BET proteins, reduces BRD4-target FOSL1 and induces apoptosis; MZ1-R cells were treated with escalating doses of ARV825 and protein levels assessed by Western blot.
FIG. 2L shows that that cells resistant to Cells resistant to ARV825 show cross-resistance to CRBN and VHL-based BBDs; ARV-R cells were treated with escalating doses of VHL-based BBD ARV-771 for 5 days and cell viability was assessed by CellTiter-Glo.
FIG. 2M shows that that cells resistant to Cells resistant to ARV825 show cross-resistance to CRBN and VHL-based BBDs; ARV-R cells were treated with escalating doses of CRBN-based BBD, ARV825 for 5 days and cell viability was assessed by CellTiter-Glo.
FIG. 2N shows that treatment of ARV-R cells with VHL or CRBN-based BBDs fails to induce apoptosis observed with ARV825-treatment of parental cells as determined measuring cleaved PARP via Western blot.
FIG. 2O shows that BBD-R cells exhibit sensitivity towards BBI therapies; OVCAR8 MZ1-R cells were treated with escalating doses of JQ1 for 5 days and cell viability was assessed by CellTiter-Glo.
FIG. 2P shows that BBD-R cells exhibit sensitivity towards BBI therapies; OVCAR8 ARV-R cells were treated with escalating doses of JQ1 for 5 days and cell viability was assessed by CellTiter-Glo.
FIG. 2Q shows that BBI-R cells exhibit sensitivity to BBD-treatment; OVCAR8 JQ1-R cells were treated with escalating doses of BBIs, JQ1, OTX015, AZD5153, INC54 or MZ1 for 5 days and cell viability was assessed by CellTiter-Glo.
FIG. 2R shows OVCAR8 JQ1-R cells were treated with increasing doses of MZ1 for 48 hours and apoptosis determined by Western blot through monitoring of cleaved PARP levels.
Figure 2:
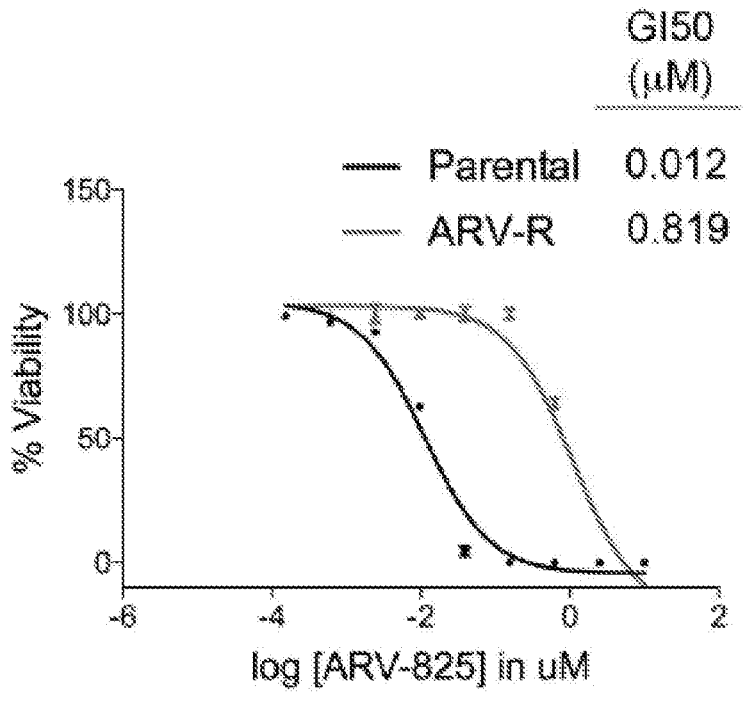
Figure 2:
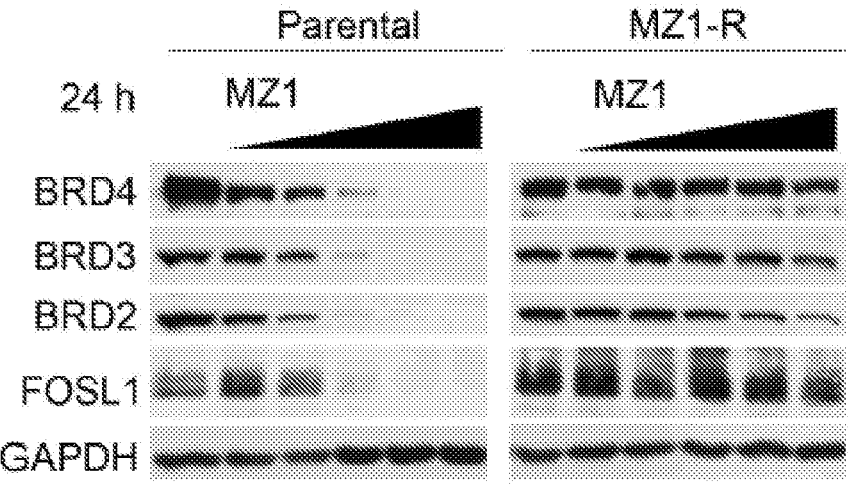
Figure 2:
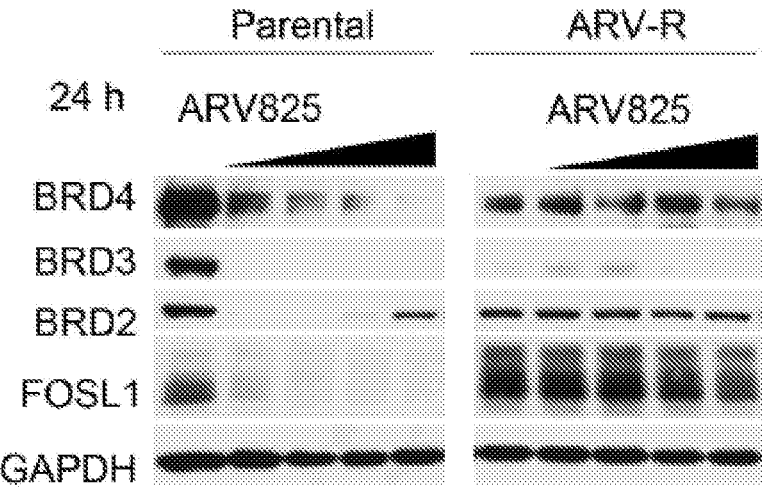
Figure 2:
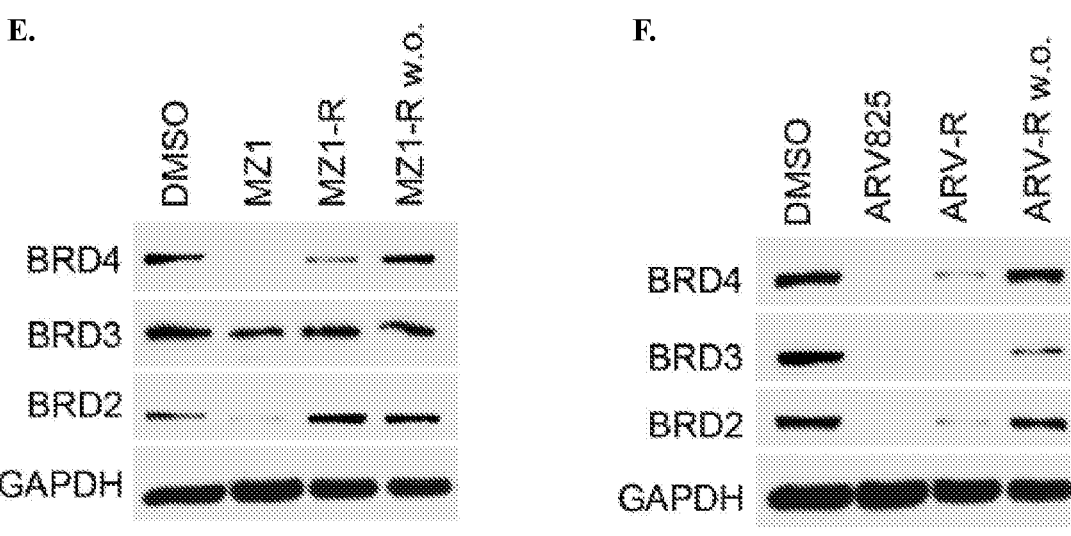
Figure 2:
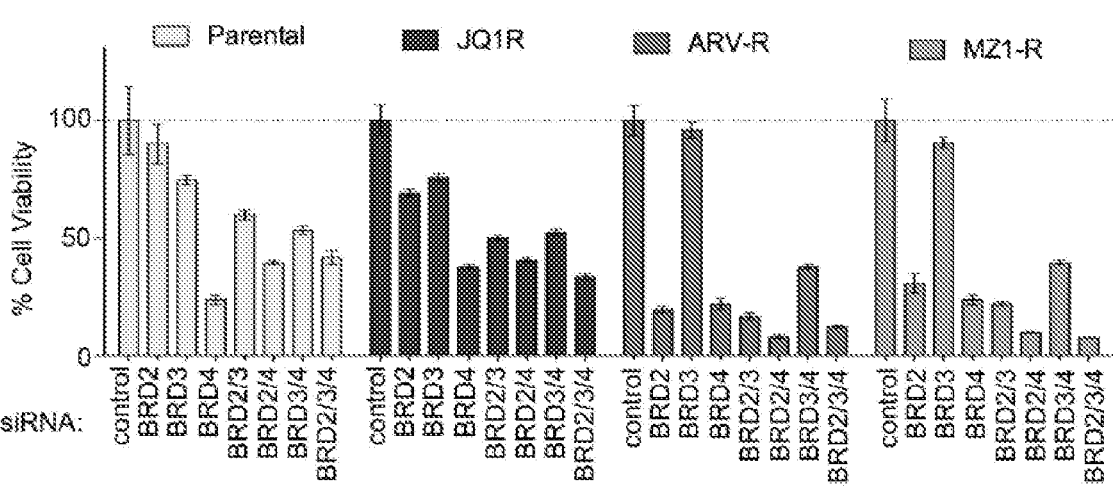
Figure 2:
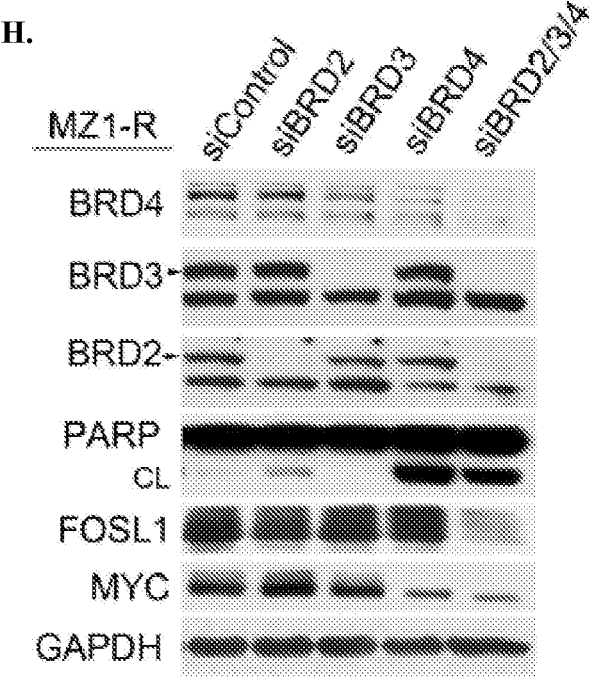
Figure 2:
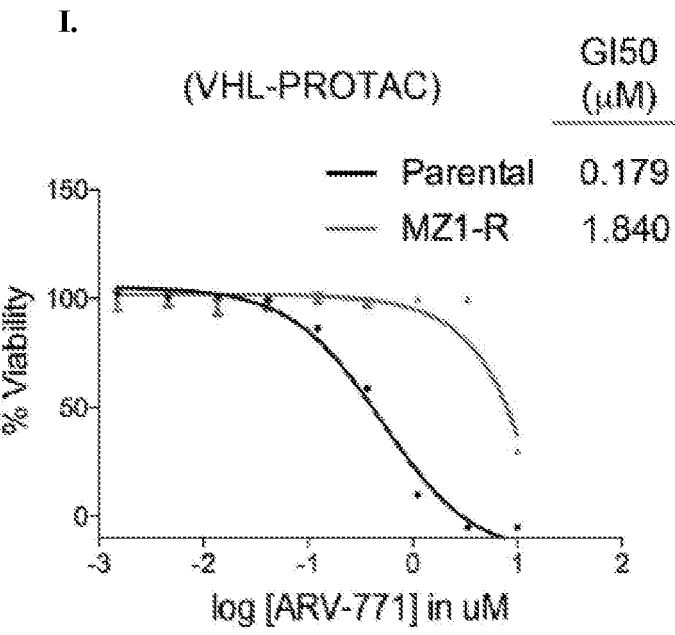
Figure 2:
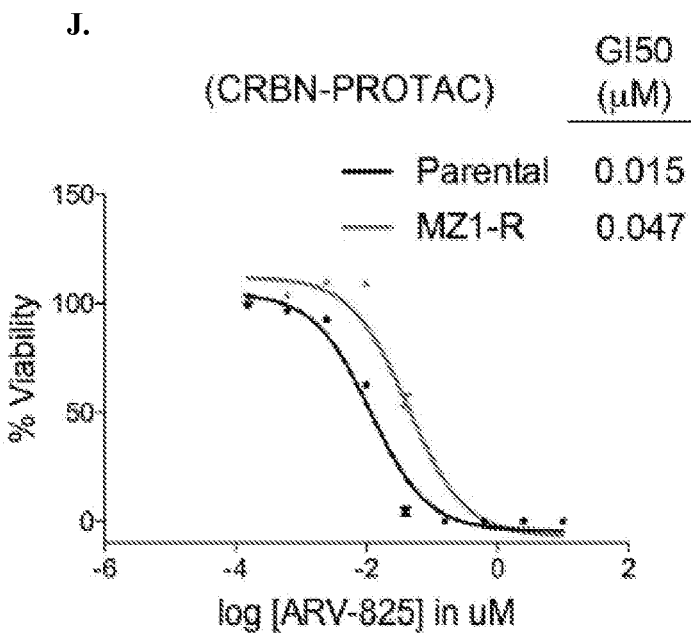
Figure 2:
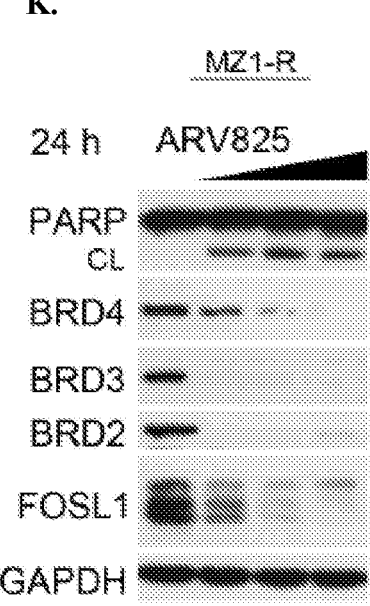
Figure 2:
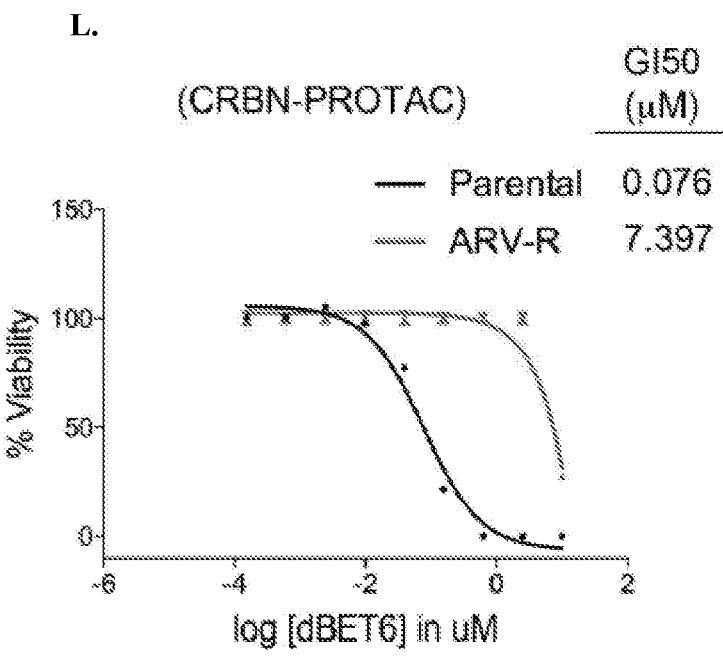
Figure 2:
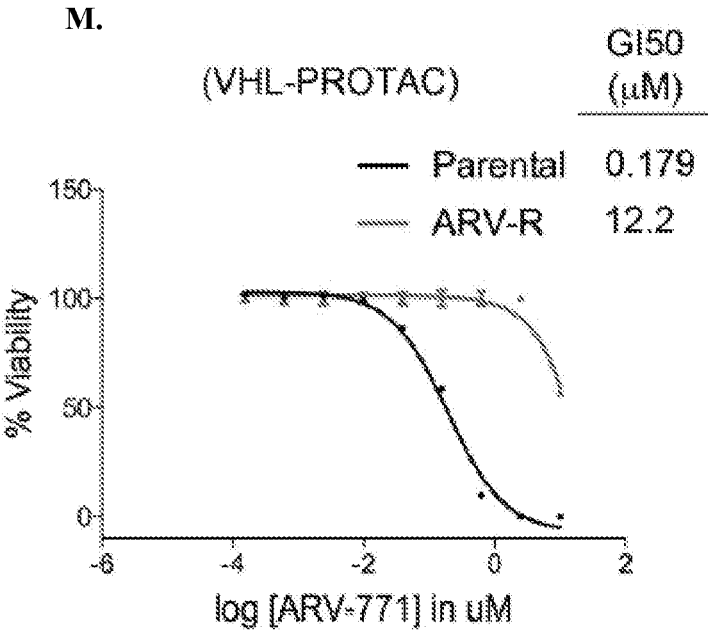
Figure 2:
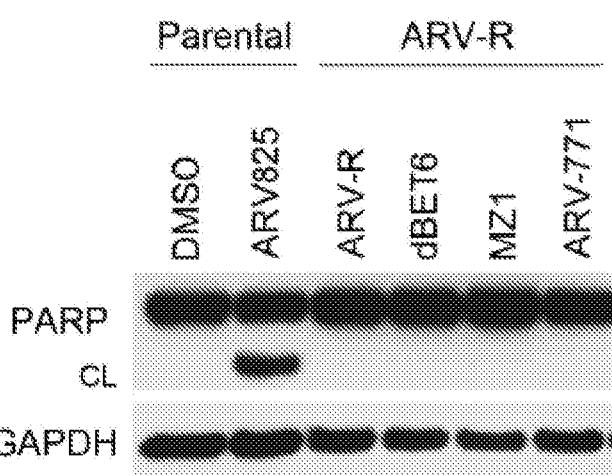
Figure 2:
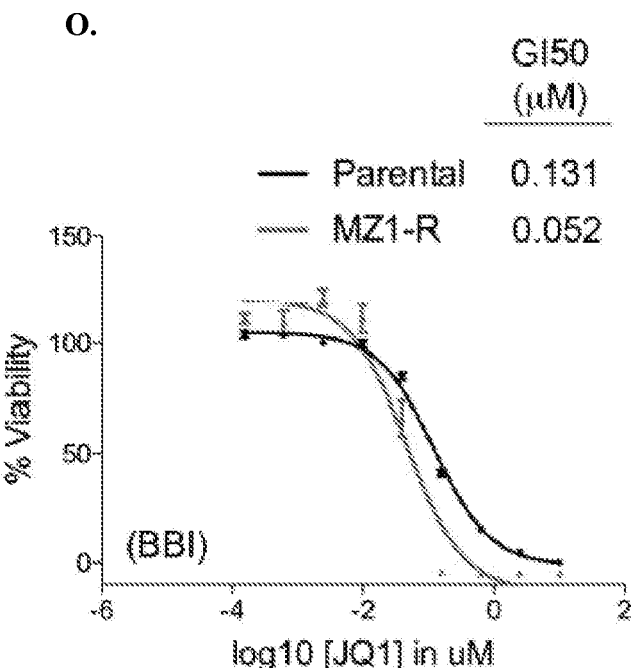
Figure 2:
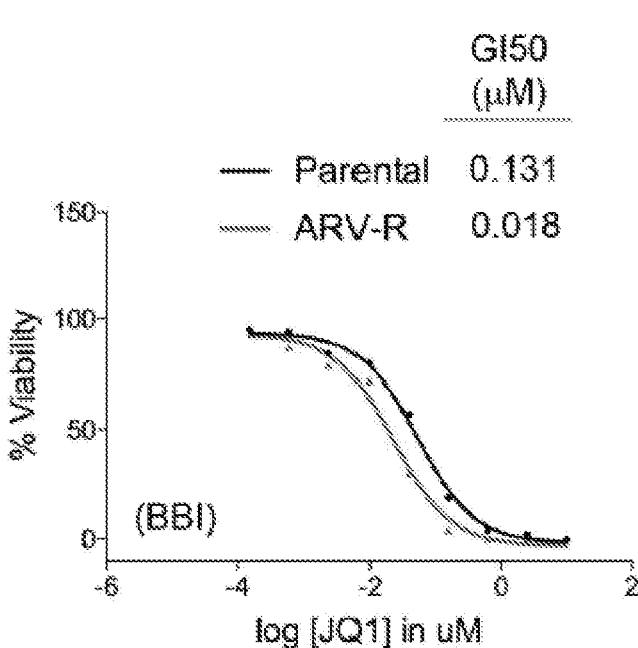
Figure 2:
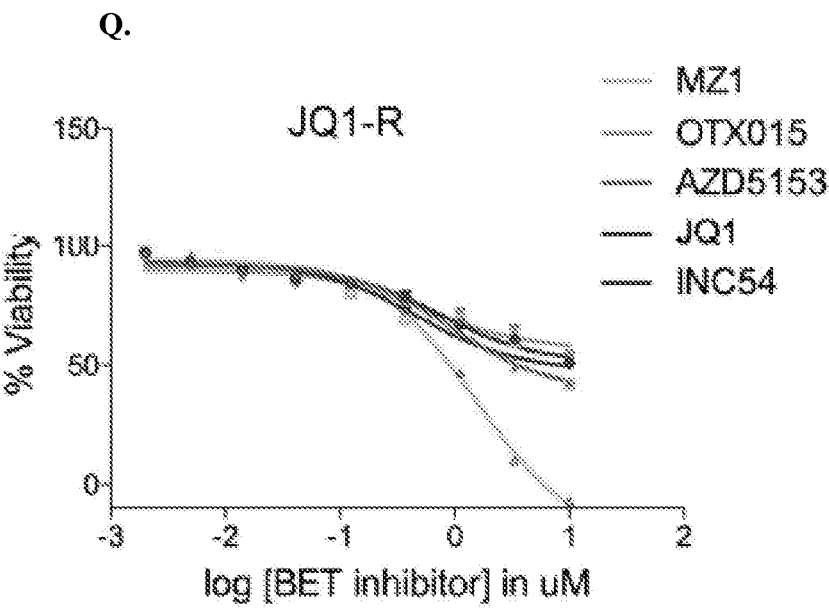
Figure 2:
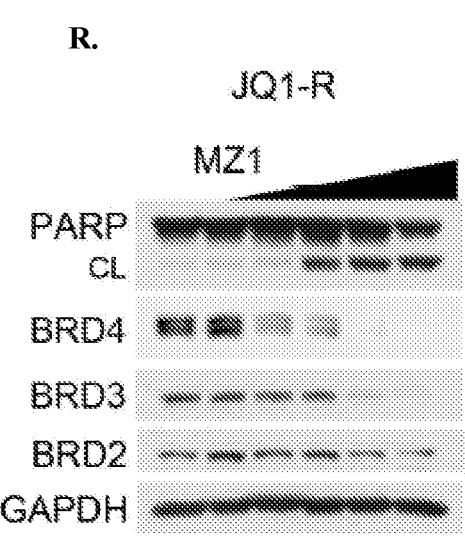
Figure 9:
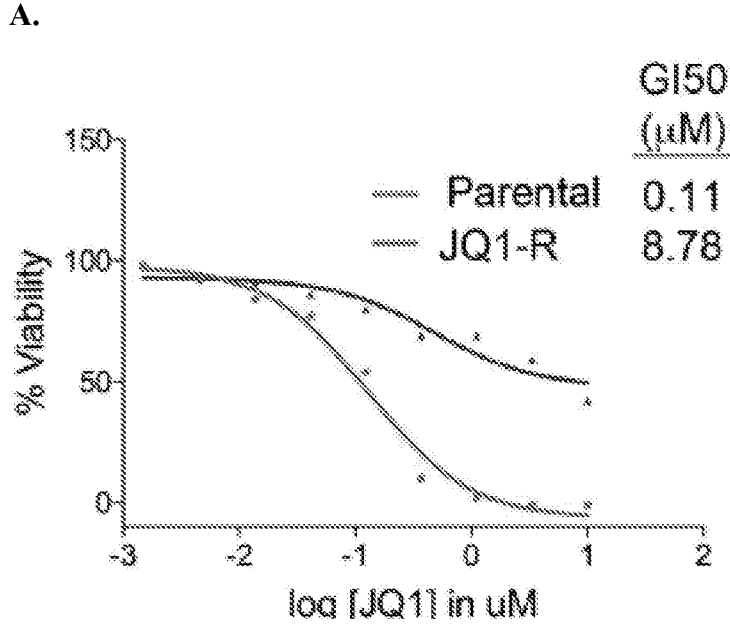
FIG. 9A shows that cells chronically exposed to JQ1 (JQ1-R) were unaffected by increasing doses of JQ1.
FIG. 9B shows that JQ1-treatment failed to reduce BRD4 target FOSL1.
FIG. 9C shows that some degree of PROTAC degradation occurs in ARV-R cells.
FIG. 9D shows that some degree of PROTAC degradation occurs in MZ1-R cells.
FIG. 9E shows RNA changes in BBD-R cells relative to parental cells.
FIG. 9F shows protein levels changes in BBD-R cells relative to parental cells.
FIG. 9G shows that BRD2 may function in contributing to MZ1 resistance through promoting MAPK signaling.
FIG. 9H shows knockdown of BRD2 reduces RAF-MEK-ERK signaling in MZ1-R cells, as shown by Western blot; OVCAR8 MZ1-R cells were transfected with siRNAs targeting BRD2 or control siRNA, cultured for 120 hours, and kinase activities assessed by Western blot using phospho-antibodies.
FIG. 9I shows MZ1-R cells display sensitivity towards CRBN-based BBD, dBET6; OVCAR8 parental or MZ1-R cells were treated with increasing doses of dBET6 for 5 days and cell viability assessed by CellTiter-Glo.
FIG. 9J shows BET proteins reduced by CRBN-based dBET6 but not VHL-based, ARV-771; OVCAR8 parental cells were treated with 100 nM MZ1 and compared to MZ1-R cells treated with 100 or 500 nM of MZ1, ARV-771 or dBET6 and BET protein levels determined by Western blot.
FIG. 9K shows ARV-R cells are cross-resistant to MZ1-treatment; OVCAR8 parental ARV-R cells were treated with increasing doses of MZ1 for 5 days and cell viability assessed by CellTiter-Glo.
FIG. 9L shows JQ1-R cells exhibit sensitivity to BBD-treatment; PEO1 JQ1-R cells were treated with escalating doses of BBIs, JQ1, OTX015, AZD5153, or ARV825 for 5 days and cell viability assessed by CellTiter-Glo.
Figure 9:
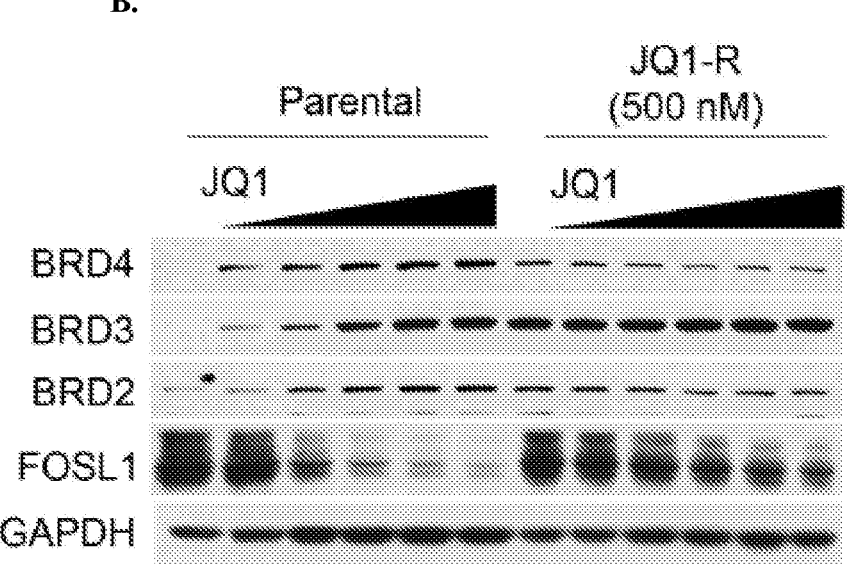
Figure 9:
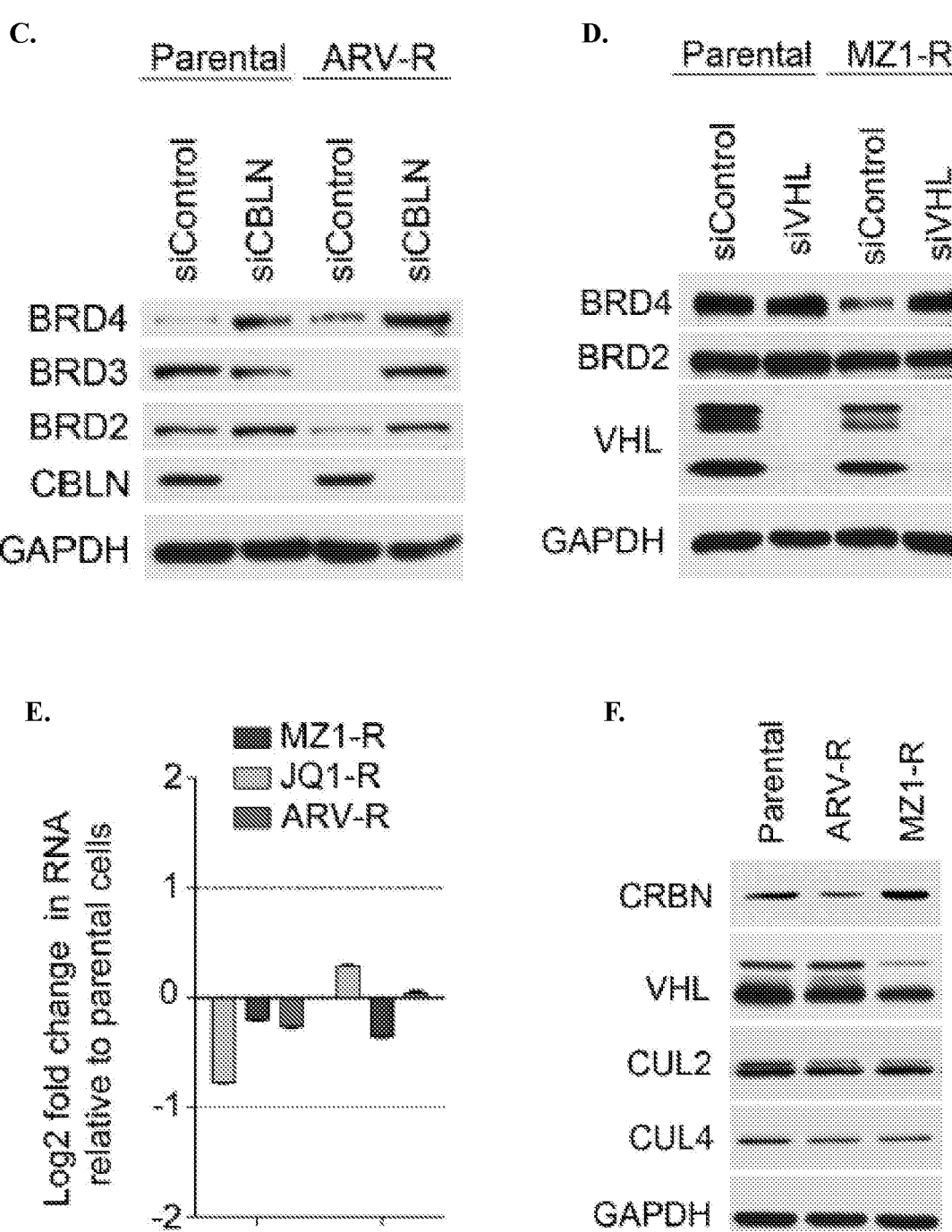
Figure 9:
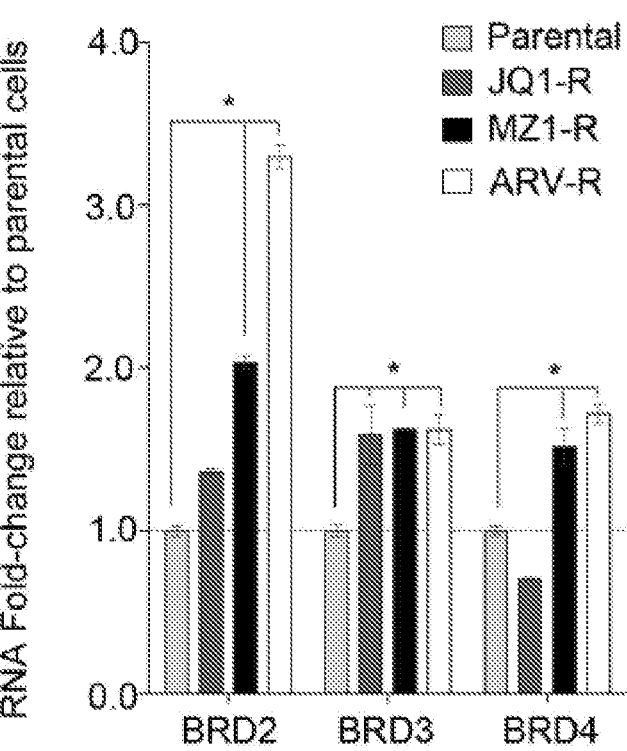
Figure 9:
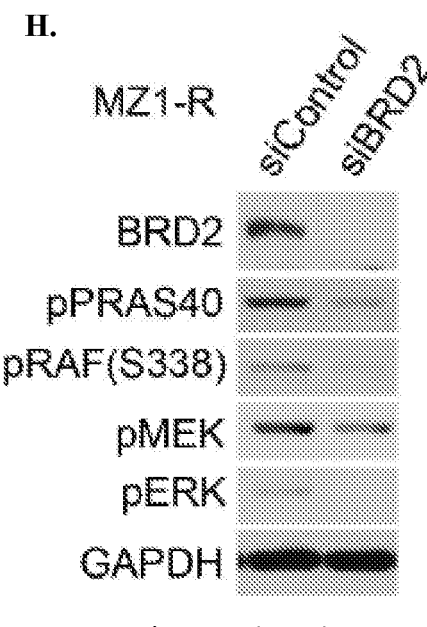
Figure 9:
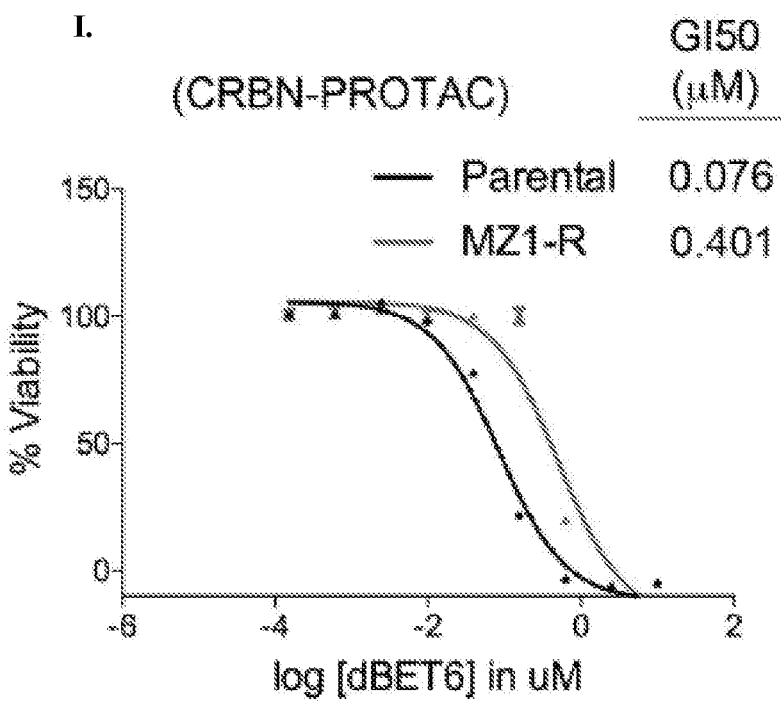
Figure 9:
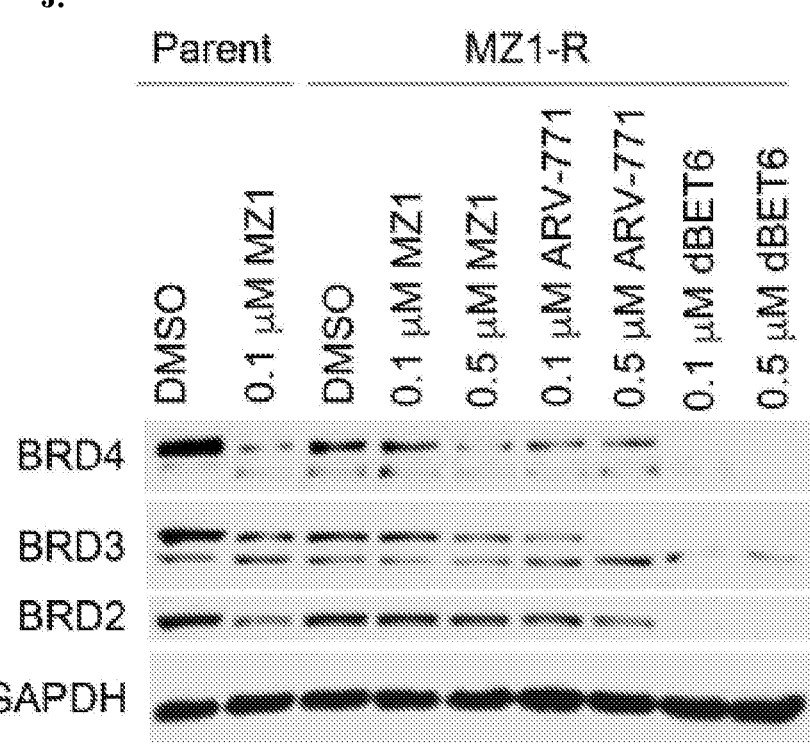
Figure 9:
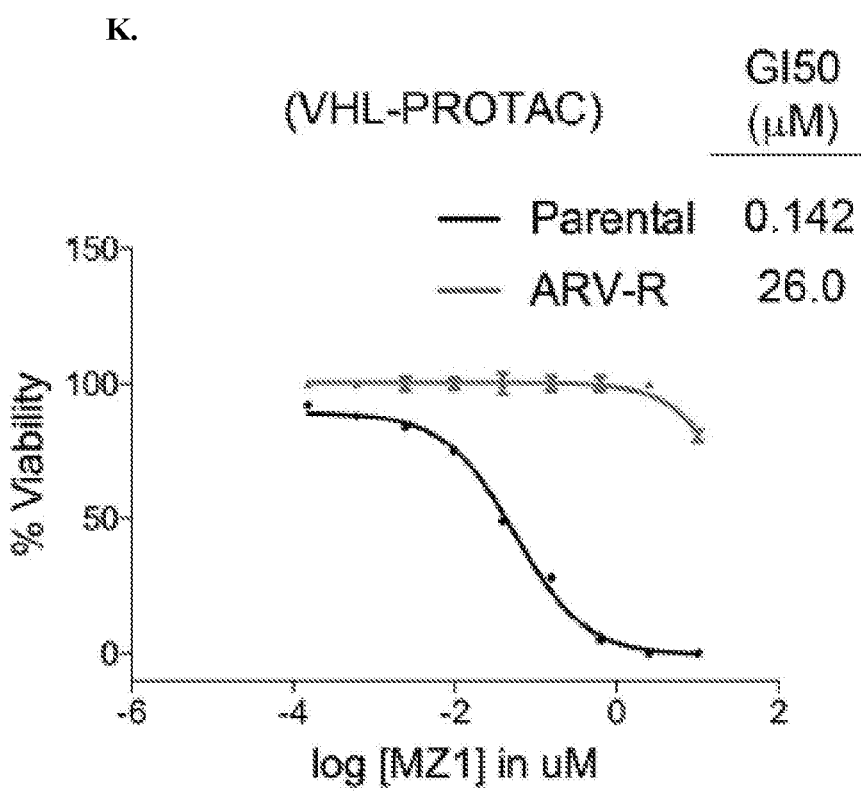
Figure 9:
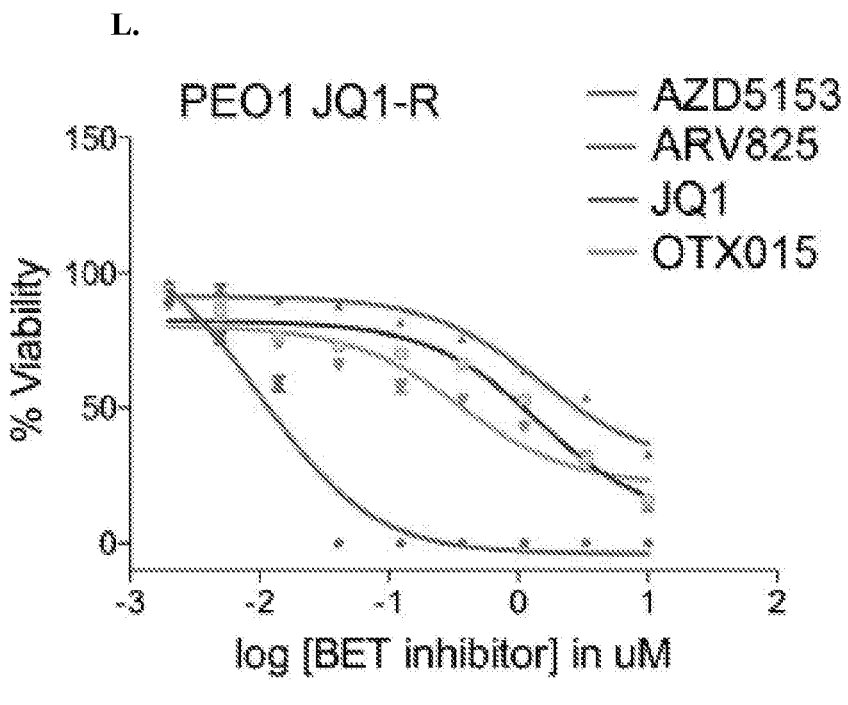

Example 2: Chronic Exposure to BBDs Fails to Maintain Sufficient Degradation of BET Proteins in OC Cells To explore acquired resistance mechanisms to BBD or BBI therapies, resistant OVCAR8 cells through chronic exposure to increasing doses of JQ1, MZ1 or ARV825 were generated. The chronically exposed OVCAR8 cells (MZ1-R) or (ARV-R) were more resistant to BBD than treatment naïve (i.e., parental cells), where they showed a rightward shift in MZ1 or ARV825 dose-response cell viability curves (FIGS. 2A and 2B). In contrast to parental OVCAR8 cells, treatment of MZ1-R or ARV-R cells with increasing doses of MZ1 or ARV825, respectfully, was insufficient to degrade BRD2, BRD3 or BRD4, as well as did not reduce BRD4-target FOSL1 protein levels to extent of parent cells (FIGS. 2C and 2D). Notably, ARV-R cells showed minimal levels of BRD3 following chronic exposure (FIG. 2D). Cells chronically exposed to JQ1 (JQ1-R) were unaffected by increasing doses of JQ1, and JQ1-treatment failed to reduce BRD4 target FOSL1 (FIGS. 9A and 9B). Characterization of BBD-R cells revealed BRD4 protein levels remained reduced in MZ1-R cells and BRD2, BRD3 and BRD4 reduced in ARV-R cells relative to parental cells (FIGS. 2E and 2F). Removal of BBDs from MZ1-R or ARV-R cells restored BET protein levels to those observed in parental cells and knockdown of CRBN (ARV-R) or VHL (MZ1-R) restored BET protein levels in BBD-R cells, demonstrating some degree of PROTAC degradation was still occurring in BBD-R cells (FIGS. 2E, 2F, 9C, and 9D). Genetic deletion of CRBN or CUL2, which is ubiquitin ligase recruited by VHL-based BBDs, was recently reported as resistance mechanisms to BBDs. Here, no significant reductions in RNA levels of CRBN were observed in ARV-R cells, though a slight reduction in CRBN protein relative to parental cells was detected by western blot (FIGS. 9E and 9F). CUL2 protein levels were unchanged in MZ1-R cells, while VHL RNA and protein levels showed a minor reduction relative to parental cells. No change in the CRBN-recruiting ubiquitin ligase CUL4 protein levels were detected in ARV-R cells (FIGS. 9E and 9F).

An increase in BRD2, BRD3 and BRD4 RNA levels was observed in MZ1-R and ARV-R cells relative to parental cells, while JQ1-R cells showed elevated BRD2 and BRD3 RNA levels, demonstrating chronic BBD treatment uniquely induced transcription of BRD4 (FIG. 9F). Importantly, MZ1-R and ARV-R cells retained reliance on residual BRD4 protein and acquired dependency on BRD2, where knockdown of BRD2, BRD4 or both significantly reduced cell viability in BBD-R cells (FIG. 2G). Moreover, depletion of BRD2 and/or BRD4 induced apoptosis and blocked BRD4-regulated MYC and FOSL1 signaling in MZ1-R cells (FIG. 2H). Knockdown of BRD2 reduced RAF, MEK and ERK activity in MZ1-R cells, suggesting BRD2 may have unique function contributing to MZ1 resistance through promoting MAPK signaling (FIG. 9G). Consistent with previous studies, knockdown of BRD4 in JQ1-R cells and to a lesser extent BRD2 also inhibited cell growth, demonstrating acquired resistance to either BBD or BBIs required BRD4 protein (FIG. 2G).

Further analysis of BBD-R cells revealed MZ1-R cells were cross-resistant to ARV-771, another VHL-based BET-PROTAC that utilized OTX015 as a warhead (FIG. 2I). Of particular interest, treatment of MZ1-R cells with CRBN-based PROTACs ARV825 (OTX015-based) or dBET6 (JQ1-based) reduced BET proteins, inhibited cell viability and promoted apoptosis, demonstrating the CRBN-based degradation machinery remained functional and could be exploited to degrade BRD4 overcoming MZ1 resistance (FIGS. 2J, 2K, 9H, and 9I). Similarly, ARV-R cells also showed cross resistance to other CRBN-based BBDs, dBET6, however, in contrast to MZ1-R cells, treatment of ARV-R cells with VHL-based MZ1 or ARV-771 failed to reduce BET proteins, block growth or induce apoptosis, demonstrating ARV-R cells were resistant to both VHL and CRBN-based BET PROTACs (FIGS. 2L, 2M, 2N, and 9J).

MZ1-R or ARV-R cells were shown to be sensitive to BET inhibition by JQ1, where increasing concentrations of JQ1 reduced cell viability to a greater extent than parental cells, suggesting the BET bromodomain function of BRD2 and BRD4 was essential for cell growth and survival of BBD-R cells (FIGS. 2O, 2P, and 9J). Resistance to BBI has been shown to occur though BET bromodomain independent functions such as interactions with MED1 rendering BBI-resistant cells sensitive to BRD4 knockdown. Treatment of JQ1-resistant OC cells with MZ1 or ARV825 degraded BET proteins, inhibited cell viability, reduced MYC/FOSL1 protein levels and induced apoptosis; demonstrating BBDs can overcome acquired resistance to BBIs (FIGS. 2Q, 2R, and 9K). PEO1 ovarian cancer cells that have acquired resistance to BET inhibitor JQ1 can be killed by treatment with BET PROTAC MZ1 but not other BET inhibitors such as JQ1, AZD5153 or OTX015 (FIG. 9L).

Figure 3:
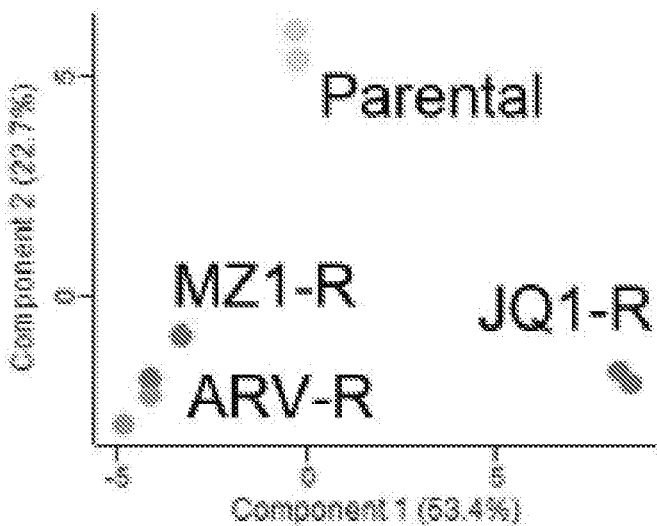
FIG. 3A shows principal component analysis of MIB-MS kinome profiles of OVCAR8 parental, JQ1-R, MZ1-R or ARV-R cells; kinase log 2 SILAC ratios were determined by comparing ratio of ratios sample/s-SILAC reference.
FIG. 3B shows Pearson correlation analysis of MIB-determined kinome profiles of MZ1-R relative to JQ1-R were determined using Perseus Software.
FIG. 3C shows kinome remodeling to chronic MZ1 treatment; Volcano plot depicts SILAC-determined log 2-fold changes in MIB-binding as a ratio of MZ1-R/Parental; statistical changes in MIB-binding were determined by paired T-Test (P<0.05) using Perseus Software.
FIG. 3D shows remodeling of the kinome similar following continuous exposure to VHL or CRBN-based BBDs; scatterplot depicts SILAC-determined log 2-fold changes in MIB-binding as a ratio of MZ1-R/Parental or ARV-R/Parental; statistical changes in MIB-binding were determined by paired T-Test (P<0.05) and Pearson correlation of MZ1-R and Pearson correlation of MZ1-R and ARV-R kinome responses determined using using Perseus Software.
FIG. 3E shows volcano plot depicting kinases predicted to be activated or inhibited in response to chronic MZ1 treatment using Kinase Substrate Enrichment Analysis (KSEA); phosphoproteomics datasets were queried using PhosphoSitePlus at p value cutoff (0.05) and NetworkKIN score cutoff of 2; statistical differences in log 2 ratios of phosphosites comparing MZ1-R/s-SILAC relative to parental/s-SILAC were determined by paired T-Test, Benjamini-Hochberg adjusted p values at FDR of <0.05.
FIG. 3F shows upregulation of INSR and ERBB3 phosphorylation in MZ1-resistant cells; changes in RTK tyrosine phosphorylation comparing MZ1-R and Parental cells was assessed by RTK array.
FIG. 3G shows increased INSR and downstream mTOR signaling in MZ1-R cells; parental and MZ1-R OVCAR8 cells protein levels were determined by Western blot.
FIG. 3H shows candidate therapeutic kinase targets in BBD-R cells; kinome activation signature of OVCAR8 BBD-R cells was determined by MIB-MS and KSEA.
Figure 3:
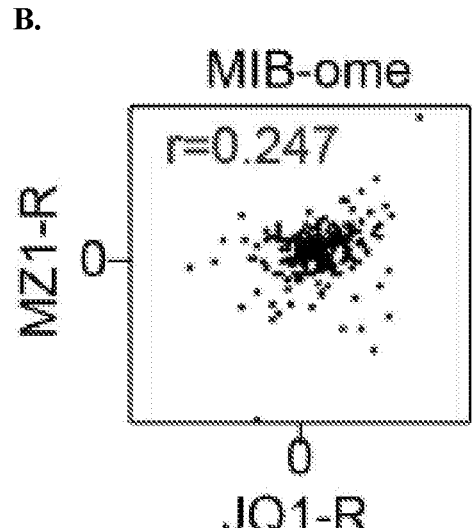
Figure 3:
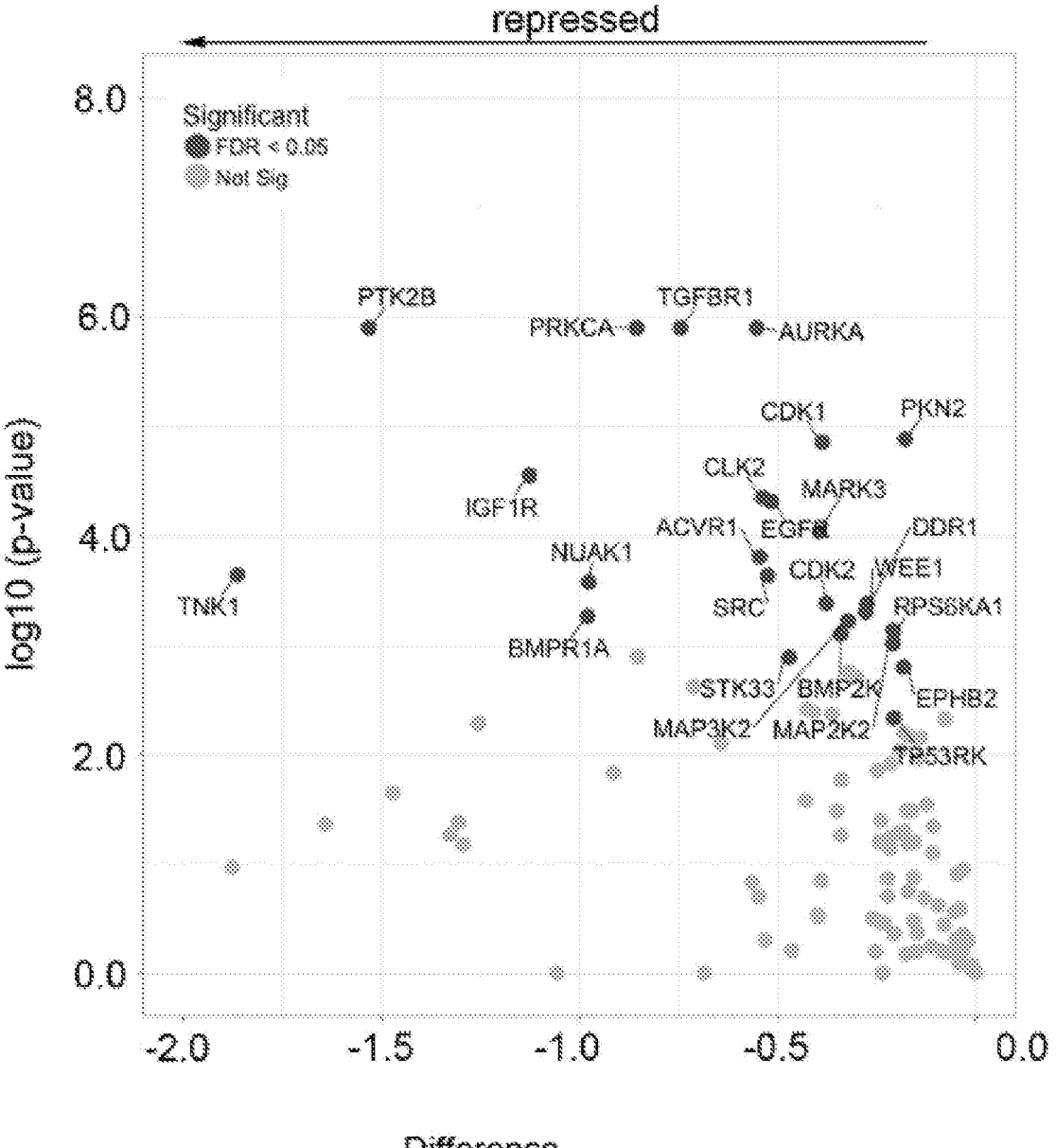
Figure 3:
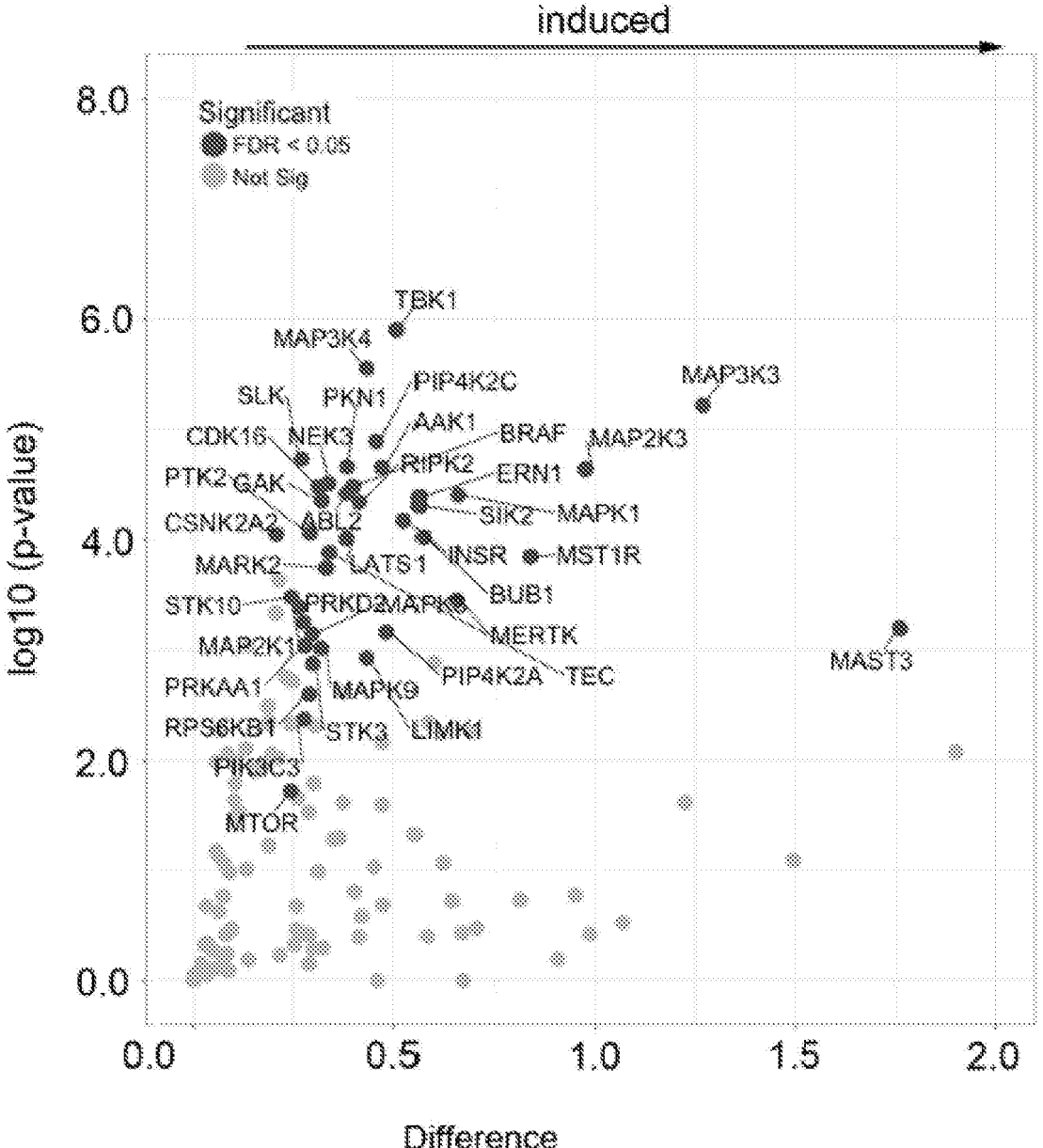
Figure 3:
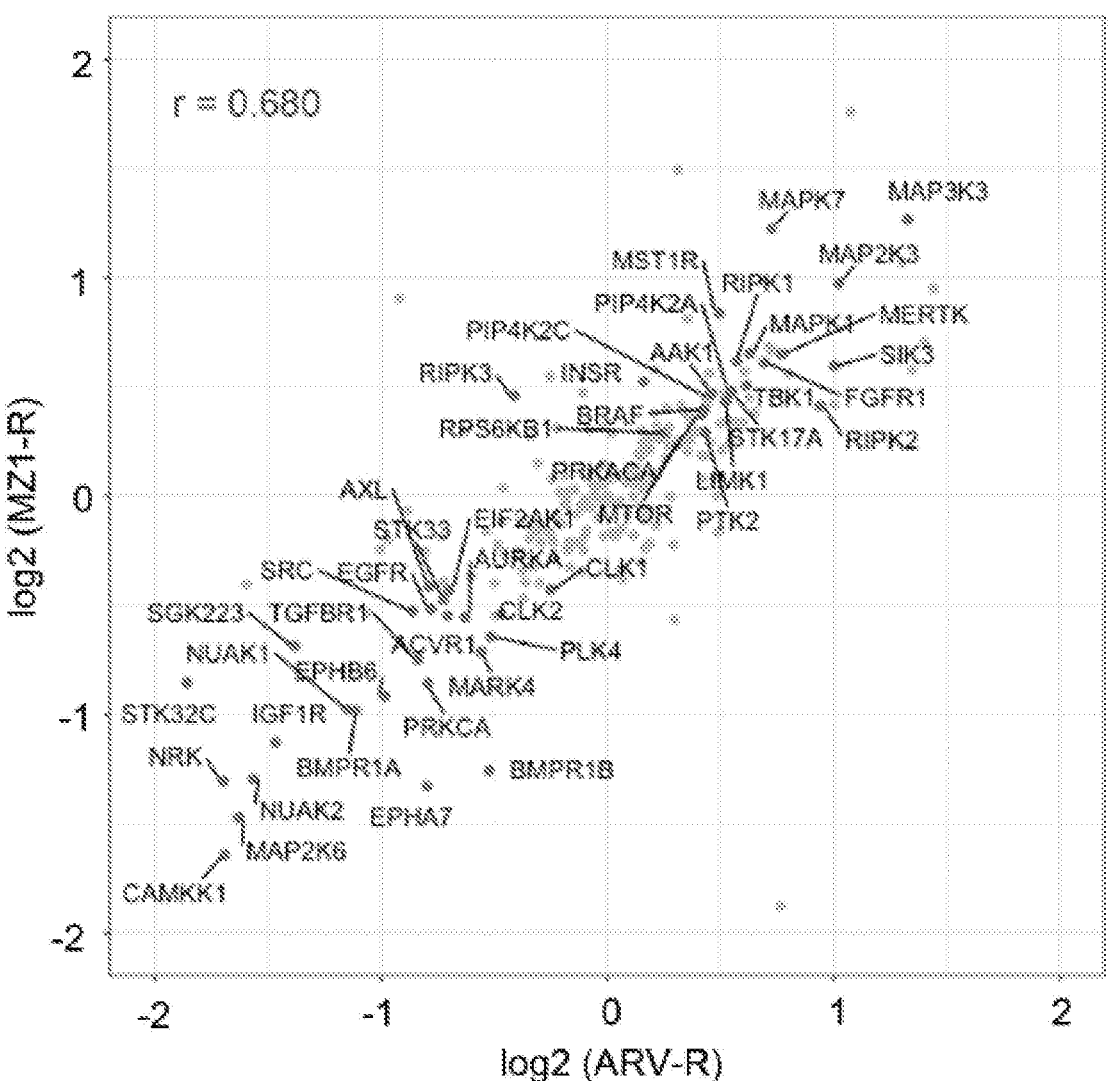
Figure 3:
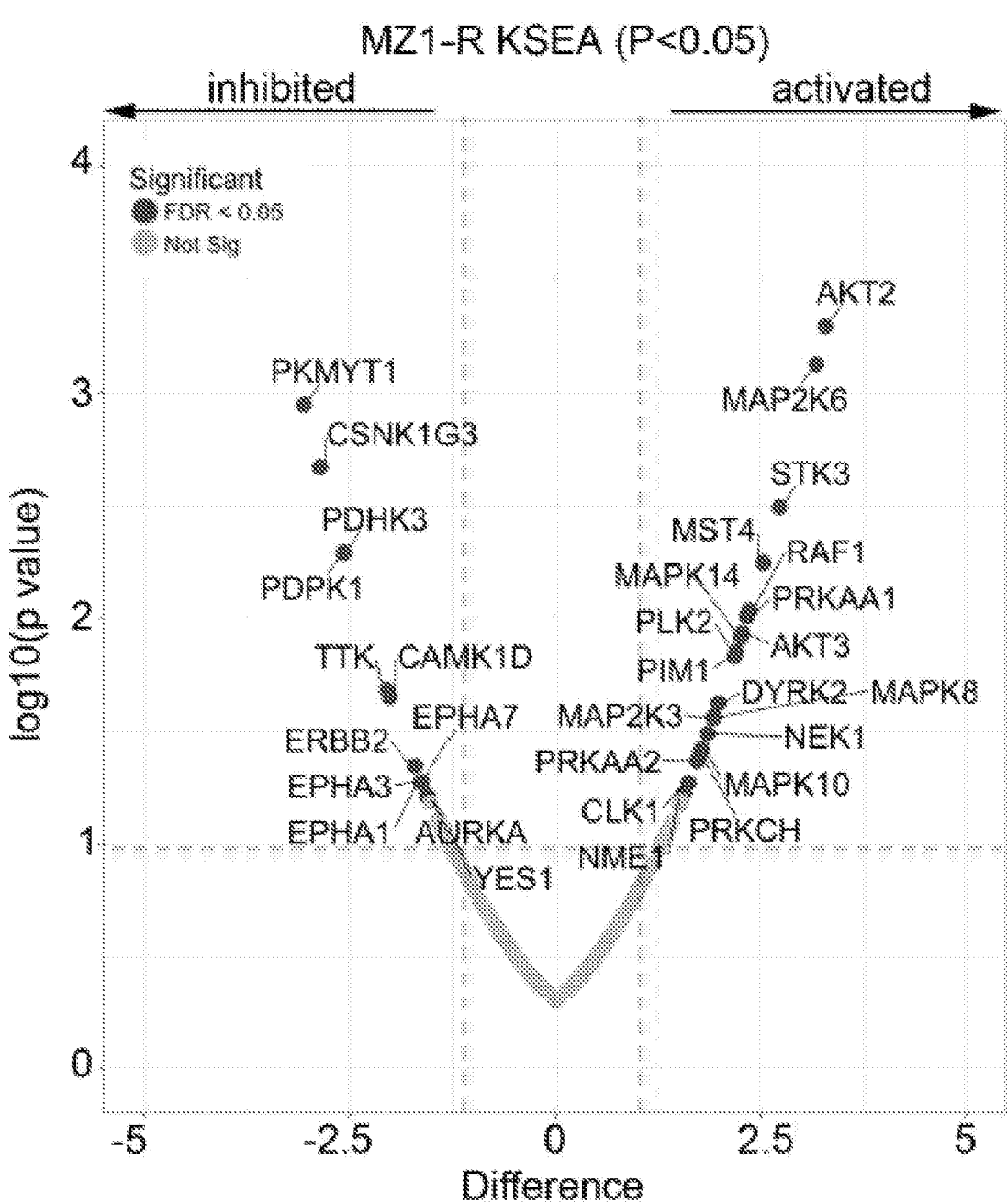
Figure 3:
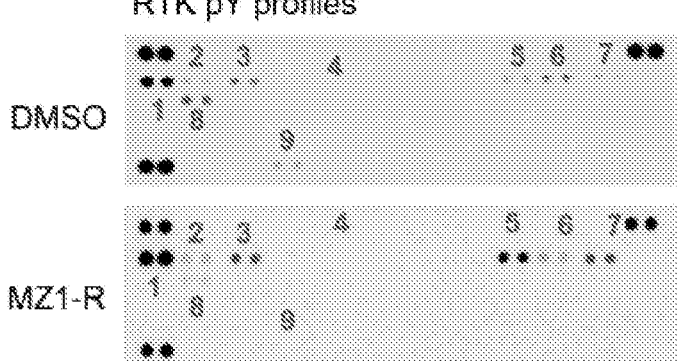
Figure 3:
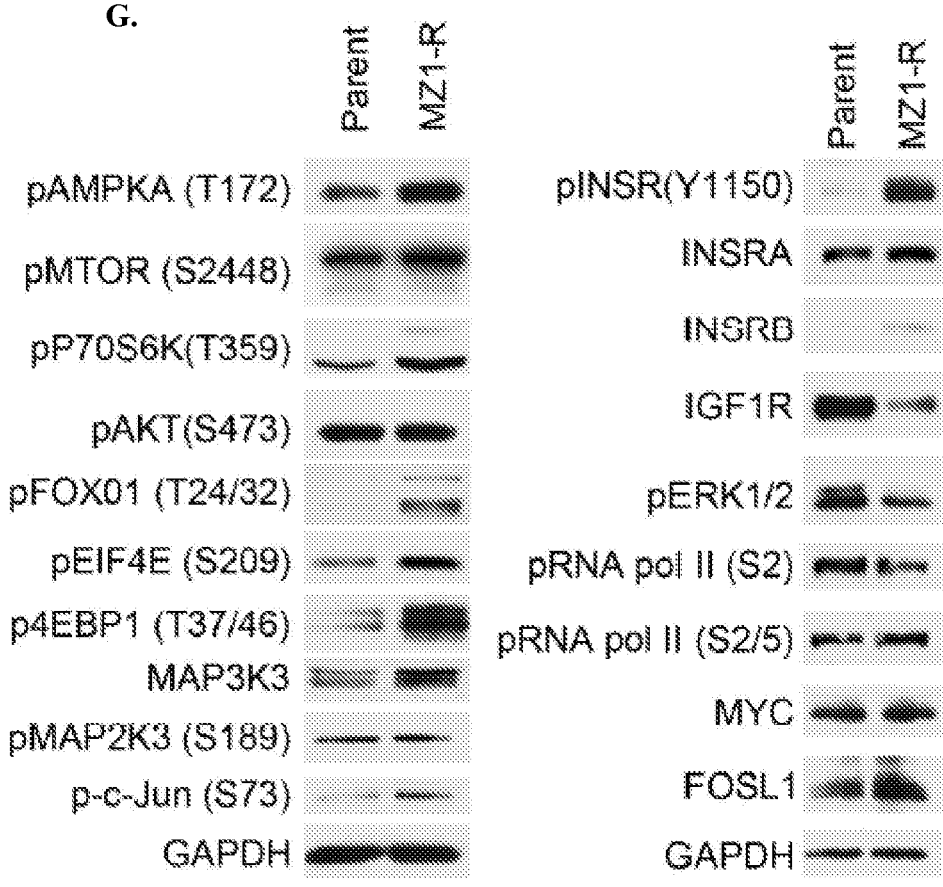
Figure 3:
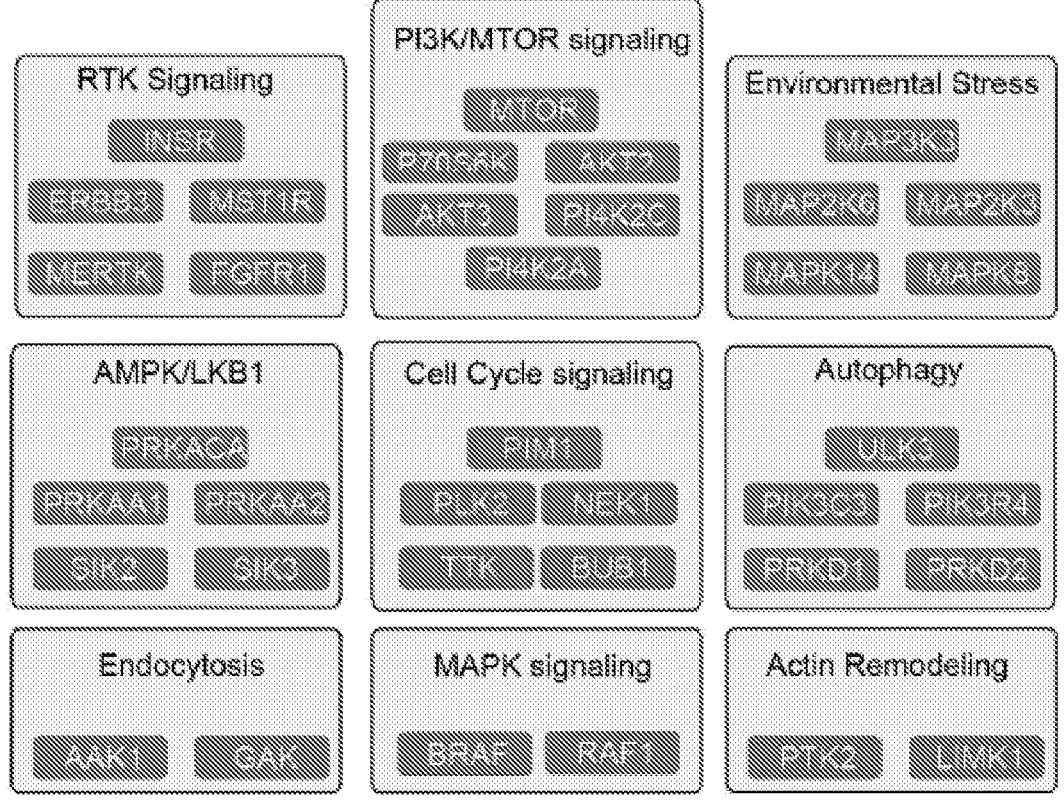

Example 3: Chronic BBD Therapy Remodels Kinome in OC Cells Upregulating INSR and mTOR/AKT Signaling To explore the mechanistic basis for acquired resistance to BBDs, kinome, phosphoproteome and global proteome profiling of BBD and BBI-resistant OVCAR8 cells were carried out. PCA and Pearson correlation analysis revealed MZ1-R and ARV-R kinome signatures were overall distinct from JQ1-R or parental OVCAR8 cells (FIGS. 3A and 3B). Volcano plots depict kinases exhibiting statistically significant changes in MIB-binding following chronic exposure to MZ1, ARV825 or JQ1 relative to parental OVCAR8 cells (FIGS. 3C, 10A, and 10B). Notably, MZ1-R and ARV-R kinome signatures were highly similar (r=0.680), with the majority of kinases commonly induced or repressed, demonstrating resistance to CRBN or VHL-based BET PROTACs elicited similar kinome adaptations (FIGS. 3D and 10C).

Figure 10:
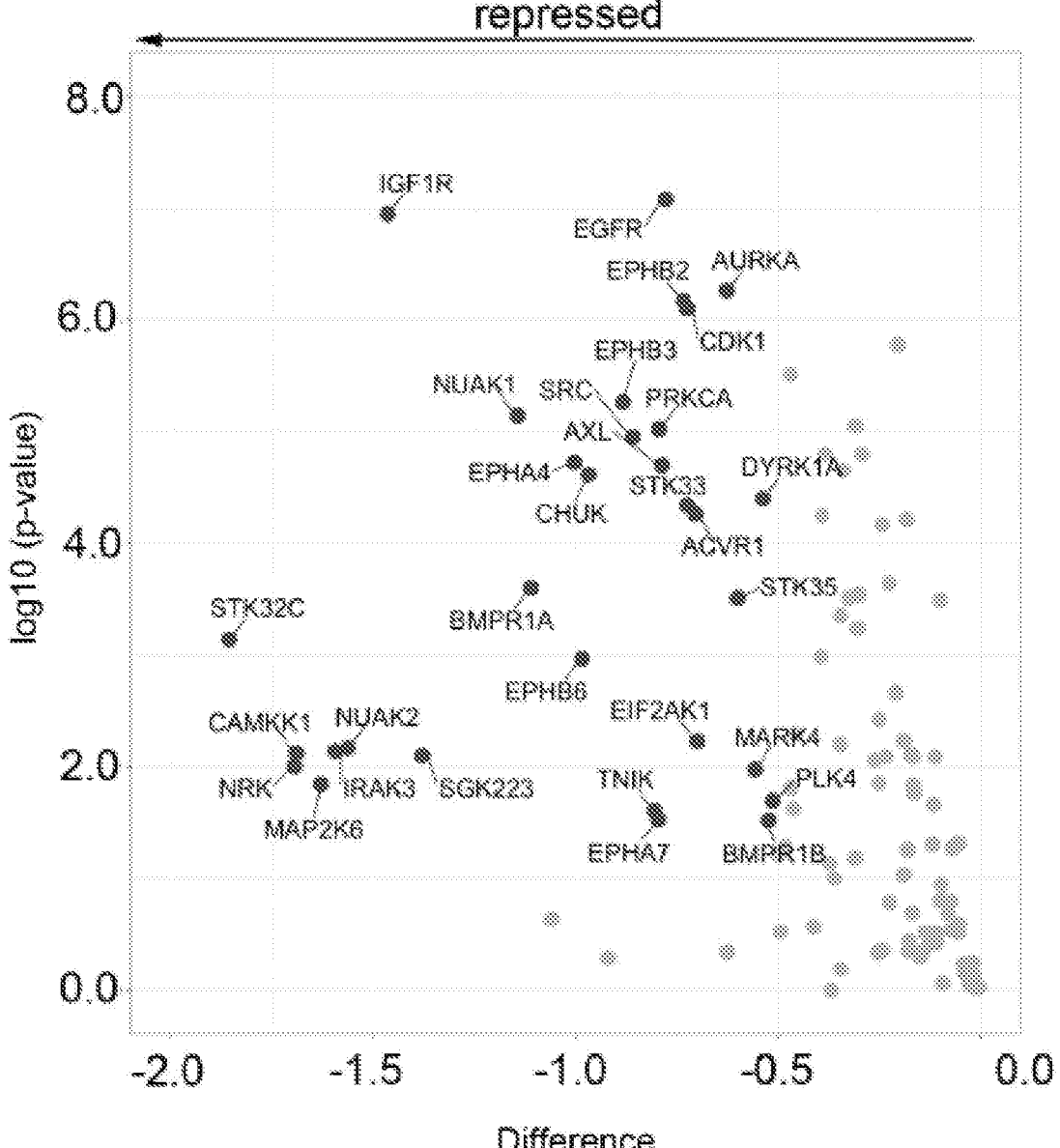
FIG. 10A shows ARV-R I Parental MIB-signature.
FIG. 10B shows JQ1-R I Parental MIB-signature.
FIG. 10C shows ARV-R and MZ1-R MIB-MS kinome profiles cluster together and are distinct from JQ1-R or parental cells as shown by PCA and hierarchical clustering.
FIG. 10D shows KEGG pathway analysis of kinases exhibiting induced MIB-binding in JQ1-R cells relative to parental cells.
FIG. 10E shows common MIB-signature MZ1-R and JQ1-R.
FIG. 10F shows KEGG pathway analysis of kinases exhibiting induced MIB-binding in MZ1-R cells relative to parental cells.
FIG. 10G shows KEGG pathway analysis of proteins reduced in MZ1-R cells relative to parental cells (P<0.05).
Figure 10:
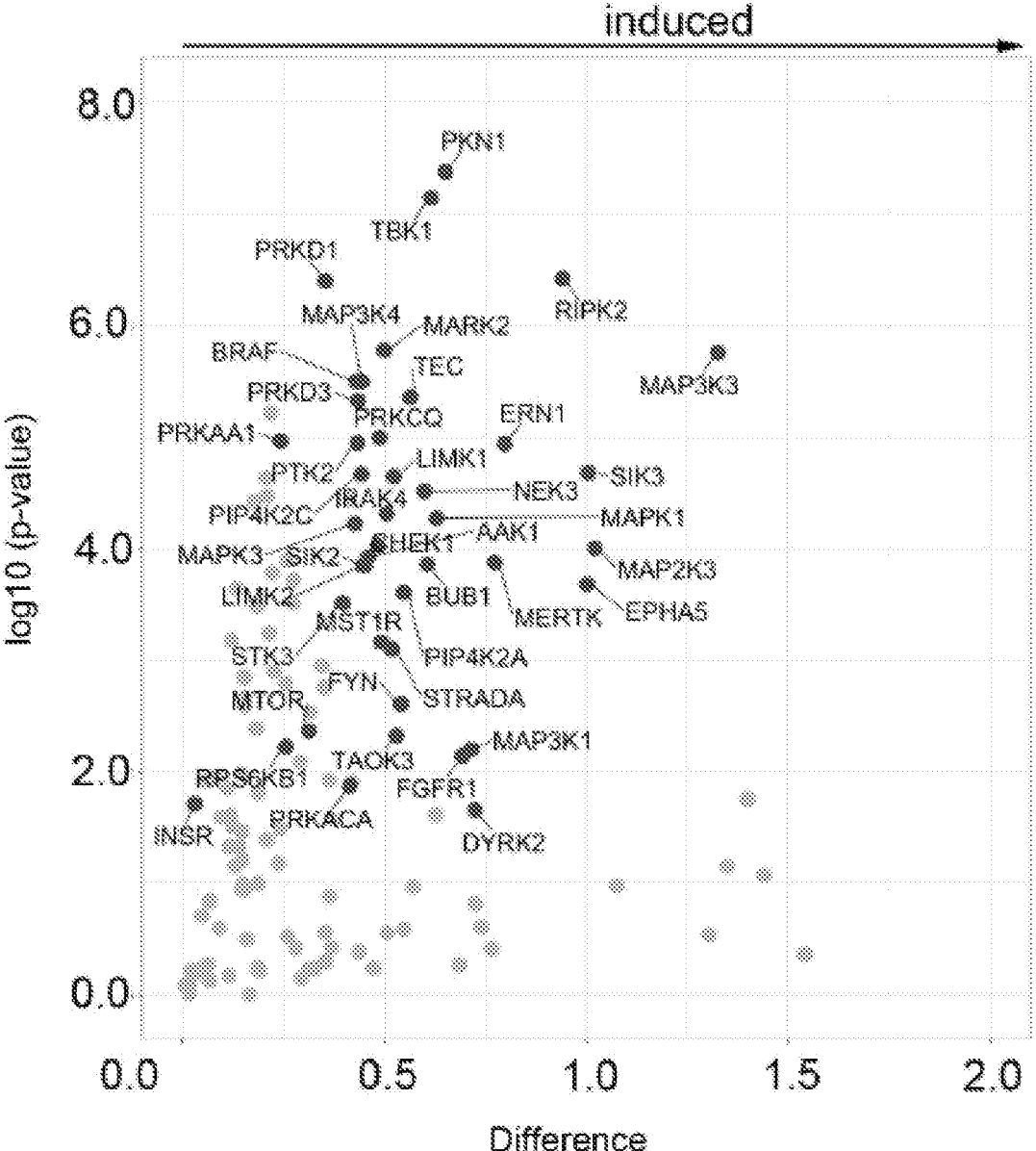
Figure 10:
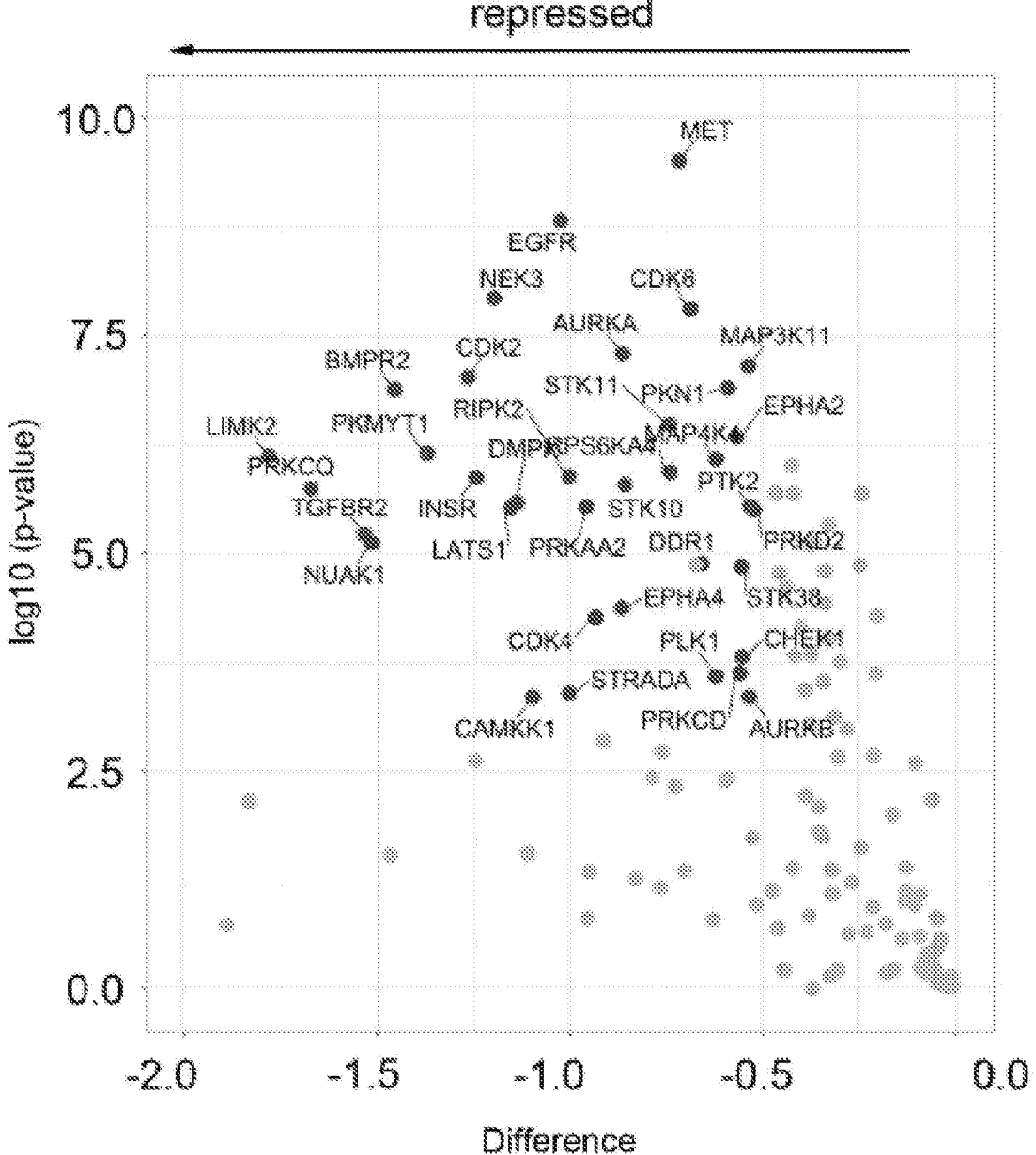
Figure 10:
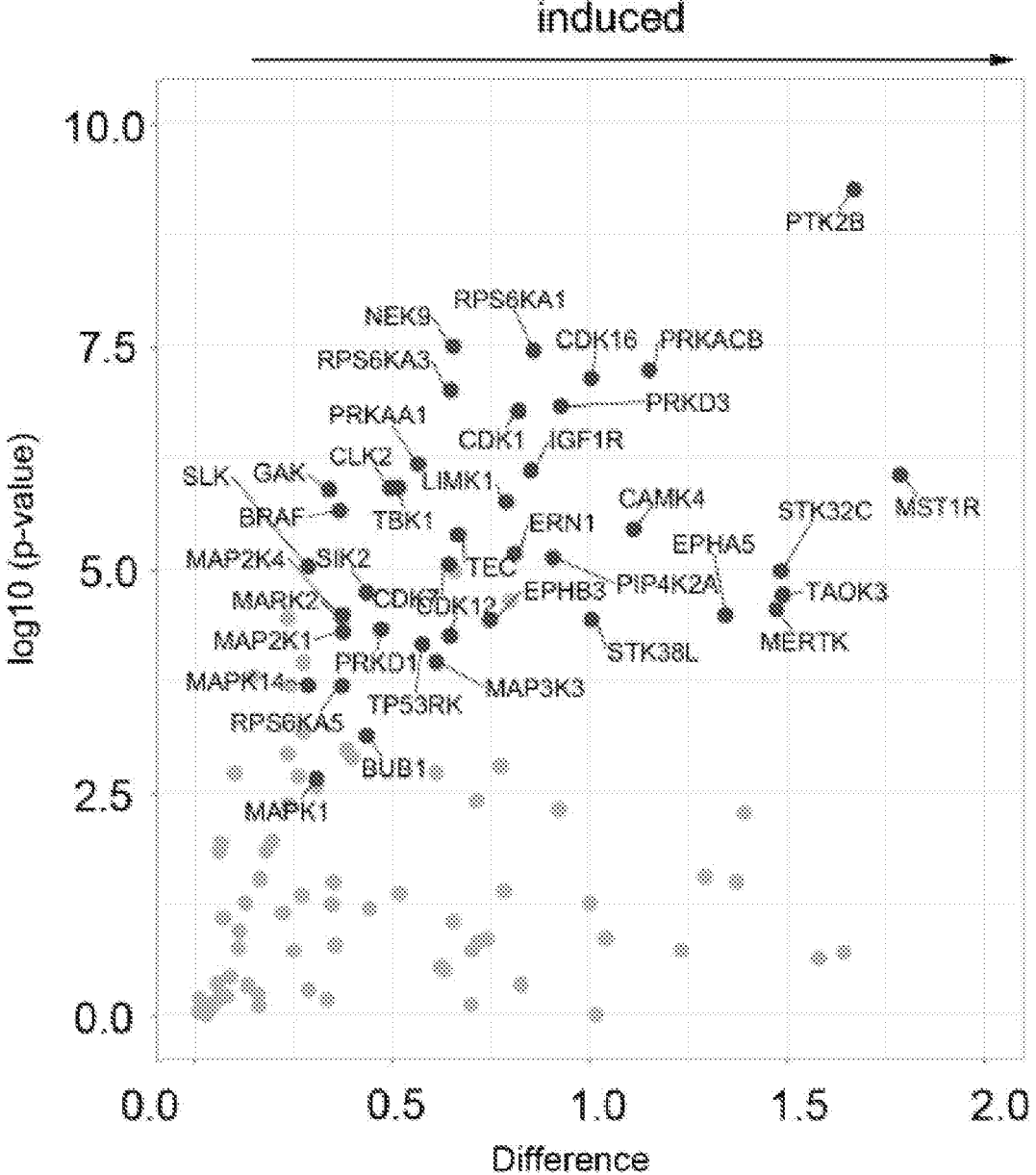
Figure 10:
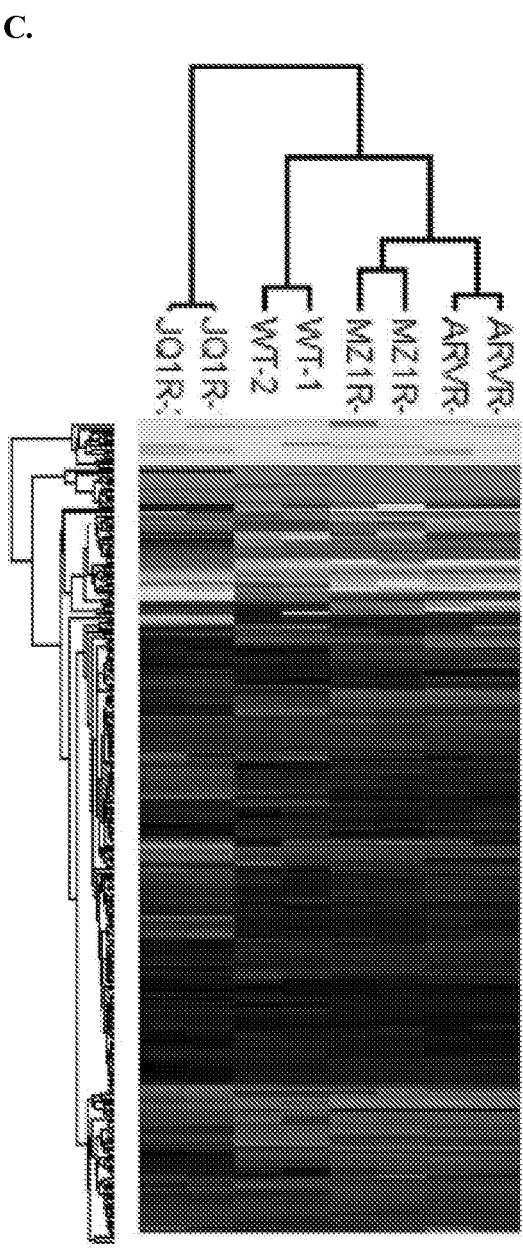
Figure 10:
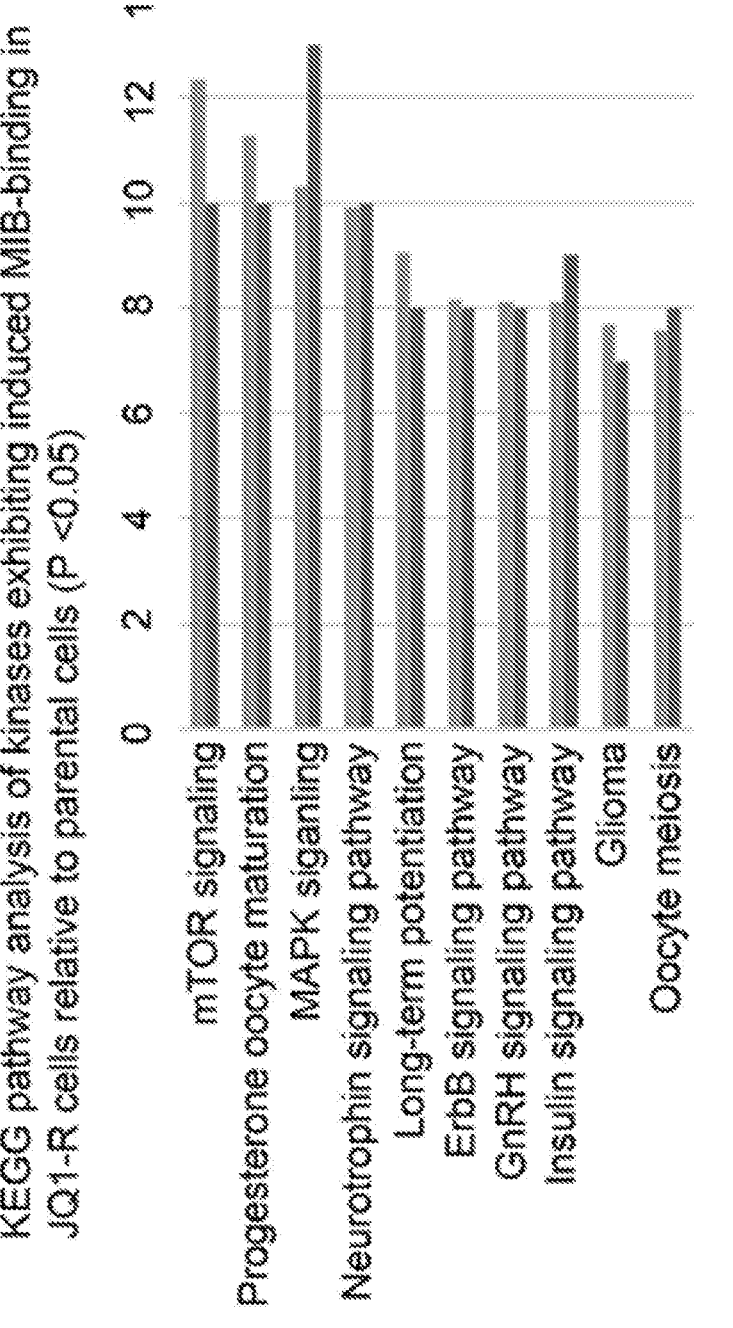
Figure 10:
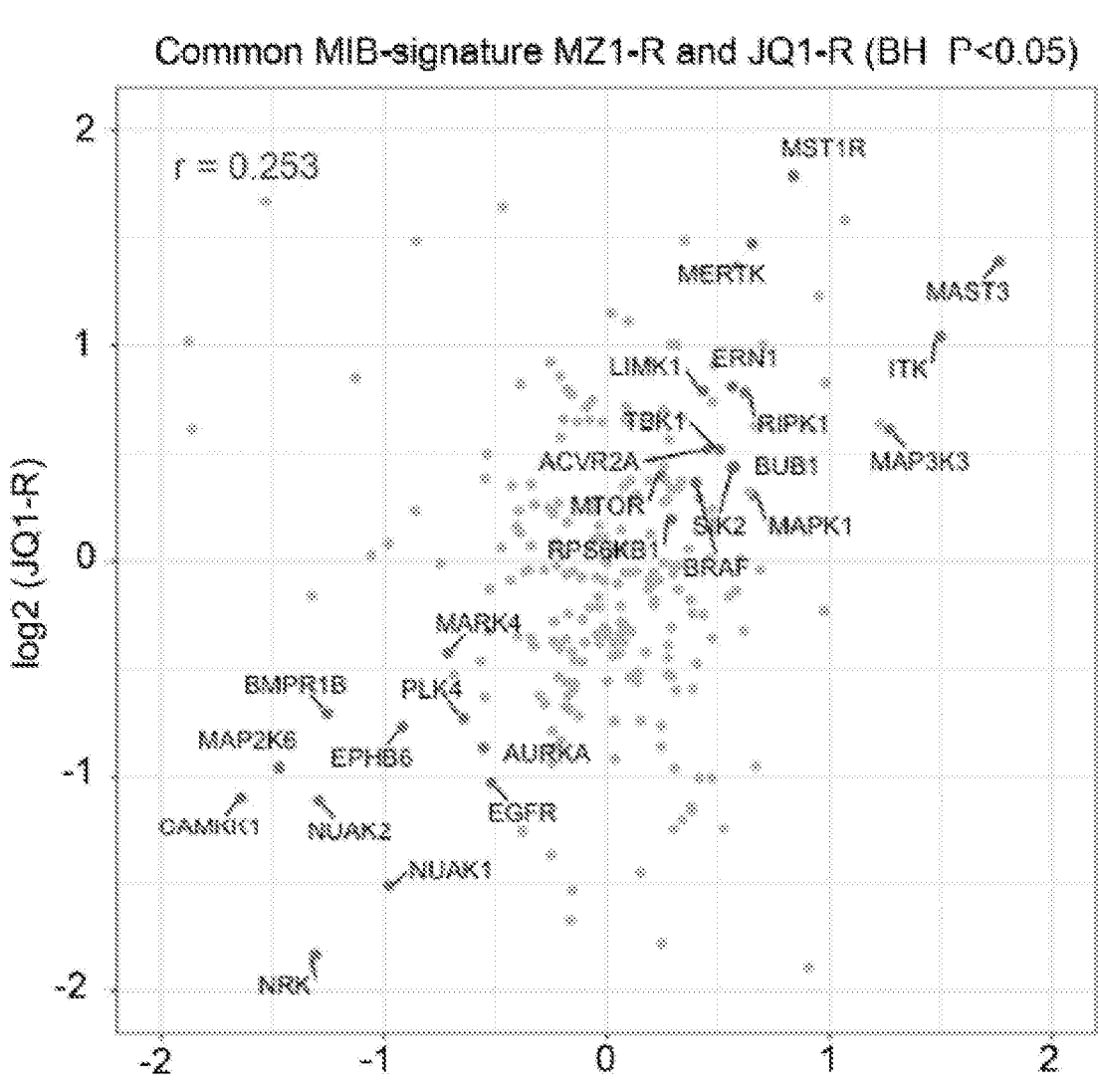
Figure 10:
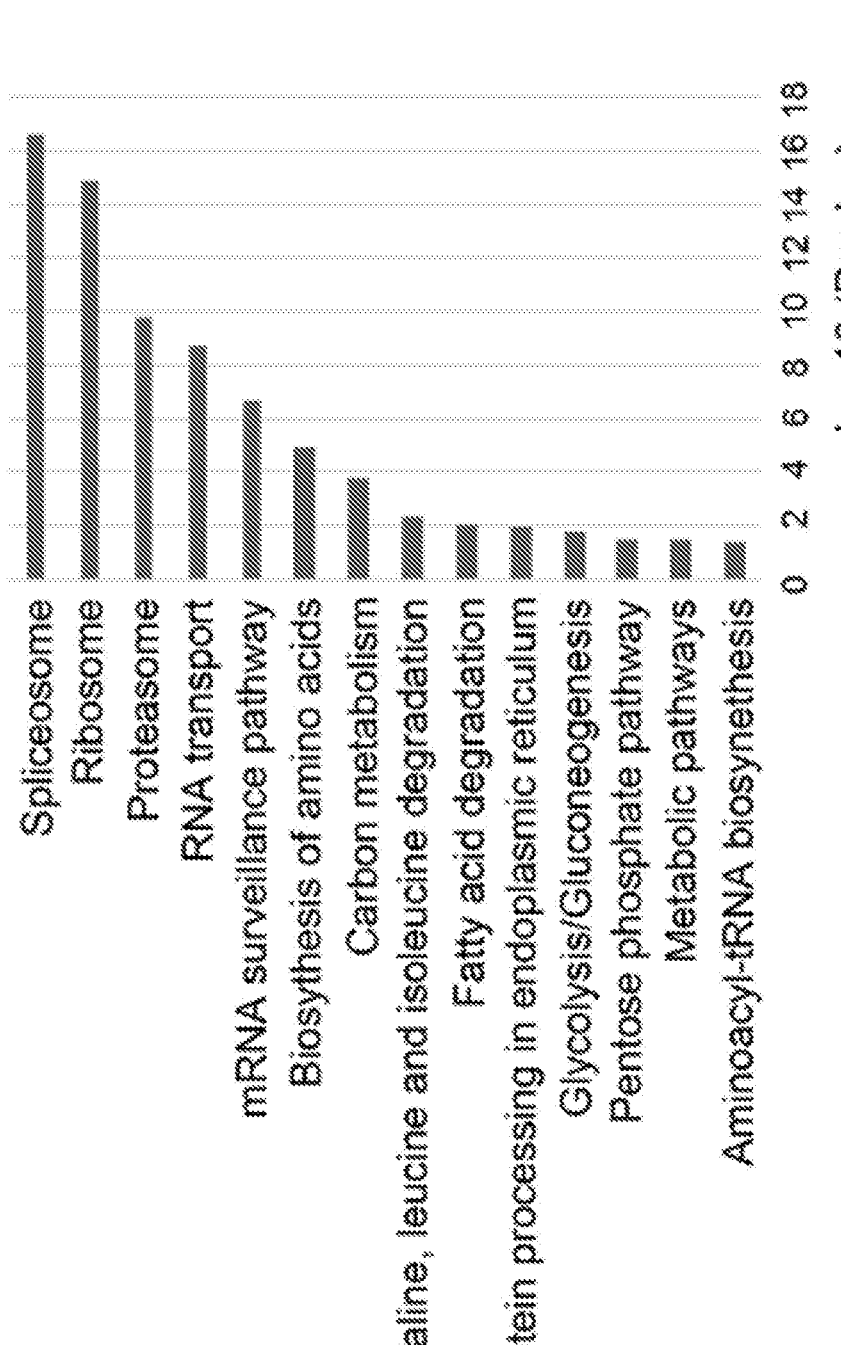

Chronic exposure to JQ1 increased MIB-binding of kinases associated with IGF1R, PI3K, mTOR, MAPK, and ErbB signaling (FIG. 10D). Similarly, increased MIB-binding of MTOR, RPS6KB1, BRAF, and MAPK1 were detected in BBD-R cells relative to parental cells, demonstrating mTOR and MAPK signaling were commonly activated by chronic BBI or BBD treatment (FIG. 10E). KEGG and STRING pathway analysis of kinases commonly unregulated in MZ1-R and ARV-R cells revealed a network enriched in mTOR signaling, insulin signaling, regulation of actin cytoskeleton, PI3K-AKT signaling, and FoxO signaling, as well as LKB1/AMPK, NF-KB, environmental stress, hippo signaling, golgi trafficking, endocytosis and autophagy signaling (data not shown). Consistent MIB-MS profiles, kinase substrate enrichment analysis (KSEA) of alterations in global phosphorylation following chronic exposure to MZ1, predicted activation of kinases involved in PI3K/AKT signaling (AKT2/3), AMPK signaling (PRKAA1/PRKAA2), hippo signaling (STK3/MST4), cell cycle signaling (PIM1, PLK2 and NEK1), as well as several kinases involved in environmental stress (MAP2K6, MAP2K3, MAPK8, MAPK14 and MAPK10) (FIG. 3E). Similarly, single-run proteome profiling of MZ1-R or parental cells showed chronic MZ1 exposure induced proteins involved in translation, mitochondrial translation, metabolism of proteins, membrane trafficking, vesicle-mediated transport, clathrin-mediated endocytosis, RHO GTPase signaling, cellular response to stress, infection signaling, and trans-golgi network vesicle budding. Proteins reduced by chronic MZ1-treatment were enriched in metabolism of RNA, RNA transport, RNA splicing, ribosome, and proteasome signaling (FIG. 10G).

Receptor tyrosine kinase (RTK) array profiling and Western blot analysis confirmed activation of INSR in MZ1-R cells relative to parental cells (FIGS. 3F and 3G). An increase in EGFR, ERBB3 and AXL tyrosine phosphorylation was also observed by RTK array analysis in MZ1-R cells relative to parental cells (FIG. 3H). Elevated phosphorylation of MTOR (S2448) and translation components p70S6K (T359), pEIF4E (S209) and p4EBP1 (T37/46), as well AKT-substrate FOX01 (T24/32) were confirmed by western blot, consistent with predicted activation of mTOR/PI3K and translation signaling by proteomics analysis (FIG. 3G). Additionally, increased protein levels of MAP3K3 and phosphorylated c-Jun (S73), as well as PRKAA1 (AMPKa) were detected in MZ1-R cells, signifying increased cellular stress response and AMPK signaling. Phosphorylated RNA pol II at (S2), MYC and FOSL1, which were rapidly lost by short-term MZ1-treatment, were detected by blot at similar levels in MZ1-R and parental cells, consistent with the return of BRD4 function in MZ1-R cells.

Collectively, proteomic analysis revealed chronic exposure to BBDs remodeled the kinome of OVCAR8 cells distinctly from BBI therapies. BBD-resistant cells activated a network of kinases involved in insulin, PI3K/mTOR, translation, MAPK signaling, environmental stress, endocytosis, autophagy and AMPK signaling, representing potential therapeutic avenues to block or overcome BBD-resistance in OC cells (FIG. 3H).

Figure 4:
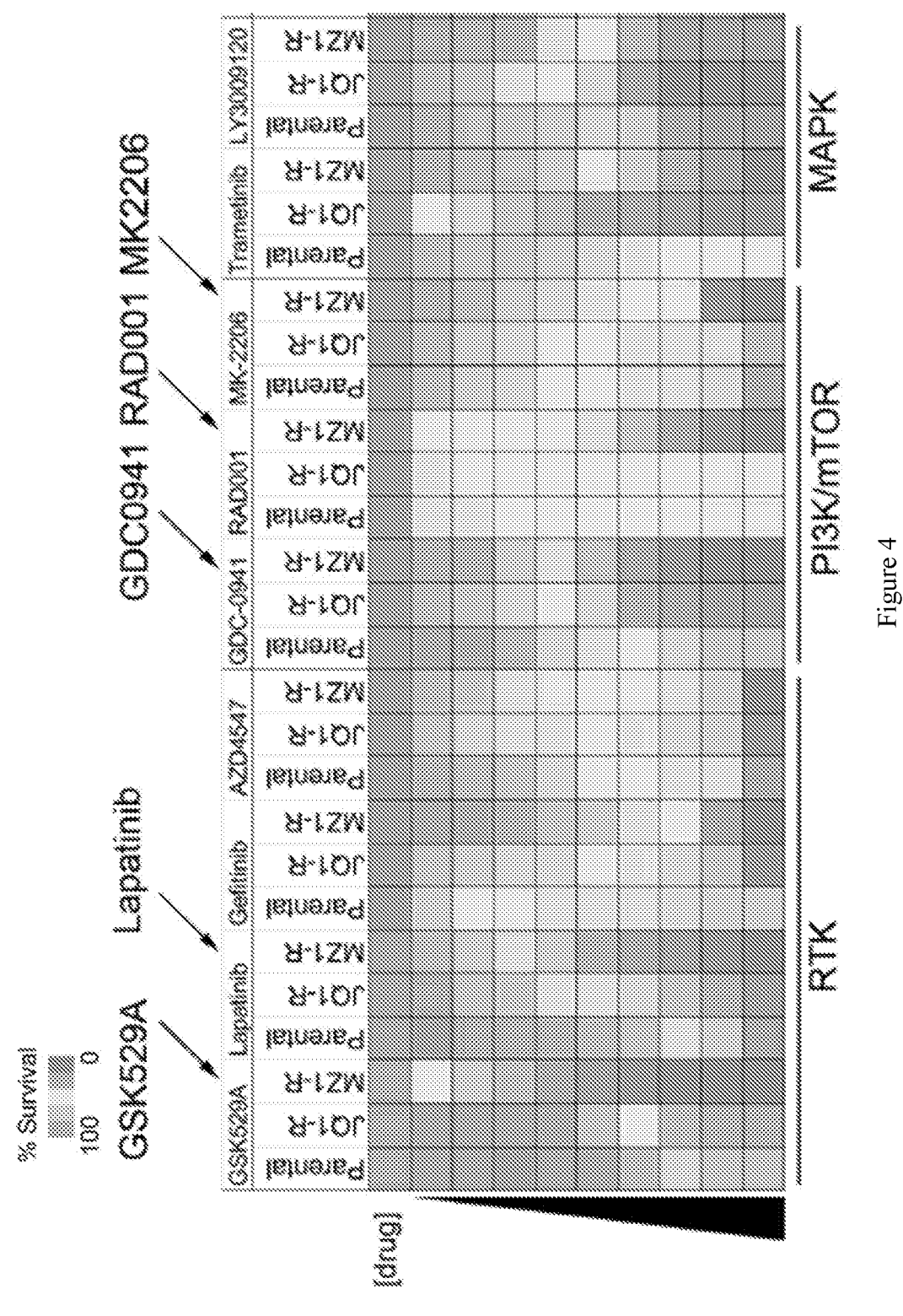
FIG. 4A shows that Chronic MZ1-treatment promotes increased sensitivity towards inhibitors targeting INSR, ErbB and MTOR pathways; parental, JQ1-R or MZ1-R cells were treated with escalating doses of inhibitors for 5 days and cell viability was assessed by CellTiter-Glo.
FIG. 4B shows that MZ1-R cells are more sensitive to INSR, ErbB or MTORC1 inhibition than JQ1-R or parental cells; parental, JQ1-R or MZ1-R OVCAR8 cells were treated with escalating doses of GSK1904529A for 5 days and cell viability was assessed by CellTiter-Glo; MZ1-R or JQ1-R inhibitor treated cell viabilities normalized to DMSO treated JQ1-R or MZ1-R cells, respectfully.
FIG. 4C shows parental, JQ1-R or MZ1-R OVCAR8 cells treated with escalating doses of lapatinib for 5 days and cell viability was assessed by CellTiter-Glo; MZ1-R or JQ1-R inhibitor treated cell viabilities normalized to DMSO treated JQ1-R or MZ1-R cells, respectfully.
FIG. 4D shows parental, JQ1-R or MZ1-R OVCAR8 cells treated with escalating doses of or RAD001 for 5 days and cell viability was assessed by CellTiter-Glo; MZ1-R or JQ1-R inhibitor treated cell viabilities normalized to DMSO treated JQ1-R or MZ1-R cells, respectfully.
FIG. 4E shows parental, JQ1-R or MZ1-R OVCAR8 cells treated with escalating doses of or MK2206 for 5 days and cell viability was assessed by CellTiter-Glo; MZ1-R or JQ1-R inhibitor treated cell viabilities normalized to DMSO treated JQ1-R or MZ1-R cells, respectfully.
FIG. 4F shows parental, JQ1-R or MZ1-R OVCAR8 cells treated with escalating doses of or NVP-2 for 5 days and cell viability was assessed by CellTiter-Glo; MZ1-R or JQ1-R inhibitor treated cell viabilities normalized to DMSO treated JQ1-R or MZ1-R cells, respectfully.
FIG. 4G shows acquired dependency on INSR, ErbB, MTOR and AKT signaling in MZ1-R cells; parental OVCAR8 cells or MZ1-R OVCAR8 cells were transfected with siRNAs targeting EGFR, ERBB2, INSR, IGF1R, MTOR or AKT1/2 and cultured for 72 hours; MZ1-R knockdown cells were normalized to MZ1-R cells transfected with non-targeting siRNA.
FIG. 4H shows that GSK529A-treatment blocks INSR and downstream MTOR, BRAF and cell cycle signaling; MIB-MS kinome profiles of OVCAR8 MZ1-R cells treated with GSK529A (1 µM) or DMSO for 48 hours; heat map depicts kinase log 2 LFQ z-scores; statistical differences in kinase log 2 LFQ z-scores comparing GSK529A-treated to control treated cells was determined by paired T-Test Benjamini-Hochberg adjusted p values at FDR of <0.05 using Perseus Software.
FIG. 4I shows treatment of MZ1-R cells with GSK529A blocks INSR and downstream MTOR, AKT and MAPK signaling; OVCAR8 MZ1-R cells were treated with escalating doses of GSK529A or DMSO for 48 hours and the activity of kinases was assessed by Western blot using phospho-antibodies.
Figure 4:
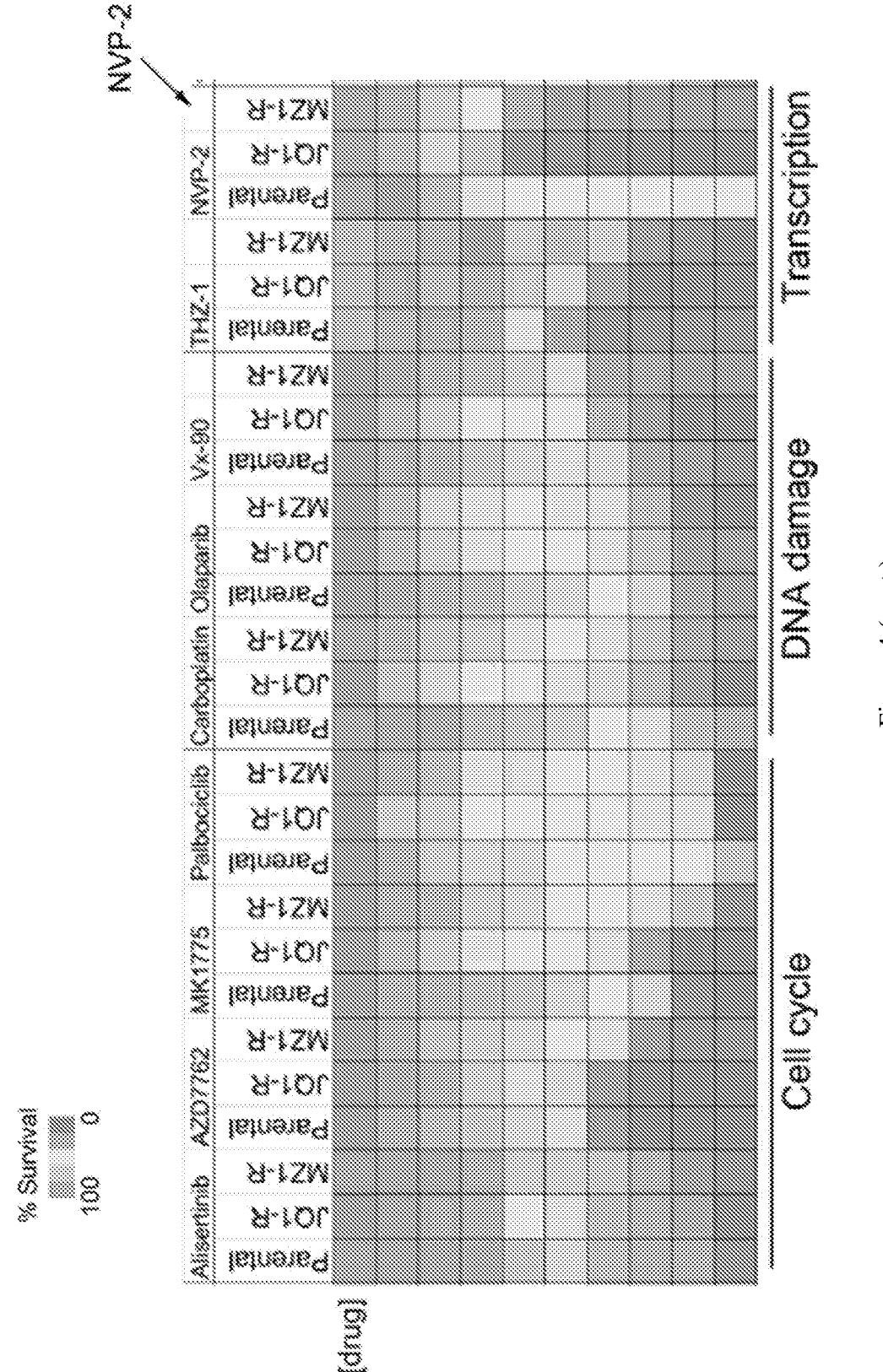
Figure 4:
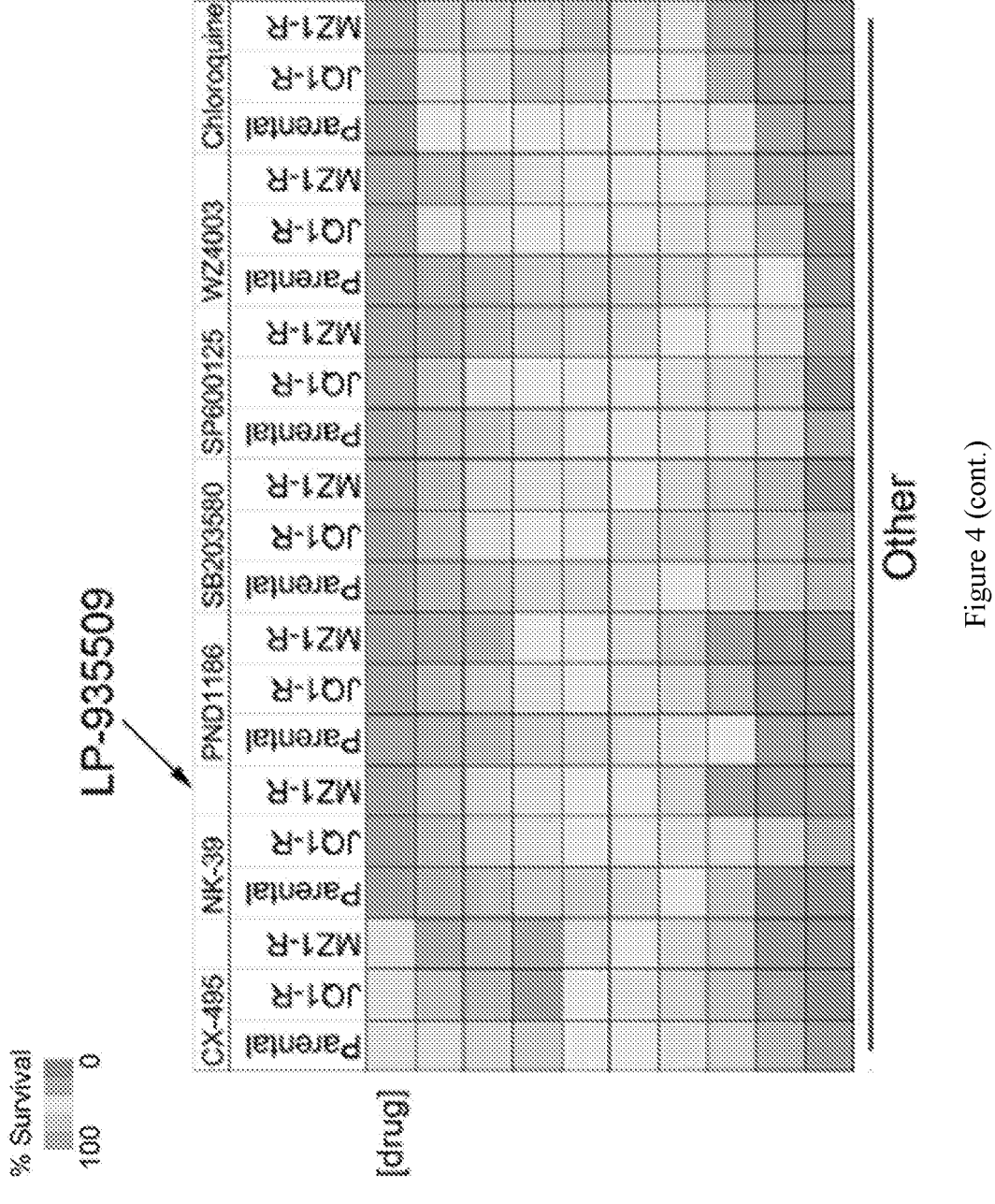
Figure 4:
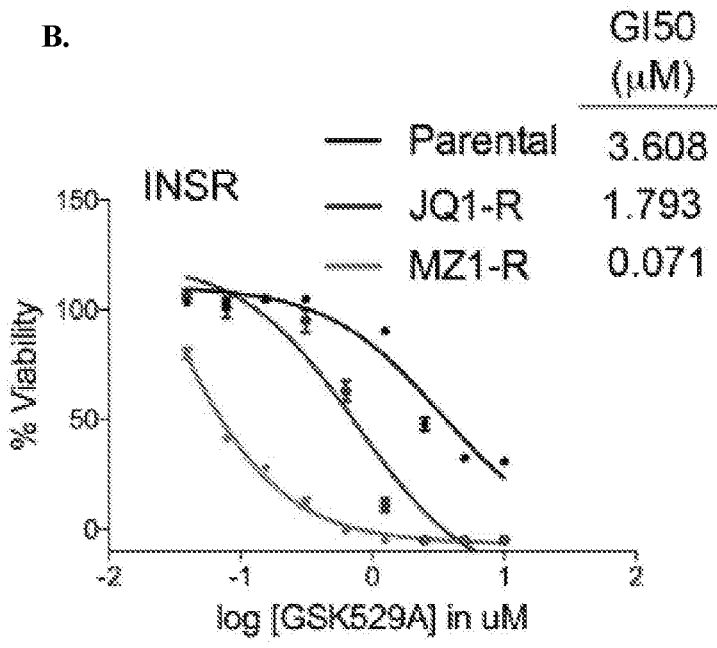
Figure 4:
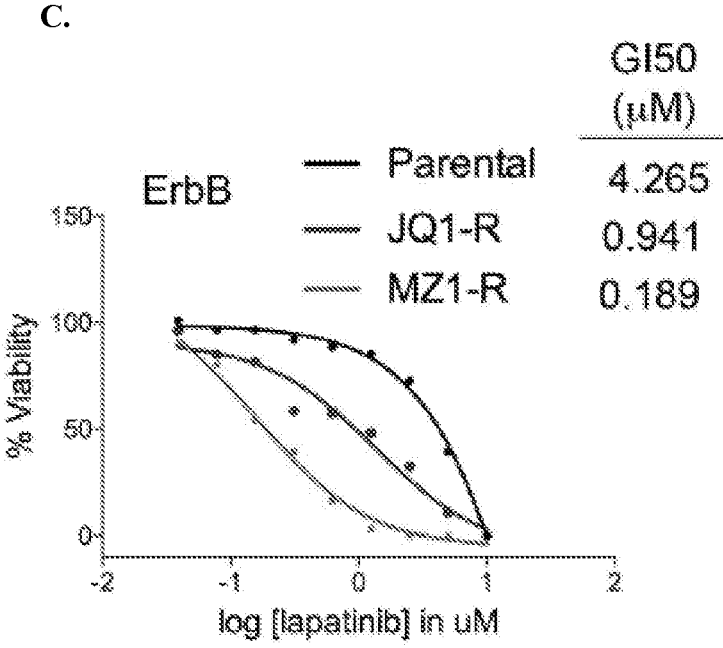
Figure 4:
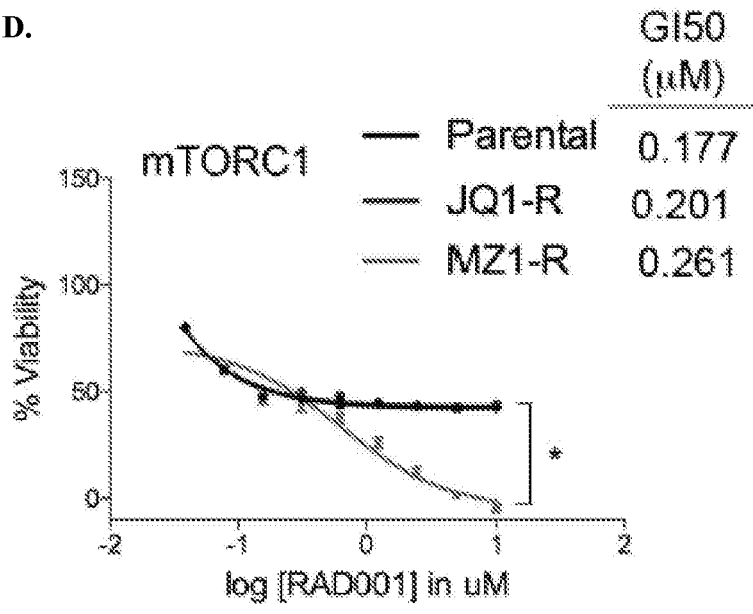
Figure 4:
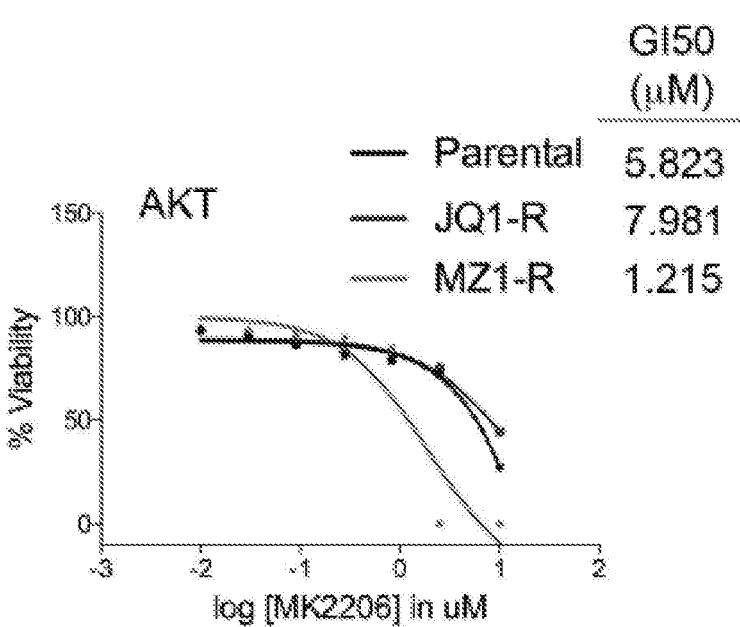
Figure 4:
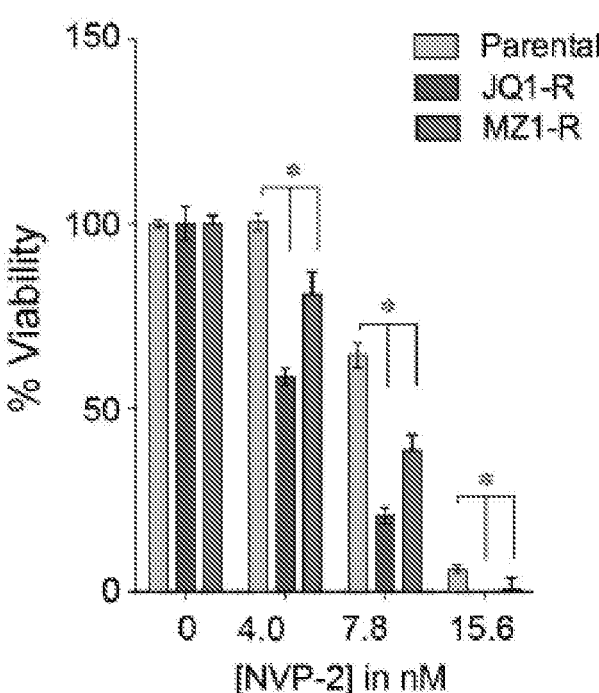
Figure 4:
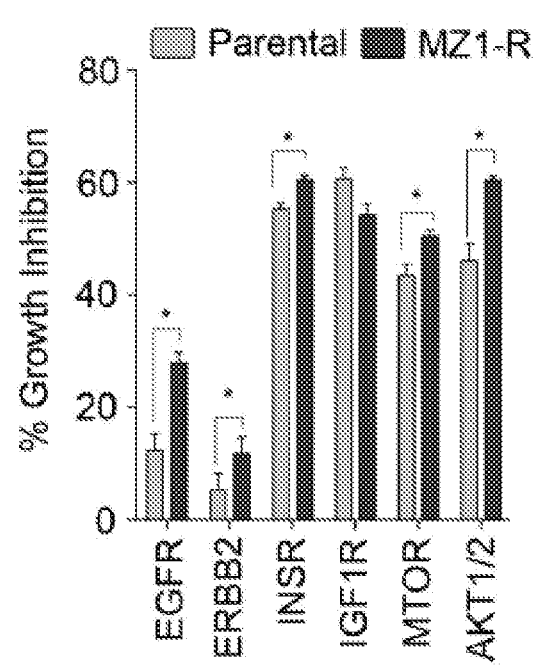
Figure 4:
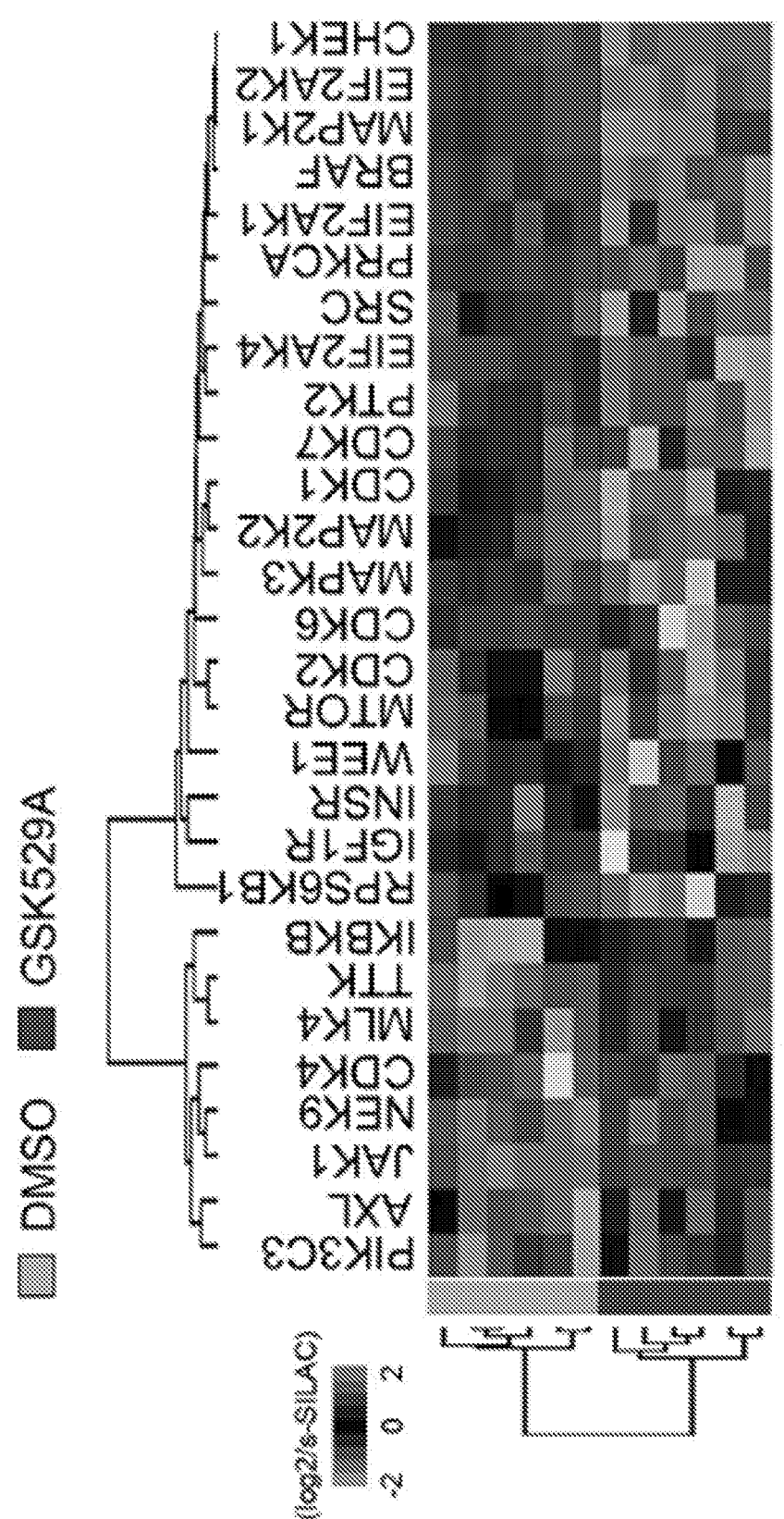
Figure 4:
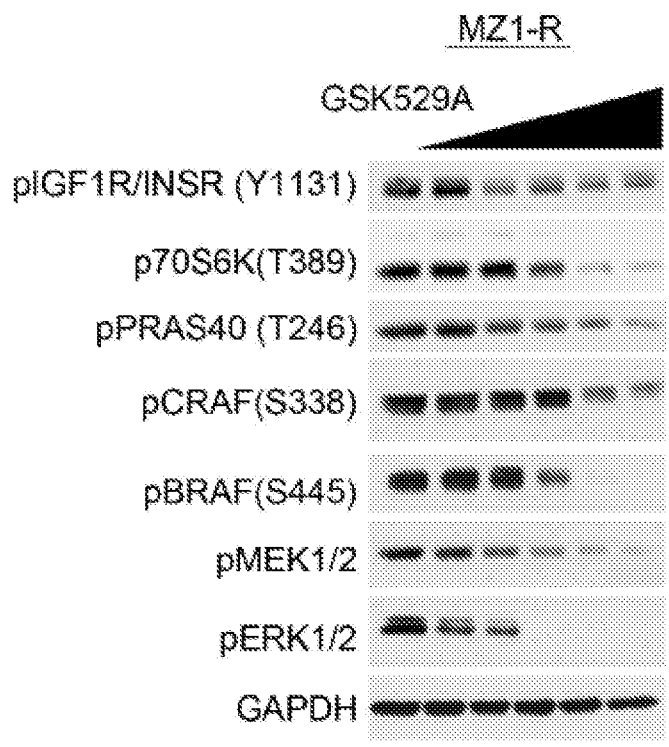

Example 4: Chronic Exposure to BBDs Promotes Enhanced Sensitivity Towards INSR, ErbB and MTOR Inhibitors To define growth and survival functions of kinases remodeled by chronic BBD treatment, an inhibitor screen in MZ1-R, JQ1-R or parental OVCAR8 cells was carried out (FIG. 4A). The screen revealed MZ1-R cells were more sensitive to inhibitors targeting INSR/IGF1R (GSK1904529A), ErbB family (lapatinib), AKT (MK-2206), mTORC1 (RAD001), AAK1 (LP-935509) and FAK1 (PND-1186) relative to JQ1-R cells or parental cells, consistent with predicted activation/upregulation of these kinases by MIB-MS and KSEA profiling (FIGS. 4B, 4C, 4D, 4E, 11A, and 11B). Inhibition of MEK (trametinib) or RAF (LY3009120) had the most profound impact on JQ1-R cell viability, while both MZ1-R and JQ1-R cells were more sensitive to PI3K inhibitor (GDC-0941), CDK9 inhibitor (NVP-2), or CK2 inhibitor (Cx-4945) than parental cells (FIGS. 4F, 11C, 11D, 11E, and 11F). Additionally, MZ1-R and JQ1-R cells were shown to be more sensitive to PARP inhibitor (olaparib), as well as the autophagy inhibitor (hydroxychloroquine). These findings show BRD4 functions as a positive regulator of homologous recombination (HR), as well as negative regulator of autophagy in cancer cells (FIG. 4A).

Knockdown of INSR, EGFR, ERBB2, MTOR or AKT1/2 reduced cell viability in MZ1-R cells to a greater extent than parental cells, suggesting BBD-R cells acquired greater dependency on these kinases for cell growth and survival in the presence of continued BBD exposure (FIG. 4G). Treatment of ARV-R cells with GSK1904529A, lapatinib, RAD001, MK2206 and LP-935509 also reduced cell viability more than in parental cells, demonstrating VHL or CRBN-based BBD-resistant cells acquire common kinase dependencies (FIGS. 11F, 11G, and 11H). Moreover, treatment of ARV-R or MZ1-R cells with GSK1904529A (GSK529A) inhibited colony formation to a greater extent than parental cells (FIG. 11I). MZ1-R cells were more sensitive to AKT inhibition than JQ1-R or parental cells. Parental, JQ1-R or MZ1-R OVCAR8 cells were treated with escalating doses of MK2206 for 5 days and cell viability assessed by CellTiter-Glo. MZ1-R or JQ1-R inhibitor treated cell viabilities normalized to DMSO treated JQ1-R or MZ1-R cells, respectfully (FIG. 11J). MZ1-R cells were more sensitive to AAK1 inhibition than JQ1-R or parental cells. Parental, JQ1-R or MZ1-R OVCAR8 cells were treated with escalating doses of LP-935509 for 5 days and cell viability assessed by CellTiter-Glo. MZ1-R or JQ1-R inhibitor treated cell viabilities normalized to DMSO treated JQ1-R or MZ1-R cells, respectfully (FIG. 11K). GSK529A-treatment blocked colony formation of MZ1-R and ARV-R cells to a greater extent than parental cells. Long-term 14-day colony formation assay of OVCAR8 parental, MZ1-R or ARV-R were treated with escalating doses of GSK529A or DMSO. Colony formation was assessed by crystal violet staining (FIG. 11L).

MIB-MS analysis of GSK529A-treated MZ1-R cells showed reduced MIB-binding of drug targets INSR and IGF1R and established downstream INSR signaling kinases MTOR, RPS6KB1, BRAF, MAP2K1/2 and MAPK3 (ERK1) (FIG. 4H). Reduced MIB-binding of kinases involved in cell cycle (WEE1, CHEK1, CDK2, CDK6 and PLK1), as well as kinases required for translation (EIF2AK1, EIF2AK2, and EIF2AK4) were also observed following GSK529A treatment. Inhibition of INSR/IGF1R, MTOR, P70S6K, BRAF and ERK activity in MZ1-R cells was confirmed by phospho-blot (FIG. 4I). Single-run proteome analysis of GSK529A treated MZ1-R cells showed inhibition of INSR signaling repressed mRNA processing, RNA splicing, translation initiation and mitosis signaling, consistent with inhibition of mTOR signaling and cycle arrest. Enrichment maps of pathways repressed by INSR inhibition generated from MIB-MS profiles of OVCAR8 cells treated with GSK529A (1 µM) treatment for 48 hours. Statistical differences in protein log 2 LFQ z-scores comparing GSK529A to control treated MZ1-R cells was determined by paired T-Test Benjamini- Hochberg adjusted p values at FDR of <0.05 using Perseus Software. Proteins significantly repressed by GSK529A therapies were then analyzed by gProfiler to determine pathway enrichments (BH P<O5). Enrichment maps were generated in Cytoscape using the Enrichment Map app v2.2.1. (data not shown).

Figure 5:
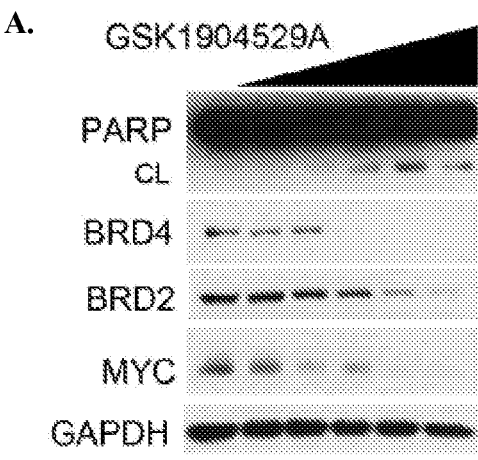
FIG. 5A shows that blockade of INSR signaling reduces BRD2 and BRD4, as well as BRD4-target MYC protein levels; OVCAR8 MZ1-R cells were treated with escalating doses of GSK529A or DMSO for 48 hours and protein levels were determined by Western blot.
FIG. 5B shows depletion of BRD2 and BRD4 protein levels by GSK529A distinct to MZ1-R cells; parental, MZ1-R or JQ1-R cells were treated with escalating doses of GSK529A or DMSO and BET protein levels were determined by Western blot.
FIG. 5C shows that inhibition of INSR, ErbB or MTOR commonly reduce BRD2 and BRD4 proteins; MZ1-R OVCAR8 cells were treated with 1 µM of kinase inhibitors or DMSO for 4 hours and BET protein levels were determined by western blot.
FIG. 5D shows ARV-R OVCAR8 cells treated with 1 µM of kinase inhibitors or DMSO for 4 hours and BET protein levels were determined by Western blot.
FIG. 5E shows that inhibition of MTORC1 promotes BET protein loss selectively in MZ1-R cells; OVCAR8 MZ1-R cells were treated with escalating doses of RAD001 or DMSO for 48 hours and protein levels were determined by Western blot.
FIG. 5F shows that inhibition of MTOR does not influence BRD4 RNA levels; OVCAR8 MZ1-R or parental cells were treated with DMSO or (1 µM) of GSK529A, lapatinib or RAD001 for 48 hours and BRD4 RNA levels were determined by qRT-PCR.
FIG. 5G shows that inhibition of proteasome rescues GSK529A or RAD001-mediated reduction of BET proteins in MZ1-R cells; OVCAR8 MZ1-R cells were treated with GSK529A (2 µM), bortezominb (10 nM) or the combination for 4 or 24 hours and BET protein levels were determined by Western blot.
FIG. 5H shows OVCAR8 MZ1-R cells treated with RAD001 (2 µM), bortezominb (10 nM) or the combination for 4 or 48 hours and BET protein levels were determined by Western blot.
Figure 5:
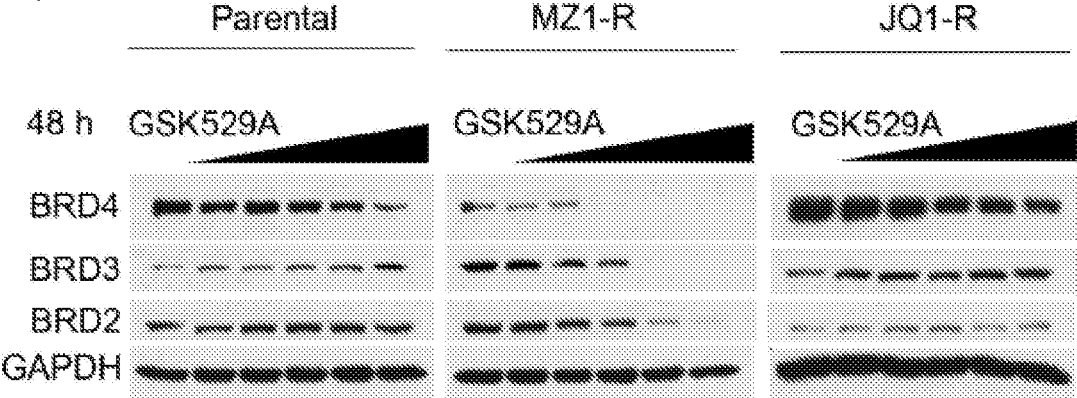
Figure 5:
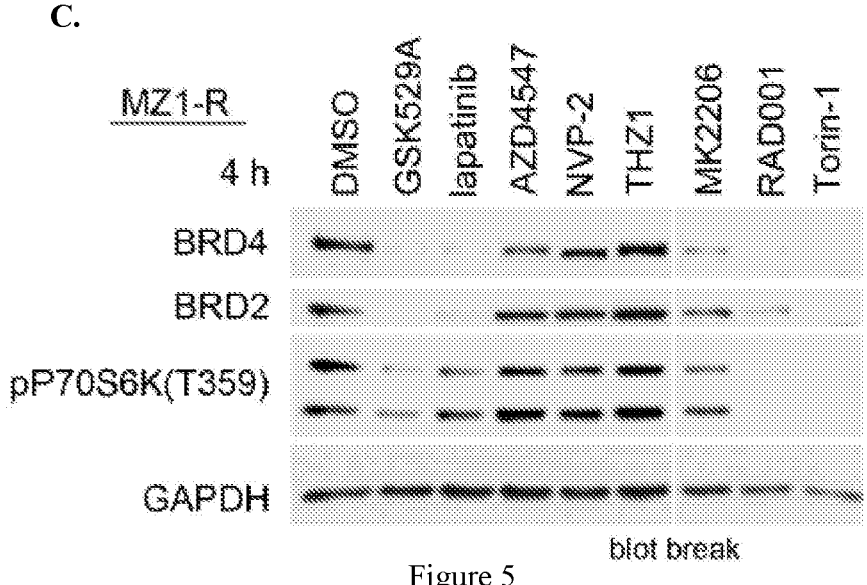
Figure 5:
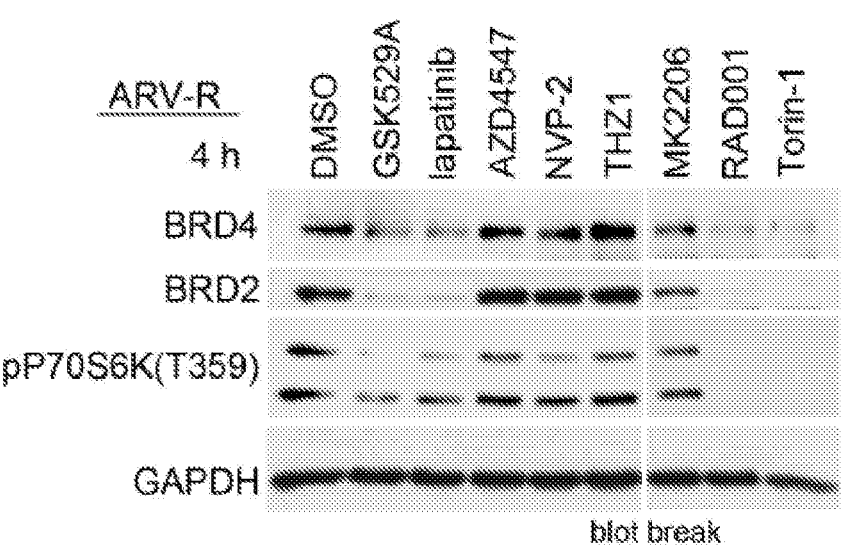
Figure 5:
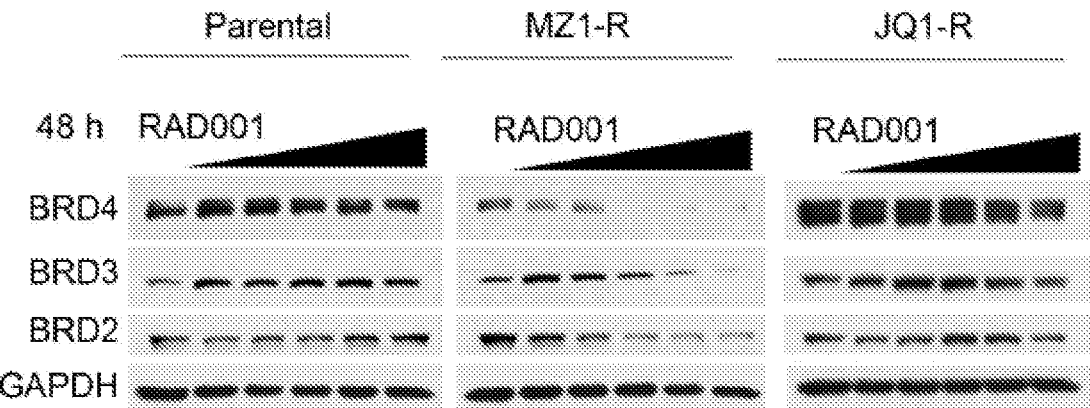
Figure 5:
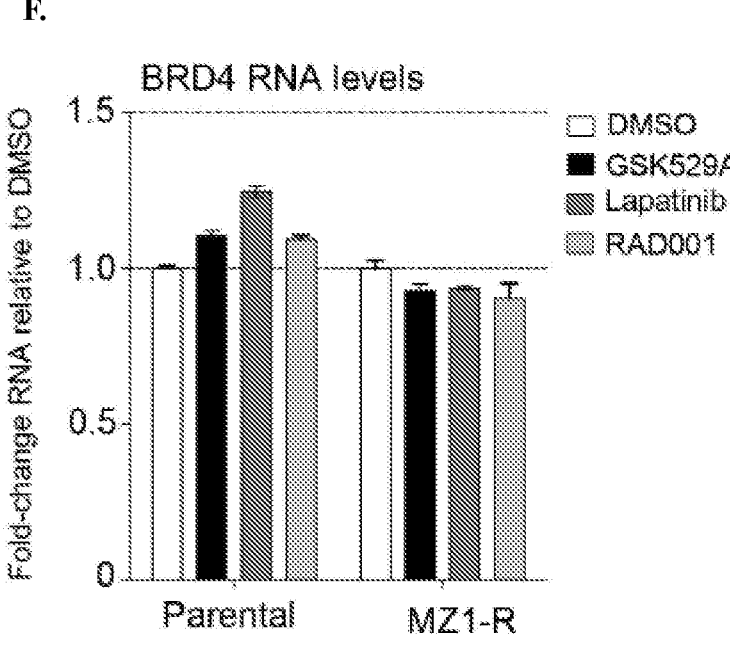
Figure 5:
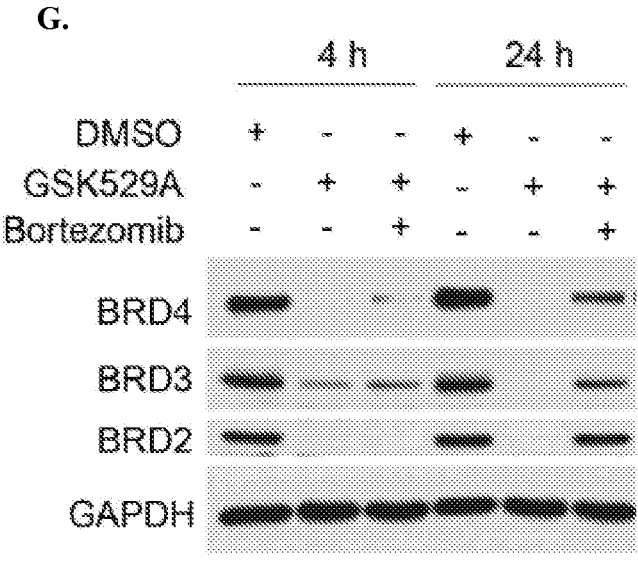
Figure 5:
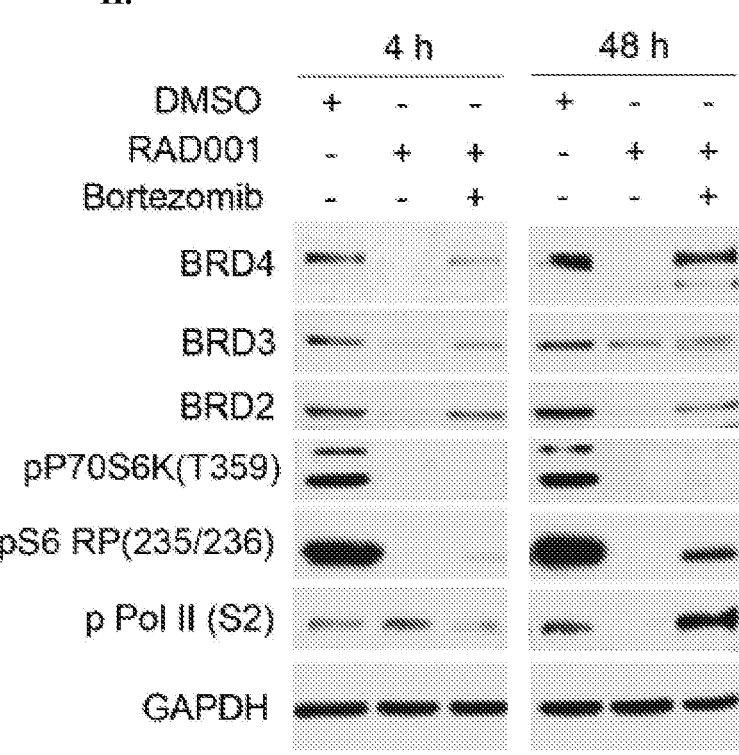

Example 5: Blockade of MTOR Signaling Destabilizes BET Proteins Overcoming Resistance to BET Degraders Proteomics profiling and Western blot analysis showed BRD2 and BRD4 protein levels were significantly reduced by GSK529A treatment in MZ1-R cells, suggesting inhibition of INSR and downstream mTOR signaling may impact BRD2 and BRD4 protein stability in BBD-R cells (FIGS. 5A and 12A). Moreover, a dose dependent reduction in MYC protein levels and an induction of apoptosis was also observed in response to GSK529A-treatment that coincided with BET protein loss. Treatment of parental cells or JQ1-R cells with GSK529A did not reduce BET protein levels, suggesting the response uniquely occurred in BBD-R cells (FIG. 5B).

Additionally, treatment of MZ1-R or ARV-R cells with lapatinib (ErbB), RAD001 (mTORC1), or Torin-1 (mTORC1/2) but not CDK9, CDK7, FGFR CK2 or AKT inhibitors, reduced BRD2 and BRD4 levels in MZ1-R and ARV-R cells (FIGS. 5C, 5D, 12B, 12C, and 12D). Notably, GSK529A, lapatinib, RAD001 and Torin-1 treatment reduced MTOR-mediated phosphorylation of P70S6K (T359), suggesting these inhibitors commonly blocked MTOR signaling in BBD-R cells. Treatment of MZ1-R but not parental or JQ1-R cells with RAD001 reduced BRD4 protein levels, signifying the MTOR-dependent protection of BRD2/4 was distinct to cells chronically exposed to BBDs (FIGS. 5E and 12E). BRD2, BRD3 or BRD4 RNA levels were unaffected by GSK529A, Lapatinib or RAD001 treatment in MZ1-R cells, demonstrating the reduced levels of BRD2 and BRD4 were not due to blockade of transcription (FIG. 5F). The reduction in BET proteins mediated by 4 or 48 hours GSK529A or RAD001 treatment was rescued by proteasome inhibitor treatment, signifying blockade of MTOR activity impacts BRD4 post transcriptionally (FIGS. 5G and 5H). Furthermore, inhibition of phosphorylated RNA pol II (S2) was observed in MZ1-R cells following a 48 hour treatment with RAD001 that could be reversed by bortezomib treatment, consistent with MTOR signaling regulating BRD4 protein function in MZ1-R cells.

Figure 6:
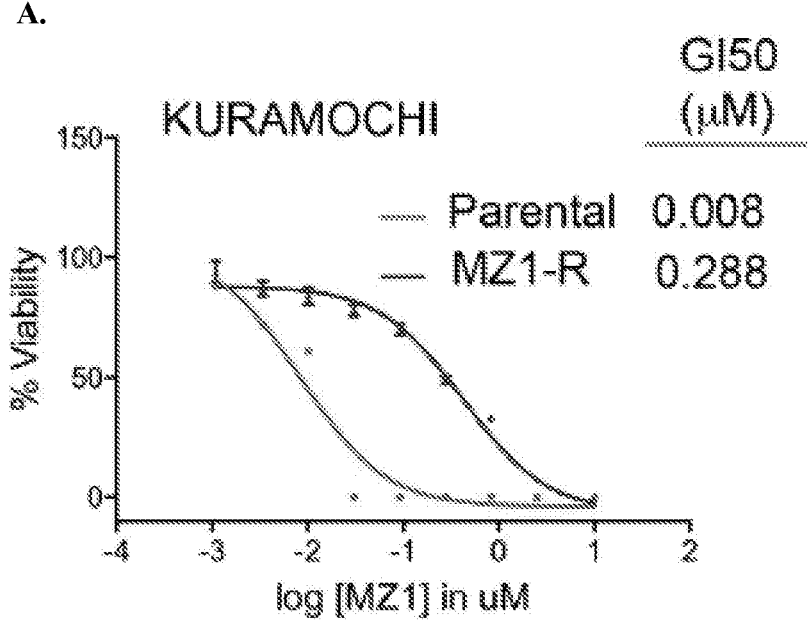
FIG. 6A shows that KURAMOCHI cells acquire resistance to MZ1; parental and MZ1-resistant cells were treated with escalating doses of MZ1 for 5 days and cell viability was assessed by CellTiter-Glo; MZ1-R treated cell viabilities normalized to DMSO treated MZ1-R cells.
FIG. 6B shows that COV362 cells acquire resistance to MZ1; parental and MZ1-resistant cells were treated with escalating doses of MZ1 for 5 days and cell viability was assessed by CellTiter-Glo; MZ1-R treated cell viabilities normalized to DMSO treated MZ1-R cells.
FIG. 6C shows that OVCAR5 EOC cells acquire resistance to MZ1; parental and MZ1-resistant cells were treated with escalating doses of MZ1 for 5 days and cell viability was assessed by CellTiter-Glo; MZ1-R treated cell viabilities normalized to DMSO treated MZ1-R cells.
FIG. 6D shows that escalating doses of MZ1 fails to promote degradation of BRD4 in MZ1-R cells; KURAMOCHI parental or MZ1-R cells were treated with escalating doses of MZ1 for 24 hours and BET proteins levels were determined by Western blot.
FIG. 6E shows COV362 parental or MZ1-R cells treated with escalating doses of MZ1 for 24 hours and BET proteins levels were determined by Western blot.
FIG. 6F shows OVCAR5 parental or MZ1-R cells treated with escalating doses of MZ1 for 24 hours and BET proteins levels were determined by Western blot.
FIG. 6G shows that MZ1-R cells exhibit increased sensitivity towards INSR, ErbB or MTORC1 inhibition; KURAMOCHI parental or MZ1-R cells were treated with escalating doses of GSK1904529A, lapatinib or RAD001 for 5 days and cell viability was assessed by CellTiter-Glo; MZ1-R or treated cell viabilities normalized to DMSO treated MZ1-R cells, respectfully.
FIG. 6H shows COV362 parental or MZ1-R cells treated with escalating doses of GSK1904529A, lapatinib or RAD001 for 5 days and cell viability was assessed by CellTiter-Glo; MZ1-R or treated cell viabilities normalized to DMSO treated MZ1-R cells, respectfully.
FIG. 6I shows OVCAR5 parental or MZ1-R cells treated with escalating doses of GSK1904529A, lapatinib or RAD001 for 5 days and cell viability was assessed by CellTiter-Glo; MZ1-R or treated cell viabilities normalized to DMSO treated MZ1-R cells, respectfully.
FIG. 6J shows that inhibition of INSR, ErbB, or MTORC1 promotes BET protein loss in MZ1-R cells; KURAMOCHI MZ1-R cells were treated with escalating doses of GSK529A, lapatinib, RAD001 or DMSO for 48 hours and protein levels were determined by Western blot.
FIG. 6K shows COV362 MZ1-R cells treated with escalating doses of GSK529A, lapatinib, RAD001 or DMSO for 48 hours and protein levels were determined by Western blot.
FIG. 6L shows OVCAR5 MZ1-R cells treated with escalating doses of GSK529A, lapatinib, RAD001 or DMSO for 48 hours and protein levels were determined by Western blot.
Figure 6:
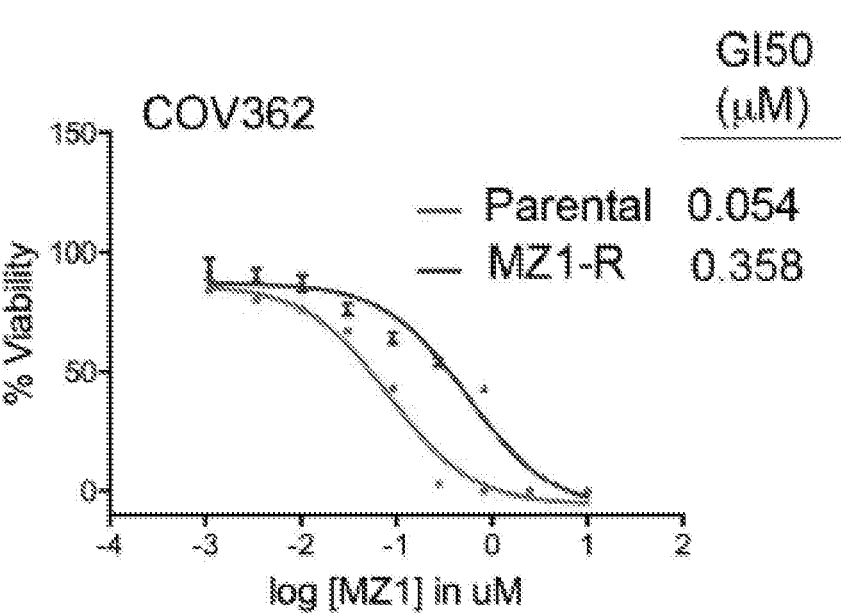
Figure 6:
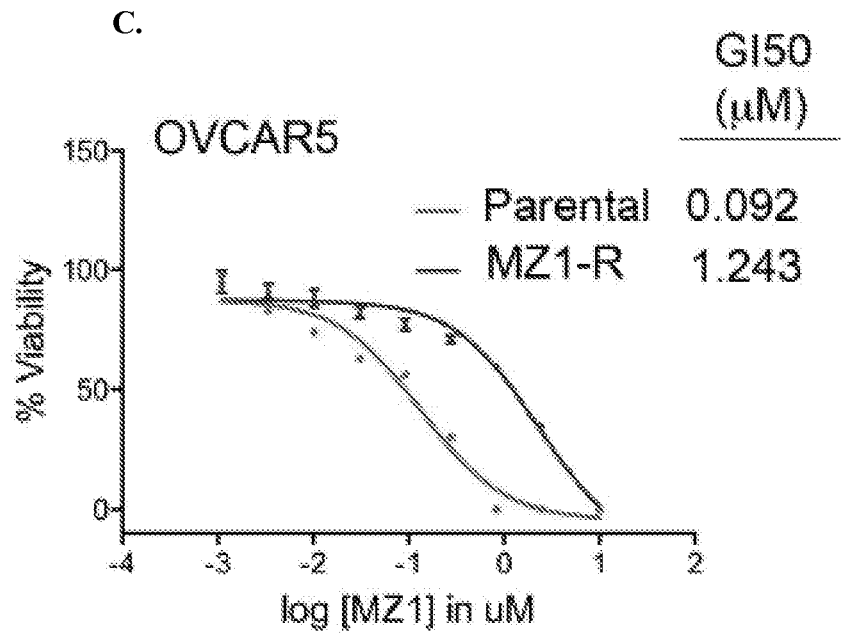
Figure 6:
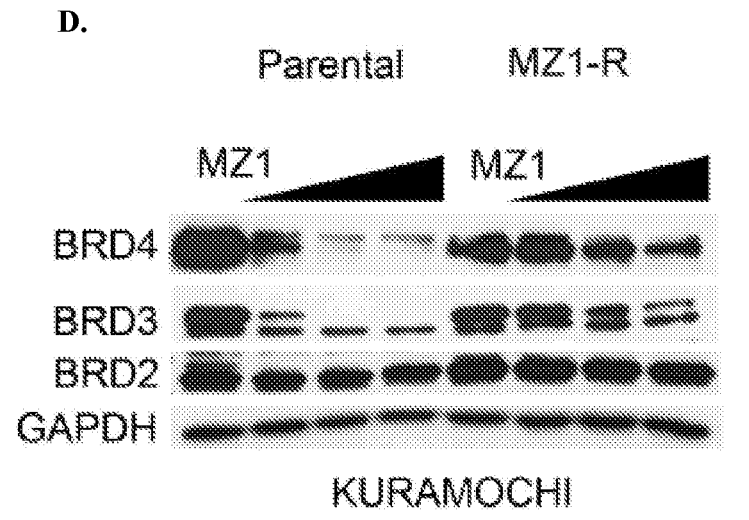
Figure 6:
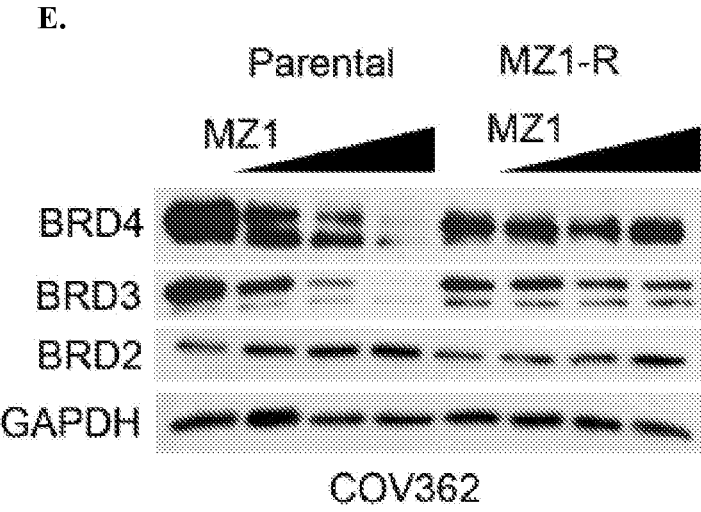
Figure 6:
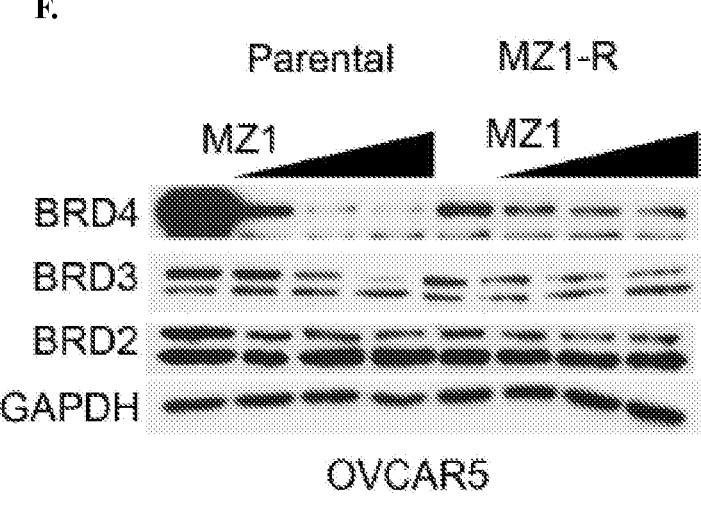
Figure 6:
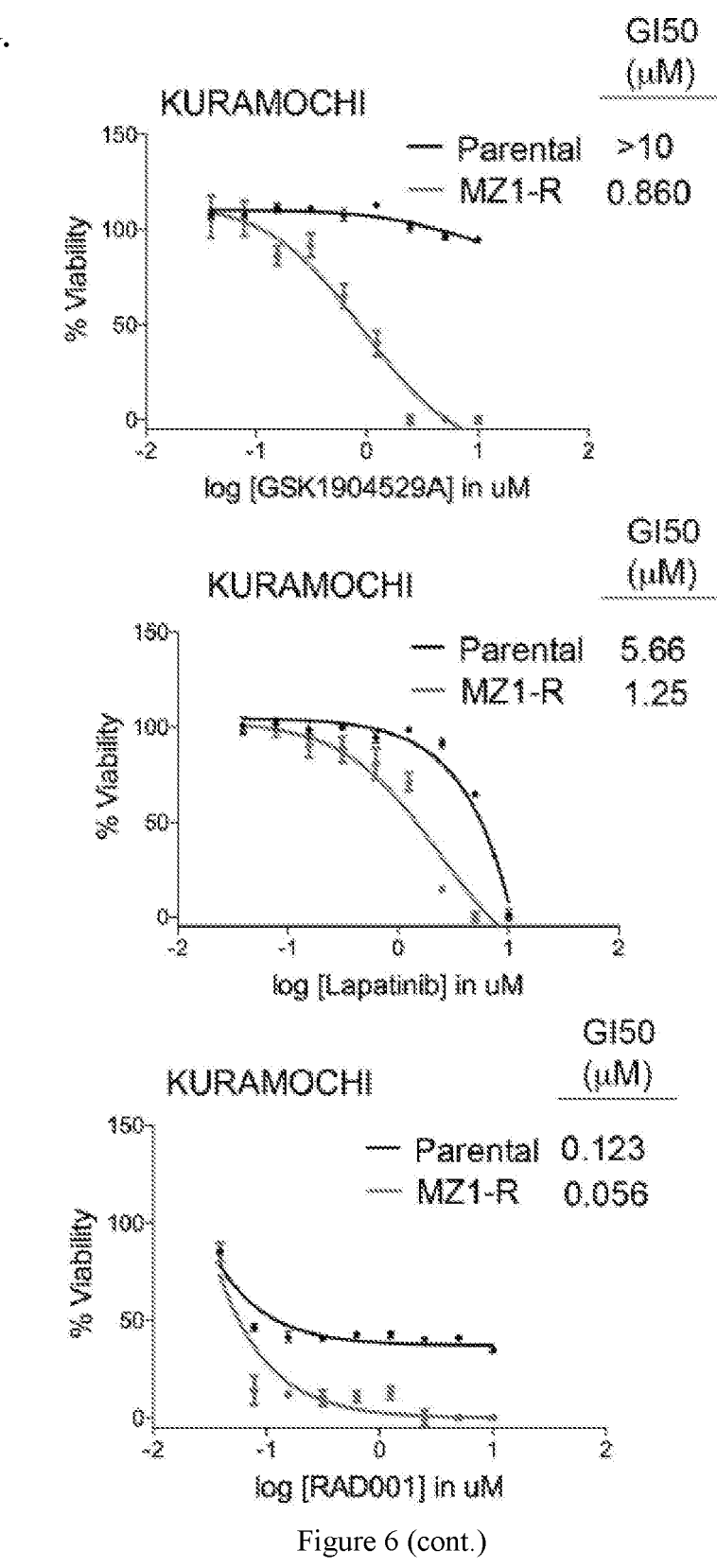
Figure 6:
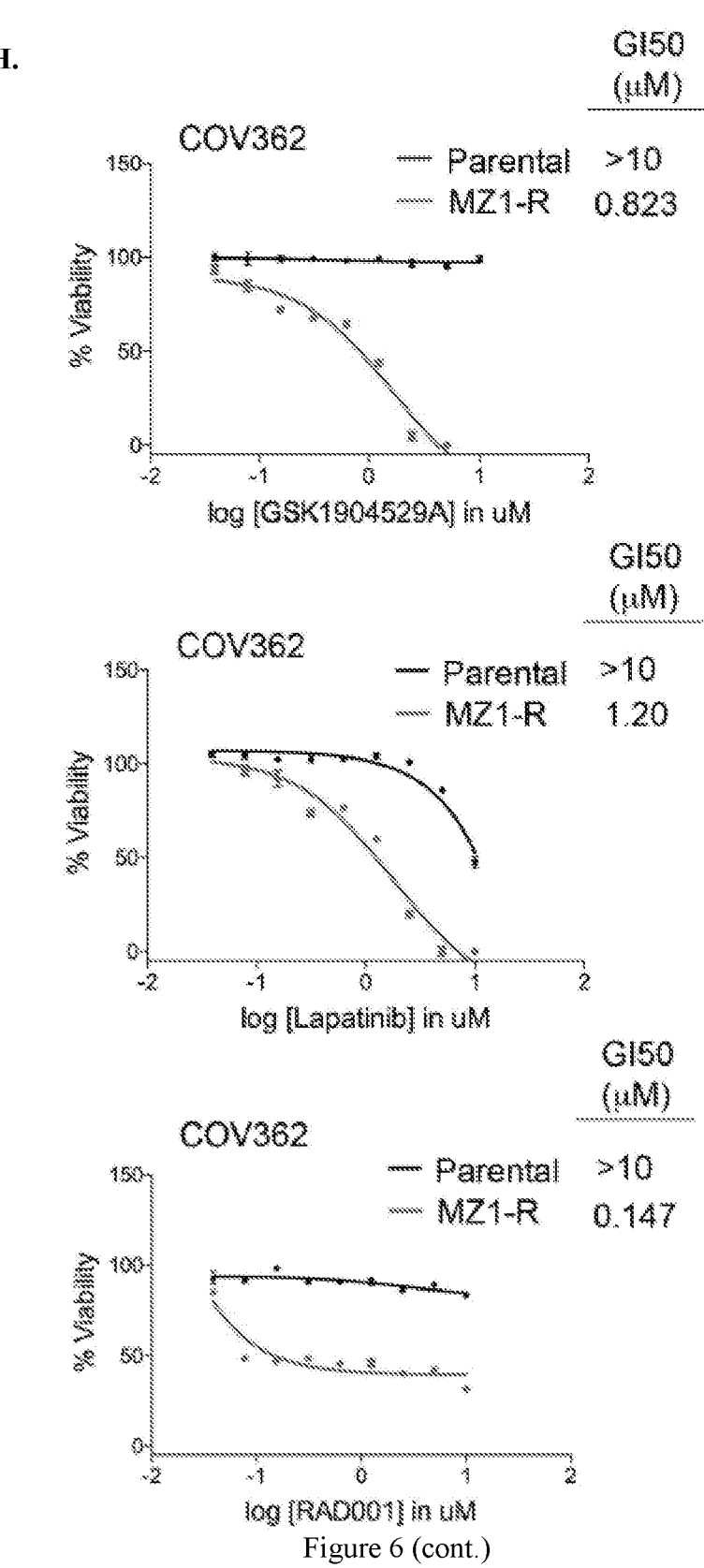
Figure 6:
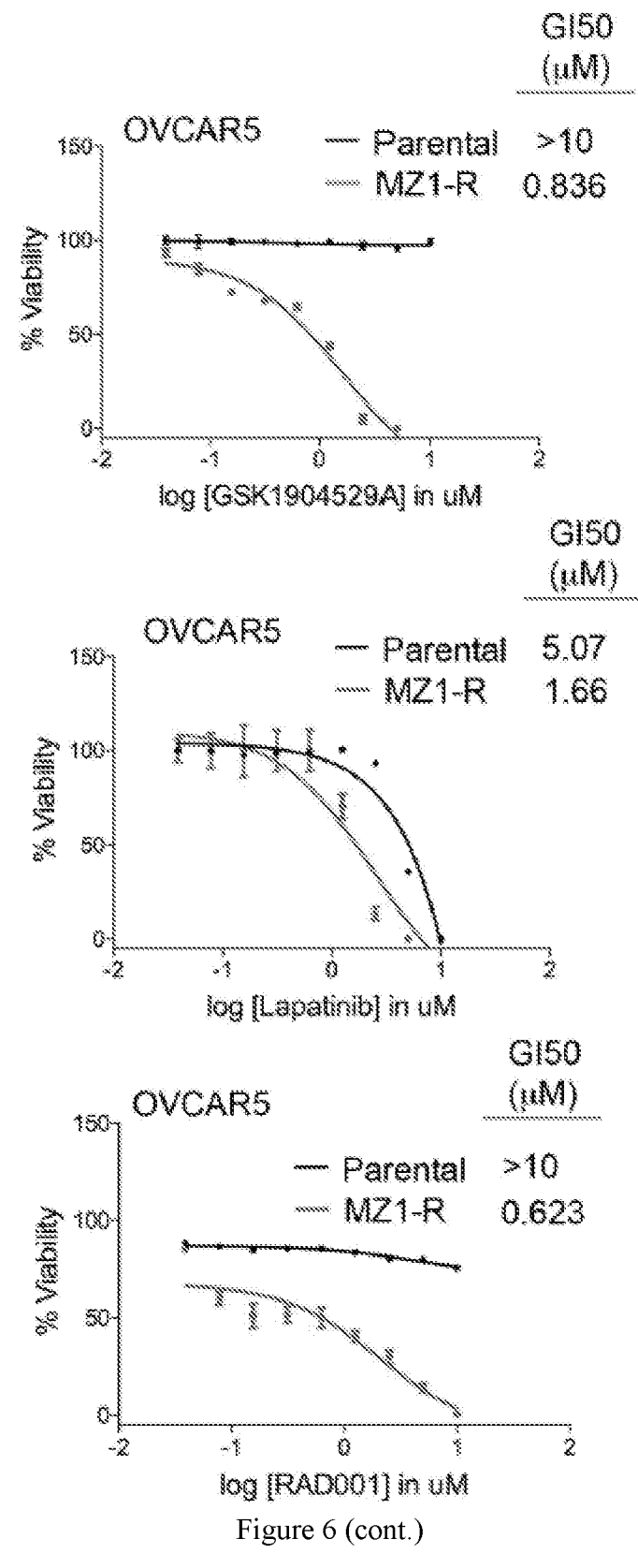
Figure 6:
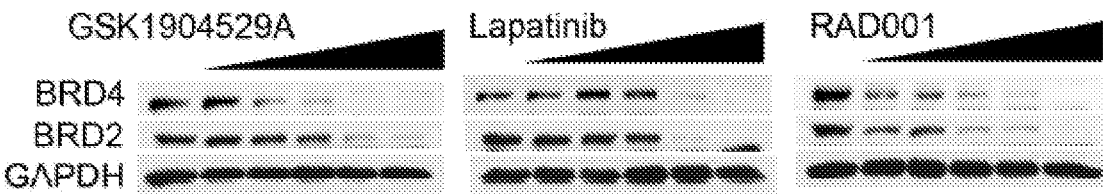
Figure 6:
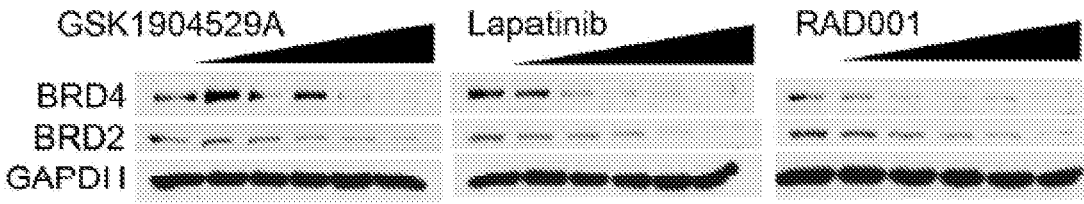
Figure 6:
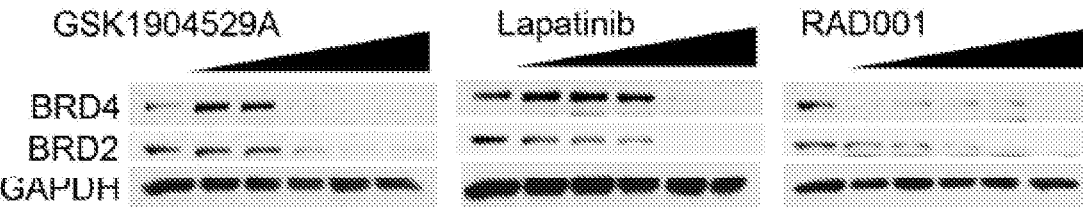

Example 6: MTOR-Driven Stabilization of BRD4 A Global Mechanism of Resistance to BBD Therapies in OC Cells To further define the role of MTOR signaling in resistance to BBD therapies, additional BBD-R OC cell lines were characterized. The chronically exposed MZ1-R cells (KURAMOCHI, COV362 and OVCAR5) were more resistant to BBD than treatment naïve (i.e., parental cells), where they showed a rightward shift in MZ1 dose-response cell viability curves and treatment with MZ1 failed to mediated degradation of BET proteins (FIGS. 6A, 6B, 6C, 6D, 6E, and 6F). Consistent with OVCAR8 MZ1-R cells, knockdown of BRD4 and to a lesser extent BRD2 inhibited cell viability of OVCAR5, COV362 or KURAMOCHI MZ1-R cells, confirming the dependency of MZ1-R cells for residual BRD4 protein levels (FIGS. 13A, 13B, and 13C). Treatment of OVCAR5, COV362 and KURAMOCHI MZ1-R cells with GSK529A, lapatinib or RAD001 significantly blocked cell growth to a greater extent than parental cells (FIGS. 6G, 6H, and 6I). Treatment of OVCAR5 JQ1-R cells with GSK529A, lapatinib or RAD001 showed minimal growth inhibition, further demonstrating exquisite sensitivity to INSR/IGF1R, EGFR and mTORC1 inhibition was uniquely acquired by chronic BBD treatment but not BBI therapies (FIGS. 13D, 13E, and 13F). Lastly, GSK529A, lapatinib or RAD001 treatment in COV362, OVCAR5 and KURAMOCHI MZ1-R cells reduced BRD2 and BRD4 proteins, suggesting the INSR, ErbB and mTORC1-mediated stabilization of BET proteins in response to chronic exposure to BBD was a common mechanism of resistance to BBD therapies amongst OC cell lines (FIGS. 6J, 6K, and 6L).

Figure 7:
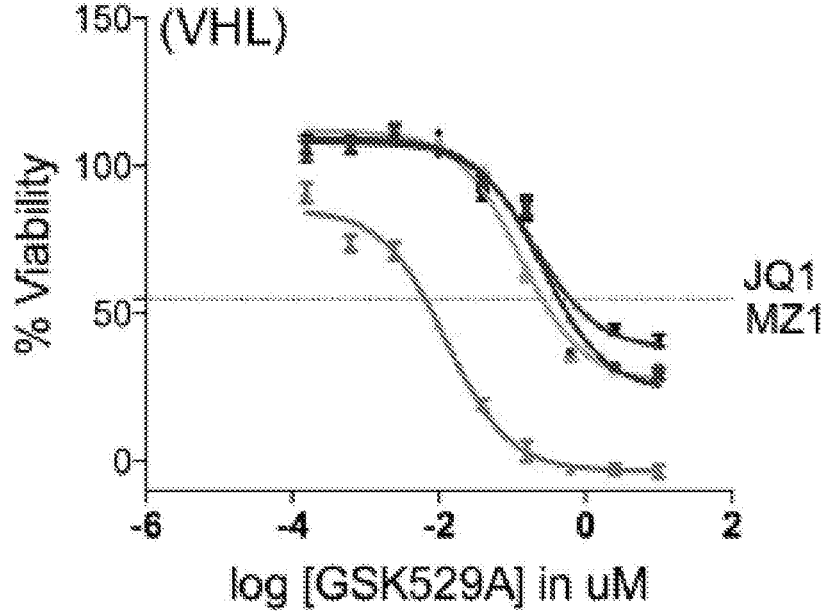
FIG. 7A shows that combination therapies involving GSK529A, lapatinib or RAD001 and MZ1 but not JQ1 improve growth repression of OVCAR8 cells; OVCAR8 cells were treated with 100 nM JQ1, MZ1 or cis-MZ1, escalating doses of GSK529A, lapatinib or RAD001, or the combination of JQ1, MZ1 or cis-MZ1 and kinase inhibitors for 5 days and cell viability was assessed by CellTiter-Glo.
FIG. 7B shows that CRBN-based BBDs synergize with GSK529A, lapatinib or RAD001; OVCAR8 cells were treated with 100 nM dBET6, escalating doses of GSK529A, lapatinib or RAD001, or the combination of dBET6 and kinase inhibitors for 5 days and cell viability was assessed by CellTiter-Glo.
FIG. 7C shows that treatment of cells with GSK529A, lapatinib or RAD001 and MZ1 but not JQ1 increased apoptosis and reduced BET proteins to a greater extent than MZ1-treatment alone; OVCAR8 cells were treated with DMSO, 100 nM MZ1, (1 μM) GSK529A, RAD001, Lapatinib or the combination of MZ1 or JQ1 and kinase inhibitors; BET protein levels and the apoptotic marker cleaved PARP were determined by Western blot.
FIG. 7D shows OVCAR8 cells were treated with DMSO, 100 nM JQ1, (1 μM) GSK529A, RAD001, Lapatinib or the combination of MZ1 or JQ1 and kinase inhibitors; BET protein levels and the apoptotic marker cleaved PARP were determined by Western blot.
FIG. 7E shows that co-treating cells with BBDs and GSK529A or RAD001 enhances PROTAC degradation of BRD4, and increases apoptosis; OVCAR8 cells were treated with DMSO, 50 nM MZ1, (1 μM) GSK529A, or MZ1 and escalating doses of GSK529A or RAD001 and BRD4 levels and the apoptotic marker cleaved PARP were determined by Western blot.
FIG. 7F shows OVCAR8 cells treated with DMSO, 50 nM MZ1, (1 μM) RAD001, or MZ1 and escalating doses of GSK529A or RAD001 and BRD4 levels and the apoptotic marker cleaved PARP were determined by Western blot.
FIG. 7G shows selective BRD4 degradation but not BET protein inhibition sensitizes OC cells to RAD001, GSK529A or Lapatinib; OC cell lines were treated with 0.1 μM MZ1, 0.1 μM JQ1, escalating doses of GSK529A, Lapatinib, RAD001 or the combination of 0.1 μM MZ1 or JQ1 and escalating doses of GSK529A, Lapatinib or RAD001 for 5 days and cell viability determined by Cell-Titer-Glo.
FIG. 7H shows that KURAMOCHI cells exhibit pronounced growth inhibition in response to dBET6 in combination with GSK529A; KURAMOCHI cells were treated with 100 nM GSK529A together with dBET6 or JQ1 for 5 days and cell viability was assessed by CellTiter-Glo.
FIG. 7I shows KURAMOCHI cells treated with 100 nM RAD001 together with dBET6 or JQ1 for 5 days and cell viability was assessed by CellTiter-Glo.
FIG. 7J shows a model of kinome adaptive bypass remodeling underlying protection of BRD4 from PROTAC-mediated degradation in OC cells and promoting resistance to BBDs.
Figure 7:
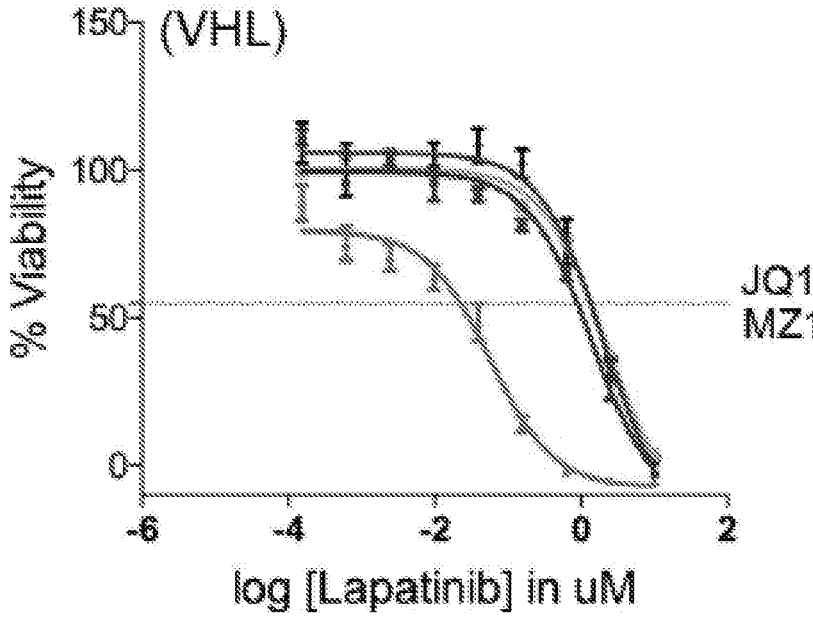
Figure 7:
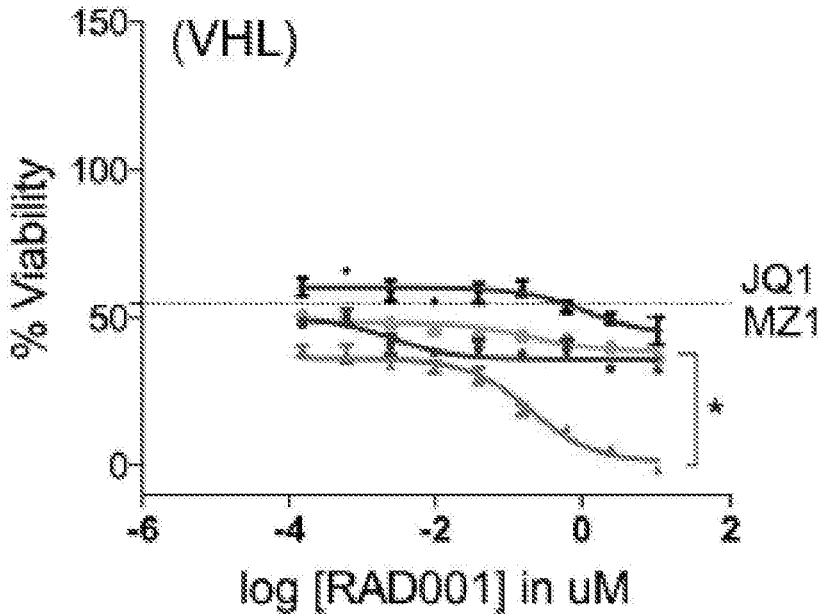
Figure 7:
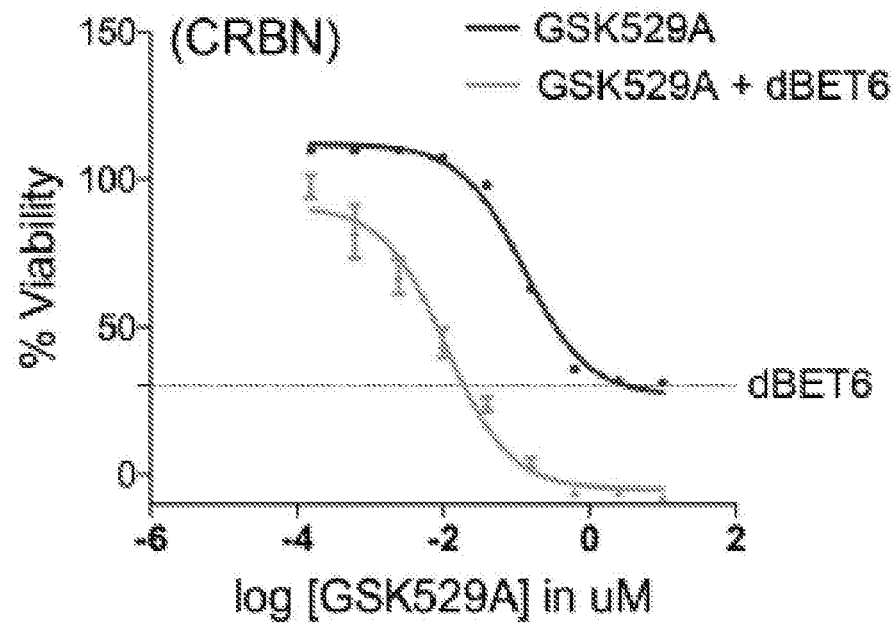
Figure 7:
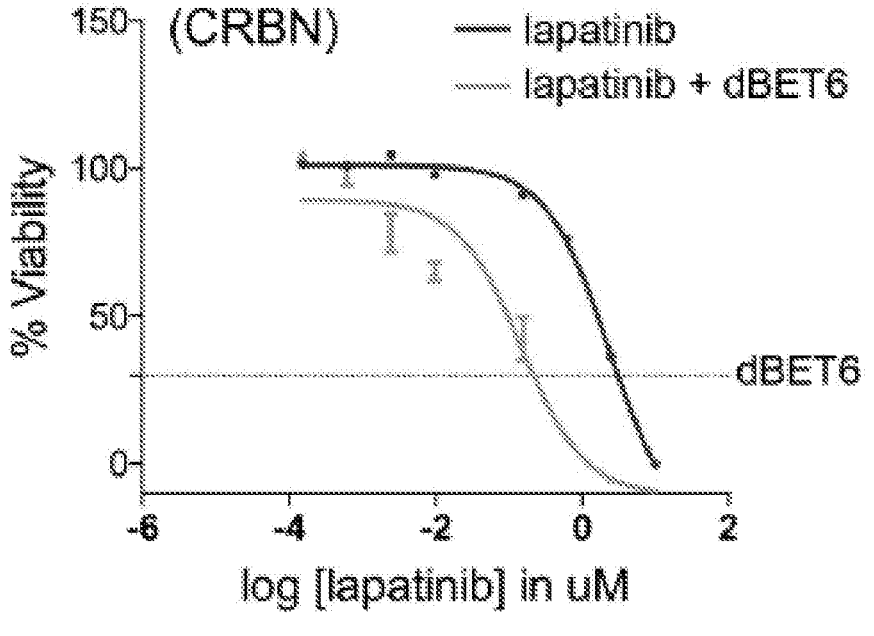
Figure 7:
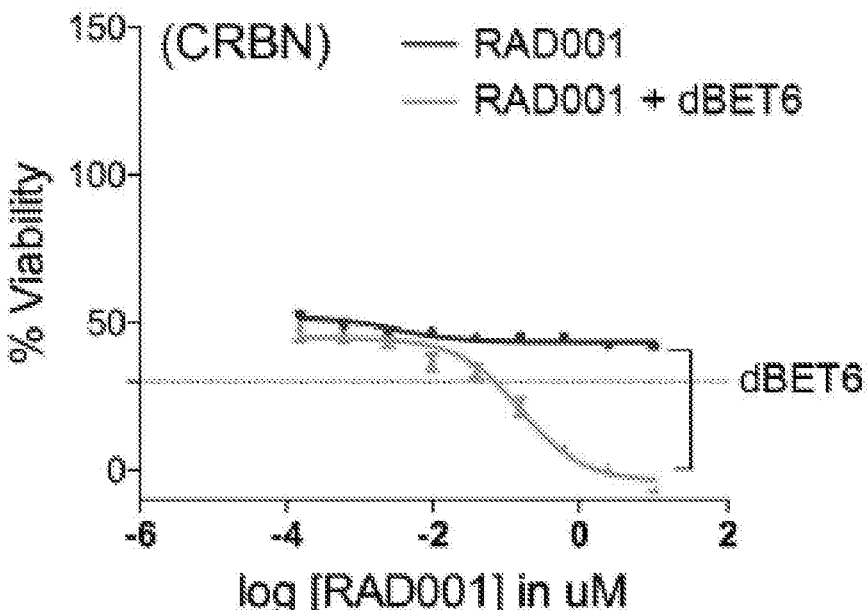
Figure 7:
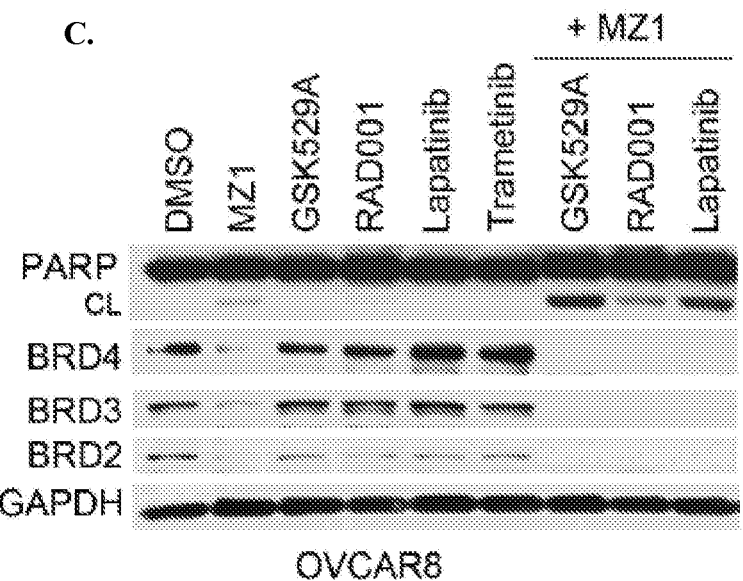
Figure 7:
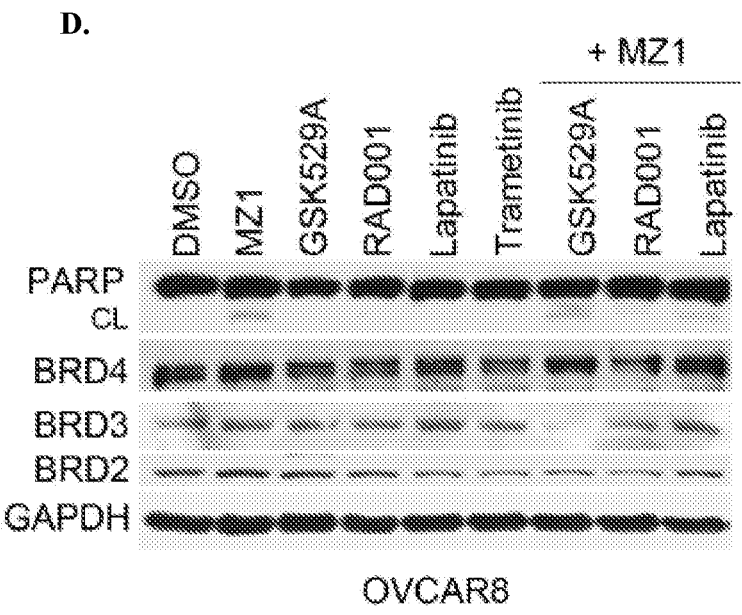
Figure 7:
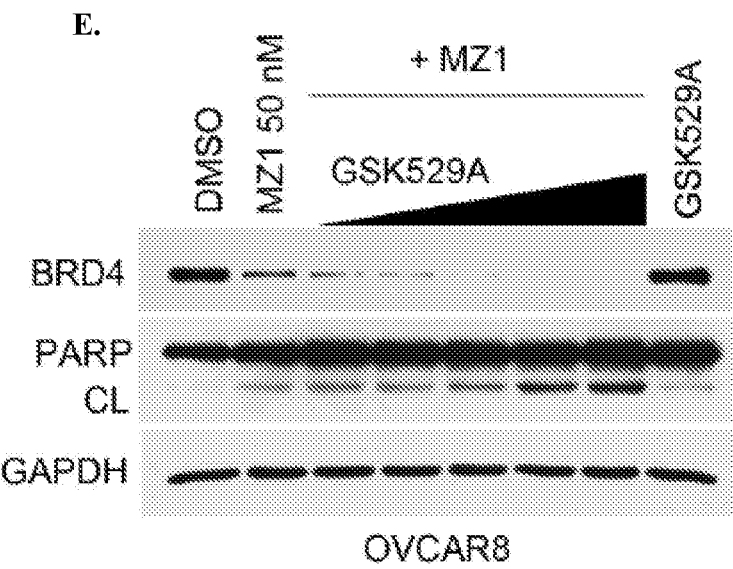
Figure 7:
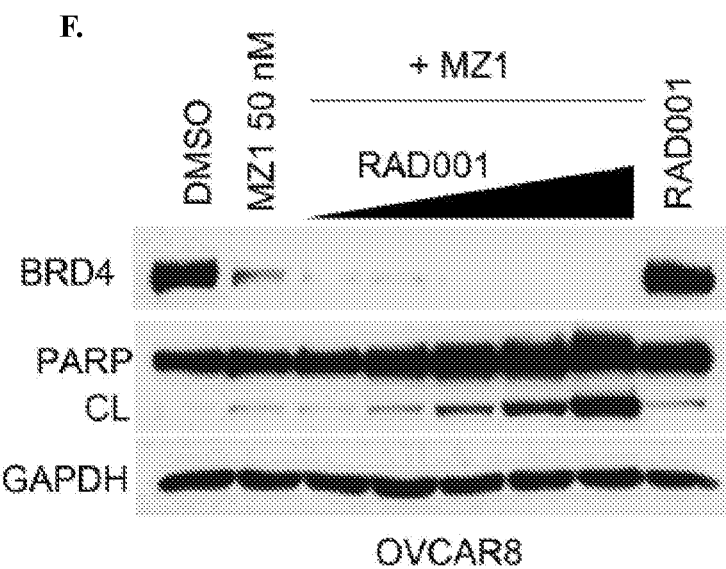
Figure 7:
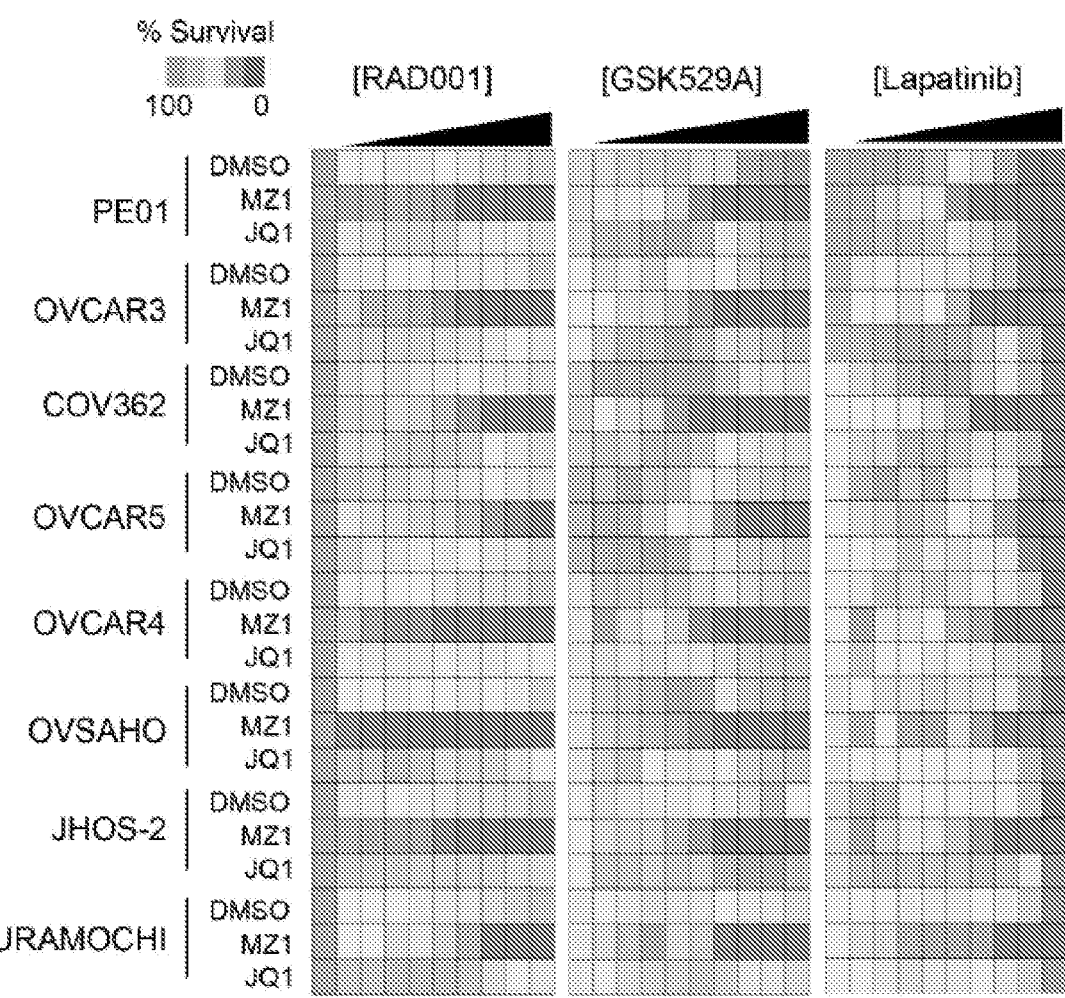
Figure 7:
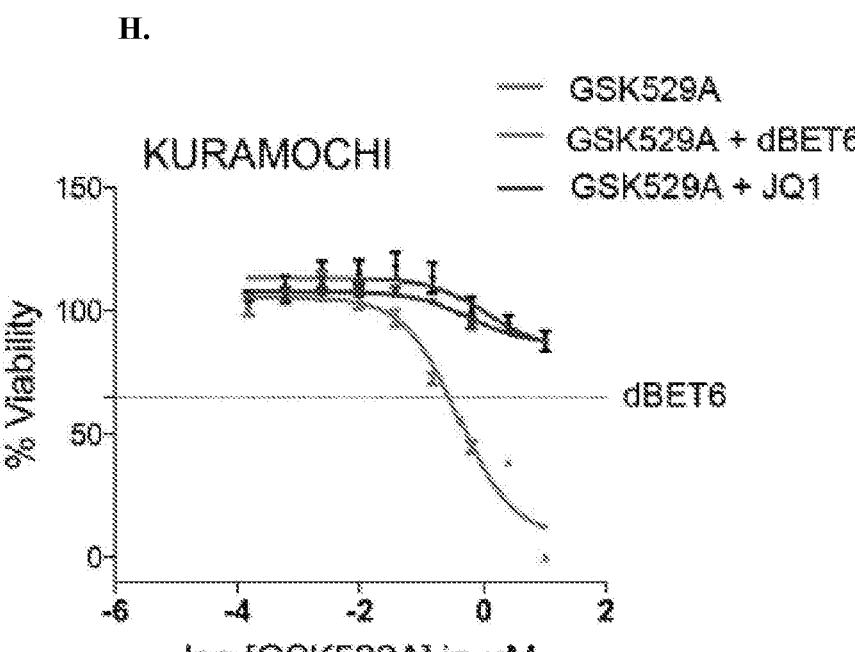
Figure 7:
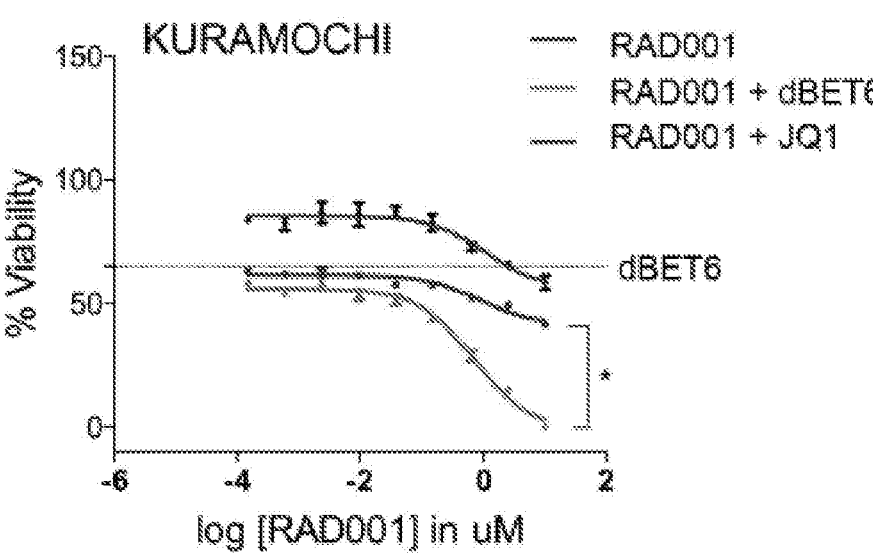
Figure 7:
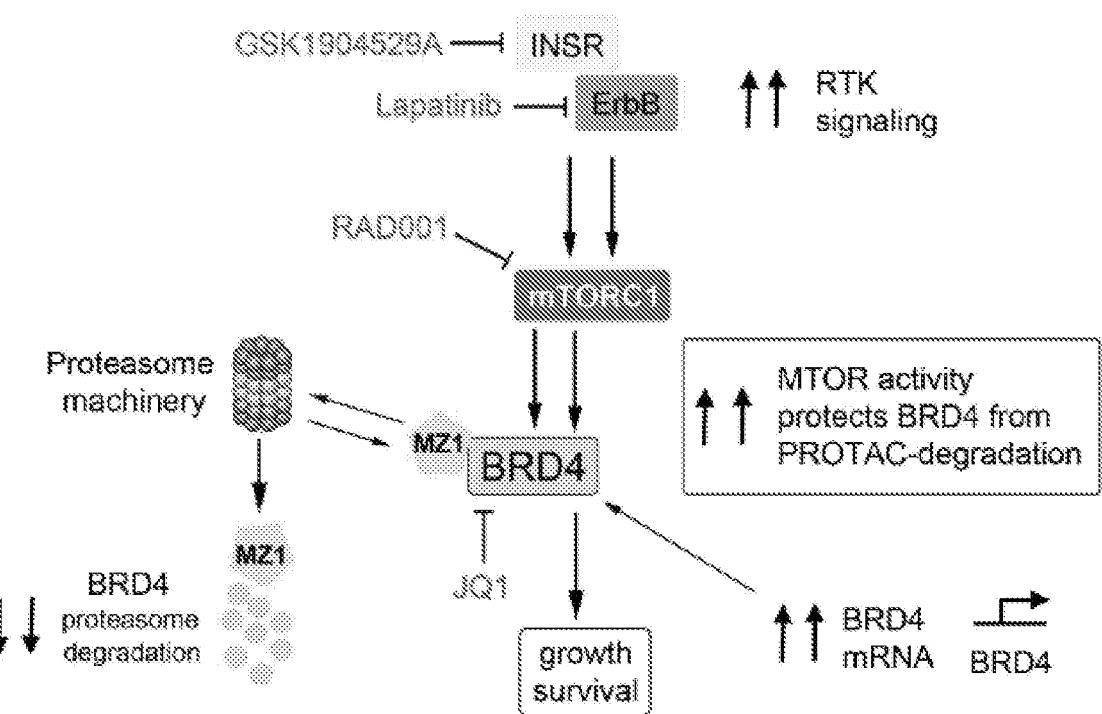

Example 7: INSR, ErbB and/or mTORC1 Inhibition Improves PROTAC-mediated Degradation of BRD4 Providing Superior Growth Repression and Apoptosis of OC Cells Combined treatment of OVCAR8 cells with either JQ1 or MZ1 and Ms targeting ATR, PI3K, MEK, CK2, CDK7, or CDK9 enhanced growth repression, demonstrating BBDs similarly synergizes with Ms previously shown to improve JQ1 efficacy in OC cells (FIGS. 14A, 14B, 14C, 14D, 14E, and 14F). Co-treatment of OVCAR8 cells with MZ1 or GSK529A, lapatinib or RAD001 uniquely enhanced growth inhibition and increased apoptosis relative to single agent therapies, whereas combined treatment with JQ1 or cis-MZ1 showed no synergy (FIG. 7A). Moreover, increasing JQ1 concentrations to 500 nM did not improve synergy with GSK529A, lapatinib or RAD001, demonstrating the combination therapies were only active using BBDs (FIGS. 14G and 14H). The drug synergy was also observed when combining CRBN-based BBD, dBET6, demonstrating either VHL or CRBN-based BBD therapies can be used for the kinase inhibitor combination therapies (FIG. 7B).

Increased apoptosis and a complete reduction in BET proteins was observed in OVCAR8 cells when MZ1 was combined with GSK529A, RAD001, or lapatinib, suggesting blockade of INSR, ErbB and/or MTOR enhanced MZ1-mediated degradation of BET proteins improving OC cell killing (FIGS. 7C and 7D). The benefit of co- treating cells with MZ1 and GSK529A, RAD001, or lapatinib was further illustrated, where dose escalation of RAD001 or GSK529A promoted enhanced degradation of BRD4, as well as increased levels of cleaved PARP than single agent therapies (FIGS. 7E and 7F). These findings suggest MTOR signaling may be promoting BRD4 stability following short-term BBD-therapy, similar to that observed when OC cells were chronically exposed to BBDs. Contrary, co-treatment of OVCAR8 cells with JQ1 and RAD001 or GSK529A had no impact on BRD4 protein levels (FIG. 14I).

Combination therapies involving GSK529A, lapatinib or RAD001 and MZ1 but not JQ1 significantly enhanced growth repression across a panel EOC cell lines harboring genomic alterations frequently observed in OC patient tumors (FIGS. 7G, 14J, 14K, and 14L). Cancer cell lines harboring MYC amplifications have been shown to exhibit enhanced sensitivity towards BBI therapies. Here, MYC-amplified HGSOC cell lines KURMAOCHI, OVCAR4, and COV362 showed pronounced synergy to combinations of BBDs and GSK529A, lapatinib, or RAD001 (FIGS. 7G and 7H). Moreover, BRD4 amplification and/or overexpression has been associated with poor prognosis and survival in HGSOC. Importantly, doses as low as 10 nM of MZ1 were sufficient to induce sensitivity towards GSK529A, lapatinib or RAD001 in BRD4 overexpressing HGSOC cell line OVSAHO (FIGS. 14M and 14N). Alterations in P13K and RAS signaling including activating KRAS or PIK3CA mutations have been shown to promote intrinsic resistance to BBI therapies. Notably, treatment of RAS-altered EOC cell lines OVCAR5, JHOS-2, A1847, COV362 and CAOV3, or PIK3CA mutant SKOV3 cells with the BBD/kinase combination therapies significantly enhanced growth inhibition compared to single agents, without the requirement of MEK or P13K inhibitors (FIGS. 7G, 14J, 14K, and 14L). KURAMOCHI cells were sensitive to the combination of dBET6 and MTOR inhibitor RAD001, while single agents were less effective. KURAMOCHI cells were treated with 100 nM dBET6, 100 nM JQ1 or the combination of dBET6 and RAD001 or JQ1 and RAD001 for 5 days and cell viability assessed by CellTitr Glo (FIG. 7I). The proposed model of the protection of BRD4 from PROTAC-degradation by MTOR signaling in ovarian cancer cells is shown in FIG. 7J. PROTAC-mediated degradation of BRD4 induces RTK signaling resulting in increased MTOR signaling which prevents the degradation of BRD4 in cells resistant to BET PROTACs.

Overall, combining BBDs and kinase inhibitors GSK529A, lapatinib or RAD001 was superior at blocking growth of EOC cells than BBI-KI combinations or single agent therapies, representing promising BBD-selective combination therapies for the treatment of ovarian cancer. In contrast to BBI therapy, BET degradation uniquely blocked translation signaling, preventing kinome reprogramming observed with BBI-treatments, leading to superior blockade of MYC signaling and induction of apoptosis. OC cells overcame chronic BBD therapy via CDK9-dependent upregulation of BRD4 transcription and activation of INSR, ErbB and mTORC1-signaling, which protected BRD4 from PROTAC-mediated degradation. Inhibition of INSR, ErbB or mTORC1 in BBD-R cells resulted in proteasome-dependent degradation of BRD4 and subsequent apoptosis, while inhibition of CDK9 blocked BRD4 transcription in BBD-R cells overcoming BBD-resistance. Moreover, combination therapies involving BBDs and INSR, ErbB, or mTORC1 inhibitors improved PROTAC-mediated degradation of BRD4 in parental OC cells enhancing BBD-induced apoptosis, representing a promising therapy for the treatment of OC.

Example 8: CDK9 PROTAC Resistance is Overcome by Co-administration of Kinase Inhibitors Chronic exposure of OVCAR8 cells to CDK9 PROTAC (Thal SNS 032) sensitized cells to RAD001 or GSK1904529A. Treatment of OVCAR8 Thal SNS 032 resistant cells with RAD001 or GSK529A resulted in downregulation of CDK9, demonstrating blockade of MTOR signaling re-sensitizes OVCAR8 cells to PROTAC-degradation. Moreover, these studies show both BET PROTACs and CDK9 PROTACs elicit a similar dependency on MTOR signaling to promote drug resistance. Co-treatment of parental OVCAR8 cells with Thal SNS 032 and RAD001 or GSK1904529A reduced cell viability to a greater extent than single agents alone, signifying blockade of MTOR signaling can improve the efficacy of CDK9-PROTAC degradation. In particular, OVCAR8 cells were treated with CDK9-degrader Thal SNS 032, resulting in the reduction of CDK9 protein levels. OVCAR8 cells were treated with escalating doses of Thal SNS 032 and CDK9 protein levels were determined by Western blot (FIG. 15A). Chronic exposure to Thal SNS 032 failed to degrade CDK9 that is overcome by GSK529A, lapatinib or RAD001 treatment. OVCAR8 Thal-R cells were treated with Thal (500 nM) or (2 μM) GSK529A, lapatinib, or RAD001 for 4 hours and protein levels were assessed by Western blot. (FIG. 15B). Thal-R cells were more sensitive to INSR, ErbB or MTORC1 inhibition than parental cells. Parental or Thal-R OVCAR8 cells were treated with escalating doses of GSK1904529A (FIG. 15C), lapatinib (FIG. 15D), or RAD001 (FIG. 15E) for 5 days and cell viability was assessed by CellTiter-Glo. Thal-R inhibitor treated cell viabilities were normalized to DMSO treated Thal-R cells. Combination therapies involving GSK529A or RAD001 and Thal SNS 032 improved growth repression of OVCAR8 cells. OVCAR8 cells were treated with 100 nM Thal SNS 032, escalating doses of GSK529A or RAD001, or the combination of Thal SNS 032 and kinase inhibitors, for 5 days and cell viability was assessed by CellTiter-Glo (FIGS. 15F and 15G).

Example 9: MTORC1 Inhibition Enhances PROTAC-Mediated Degradation of Protein Targets MTORC1 inhibition enhanced PROTAC-meditated degradation of BRD4, CDK9 or FAK1 proteins in cancer cells. Briefly, A1847 cells were treated with DMSO, 2 μM RAD001, increasing doses of dBET6 or 2 μM RAD001+ increasing doses of dBET6 for 4 hours and BRD4 protein was assessed by Western blot (FIG. 16, Panel A). A1847 cells were treated with DMSO, 2 μM RAD001, increasing doses of Thal SNS 032 or 2 μM RAD001+increasing doses of Thal SNS 032 for 4 hours and CDK9 protein was assessed by Western blot (FIG. 16, Panel B). A1847 cells were treated with DMSO, 2 μM RAD001, increasing doses of FAK-Protac or 2 RAD001+increasing doses of FAK-Protac for 4 hours and CDK9 protein was assessed by Western blot (FIG. 16, Panel C).

Immunoblot analysis showed inhibition of mTORC1 signaling by RAD001 improved MZ1 or dBET6-mediated degradation of BRD4 lowering the concentration of BBD required to achieve maximal protein degradation (FIG. 1g, Panel A). Notably, a 100-fold reduction in concentration required to degrade BRD4 was observed when dBET6 was combined with RAD001, while potent enhancement was observed with MZ1-treatment. Importantly, the improved degradation at lower concentration of BBDs was also observed in additional cancer cell lines MOLT4, SUM159 and HCT116. Furthermore, blockade of mTORC1 also enhanced degradation of CDK9 by Thal SNS 032, where RAD001 co-treatment significantly reduced the concentration of Thal SNS 032 required to achieve maximal degradation of CDK9 in A1847 cells (FIG. 16, Panel B). Notably, RAD001-treatment improved degradation efficiency of other PROTACs targeting FAK1 (FAK-PROTAC), suggesting blockade of mTORC1 may enhance degradation of PROTACs targets, reducing the concentration of degraders required to deplete proteins (FIG. 16, Panel C). Thus, MTORC1 inhibition may represent a general therapeutic strategy to improve PROTAC-induced degradation of protein targets and improve efficacy of PROTACs by minimizing concentrations of PROTACs required for reduce protein targets in cells.

Example 10: MTORC1 Inhibition Facilitates
Degradation of Protein Targets in Cancer Cells
Intrinsically Resistant to PROTAC Therapy Blockade of MTORC1 signaling sensitizes cancer cells resistant to BET-PROTACs. Briefly, a Cell-Titer Glo assay was performed for cell viability of A1847 cell lines treated with increasing concentrations of RAD001, dBET6 or the combination of RAD001 and dBET6 and cultured for 120 hours. Data were analyzed as % cell viability of DMSO control, presented as means of 3 independent assays. A dose response matrix of RAD001 or dBET6 in A1847 cells is shown in FIG. 17, Panel A. DLD-1 cells were treated with DMSO, 2 µM RAD001, increasing doses of dBET6 or 2 µM RAD001+increasing doses of dBET6 for 4 hours and BRD4 protein assessed by Western blot. An immunoblot analysis of BRD4 protein levels is shown in FIG. 17, Panel B. A drug synergy analysis of RAD001 and dBET6 in DLD-1 cells (N=3) is shown in FIG. 17, Panel C. Spheroid assays were performed wherein DLD-1 cells were treated with DMSO, 2 µM RAD001, 1 nM dBET6 or 2 µM RAD001+1 nM dBET6 and spheroid formation was assessed (see, Fure 17, Panel D).

Several cancer cell lines have been reported to be intrinsically resistant to BBDs, including the colorectal cancer cell line DLD-1. Here, DLD-1 cells were shown to be resistant to dBET6 (FIG. 17, panel A) with GI5O's >1 µM requiring high concentrations of dBET6 to reduce BET proteins and inhibit protein synthesis (FIG. 17, Panel B). DLD-1 cells harbor activating mutations in the K-Ras and PIK3CA genes, both known to strongly potentiate mTORC1 signaling. Notably, combined treatment of RAD001 and dBET6 enhanced the degradation of BRD4 in DLD-1 cells, markedly reducing BRD4 levels, compared to treatment with single agent dBET6 (FIG. 17, Panel B). Strong drug synergy was observed in RAD001 and dBET6 treated cells with Bliss synergy score of 24.17 (FIG. 17, Panel C) and the combination blocked spheroid growth in 3D assays while single agents were ineffective, demonstrating RAD001-treatment can sensitize resistant cells to BBDs (FIG. 17, Panel D). Thus, cancer cells intrinsically resistant to BET protein PROTACs can be made sensitive by blocking mTORC1 signaling, supporting combination therapies involving MTORC1 and BET protein degraders for the treatment of these types of cancers.

Example 11: Activation of K-ras Signaling
Promotes Resistance to BET-PROTACs that can be
Reversed by MTORC1 Inhibitors K-ras mutations promote resistance to BET protein degraders that can be overcome by MTORC1 inhibitors. Briefly, isogenic SW48 colorectal cancer cells expressing wild-type or mutant (G12D) K-ras were treated with increasing doses of MZ1 and cell viability was assessed. Expression of K-ras mutants promote resistance to MZ1 therapy (FIG. 18, Panel A). Immunoblot analysis depicts activation of translation by forced expression of K-ras G12D mutants in SW48 cells (FIG. 18, Panel B). SW48 cells expressing wild-type or K-ras G12D mutants were treated with DMSO, 2 µM RAD001, increasing doses of MZ1 or 2 µM RAD001+ increasing doses of MZ1 for 4 hours and BRD4 protein assessed by Western blot. Immunoblot analysis of BRD4 protein levels are shown in FIG. 18, Panel C. A Cell-Titer Glo assay was performed for cell viability of SW48 (KRAS G12D) cell lines treated with increasing concentrations of RAD001, MZ1 or the combination of RAD001 and MZ1 and cultured for 120 hours. Data were analyzed as % cell viability of DMSO control, presented as means of 3 independent assays. A dose synergy analysis of RAD001 or MZ1 in K-ras G12D mutant SW48 cells is shown in FIG. 18, Panels D and E. Immunoblot analysis for BRD4 protein levels in response to combination is shown in FIG. 18, Panel F. A Cell-Titer Glo assay was performed for cell viability of SW48 (KRAS WT) cell lines treated with increasing concentrations of RAD001, MZ1 or the combination of RAD001 and MZ1 and cultured for 120 hours. Data were analyzed as % cell viability of DMSO control, presented as means of 3 independent assays. A dose synergy analysis of RAD001 or MZ1 in K-ras wild-type SW48 cells is shown in FIG. 18, Panels G and H. An immunoblot analysis for BRD4 protein levels in response to combination is shown in FIG. 18, Panel I.

To explore the impact of K-ras mutations on BBD responses, isogenic colorectal cancer cell lines harboring a knocking G12D K-Ras mutation or wild-type K-Ras were treated with MZ1 (FIG. 18, Panel A). Cells harboring K-Ras mutations displayed elevated translation signaling (FIG. 18, Panel B), and were less sensitive to MZ1 than parental cells exhibiting a 10-fold shift in GI50 from 0.63 to 63 nM. Moreover, knock-in of the K-Ras mutation impaired the degradation of BRD4 by MZ1 relative to parental cells, requiring higher concentrations of MZ1 to achieve complete degradation of BRD4 (FIG. 18, Panel C). Inhibition of mTORC1 signaling with RAD001 improved MZ1-mediated degradation of BRD4 in K-Ras expressing cells lowering the concentration of MZ1 required to achieve maximal degradation. Combined treatment of K-Ras isogeneic cells with RAD001 and MZ1 was highly synergistic at inhibiting cell viability with a Bliss synergy score of 21.041, as well as improved degradation of BRD4 relative to single agents (FIG. 18, Panels D, E, and F). In contrast, the combination therapy displayed less synergy (bliss synergy score of 7.59) in K-Ras WT cells, as single agent MZ1 inhibited viability >50% at low concentrations (FIG. 18, Panels G, H, and I). To summarize, these experiments indicate that cancer cells harboring K-Ras mutations or other mutations that strongly activate mTORC1 signaling can promote intrinsic resistance to BBDs representing a patient population that may benefit from combined mTORC1 and PROTAC-treatment.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A pharmaceutical composition comprising:
   one or more bromodomain and extra terminal domain (BET) proteolysis targeting chimera (PROTAC) (BET-PROTAC) therapeutic agents; and
   one or more casein kinase 2 (CK2) inhibitors or adaptor-associated kinase 1 (AAK1) inhibitors, wherein the one or more CK2 kinase inhibitors are GSK269962 or TBB, wherein the one or more AAK1 inhibitors are LP-935509, LP-922761, BMT-124110, LP-927443 or BMS-901715.

2. The pharmaceutical composition according to claim 1, comprising one or more BET-PROTAC therapeutic agents selected from the group consisting of a BRD2 PROTAC, a BRD3 PROTAC, a BRD4 PROTAC, a VHL ligand-based BET-PROTAC, a CRBN ligand-based BET-PROTAC, a phthalimide-based BET-PROTAC, a Nutlin-based BET-PROTAC, or CFT-2718, or any combination thereof.

3. The pharmaceutical composition of claim 1, wherein the one or more BET-PROTAC therapeutic agents is MZ1 or ARV825.

4. A method for augmenting the therapeutic effect in a human cancer patient undergoing treatment with one or more BET-PROTAC therapeutic agents comprising administering one or more kinase inhibitors to the patient, wherein the one or more kinase inhibitors are a casein kinase 2 (CK2) inhibitor or an adaptor-associated kinase 1 (AAK1) inhibitor, wherein the one or more CK2 kinase inhibitors are GSK269962 or TBB, wherein the one or more AAK1 inhibitors are LP-935509, LP-922761, BMT-124110, LP-927443, or BMS-901715.

5. The method according to claim 4, wherein the one or more BET-PROTAC therapeutic agents the human cancer patient is undergoing treatment with is a BRD2 PROTAC, a BRD3 PROTAC, a BRD4 PROTAC, a VHL ligand-based BET-PROTAC, a CRBN ligand-based BET-PROTAC, a phthalimide-based BET-PROTAC, a Nutlin-based BET-PROTAC, or CFT-2718, or any combination thereof.

6. A method of treating cancer in a human patient in need thereof, the method comprising administering to the patient a therapeutically effective amount of a pharmaceutical composition comprising:
   one or more BET-PROTAC therapeutic agents; and
   one or more kinase inhibitors, wherein the one or more kinase inhibitors are a casein kinase 2 (CK2) inhibitor or an adaptor-associated kinase 1 (AAK1) inhibitor, wherein the one or more CK2 kinase inhibitors are GSK269962 or TBB, wherein the one or more AAK1 inhibitors are LP-935509, LP-922761, BMT-124110, LP-927443 or BMS-901715.

7. The method according to claim 6, wherein the human patient is administered one or more BET-PROTAC therapeutic agents selected from the group consisting of a BRD2 PROTAC, a BRD3 PROTAC, a BRD4 PROTAC, a VHL ligand-based BET-PROTAC, a CRBN ligand-based BET-PROTAC, a phthalimide-based BET-PROTAC, a Nutlin-based BET-PROTAC, or CFT-2718, or any combination thereof.

8. The method according to claim 6, wherein the cancer is acute myeloid leukemia, acute monocytic leukemia, prostatic adenocarcinoma, ovarian carcinoma, or epithelial ovarian cancer.

* * * * *